US006544727B1

(12) United States Patent
Hei

(10) Patent No.: US 6,544,727 B1
(45) Date of Patent: *Apr. 8, 2003

(54) METHODS AND DEVICES FOR THE REMOVAL OF PSORALENS FROM BLOOD PRODUCTS

(75) Inventor: Derek J. Hei, Concord, CA (US)

(73) Assignee: Cerus Corporation, Concord, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/659,249

(22) Filed: Jun. 7, 1996

Related U.S. Application Data

(63) Continuation-in-part of application No. 08/484,926, filed on Jun. 7, 1995, now abandoned.

(51) Int. Cl.[7] .......................... A01N 1/02; A61M 37/00; A61B 19/00
(52) U.S. Cl. ..................... 435/2; 435/173.1; 435/173.9; 424/529; 424/530; 424/531; 604/5.01; 604/5.02; 604/6.08; 604/6.09; 604/6.1; 604/6.15; 604/262; 604/403; 604/406; 604/408; 604/409; 604/410
(58) Field of Search ...................... 435/2, 173.1, 173.9; 604/529, 530, 531, 5.01, 5.02, 6.08, 6.09, 262, 403, 408, 406, 409, 410, 6.1, 6.15

(56) References Cited

U.S. PATENT DOCUMENTS

| 4,160,059 A | 7/1979 | Samejima |
|---|---|---|
| 4,202,775 A | 5/1980 | Abe et al. |
| 4,460,530 A | 7/1984 | Hanson et al. |
| 4,594,202 A | 6/1986 | Pall et al. |
| 4,728,432 A | 3/1988 | Sugiyama et al. |
| 4,935,141 A | 6/1990 | Buck et al. |
| 4,959,148 A | * 9/1990 | Clark, III .................... 210/635 |
| 4,985,153 A | 1/1991 | Kuroda et al. |

(List continued on next page.)

FOREIGN PATENT DOCUMENTS

| AU | 6339190 | 4/1991 |
|---|---|---|
| JP | 62283198 | * 1/1990 |
| WO | WO 91/03933 | 4/1991 |
| WO | WO 9500631 | * 1/1995 |

OTHER PUBLICATIONS

Goodrich et al. "Selective inactivation of viruses in the presence of human platelets: UV sensitization with psoralen derivatives" Proc. Natl. Acad. Sci. USA vol. 91 5552–5556 (1994).

(List continued on next page.)

Primary Examiner—Michael P. Woodward
Assistant Examiner—Mary K Zeman
(74) Attorney, Agent, or Firm—Morrison & Foerster LLP

(57) ABSTRACT

Methods and devices for the removal of psoralens and psoralen photoproducts from blood products are described. The methods include contacting a psoralen- and irradiation-treated blood product with a resin capable of adsorbing psoralens and psoralen photoproducts. The removal process is particularly suitable for use with platelet concentrates and plasma because the process does not have a significant adverse effect on clotting factor function. The methods and devices can be incorporated with apheresis systems and other devices and procedures currently used to process blood products for transfusion.

47 Claims, 70 Drawing Sheets

U.S. PATENT DOCUMENTS

| | | | |
|---|---|---|---|
| 5,094,960 A | * | 3/1992 | Bonomo |
| 5,100,564 A | | 3/1992 | Pall et al. |
| 5,128,048 A | * | 7/1992 | Stewart et al. |
| 5,234,608 A | | 8/1993 | Duff |
| 5,328,758 A | | 7/1994 | Markell et al. |
| 5,354,262 A | * | 10/1994 | Boehinger et al. |
| 5,407,581 A | | 4/1995 | Onodera et al. |
| 5,418,130 A | | 5/1995 | Platz et al. |
| 5,456,845 A | | 10/1995 | Nishimura et al. |
| 5,486,410 A | | 1/1996 | Groeger |
| 5,501,795 A | | 3/1996 | Pall et al. |
| 5,504,163 A | | 4/1996 | Tegen et al. |
| 5,531,902 A | | 7/1996 | Gallup |
| 5,543,062 A | | 8/1996 | Nishimura |
| 5,556,541 A | | 9/1996 | Ruschke |
| 5,559,250 A | | 9/1996 | Cook et al. |
| 5,593,823 A | | 1/1997 | Wollowitz et al. |
| 5,605,746 A | | 2/1997 | Groeger |
| 5,607,766 A | | 3/1997 | Berger |
| 5,616,254 A | | 4/1997 | Pall et al. |
| 5,660,731 A | * | 8/1997 | Piechocki |
| 5,662,728 A | | 9/1997 | Groeger |
| 5,773,384 A | | 6/1998 | Davankov et al. |
| 5,817,354 A | | 10/1998 | Mozaffar et al. |
| 5,883,256 A | | 3/1999 | Schüler et al. |
| 6,228,995 B1 | | 5/2001 | Lee |
| 6,319,662 B1 | | 11/2001 | Foley et al. |
| 6,348,309 B1 | | 2/2002 | Mohr et al. |

OTHER PUBLICATIONS

Bulletin 871 A, (1994) "Sterile Pyrogen–Free Adsorbent Cartridges for Purifying Biological Preparations," Supelco, Inc., 8 pages.

Hayes, J.S., (Jun. 1994) "Activated Carbon Fibers and Textiles" *American Kynol, Inc.*, Pleasantville, NY, p.1–20.

Hayes, J. S., (Apr. 20, 1993) "Novoloid and Related Fibers in Nonwoven Structures" Index 93 C Congress, Session 2C, Geneva, *American Kynol, Inc.*, Pleasantville, NY, p. 1–24.

Bogusz, Maciej et al. "Isolation of drugs from blood and tissues with XAD–2 bags" Forensic Sci. Int'l. 12:73–72 (1978).

Carmen, R., "The selection of plastic materials for blood bags," *Trans. Med. Rev.* (1993) 7:1 1–10.

Kiremitci & Piskin, "Properties of new sorbents containing activated carbon–PHEMA–PEG," Int'l. J. of Art. Org. (1985) 8:4 201–208.

Moroff et al. (1992) "Factors influencing virus inactivation and retention of platele properties following treatment with aminomethyltrimethylpsoralen and ultraviolet A light" Blood Cells 18:43–56.

Tishler & Winston "Sorbent therapy of the porphyrias. III. Comparative efficacy of experimental plasma perfusion with several commercial hemoperfusion cartridges" (1984) Meth & Find Exptl Clin. Pharmacol (1984) 6:7 389–393.

Valeri, Capt. C.R. et al. "Freeze–preserved baboon red blood cells: effects of biochemical modification and perfusion in vitro", Am J Vet Res, 42:1590–1594 (1981).

Tsyurupa et al. Reactive Polymers 25:69–78, 1995.*

Margolis–Nunno et al. (1995a) Transfusion 35: 855–862, 1995.*

Verified Translation of PCT Application PCT/DE90/00691.

* cited by examiner

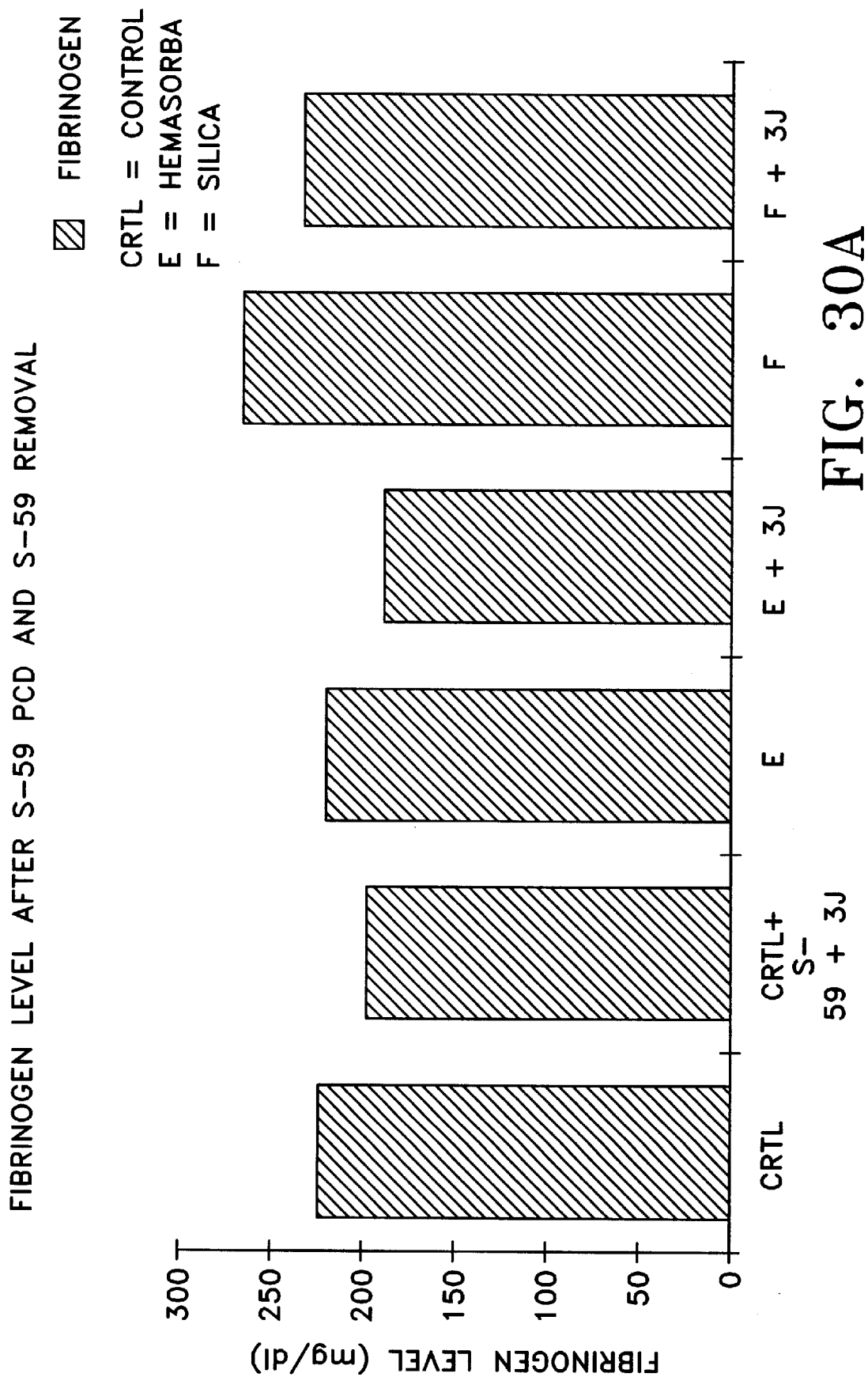

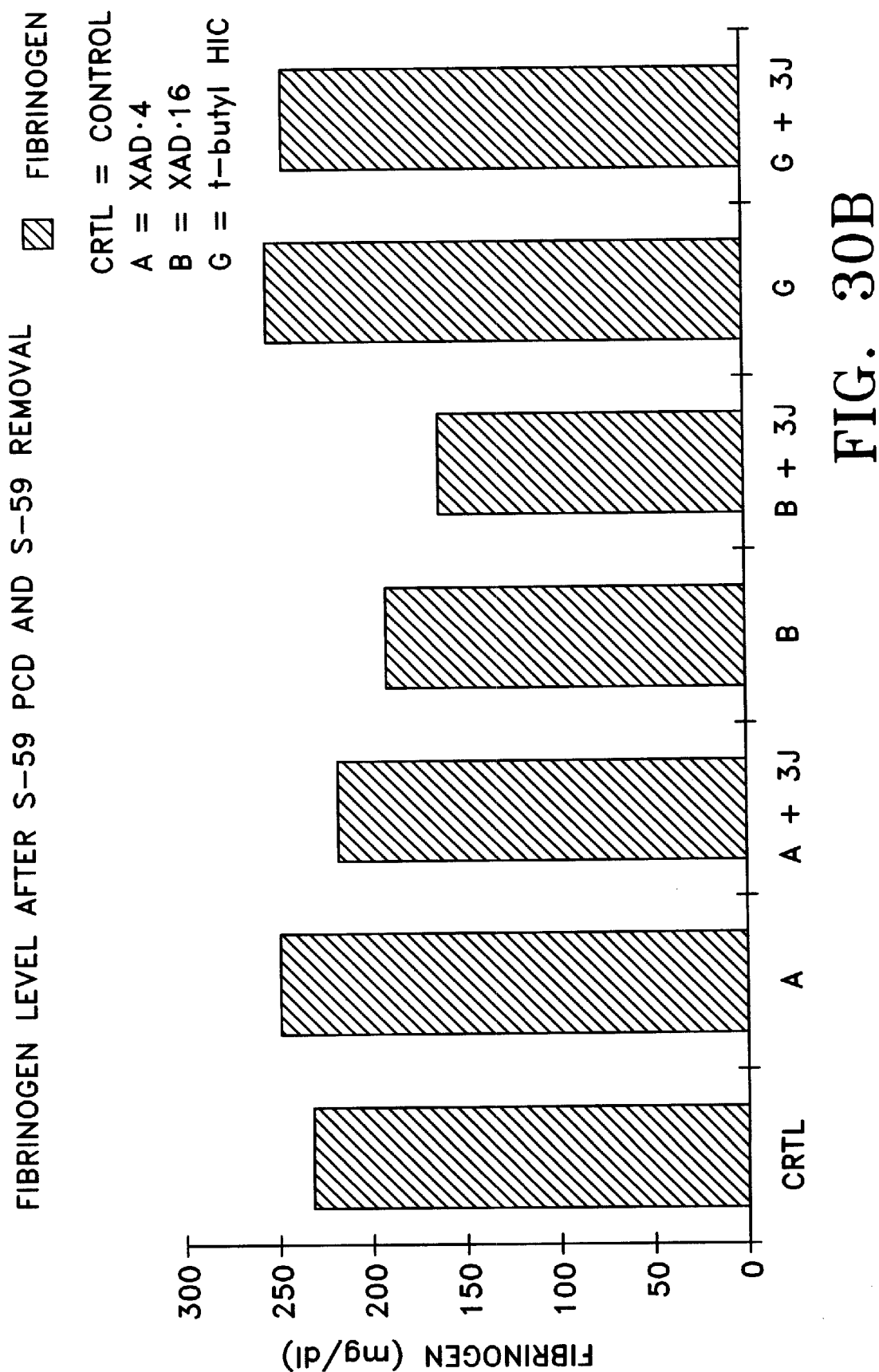

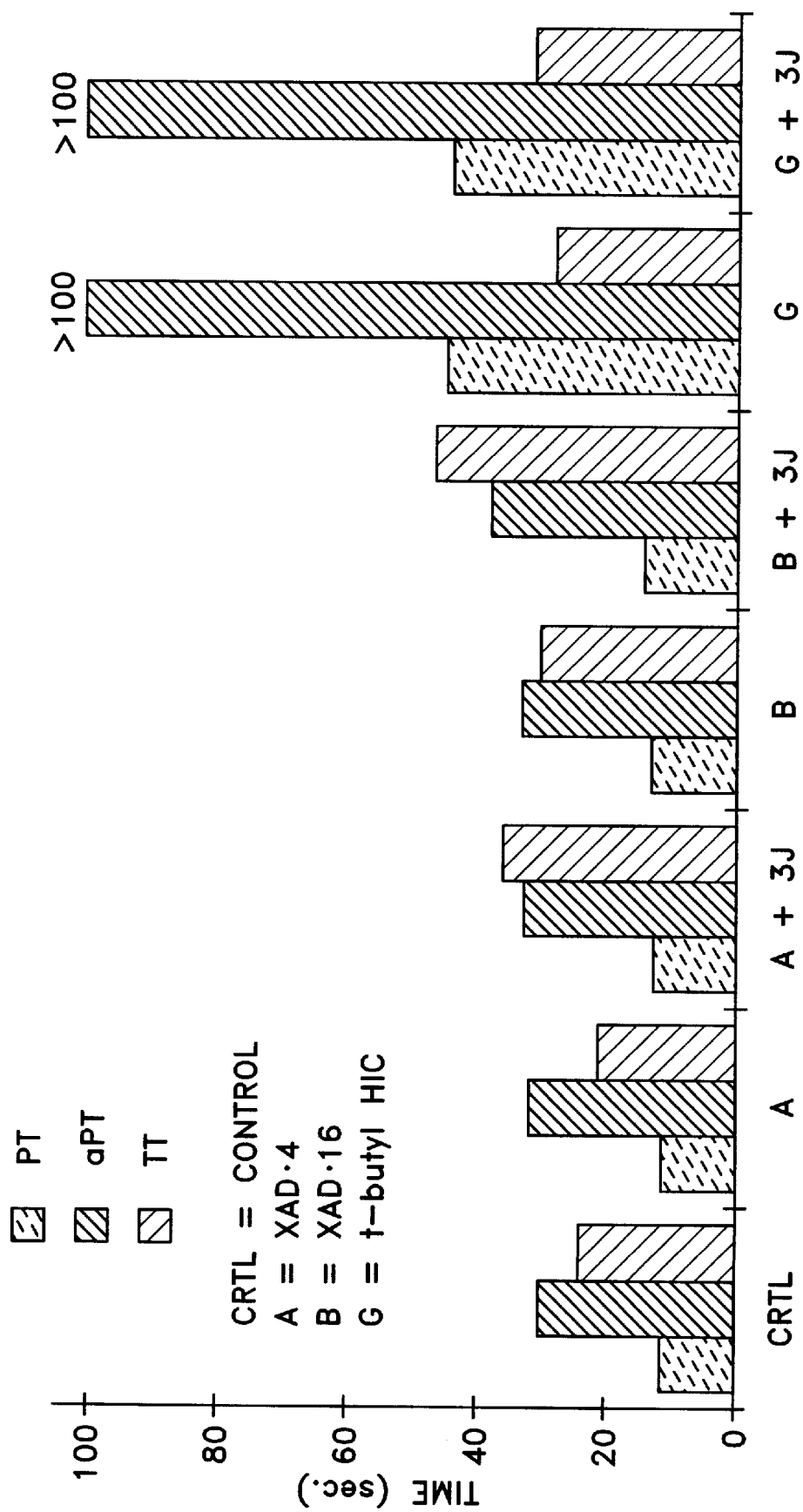

| Manufacture of Port Seal Subassembly | | Manufacture of Filled Mesh Pouch | |
|---|---|---|---|
| A1<br>Mesh (PL 1144 Plastic) arrives cleaned and cut to final dimension |  | B1<br>Mesh (PL 1144 Plastic) arrives cleaned and cut to final dimension |  |
| A2<br>Mesh is folded longitudely and sealed transversely forming port filter open on one end |  | B2<br>Mesh is folded longitudely and sealed transversely forming mesh bag, open on one end |  |
| A3<br>Port filter is sealed to port bushing completing port seal subassembly |  | B3<br>Mesh pouch is precision filled by weight with adsorbent beads and sealed closed | 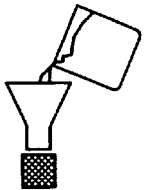 |
| | | B4<br>Pouches are cleaned in vacuum and subject to 100% inspection |  |

FIG. 38A

Configuration A

Configuration B

METHODS AND DEVICES FOR THE REMOVAL OF PSORALENS FROM BLOOD PRODUCTS

This application is a continuation in part of application Ser. No. 08/484,926, filed Jun. 7, 1995, now abandoned.

FIELD OF THE INVENTION

The present invention relates to methods and devices for the removal of substances from blood products and particularly to methods and devices for the removal of psoralens and psoralen photoproducts from plasma that contains platelets without significantly affecting platelet function.

BACKGROUND

Pathogen contamination within the blood supply remains an important medical problem throughout the world. Although improved testing methods for hepatitis B (HBV), hepatitis C (HCV), and HIV have markedly reduced the incidence of transfusion associated diseases, the public is losing trust in the safety of the blood supply due to publicity of cases of transfusion related transmission of these viruses.

For example, the recent introduction of a blood test for HCV will reduce transmission of this virus; however, it has a sensitivity of only 67% for detection of probable infectious blood units. HCV is responsible for 90% of transfusion associated hepatitis. Melnick, J. L., Abstracts of Virological Safety Aspects of Plasma, Cannes, Nov. 3–6, 1992 (page 9). It is estimated that, with the test in place, the risk of infection is 1 out of 3300 units transfused.

Similarly, while more sensitive seriological assays are in place for HIV-1 and HBV, these agents can nonetheless bed transmitted by seronegative blood donors. International Forumn: Vox Sang 32:346 (1977). Ward, J. W., et al., N. Engl. J. Med., 318:473 (1988). Up to 10% of total transfusion-related hepatitis and 25% of severe icteric cases are due to the HBV transmitted by hepatitis B surface antigen (HBasAg) negative donors. To date, fifteen cases of transfusion-associated HIV infections have been reported by the Center for Disease Control (CDC) among recipients of blood pre tested negative for antibody to HIV-1.

Furthermore, other viral, bacterial, and agents are not routinely tested for, and remain a potential threat to transfusion safety. Schmunis, G. A., Transfusion 31:547–557 (1992). In addition, testing will not insure the safety of the blood supply against future unknown pathogens that may enter the donor population resulting in transfusion associated transmission before sensitive tests can be implemented.

Even if seroconversion tests were a sufficient screen, they may not be practical in application. For example, CMV (a herpes virus) and parvo B19 virus in humans are common. When they occur in healthy, immunocompetent adults, they nearly always result in asymptomatic seroconversion. Because such a large part of the population is seropositive, exclusion of positive units would result in substantial limitation of the blood supply.

An alternative approach to eliminate transmission of viral diseases through blood products is to develop a means to inactivate pathogens in transfusion products. Development of an effective technology to inactivate infectious pathogens in blood products offers the potential to improve the safety of the blood supply, and perhaps to slow the introduction of new tests, such as the recently introduced HIV-2 test, for low frequency pathogens. Ultimately, decontamination technology could significantly reduce the cost of blood products and increase the availability of scarce blood products.

To be useful, such an inactivation method i) must not adversely affect the function for which the blood product is transfused, ii) must thoroughly inactivate existing pathogens in the blood product, and iii) must not adversely affect the recipients of the blood product. Several methods have been reported for the inactivation or elimination of viral agents in erythrocyte-free blood products. However, most of these techniques are completely incompatible with maintenance of the function of platelets, an important blood product. Examples of these techniques are: heat (Hilfenhous, J., et al., J. Biol. Std. 70:589 (1987)), solvent/detergent treatment (Horowitz, B., et al., Transfusion 25:516 (1985)), gamma-irradiation (Moroff, G., et al., Transfusion 26:453 (1986)), UV radiation combined with beta propriolactone, (Prince A. M., et al., Reviews of Infect. Diseases 5:92–107 (1983)), visible laser light in combination with hematoporphyrins (Matthews J. L., et al., Transfusion 28:81–83 (1988); North J., et al., Transfusion 32:121–128 (1992)), use of the photoactive dyes aluminum phthalocyananine and merocyanine 540 (Sieber F., et al., Blood 73:345–350 (1989); Rywkin S., et al., Blood 78(Suppl 1):352a (Abstract) (1991)) or UV alone (Proudouz, K. N., et al., Blood 70:589 (1987)).

Other methods inactivate viral agents by treatment with furocoumarins, such as psoralens, in the presence of ultraviolet light. Psoralens are tricyclic compounds formed by the linear fusion of a furan ring with a coumarin. Psoralens can intercalate between the base pairs of double-stranded nucleic acids, forming covalent adducts to pyrimidine bases upon absorption of long wave ultraviolet light (UVA). G. D. Cimino et al., Ann. Rev. Biochem. 54:1151 (1985); Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977); S. T. Isaacs et al., Trends in Photobiology (Plenum) pp. 279–294 (1982); J. Tessman et al., Biochem. 24:1669 (1985); Hearst et al., U.S. Pat. Nos. 4,124,598, 4,169,204, and 4,196,281, hereby incorporated by reference.

The covalently bonded psoralens act as inhibitors of DNA replication and thus have the potential to stop the replication process. Due to this DNA binding capability, psoralens are of particular interest in relation to solving the problems inherent in creating and maintaining a pathogen-free blood supply. Some known psoralens have been shown to inactivate viruses in some blood products. H. J. Alter et al., The Lancet (ii:1446) (1988); L. Lin et. al., Blood 74:517 (1989) (decontaminating platelet concentrates); G. P. Wiesehahn et al., U.S. Pat. Nos. 4,727,027 and 4,748,120, hereby incorporated by reference, describe the use of a combination of 8-methoxypsoralen (8-MOP) and irradiation. P. Morel et al., Blood Cells 18:27 (1992) show that 300 µg/mL of 8-MOP together with ten hours of irradiation with ultraviolet light can effectively inactivate viruses in human serum. Similar studies using 8-MOP and aminomethyltrimethyl psoralen (AMT) have been reported by other investigators. Dodd RY, et al., Transfusion 31:483–490 (1991); Margolis-Nunno, H., et al., Thromb Haemostas 65:1162 (Abstract)(1991). Indeed, the photoinactivation of a broad spectrum of microorganisms has been established, including HBV, HCV, and HIV, under conditions different from those used in the present invention and using previously known psoralen derivatives. [Hanson, C. V., Blood Cells, 18:7–24 (1992); Alter, H. J., et al., The Lancet ii:1446 (1988); Margolis-Nunno, H. et al., Thromb Haemostas 65:1162 (Abstract) (1991).]

Psoralen photoinactivation is only feasible if the ability of the psoralen to inactivate viruses is sufficient to ensure a safety margin in which complete inactivation will occur. On the other hand, the psoralen must not be such that it will cause damage to blood products. The methods just described, when applied using known psoralens, require the use of difficult and expensive procedures to avoid causing damage to blood products. For example, some compounds and protocols have necessitated the removal of molecular oxygen from the reaction before exposure to light, to prevent damage to blood products from oxygen radicals produced during irradiation. See L. Lin et al., Blood 74:517 (1989); U.S. Pat. No. 4,727,027, to Wiesehahn. This is a costly and time consuming procedure.

Finally, some commonly known compounds used in photochemical decontamination (PCD) exhibit undesirable mutagenicity which appears to increase with increased ability to kill virus. In other words, the more effective the known compounds are at inactivating viruses, the more injurious the compounds are to the recipient, and thus, the less useful they are at any point in an inactivation system of products for in vivo use.

A new psoralen compound is needed which displays improved ability to inactivate pathogens and low mutagenicity, without causing significant damage to blood products for which it is used, and without the need to remove oxygen, thereby ensuring safe and complete inactivation of pathogens in blood decontamination methods. In addition, a device is needed that is capable of removing from blood products both residual levels of and photoproducts created by a suitable psoralen, thereby allowing efficient and economical widespread use of PCD treatment of such blood products.

SUMMARY OF THE INVENTION

The present invention provides new psoralens and methods of synthesis of new psoralens having enhanced ability to inactivate pathogens in the presence of ultraviolet light which is not linked to mutagenicity. The present invention also provides methods of using new and known compounds to inactivate pathogens in health related products to be used in vivo and in vitro, and particularly, in blood products and blood products in synthetic media.

The present invention contemplates a method of inactivating pathogens in a platelet preparation comprising, in the following order: a) providing, in any order, i) a synthetic media comprising a compound selected from the group consisting of 4'-primaryamino-substituted psoralens and 5'-primaryamino-substituted psoralens; ii) photoactivating means for photoactivating said compound; and iii) a platelet preparation suspected of being contaminated with a pathogen having nucleic acid; b) adding said synthetic media to said platelet preparation; and c) photoactivating said compound so as to prevent the replication of substantially all of said pathogen nucleic acid, without significantly altering the biological activity of said platelet preparation. The pathogen may be a virus, or a bacteria. Its nucleic acid may be single stranded or double stranded, DNA or RNA. The photoactivating means comprises a photoactivation device capable of emitting a given intensity of a spectrum of electromagnetic radiation comprising wavelengths between 180 nm and 400 nm. The intensity may be between 1 and 30 mW/cm$^2$ and the platelet preparation is exposed to said intensity for between 1 second and thirty minutes. The spectrum of electromagnetic radiation may be wavelengths between 320 nm and 380 nm.

In one embodiment the compound displays low mutagenicity. It may be added to said platelet preparation at a concentration of between 0.1 and 250 μM. And the method may be performed without limiting the concentration of molecular oxygen.

The 4'-primaryamino-substituted psoralen may comprise: a) a substituent $R_1$ on the 4' carbon atom, selected from the group comprising:

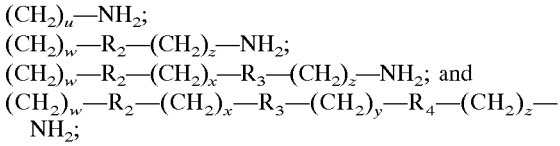

wherein $R_2, R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_vCH_3$, where v is a whole number from 0 to 5; or a salt thereof Alternatively, the 5'-primaryamino-substituted psoralen comprises: a) a substituent $R_1$ on the 5' carbon atom, selected from the group comprising:

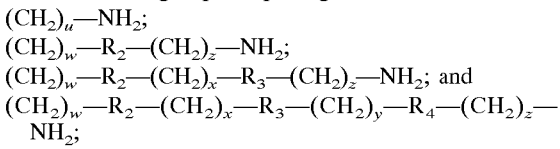

wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, and where when $R_1$ is selected from the group comprising —$(CH_2)_u$—$NH_2$, $R_6$ is H; or a salt thereof Finally, the 5'-primaryamino-substituted psoralen may comprise: a) a substituent $R_1$ on the 5' carbon atom, selected from the group comprising:

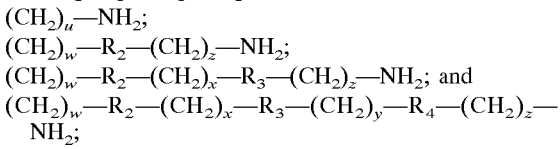

wherein $R_2R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5; or a salt thereof.

In one embodiment, at least two compounds are present. In another embodiment, the synthetic media further comprises sodium acetate, potassium chloride, sodium chloride, sodium citrate, sodium phosphate and magnesium chloride, and may also include mannitol and/or glucose.

In one embodiment, the synthetic media is contained in a first blood bag and said platelet preparation is contained in a second blood bag, the synthetic media being added to the platelet preparation in step (b) by expressing the synthetic media from the first blood bag into the second blood bag via a sterile connection.

In a preferred embodiment, the compound is either 5'-(4-amino-2-oxa)butyl-4,4',8-trimethylpsoralen or 4'-(4-amino-2-oxa)butyl-4,5',8-trimethylpsoralen.

In one embodiment, the method described above includes administering said platelet preparation by intravenous infusion to a mammal.

The present invention contemplates a method of inactivating pathogens in a platelet preparation comprising, in the following order: a) providing, in any order, i) a synthetic media comprising a buffered saline solution and a compound displaying low mutagenicity, selected from the group consisting of 4'-primaryamino-substituted psoralens and 5'-primaryamino-substituted psoralens, contained in a first blood bag; ii) photoactivating means for photoactivating said compound; and iii) a platelet preparation suspected of being contaminated with a pathogen having nucleic acid, contained in a second blood bag; b) adding said synthetic media to said platelet preparation by expressing said synthetic media from said first blood bag into said second blood bag via sterile connection means; and c) photoactivating said compound so as to prevent the replication of substantially all of said pathogen nucleic acid, without significantly altering the biological activity of said platelet preparation. The pathogen may be a virus or a bacteria. Its nucleic acid may be single stranded or double stranded, DNA or RNA. The photoactivating means comprises a photoactivation device capable of emitting a given intensity of a spectrum of electromagnetic radiation comprising wavelengths between 180 nm and 400 nm. The intensity may be between 1 and 30 mW/cm$^2$ and the platelet preparation is exposed to said intensity for between 1 second and thirty minutes. The spectrum of electromagnetic radiation may be wavelengths between 320 nm and 380 nm.

In one embodiment the compound displays low mutagenicity. It may be added to said platelet preparation at a concentration of between 0.1 and 250 $\mu$M. And the method may be performed without limiting the concentration of molecular oxygen.

The 4'-primaryamino-substituted psoralen may comprise: a) a substituent $R_1$ on the 4' carbon atom, selected from the group comprising:

$(CH_2)_u$—$NH_2$;
$(CH_2)_w$—$R_2$—$(CH_2)_z$—$NH_2$;
$(CH_2)_w$—$R_2$—$(CH_2)_x$—$R_3$—$(CH_2)_z$—$NH_2$; and
$(CH_2)_w$—$R_2$—$(CH_2)_x$—$R_3$—$(CH_2)_y$—$R_4$—$(CH_2)_z$—$NH_2$;

wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_v CH_3$, where v is a whole number from 0 to 5; or a salt thereof.

Alternatively, the 5'-primaryamnino-substituted psoralen comprises: a) a substituent $R_1$ on the 5' carbon atom, selected from the group comprising:

$(CH_2)_u$—$NH_2$;
$(CH_2)_w$—$R_2$—$(CH_2)_z$—$NH_2$;
$(CH_2)_w$—$R_2$—$(CH_2)_x$—$R_3$—$(CH_2)_z$—$NH_2$; and
$(CH_2)_w$—$R_2$—$(CH_2)_x$—$R_3$—$(CH_2)_y R_4$—$(CH_2)_z$—$NH_2$;

wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5, and where when $R_1$ is selected from the group comprising —$(CH_2)_u$—$NH_2$, $R_6$ is H; or a salt thereof Finally, the 5'-primaryamino-substituted psoralen may comprise: a) a substituent $R_1$ on the 5' carbon atom, selected from the group comprising:

$(CH_2)_u$—$NH_2$;
$(CH_2)_w$—$R_2$—$(CH_2)_z$—$NH_2$;
$(CH_2)_w$—$R_2$—$(CH_2)_x$—$R_3$—$(CH_2)_z$—$NH_2$; and
$(CH_2)_w$—$R_2$—$(CH_2)_x$—$R_3$—$(CH_2)_y R_4$—$(CH_2)_z$—$NH_2$;

wherein $R_2$, $R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5; or a salt thereof.

In one embodiment, at least two compounds are present. In another embodiment, the synthetic media further comprises sodium acetate, potassium chloride, sodium chloride, sodium citrate, sodium phosphate and magnesium chloride, and may also include mannitol and/or glucose.

In one embodiment, the synthetic media is contained in a first blood bag and said platelet preparation is contained in a second blood bag, the synthetic media being added to the platelet preparation in step (b) by expressing the synthetic media from the first blood bag into the second blood bag via a sterile connection.

In a preferred embodiment, the compound is either 5'-(4-amino-2-oxa)butyl-4,4',8-trimethylpsoralen or 4'-(4-amino-2-oxa)butyl-4,5',8-trimethylpsoralen.

In one embodiment, the method described above includes administering said platelet preparation by intravenous infusion to a mammal.

The present invention also contemplates a method of synthesizing 4,8-dialkyl-5'-bromomethyl-4'-methylpsoralens, without performing chloromethylation, comprising: a) providing 4,8-dialkyl-7-(1-methyl-2-oxopropyloxy)psoralen; d) stirring 4,8-dialkyl-4',5'-dimethylpsoralen in carbon tetrachloride to obtain 4,8-dialkyl-5-bromomethyl-4'-methylpsoralen. A method of synthesizing 4,8-dialkyl-4'-bromomethyl-5'-methylpsoralens, without performing chloromethylation, is contemplated, comprising: a) providing 4,8-dialkyl-7-(1-methyl-2-oxopropyloxy)psoralen; d) stirring 4,8-dialkyl-4',5'-dimethylpsoralen in methylene chloride to obtain 4,8-dialkyl-4'-bromomethyl-5'-methylpsoralen.

A novel compound is also contemplated, having the formula:

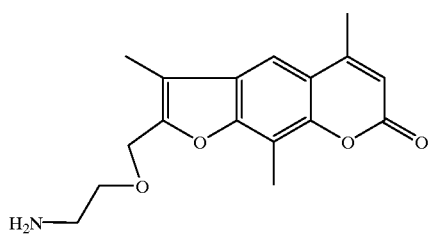

or a salt thereof.

Finally, the present invention contemplates compositions having anti-viral properties. The first comprising an aqueous solution of a 4'-primaryamino-substituted psoralen and platelets suitable for in vivo use. One embodiment, further comprises a synthetic media, comprising sodium acetate, potassium chloride, sodium chloride, sodium citrate, sodium phosphate and magnesium chloride and optionally mannitol or glucose. These same compositions are contemplated that contain a 5'-primaryamino-substituted psoralen rather than a 4'-primaryamino-substituted psoralen.

A novel synthetic platelet storage media, is also contemplated, comprising an aqueous solution of:
45–100 mM sodium chloride;
4–5 mM potassium chloride;
10–15 mM sodium citrate;
20–27 mM sodium acetate;
0–2 mM glucose;
0–30 mM mannitol;
approximately 20 mM sodium phosphate;
2–3 mM magnesium chloride; and
a psoralen selected from the group consisting of 4'-primaryaminopsoralen and a
5'-primaryaminopsoralen, at a concentration between approximately 0.1 and 250 µM.

The present invention provides a method of inactivating nucleic acid-containing pathogens in blood products, comprising providing, in any order, psoralen, photoactivation means, a blood product intended for in vivo use suspected of being contaminated with at least one pathogen, adding psoralen to the blood product to create a solution of psoralen at a concentration, treating the solution with photoactivation means so as to create a treated blood product, wherein pathogens are inactivated, and wherein at least a portion of the psoralen concentration is free in solution; and removing substantially all of the portion of psoralen concentration free in solution in treated blood product. In one embodiment, the removing step comprises contacting treated blood product with a resin. It is contemplated that various resins will be used with the present invention, including but not limited to adsorbents, polystyrene, polyacrylic ester, silica, activated charcoal, and activated charcoal coated with poly-(2-hydroxyethyl methacrylate). In an alternative embodiment, the contacting step comprises perfusing blood product through an in-line column containing resin.

In another embodiment, the method of the present invention comprises passing blood product through a flow adapter in fluidic contact with an in-line column after the blood product has passed through the in-line column. In another embodiment the contacting occurs within a bag containing resin. In a particularly preferred embodiment, the resin is contained within a mesh enclosure in the bag, wherein the mesh enclosure is adapted to allow blood product to contact the resin.

In another embodiment, the method of the present invention further comprises a partition mounted external to, and in contact, with the bag, wherein the partition is adapted to separate blood product from the mesh enclosure and adapted to be removed from the bag at a predetermined time. In an alternative embodiment, the method further comprises mixing the resin-containing bag with a shaker device. It is contemplated that various psoralen compounds will be useful in the present invention, including, but not limited to 4'-(4-amino-2-oxa)butyl-4,5',8-trimethylpsoralen. It is also contemplated that the blood product comprise any blood components, including but not limited to platelets, plasma, red cells, and white cells, as well as whole blood.

In another embodiment, the present invention provides a method of inactivating nucleic acid-containing pathogens in blood products, comprising the steps of, providing in any order, 4'-(4-amino-2-oxa)butyl-4,5',8-trimethylpsoralen, photoactivation means, a platelet mixture intended for in vivo use suspected of being contaminated with pathogens, adding 4'-(4-amino-2-oxa)butyl-4,5',8-trimethylpsoralen to the platelet mixture to create a solution of 4'-(4-amino-2-oxa)butyl-4,5',8-trimethylpsoralen at a concentration; treating the solution with photoactivation means so as to create a treated platelet mixture wherein pathogens are inactivated and wherein at least a portion of 4'-(4-amino-2-oxa)butyl-4,5',8-trimethylpsoralen concentration is free in solution; and removing substantially all of the portion of 4'-(4-amino-2-oxa)butyl-4,5',8-trimethylpsoralen concentration free in solution in the treated platelet mixture.

In one embodiment of this method, the removing step comprises contacting treated platelet mixture with a resin. The present invention contemplates greater than 99% removal of 4'-(4-amino-2-oxa)butyl-4,5',8-trimethylpsoralen at two hours with contacting with a resin. It is contemplated that various resins will be used with the present invention, including but not limited to adsorbents, polystyrene, polyacrylic ester, silica, activated charcoal, and activated charcoal coated with poly-(2-hydroxyethyl methacrylate). In an alternative embodiment, the contacting step comprises perfusing blood product through an in-line column containing resin. In yet another embodiment, this method further comprises passing blood product through a flow adapter in fluidic contact with an in-line column after blood product has passed through the in-line column.

In one embodiment of this method, the contacting occurs within a bag containing resin. In a preferred embodiment, the resin is contained within a mesh enclosure in the bag, wherein the mesh enclosure is adapted to allow blood product to contact resin. In another preferred embodiment, the method further comprises a partition mounted external to, and in contact, with the bag, wherein the partition is adapted to separate the blood product from the mesh enclosure and adapted to be removed from the bag at a predetermined time. It is contemplated that this method further comprises mixing the resin-containing bag with a shaker device.

The present invention also provides a blood decontamination system, comprising a first blood bag and an in-line column containing resin capable of removing psoralen, where the in-line column has an input end in fluidic communication with first blood bag, an output end, and a capacity. In one embodiment, the output end is in fluidic contact with a second blood bag. In a preferred embodiment, the capacity of the in-line column is approximately 5–10 mL. In another embodiment, the method further comprises a flow adapter positioned in fluidic contact with the in-line column and positioned after the output end of the inline column and before the second bag.

In one embodiment of this method, the removing step comprises contacting treated platelet mixture with a resin. It is contemplated that various resins will be used with the present invention, including but not limited to adsorbents, polystyrene, polyacrylic ester, silica, activated charcoal, and activated charcoal coated with poly-(2-hydroxyethyl methacrylate). In an alternative embodiment, the contacting step comprises perfusing blood product through an in-line column containing resin. In yet another embodiment, this method further comprises passing blood product through a flow adapter in fluidic contact with an in-line column after blood product has passed through the in-line column.

The present invention also provides a blood bag, comprising a biocompatible housing and a compartment within the housing which contains a resin capable of removing psoralen. In one embodiment, the blood bag further comprises a mesh enclosure disposed within the compartment and containing resin, wherein the mesh enclosure is adapted to allow a blood product to contact the resin. It is contemplated that the mesh enclosure is fixed in location within the compartment.

In an alternative embodiment, the blood bag further comprises a partition mounted external to, and in contact with, the biocompatible housing, wherein the partition is adapted to separate blood product from the mesh enclosure and to be removed from the bag at a predetermined time to allow blood product to contact the resin. In yet another embodiment, the blood bag further comprises a flow adapter in fluidic contact with the biocompatible housing and having a 50–100 $\mu$m opening mesh filter. It is contemplated that the resin of this invention comprise various materials, including, but not limited to adsorbents, polystyrene, polyacrylic ester, silica, activated charcoal, and activated charcoal coated with poly-(2-hydroxyethyl methacrylate).

It is contemplated that various blood bags will be used. It is not intended that the blood bag be limited to a particular type or source. Indeed, it is contemplated that blood bags obtained from any commercial source will be useful in the present invention. Also, it is contemplated that the photoactivation device of the present invention may be obtained from any commercial source. Thus, it is not intended that the present invention be limited to any one source of blood bag or photoactivation device.

The present invention contemplates a container for a blood product, comprising: a) a biocompatible housing; b) a resin capable of removing psoralen from the blood product, the resin contained within the biocompatible housing; and c) means for retaining the resin within the biocompatible housing.

The present invention also contemplates a blood bag, comprising: a) a biocompatible housing; b) a resin capable of removing aminopsoralen from a blood product, the resin contained within the biocompatible housing; c) means for retaning the resin within the biocompatible housing.

In some embodiments, the retaining means of the container or the blood bag comprises a mesh enclosure disposed within the biocompatible housing, the mesh enclosure containing the resin and adapted to allow a blood product to contact the resin. In further embodiments, the mesh enclosure comprises 30 $\mu$m pores. In particular embodiments, the mesh enclosure comprises polyester.

In additional embodiments, the container or the blood bag further comprises an inlet/outlet line. In still further embodiments, the retaining means comprises a mesh filter positioned in the inlet/oulet line and in fluidic communication with the biocompatible housing. The mesh filter comprises 30 $\mu$m pores in particular embodiments, while the mesh of the mesh filter comprises polyester in still other embodiments.

In particular embodiments of the present invention, the resin is adsorbent. When the resin is adsorbent it comprises a polymer in some embodiments. The polymer may be polystyrene in additional embodiments, and the polystyrene is crosslinked in still further embodiments.

In certain embodiments, the aminopsoralen is 4'-(4-amino-2-oxa)butyl-4,5',8-trimethylpsoralen.

The present invention also contemplates a method of inactivating nucleic acid-containing pathogens in blood products, comprising: a) providing, in any order: i) psoralen, ii) photoactivation means, iii) a first container containing a blood product intended for in vivo use suspected of being contaminated with the pathogens; b) adding the psoralen to the blood product in the first container to create a solution of psoralen at a concentration; c) treating the solution with the photoactivation means so as to create a treated blood product wherein the pathogens are inactivated and wherein at least a portion of the psoralen concentration is free in the solution; and d) removing some of the portion of the psoralen free in solution in the treated blood product. It should be emphasized that the present invention is not limited to the removal of a particular amount of psoralen free in solution. Indeed, the present invention contemplates the removal of any portion of psoralen free in solution.

In particular embodiments, the psoralen is 4'-(4-amino-2-oxa)butyl-4,5',8-trimethylpsoralen. In other embodiments, the psoralen is brominated. When a brominated psoralen is used, the brominated psoralen may be 5-bromo-8-methoxypsoralen or 5-bromo-8-(diethylaminopropyloxy)-psoralen. Moreover, the psoralen is a quaternary amine in some embodiments, and the quaternary amine psoralen is 4'-(triethylamino) methyl-4,5',8-trimethylpsoralen in still further embodiments.

In some embodiments of the present invention, the removing step comprises transferring the treated blood product into a second container, comprising: i) a biocompatible housing; ii) a resin capable of removing psoralen from the blood product, the resin contained within the biocompatible housing; and iii) retaining means for retaining the resin within the biocompatible housing under conditions such that some of the portion of the psoralen concentration free in solution is removed in the treated blood product.

In some embodiments, the retaining means of the container or the blood bag comprises a mesh enclosure disposed within the biocompatible housing, the mesh enclosure containing the resin and adapted to allow a blood product to contact the resin. In further embodiments, the mesh enclosure comprises 30 $\mu$m pores. In particular embodiments, the mesh enclosure comprises polyester.

In additional embodiments, the container or the blood bag further comprises an inlet/outlet line. In still further embodiments, the retaining means comprises a mesh filter positioned in the inlet/oulet line and in fluidic communication with the biocompatible housing. The mesh filter comprises 30 $\mu$m pores in particular embodiments, while the mesh of the mesh filter comprises polyester in still other embodiments.

The present invention also contemplates a method of inactivating nucleic acid-containing pathogens in blood products, comprising: a) providing, in any order: i) a donor, the donor capable of providing blood suspected of being contaminated with the pathogens, ii) blood separation means for separating the blood into blood products, iii) psoralen, iv) photoactivation means, and v) psoralen removal means; b) withdrawing the blood from the donor and introducing blood into said blood separation means; c) isolating a blood product from the blood with the blood separation means; d) adding the psoralen to the blood product to create a solution of psoralen at a concentration; e) treating the solution with the photoactivation means so as to create a treated blood product wherein the pathogens are inactivated and wherein at least a portion of the psoralen concentration is free in the solution; and f) removing substantially all of the portion of the psoralen free in solution in the treated blood product with the psoralen removal means.

In particular embodiments, the blood separation means is an apheresis system. The blood product is platelets in certain embodiments, and plasma in other embodiments.

In some embodiments, the psoralen removal means comprises a mesh enclosure containing a resin, the mesh enclosure adapted to allow a blood product to contact the resin. The resin is adsorbent in some embodiments. When the resin is adsorbent, it may be a polymer in further embodiments. In particular embodiments, the polymer comprises polystyrene, while the polystyrene is crosslinked in still further embodiments.

The psoralen may be an aminopsoralen in some embodiments, and a brominated psoralen in others.

Additionally, the present invention contemplates a method of inactivating nucleic acid-containing pathogens in blood products, comprising: a) providing, in any order: i) a donor, the donor capable of providing blood suspected of being contaminated with the pathogens, ii) an apheresis system for separating platelets from the blood, iii) an aminopsoralen, iv) photoactivation means, and v) psoralen removal means; b) withdrawing the blood from the donor and introducing the blood into the apheresis system; c) isolating the platelets from the blood with the apheresis system; d) producing a platelet mixture comprising the platelets; e) adding the aminopsoralen to the platelet mixture to create a solution of aminopsoralen at a concentration; f) treating the solution with the photoactivation means so as to create a treated platelet mixture wherein the pathogens are inactivated and wherein at least a portion of the aminopsoralen concentration is free in the solution; and g) removing substantially all of the portion of the aminopsoralen free in solution in the treated platelet mixture with the psoralen removal means.

In some embodiments, the psoralen removal means comprises a mesh enclosure containing the resin, the mesh enclosure adapted to allow a platelet mixture to contact the resin. The resin is adsorbent in some embodiments. When the resin is adsorbent, it may be a polymer in further embodiments. In particular embodiments, the polymer comprises polystyrene, while the polystyrene is crosslinked in still further embodiments. Finally, the resin is subjected to a wetting process in still additional embodiments.

In still further embodiments, the aminopsoralen is 4'-(4-amino-2-oxa)butyl-4',5',8-trimethylpsoralen.

The present invention also contemplates a method of inactivating nucleic acid-containing pathogens in blood products, comprising: a) providing, in any order: i) a donor, the donor capable of providing blood suspected of being contaminated with the pathogens, ii) an apheresis system for separating platelets from the blood, iii) synthetic media, iv) a platelet collection container, v) 4'-(4-amino-2-oxa)butyl-4',5',8-trimethylpsoralen, vi) photoactivation means, and vii) psoralen removal means; b) withdrawing the blood from the donor and introducing the blood into the apheresis system; c) isolating the platelets from the blood with the apheresis system; d) collecting the platelets in a platelet container over a period of time; e) adding the synthetic media to the platelets in the platelet container, thereby producing a platelet mixture comprising platelets and synthetic media; f) adding the 4'-(4-amino-2oxa)butyl-4',5',8-trimethylpsoralen to the platelet mixture to create a solution of 4'-(4amino-2-oxa)butyl-4',5',8-trimethylpsoralen at a concentration; g) treating the solution with the photoactivation means so as to create a treated platelet mixture wherein the pathogens are inactivated and wherein at least a portion of the 4'-(4-amino-2oxa)butyl-4',5',8-trimethylpsoralen concentration is free in the solution; and h) removing substantially all of the portion of the 4'-(4-amino-2-oxa)butyl-4',5',8trimethylpsoralen free in solution in the treated platelet mixture with the psoralen removal means.

In some embodiments, the synthetic media comprises phosphate. In still further embodiments, the synthetic media is added to the platelets over the period of time the platelets are being collected.

In some embodiments, the psoralen removal means comprises a mesh enclosure containing the resin, the mesh enclosure adapted to allow a platelet mixture to contact the resin. The resin is adsorbent in some embodiments. When the resin is adsorbent, it may be a polymer in further embodiments. In particular embodiments, the polymer comprises polystyrene, while the polystyrene is crosslinked in still further embodiments. Finally, the resin is subjected to a wetting process in still additional embodiments.

DEFINITIONS

The term "blood product" refers to all formulations of the fluid and/or associated cellular elements and the like (such as erythrocytes, leukocytes, platelets, etc.) that pass through the body's circulatory system; blood products include, but are not limited to, platelet mixtures, serum, and plasma. The term "platelet mixture" refers to one type of blood product wherein the cellular element is primarily or only platelets. A platelet concentrate (PC) is one type of platelet mixture where the platelets are associated with a smaller than normal portion of plasma. A synthetic media may make up that volume normally occupied by plasma; for example, a platelet concentrate may entail platelets suspended in 35% plasma/65% synthetic media. Frequently, the synthetic media comprises phosphate.

The term "photoproduct" refers to products that result from the photochemical reaction that a psoralen undergoes upon exposure to ultraviolet radiation.

The term "resin" refers to a solid support (such as beads/particles etc.) capable of interacting and attaching to various elements, including psoralens, in a solution or fluid (e.g., a blood product), thereby removing those elements. The removal process is not limited to any particular mechanism. For example, a psoralen may be removed by an adsorbent or by charge (i.e., affinity interaction). The term "adsorbent resin" refers broadly to both natural organic substances and synthetic substances. Various adsorbent resins differ in surface area, pore size, chemical nature (e.g., polystyrene divinylbenzene and acrylic ester), polarity, etc., to allow optimum performance for particular applications (e.g., adsorption of pharmaceuticals). The adsorbent resins may be packaged in a number of arrangements, including a column through which a substance like blood can be perfused, and a mesh having apertures sized to allow contact of the adsorbent with the substance while retaining the adsorbent resin within the area defined by the mesh.

The term "psoralen removal means" refers to a substance or device that is able to remove psoralen from, e.g., a blood product. A psoralen removal means may also remove other components of the blood product, such as psoralen photoproducts. A preferred psoralen removal means is an adsorbent resin.

The term "in-line column" refers to a container, usually cylindrically shaped, having an input end and an output end and containing a substance disposed therein to remove substances from a blood product. The present invention contemplates the use of a column having a capacity of at least 1 mL, and preferably 5–10 mL that is packed with an adsorbent resin for removing psoralens and psoralen photoproducts from the blood product. A blood product enters the input end, comes in contact with the adsorbent resin, and then exits the output end.

The term "partition" refers to any type of device or element that can separate or divide a whole into sections or parts. For example, the present invention contemplates the use of a partition to divide a blood bag, adapted to contain a blood product, into two parts. The blood product occupies one part of the bag prior to and during treatment, while the adsorbent resin occupies the other part. In one embodiment, after treatment of the blood product, the partition is removed (e.g., the integrity of the partition is altered), thereby allowing the treated blood product to come in contact with the adsorbent resin. The partition may either be positioned in the bag's interior or on its exterior. When used with the term "partition," the term "removed" means that the isolation of the two parts of the blood bag no longer exists; it does not necessarily mean that the partition is no longer associated with the bag in some way.

The term "flow adapter" refers to a device that is capable of controlling the flow of a particular substance like a blood product. The flow adapter may perform additional functions, such as preventing the passage of pieces of adsorbent resin material.

The term "resin retaining means" refers to any mechanism that confines resin to a defined area, like a biocompatible housing. For example, a mesh enclosure, housed within a platelet storage container, may be used to hold the resin within the container. Similarly, a filter (e.g., a mesh filter) may be positioned at the inlet/outlet line of a blood product storage bag. The term "inlet/outlet line" refers to the tubing that is connected to and in fluidic communication with a blood product storage bag. There may be a single inlet/outlet line or two or more lines connected to a bag.

The terms "mesh enclosure," "mesh pouch" and the like refer to an enclosure, pouch, bag or the like manufactured to contain multiple pores. For example, the present invention contemplates a pouch, containing the adsorbent resin, with pores of a size that allow a blood product to contact the adsorbent resin, but retain the resin within the pouch. For purposes of the present invention, the adsorbent-containing mesh enclosure is referred to as a RD. In a preferred embodiment, the RD is housed in a blood product storage container (e.g., a platelet storage container). The present invention contemplates that mesh enclosures will be constructed of a woven, medical-grade polyester mesh or other suitable material like nylon. The preferred range of pore size of the mesh material is approximately 10 $\mu$m and 50 $\mu$m, while the preferred embodiment of the present invention utilizes mesh with pores of approximately 30 $\mu$m.

The terms "fluidic contact," "fluidic connection," and the like refer to the ability of a fluid component (e.g., a blood product) to flow from one element to another. For example, a blood component may flow from a platelet bag through tubing to a flow adapter; thus, the flow adapter does not have to be in direct contact with the platelet bag. Similarly, tubing from each of two or more blood product containers may be connected (e.g., sterile welded) using a sterile connection device to allow fluid to be transferred from one container to another.

The phrase "adapted to allow a blood product to contact said resin" refers to the ability of a blood product to contact and interact with a resin such that the resin is able to adsorb components (e.g., psoralen and psoralen photoproducts) from the blood product. The phrase is frequently used to describe the ability of a psoralen- and irradiation-treated blood product (e.g., platelets), contained within a blood product storage container, to pass through the pores of a mesh enclosure housed within that container; in so doing, the resin is able to adsorb the psoralen and psoralen photoproducts.

The term "shaker device" refers to any type of device capable of thoroughly mixing a blood product like a platelet concentrate. The device may have a timing mechanism to allow mixing to be restricted to a particular duration.

The term "biocompatible housing" refers broadly to housings, containers, bags, vessels, receptacles, and the like that are suitable for containing a biological material, such as whole blood, platelet concentrates and plasma. Suitable containers are biocompatible if they have minimal, if any, effect on the biological material to be contained therein. By "minimal" effect it is meant that no significant difference is seen compared to the control. Thus, blood products may be stored in biocompatible housings prior to transfusion to a recipient. In a preferred embodiment, a biocompatible housing is a platelet storage container.

The term "blood separation means" refers broadly to a device, machine, or the like that is able to separate blood into blood products (e.g., platelets and plasma). An apheresis system is one type of blood separation means. Apheresis systems generally comprise a blood separation device, an intricate network of tubing and filters, collection bags, an anticoagulant, and a computerized means of controlling all of the components. The blood separation device is most commonly a centrifuge. At least one pump is used to move the blood, separated blood components, and fluid additives through the apheresis system and ultimately back to either the donor or to a collection bag(s). Though not limited to any particular type of apheresis system, the present invention specifically contemplates the use of automated systems that are capable of collecting a particular amount of a desired blood product mixture.

The term "isolating" refers to separating a substance out of a mixture containing more than one component For example, platelets may be separated from whole blood. The product that is isolated (e.g, platelets) does not necessarily refer to the complete separation of that product from other components. For example, platelets isolated by an apheresis system frequently are associated with a small volume of plasma; in this example, the platelets would still be deemed to have been separated from the whole blood.

The term "filter" refers broadly to devices, materials, and the like that are able to allow certain components to a mixture to pass through while retaining other components. For example, a filter may comprise a mesh with pores sized to allow a blood product (e.g., plasma) to pass through, while retaining other components such as resin particles. The term "filter" is not limited to the means by which certain components are retained.

The term "polyester" refers broadly to materials comprising [poly(ethylene terephthalate)]. The polyester material may be in the form of a mesh material with pores of a definitive size.

The term "polymer" refers broadly to a material made up of a chain of identical, repeated "base units". The term encompasses materials containing styrene ($C_6H_5CH=CH_2$) monomers, which may be referred to as "polystyrene networks."

The term "crosslinked" refers broadly to linear molecules that are attached to each other to form a two- or three-dimensional network. For example, divinylbenzene (DVB) serves as the crosslinking agent in the formation of styrene-divinylbenzene copolymers. The term also encompasses "hypercrosslinking" in which hypercrosslinked networks are produced by crosslinking linear polystyrene chains either in solution or in a swollen state with bifunctional agents (described below).

The terms "aminopsoralen" "aminated psoralen" and the like refer to psoralen compounds that contain an $NH_2$ group linked to either the 4'-position (4'-primaryamino-substituted psoralens) or the 5'-position (5'-primaryamino-substituted psoralens) of the psoralen by a hydrocarbon chain. In 4'-primaryamino-substituted psoralens, the total length of the hydrocarbon chain is 2–20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)_nCH_3$, where n=0–6. By comparison, in 5'-primaryamino-substituted psoralens, the total length of the hydrocarbon chain is 1–20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)_nCH_3$, where n=0–6.

The term "brominated psoralen" refers to psoralen compounds that contain a bromine (Br) atom linked thereto. Preferred brominated psoralens contain a bromine linked to the 5-position. Examples of brominated psoralens included 5-bromo-8methoxypsoralen and 5-bromo-8-(diethylaminopropyloxy)-psoralen.

DESCRIPTION OF THE DRAWINGS

FIG. 30A graphically depicts fibrinogen levels after S-59 PCD and S-59 removal with Hemosorba CH-350™ and silica; both non-illuminated and illuminated samples were analyzed.

FIG. 30B graphically depicts fibrinogen levels after S-59 PCD and S-59 removal with Amberlite XAD-4™, Amberlite XAD-16™, and Bio-Rad t-butyl HIC™; both non-illuminated and illuminated samples were analyzed.

FIG. 30C graphically depicts PT, aPTT, and TT coagulation function after S-59 PCD and S-59 removal with Amberlite XAD-4™, Amberlite XAD-16™, and Bio-Rad t-butyl HIC™; both non-illuminated and illuminated samples were analyzed.

FIGS. 38A and 38B depict a production flow chart of many of the steps used in manufacturing a batch removal device.

DESCRIPTION OF THE INVENTION

Figure 1:
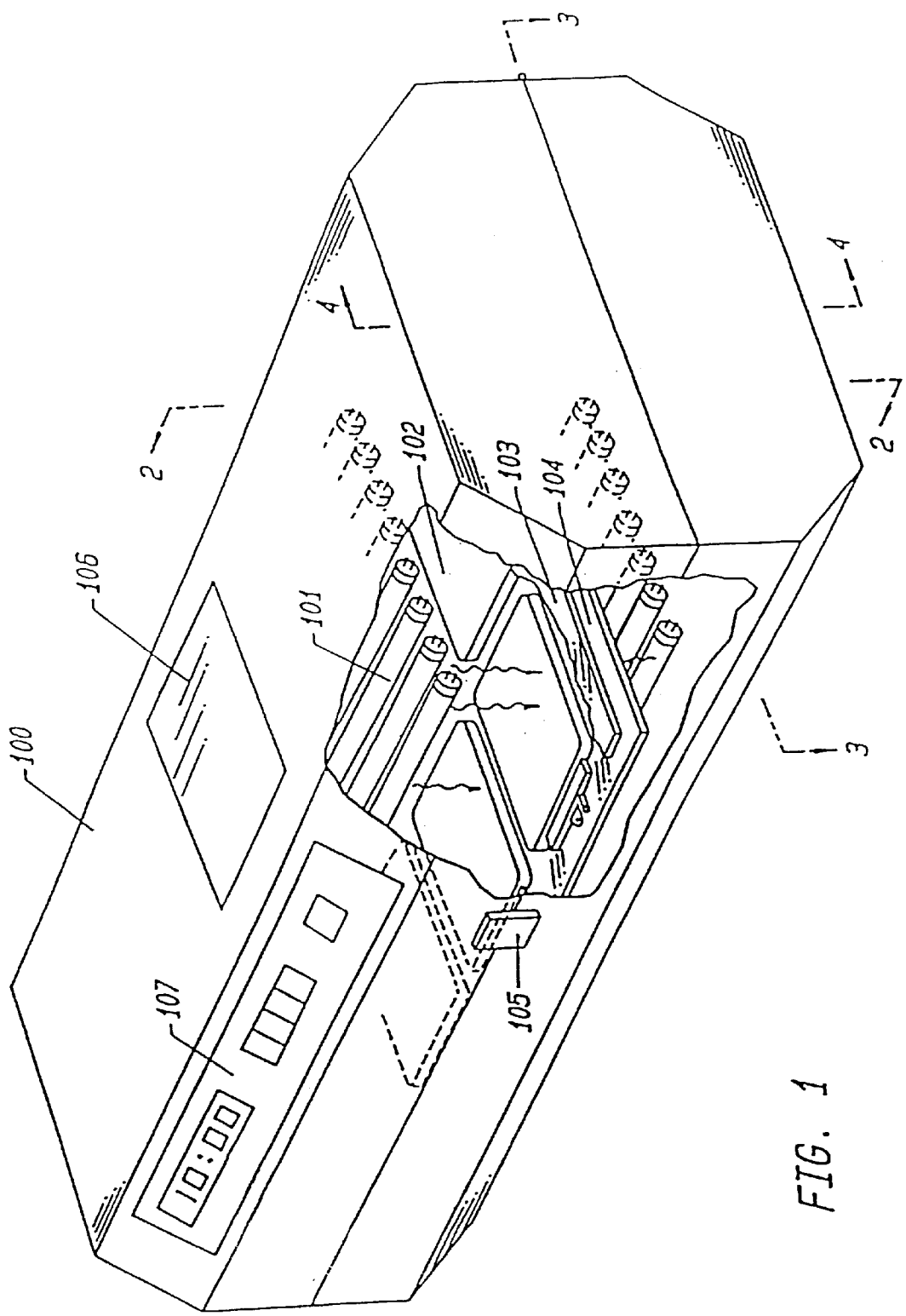
FIG. 1 is a perspective view of one embodiment of the device of the present invention.

The present invention provides new psoralens and methods of synthesis of new psoralens having enhanced ability to inactivate pathogens in the presence of ultraviolet light. The new psoralens are effective against a wide variety of pathogens. The present invention also provides methods of using new and known compounds to inactivate pathogens in health related products to be used in vivo and in vitro, and in particular, blood products, without significantly affecting blood product function or exhibiting mutagenicity.

The inactivation methods of the present invention provide methods of inactivating pathogens, and in particular, viruses, in blood products prior to use in vitro or in vivo. In contrast with previous approaches, the method requires only short irradiation times and there is no need to limit the concentration of molecular oxygen.

The description of the invention is divided into the following sections: I) Photoactivation Devices, II) Compound Synthesis, III) Binding of Compounds to Nucleic Acid, IV) Inactivation of Contaminants, V) Preservation of Biochemical Properties of Material Treated, VI) Devices and Methods for Removing Psoralens and Psoralen Photoproducts; VII) Effect of Psoralen Structural Characteristics on Adsorption; and VIII) Manufacturing A Batch Psoralen Removal Device.

I. PHOTOACTIVATION DEVICES

The present invention contemplates devices and methods for photoactivation and specifically, for photoactivation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause photoactivation of at least one photoreactive compound; b) means for supporting a plurality of samples in a fixed relationship with the radiation providing means during photoactivation; and c) means for maintaining the temperature of the samples within a desired temperature range during photoactivation. The present invention also contemplates methods, comprising: a) supporting a plurality of sample containers, containing one or more photoreactive compounds, in a fixed relationship with a fluorescent source of electromagnetic radiation; b) irradiating the plurality of sample containers simultaneously with electromagnetic radiation to cause photoactivation of at least one photoreactive compound; and c) maintaining the temperature of the sample within a desired temperature range during photoactivation.

The major features of one embodiment of the device of the present invention involve: A) an inexpensive source of ultraviolet radiation in a fixed relationship with the means for supporting the sample containers, B) rapid photoactivation, C) large sample processing, D) temperature control of the irradiated samples, and E) inherent safety.

A. Electromagnetic Radiation Source

Many sources of ultraviolet radiation can be successfully used in decontamination protocols with psoralens. For example, some groups have irradiated sample from above and below by General Electric type F20T12-BLB fluorescent UVA bulbs with an electric fan blowing gently across the lights to cool the area. Alter, H. J., et al., The Lancet, 24:1446 (1988). Another group used Type A405-TLGW/05 long wavelength ultraviolet lamp manufactured by P. W. Allen Co., London placed above the virus samples in direct contact with the covers of petri dishes containing the samples, and was run at room temperature. The total intensity delivered to the samples under these conditions was $1.3 \times 10^{15}$ photons/second cm$^2$ (or 0.7 mW/cm$^2$ or 0.0007 J/cm$^2$ sec) in the petri dish. Hearst, J. E., and Thiry, L., Nucleic Acids Research, 4:1339 (1977). However, without intending to be limited to any type of photoactivation device, the present invention contemplates several preferred arrangements for the photoactivation device, as follows.

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g., visible light).

Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source, by virtue of filters or other means, does not allow radiation below a particular wavelength (e.g., 320 nm), it is said to have a low end "cutoff" at that wavelength (e.g., "a wavelength cutoff at 300 nanometers"). Similarly, when a radiation source allows only radiation below a particular wavelength (e.g., 360 nm), it is said to have a high end "cutoff" at that wavelength (e.g., "a wavelength cutoff at 360 nanometers").

For any photochemical reaction it is desired to eliminate or least minimize any deleterious side reactions. Some of these side reactions can be caused by the excitation of endogenous chromophores that may be present during the photoactivation procedure. In a system where only nucleic acid and psoralen are present, the endogenous chromophores are the nucleic acid bases themselves. Restricting the photoactivation process to wavelengths greater than 320 nm minimizes direct nucleic acid damage since there is very little absorption by nucleic acids above 313 nm.

In human serum or plasma, for example, the nucleic acid is typically present together with additional biological constituents. If the biological fluid is just protein, the 320 nm cutoff will be adequate for minimizing side reactions (aromatic amino acids do not absorb above 320 nm). If the biological fluid includes other analytes, there may be constituents that are sensitive to particular wavelengths of light. In view of the presence of these endogenous constituents, it is intended that the device of the present invention be designed to allow for irradiation within a small range of specific and desirable wavelengths, and thus avoid damage to blood components. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmits only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiation, it is expressed in terms of intensity flux (milliwatts per square centimeter or "mW cm-2" or J/cm$^2$sec). "Output" is herein defined to encompass both the emission of radiation (yes or no; on or off) as well as the level of irradiation. In a preferred embodiment, intensity is monitored at 4 locations: 2 for each side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for approximately fifteen minutes of irradiation time, so that, when measured for the wavelengths between 320 and 350 nanometers, an intensity flux greater than approximately 1 mW cm-2 (0.001 J/cm$^2$ sec.) is provided to the sample vessels.

C. Processing of Large Numbers of Samples

As noted, another important feature of the photoactivation devices of the present invention is that they provide for the processing of large numbers of samples. In this regard, one element of the devices of the present invention is a means for supporting a plurality of blood bags. In the preferred embodiment of the present invention the supporting means comprises a blood bag support placed between two banks of lights. By accepting commonly used commercially available bags, the device of the present invention allows for convenient processing of large numbers of samples.

D. Temperature Control

As noted, one of the important features of the photoactivation devices of the present invention is temperature control. Temperature control is important because the temperature of the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (ie., an opaque housing). No irradiation is allowed to pass to the user. This allows for inherent safety for the user.

II. COMPOUND SYNTHESIS

A. Photoactivation Compounds in General

"Photoactivation compounds" (or "photoreactive compounds") defines a family of compounds that undergo chemical change in response to electromagnetic radiation. Table 1 is a partial list of photoactivation compounds.

TABLE 1

Photoactivation Compounds

Actinomycins
Anthracyclinones
Anthramycin
Benzodipyrones
Fluorenes And Fluorenones
Furocoumarins
Mitomyci
Monostral Fast Blue
Norphillin A
Many Organic Dyes Not Specifically Listed
Phenanthridines
Phenazathionium Salts
Phenazines
Phenothiazines
Phenylazides
Quinolines
Thiaxanthenones The preferred species of photoreactive compounds described herein is commonly referred to as the furocoumarins. In particular, the present invention contemplates those compounds described as psoralens: [7H-furo(3,2-g)-(1)-benzopyran-7-one, or β-lactone of 6-hydroxy-5-benzofiranacrylic acid], which are linear:

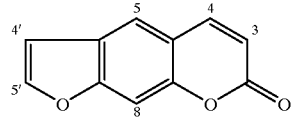

and in which the two oxygen residues appended to the central aromatic moiety have a 1, 3 orientation, and further in which the furan ring moiety is linked to the 6 position of the two ring coumarin system. Psoralen derivatives are derived from substitution of the linear furocoumarin at the 3, 4, 5,8, 4', or 5' positions.

8-Methoxypsoralen (known in the literature under various names, e.g., xanthotoxin, methoxsalen, 8-MOP) is a naturally occurring psoralen with relatively low photoactivated binding to nucleic acids and low mutagenicity in the Ames assay, which is described in the following experimental section. 4'-Aminomethyl-4,5',8-trimethylpsoralen (AMT) is one of most reactive nucleic acid binding psoralen derivatives, providing up to 1 AMT adduct per 3.5 DNA base pairs. S. T. Isaacs, G. Wiesehahn and L. M. Hallick, NCI Monograph 66:21 (1984). However, AMT also exhibits significant levels of mutagenicity. A new group of psoralens was desired which would have the best characteristics of both 8-MOP and AMT: low mutagenicity and high nucleic acid binding affinity, to ensure safe and thorough inactivation of pathogens. The compounds of the present invention were designed to be such compounds.

"4'-primaryamino-substituted psoralens" are defined as psoralen compounds which have an NH$_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)_nCH_3$, where n=0–6.

"5'-primaryamino-substituted psoralens" are defined as psoralen compounds which have an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)_nCH_3$, where n=0–6.

B. Synthesis of the Psoralens

The present invention contemplates synthesis methods for the novel compounds of the present invention, as well as new synthesis methods for known intermediates. Specifically, the novel compounds are mono, di or trialkylated 4'- or 5'-primaryamino-substituted psoralens. Several examples of the schemes discussed in this section are shown in FIGS. 5A–5F. For ease of reference, TABLE 2 sets forth the nomenclature used for the psoralen derivatives discussed herein. The structures of compounds 1–18 are also pictured in FIGS. 5A–5F. Note that this section (entitled "B. Synthesis of the Psoralens") the roman numerals used to identify compounds correlate with Schematics 1–6 only, and do not correlate with the compound numbers listed in Table 2 or FIGS. 5A–5F.

It is most logical to first describe the synthesis of intermediates useful in synthesizing many of the compounds of the present invention. While the invention is not limited to 4,5',8-trimethyl4'-primaryamino-substituted psoralens or 4,4',8-trimethyl-5'-primaryamino-substituted psoralens, some important intermediates include tri- and tetramethyl psoralens, 4'-halomethyl-4,5',8-trimethylpsoralens and 5'-halomethyl-4,4',8-trimethylpsoralens. The preparation of these critical intermediates presents difficult challenges.

TABLE 2

| # | Compound |
|---|---|
| 1 | 4'-(4-amino-2-aza)butyl-4,5',8-trimethylpsoralen |
| 2 | 4'-(4-amino-2-oxa)butyl-4,5',8-trimethylpsoralen |
| 3 | 4'-(2-aminoethyl)-4,5',8-trimethylpsoralen |
| 4 | 4'-(5-amino-2-oxa)pentyl-4,5',8-trimethylpsoralen |
| 5 | 4'-(5-amino-2-aza)pentyl-4,5',8-trimethylpsoralen |
| 6 | 4'-(6-amino-2-aza)hexyl-4,5',8-trimethylpsoralen |
| 7 | 4'-(7-amino-2,5-oxa)heptyl-4,5',8-trimethylpsoralen |
| 8 | 4'-(12-amino-8-aza-2,5-dioxa)dodecyl-4,5',8-trimethylpsoralen |
| 9 | 4'-(13-amino-2-aza-6,11-dioxa)tridecyl-4,5',8-trimethylpsoralen |
| 10 | 4'-(7-amino-2-aza)heptyl-4,5',8-trimethylpsoralen |
| 11 | 4'-(7-amino-2-aza-5-oxa)heptyl-4,5',8-trimethylpsoralen |
| 12 | 4'-(9-amino-2,6-diaza)nonyl-4,5',8-trimethylpsoralen |
| 13 | 4'-(8-amino-5-aza-2-oxa)octyl-4,5',8-trimethylpsoralen |
| 14 | 4'-(9-amino-5-aza-2-oxa)nonyl-4,5',8-trimethylpsoralen |
| 15 | 4'-(14-amino-2,6,11-triaza)tetradecyl-4,5',8-trimethylpsoralen |
| 16 | 5'-(4-amino-2-aza)butyl-4,4',8-trimethylpsoralen |
| 17 | 5'-(6-amino-2-aza)hexyl-4,4',8-trimethylpsoralen |
| 18 | 5'-(4-amino-2-oxa)butyl-4,4',8-trimethylpsoralen |

Synthesis of Intermediates

Previous syntheses of 4'-chloromethyl-4,5',8-trimethylpsoralen (4'-CMT) and 4'-methyl-4,5',8-trimethylpsoralen (4'-BrMT) start from 4,5',8-trimethylpsoralen (5'TMP)) which is commercially available (Aldrich Chemical Co., Milwaukee, Wis.) or can be prepared in four steps as described below for other alkylated psoralens. 5'-TMP is converted to 4'-CMT using a large excess (20–50 equivalents) of highly carcinogenic, and volatile chloromethyl methyl ether. Halomethylation of the 4,5',8-trialkylpsoralens with chloromethyl methyl ether or bromomethyl methyl ether is described in U.S. Pat. No. 4,124,598, to Hearst. The bromo compound, 4'-BrMT, is likewise prepared using bromomethyl methyl ether which is somewhat less volatile. Yields of only 30–60% of the desired intermediate are obtained. The 5'-chloromethyl-4,4',8-trimethylpsoralen (5'-CMT) and 5'-bromomethyl-4,4',8-trimethylpsoralen (5'-BrMT) are prepared similarly, using the isomeric starting compound, 4,4',8-trimethylpsoralen (4'-TMP) [U.S. Pat. No. 4,294,822, to Kaufman; McLeod, et al., "Synthesis of Benzofuranoid Systems. I. Furocoumarins, Benzofurans and Dibenzofurans," Tetrahedron Letters 237 (1972)].

Described herein is a much improved procedure which allows for the synthesis of either isomer of the bromomethyl-trialkylpsoralens from the same psoralen precursor by careful control of reaction conditions. See Schematic 1.

SCHEMATIC 1

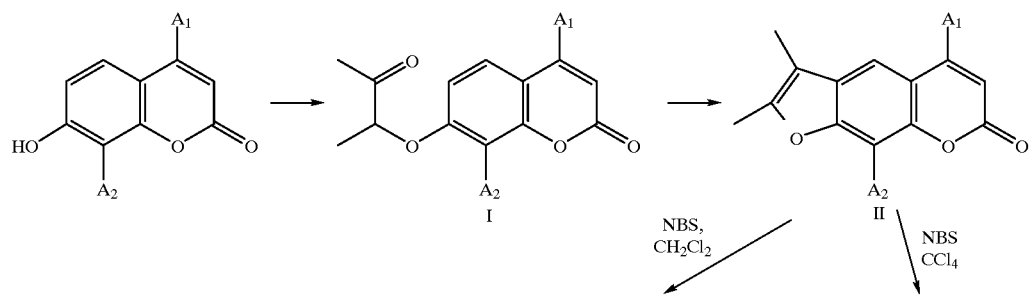

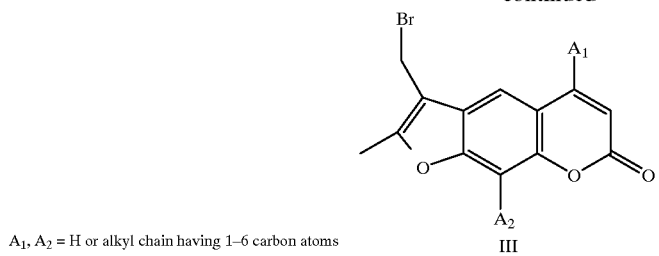
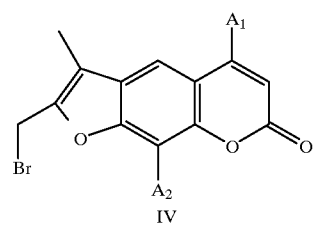

$A_1$, $A_2$ = H or alkyl chain having 1–6 carbon atoms

Reaction of the 4,8-dialkyl-7-hydroxycoumarin with 2-chloro-3-butanone under typical basic conditions, provides 4,8-dialkyl-7-(1-methyl-2-oxo)propyloxycoumarin (I). This material is cyclized by heating in aqueous NaOH to provide 4,8-dialkyl-4', 5'-dimethylpsoralen (II). Treatment of the tetrasubstituted psoralen and N-bromosuccinimide in a solvent at room temperature up to 150° C. leads to bromination at the 4'- or 5'- position, depending upon the conditions used. A catalyst such as dibenzoyl peroxide may be added, but is not necessary. If the solvent used is carbon tetrachloride at reflux, 4,8-dialkyl-5'-bromomethyl-4'-methylpsoralen (IV) is obtained in yields of 50% or greater. If methylene chloride is used at room temperature, only 4,8-dialkyl-4'-bromomethyl-5'-methylpsoralen (III) is obtained in $\geq 80\%$ yield. Benzylic bromination in other solvents can also be done, generating one of the isomeric products alone or in a mixture. These solvents include, but are not limited to 1,2-dichloroethane, chloroform, bromotrichloromethane and benzene.

General Scheme of Synthesis of 4'-Substituted Psoralens

Turning now to the synthesis of a subclass of the linear psoralens, 4,5',8-trialkylpsoralens can be made as follows. The 4,8-dialkylcoumarins are prepared from 2-alkylresorcinols and a 3-oxoalkanoate ester by the Pechmann reaction (Organic Reactions Vol VII, Chap 1, ed. Adams et al, Wiley, N.Y., (1953)). The hydroxy group is treated with an allylating reagent, $CH_2=CHX-CH(R)-Y$, where X is a halide or hydrogen, Y is a halide or sulfonate, and R is H or $(CH_2)_v CH_3$, where v is a whole number from 0 to 4. Claisen rearrangement of the resultant allyl ether gives 4,8-dialkyl-6-allyl-7-hydroxycoumarin. The coumarins are converted to the 4,5',8-trialkylpsoralens using procedures similar to one of several previously described procedures (ie., see, Bender et al, J. Org. Chem. 44:2176 (1979); Kaufinan, U.S. Pat. Nos. 4,235,781 and 4,216,154, hereby incorporated by reference). 4,5',8-Trimethylpsoralen is a natural product and is commercially available (Aldrich Chemical Co., Milwaukee, Wis.).

General Scheme of Synthesis of 5'-Substituted Psoralens

The 4,4',8-trialkylpsoralens can be prepared in two steps also starting from the 4,8-dialkyl-7-hydroxycoumarins discussed above. The coumarin is treated with an alpha-chloro ketone under basic conditions to give the 4,8-dialkyl-7-(2-oxoalkoxy)coumarin. Cyclization of this intermediate to the 4,4',8-trialkylcoumarin occurs by heating in aqueous base.

Longer chain 4'-($\omega$-haloalkyl)trialkylpsoralens (herein referred to as longer chain 4'-HATP) where the alkyl groups are selected from the group $(CH_2)_2$ to $(CH_2)_{10}$ can be prepared under Freidel-Crafts conditions as discussed elsewhere (Olah and Kahn, J. Org. Chem., 1964, 29, 2317; Friedel-Crafts and Related Reactions, Vol. II, Part 2, Olah, ed., Interscience, N.Y., 1964, p 749). While reactions of the halomethyl-intermediates with amines (e.g., Hearst et al., U.S. Pat. No. 4,124,598), and alcohols (e.g., Kaufman, U.S. Pat. No. 4,269,852) have been described, there are only two original reports on the formation of extended chain primary amines. They describe the reaction of the 4'-chloromethyl-4,5',8-trimetiyl psoralen with $H_2N-(CH_2)_n-NH_2$ (where n=2, 4, 6) (Lee, B., et al. "Interaction of Psoralen-Derivatized Oligodeoxyribonucleoside Methylphosphonates with Single-Stranded DNA," Biochemistry 27:3197 (1988), and with $H_2NCH_2CH_2SSCH_2CH_2NH_2$ (Goldenberg, M., et al., "Synthesis and Properties of Novel Psoralen Derivatives," Biochemistry 27:6971 (1988)). The utility of the resulting compounds for nucleic acid photoreaction has not previously been reported. The properties of these materials, such as decreased mutagenicity, are unexpected based on what is known about previously prepared compounds, such as AMT.

Several synthesis routes are shown in Schematic 2, below. Starting from the 4'-HATP, reaction with an excess of a bis-hydroxy compound, HO—(B)—OH, where B is either an alkyl chain (e.g., HO—(B)—OH is 1,3-propanediol) or a monoether (e.g., diethylene glycol) or a polyether (e.g., tetraethylene glycol), either neat or with a solvent such as acetone at 20–80° C., and a base for the carbon chains longer than halomethyl, gives a (w-hydroxyalkoxy)alkyl psoralen.

SCHEMATIC 2

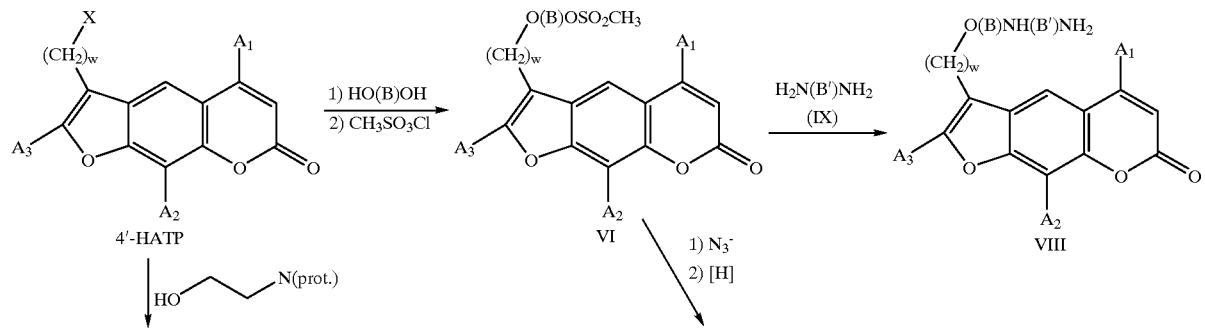

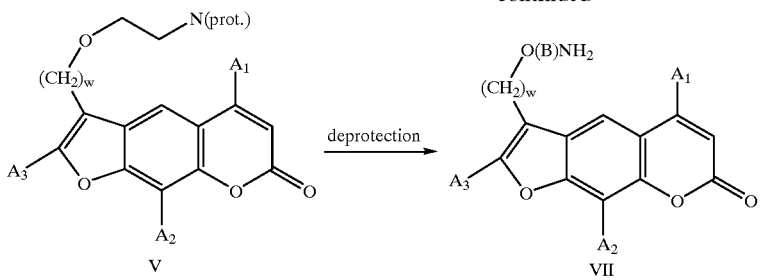

V

-continued

VII w = 1–5
B, B' = alkyl chain, monoether or polyether; ≤18 carbon atoms long
$A_1, A_2, A_3$ = H, $(CH_2)vCH_3$;
        v = 0–5
X = Br, Cl, I The terminal hydroxy group can be transformed to an amino group under a variety of conditions (e.g., see Larock, "Comprehensive Organic Transformations", VCH Publishers, N.Y., 1989). Particularly, the hydroxy group can be converted to the ester of methanesulfonic acid (structure VI). This can subsequently be converted to the azide in refluxing ethanol and the azide reduced to the final amine, structure VII (examples are Compounds 2, 4 and 7). The method described herein utilizes triphenylphosphine and water in THF for the reduction but other methods are contemplated.

A preferred method of preparation of structure VII uses the reaction of 4'-HATP with a primary linear alcohol containing a protected amine (e.g., a phthalimido group) at the terminal position in a suitable solvent such as DMF at 25–150° C. to give I. The amine is then deprotected under standard conditions (e.g., hydrazine or aqueous $MeNH_2$ to deprotect a phthalimido group [higher alkyl hydrazines, such as benzyl hydrazines, are also contemplated]) to give VII.

Conversely, structure VI can be reacted with diamines, $H_2N—(B')—NH_2$ (Structure IX), where B' is an alkyl chain (e.g., 1,4,-butanediamine), a monoether (e.g., 3-oxa-1,5-pentanediamine) or a polyether (e.g., 3,6-dioxa-1,8-octanediamine) to give the final product, compound VIII (examples are Compounds 8, 13 and 14). This reaction is carried out with an excess of diamine in acetonitrile at reflux, but other solvents and temperatures are equally possible.

Some final compounds are desired in which the carbon chain is linked to the 4'- position of the psoralen ring by an aminoalkyl group $[NH(CH_2)_w]$ rather than by an oxyalkyl group $[O(CH_2)_w]$. Synthesis pathways for these compounds are shown in Schematic 3, below. When the linkage between this nitrogen and the terminating nitrogen contains only $CH_2$ subunits and oxygen but no other nitrogens (structure X) (examples are Compounds 1, 5, 6, 9, 10 and 11), the product can conveniently be prepared from the 4'-HATP and the appropriate diamine of structure IX. This method is also applicable to final products that contain more than two nitrogens in the chain (structure XIII) (examples are Compounds 12 and 15) starting from polyamines of structure XII (e.g., norspermidine or spermine [commercially available from Aldrich, Milwaukee, Wis.]), however, in this case isomeric structures are also formed in considerable amounts. The preferred method for the preparation of structure XIII is reductive amination of the psoralen-4'-alkanal (XI) with a polyamine of structure XII and a reducing agent such as sodium cyanoborohydride. This reductive amination is applicable to the synthesis of compounds X as well. The carboxaldehydes (structure XI, w=0) have been prepared previously by hydrolysis of the 4'-halomethyl compounds and subsequent oxidation of the resultant 4'-hydroxymethyl compound. (Isaacs et al, J. Labelled Cmpds. Radiopharm., 1982, 19, 345). These compounds can also be conveniently prepared by formulation of the 4'-hydrido compounds with a formamide and $POCl_3$, or with hexamethylene tetraamine in acid. Longer chain alkanals can be prepared from the 4'-HATP compounds by conversion of the terminal halo group to an aldehyde functionality (for example, Durst, Adv. Org. Chem. 6:285 (1969)).

SCHEMATIC 3

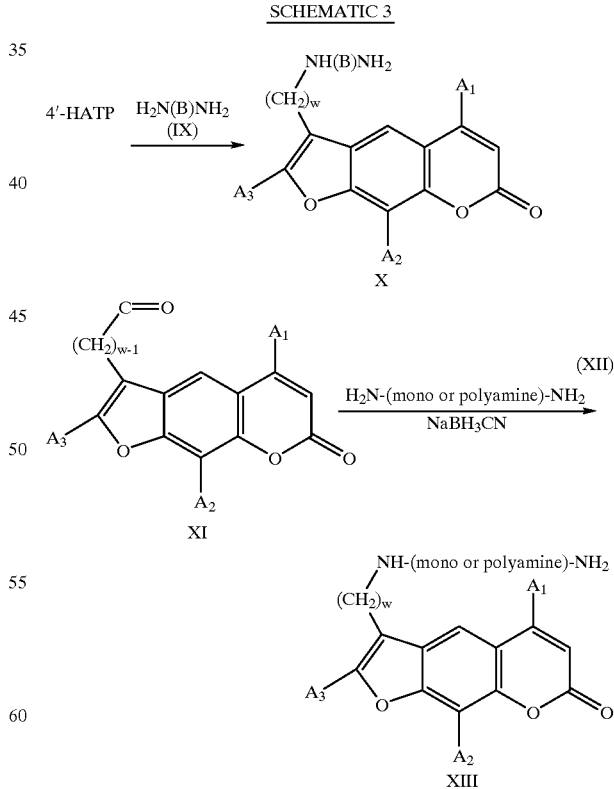

Other final products have a terminal amine linked to the psoralen by an alkyl chain. As shown in Schematic 4, below, these compounds (structures XIV) (an example is Compound 3) are prepared either by reaction of the 4'-HATP with potassium phthalimide or azide and subsequent liberation of the desired amine as before, or conversion of the 4'-HATP to the cyanide compound, followed by reduction, for example with $NaBH_4$—$CF_3CO_2H$.

SCHEMATIC 4

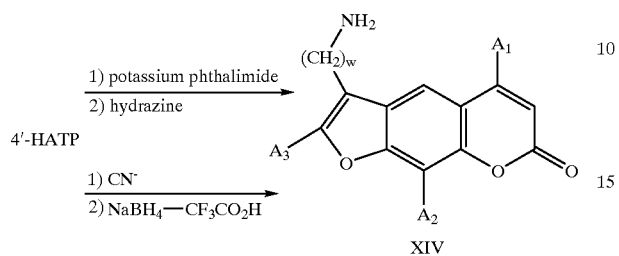

The discussion of the conversion of 4,5',8-trialkylpsoralens to 4'-aminofunctionalized-4,5',8-trialkylpsoralens applies equally well when the 4- and/or 8-position is substituted with only a hydrogen, thus providing 4'-primaryamino-substituted-5', (4 or 8)-dialkylpsoralens and 4'-primaryamino-substituted-5'-alkylpsoralens.

Synthesis of 5' Derivatives

Under identical conditions to those described above, the 4,4',8-trialkylpsoralens or the 4,4',8-trialkyl-5'-methylpsoralens can be converted to the 5'-(ω-haloalkyl))-4,4',8-trialkylpsoralens, (herein called 5'-HATP), as detailed in Schematic 5, below. (See Kaufinan, U.S. Pat. Nos. 4,294,822 and 4,298,614 for modified version).

soralens or angelicins. Thus, the 4'-halomethylangelicins (XIX) and the 5'-halomethylangelicins (XX can be prepared in a similar manner to their linear counterparts. (See Schematic 6). By analogy with the synthetic pathways presented above one can envision the synthesis of 4'-(ω-amino)alkylangelicins and 5'-(ω-amino)alkylangelicins where the alkyl linkage can contain one or more oxygen or nitrogen atoms.

SCHEMATIC 6

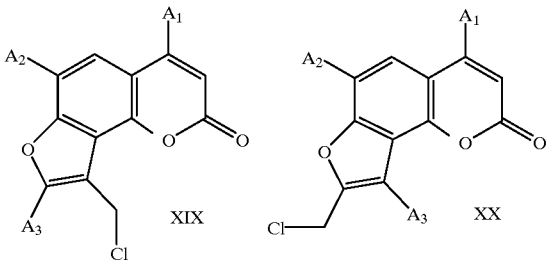

III. BINDING OF COMPOUNDS TO NUCLEIC ACID

The present invention contemplates binding new and known compounds to nucleic acid, including (but not limited to) viral nucleic acid and bacterial nucleic acid. One approach of the present invention to binding photoactivation compounds to nucleic acid is photobinding. Photobinding is defined as the binding of photobinding compounds in the presence of photoactivating wavelengths of light. Photobinding compounds are compounds that bind to nucleic acid in

SCHEMATIC 5

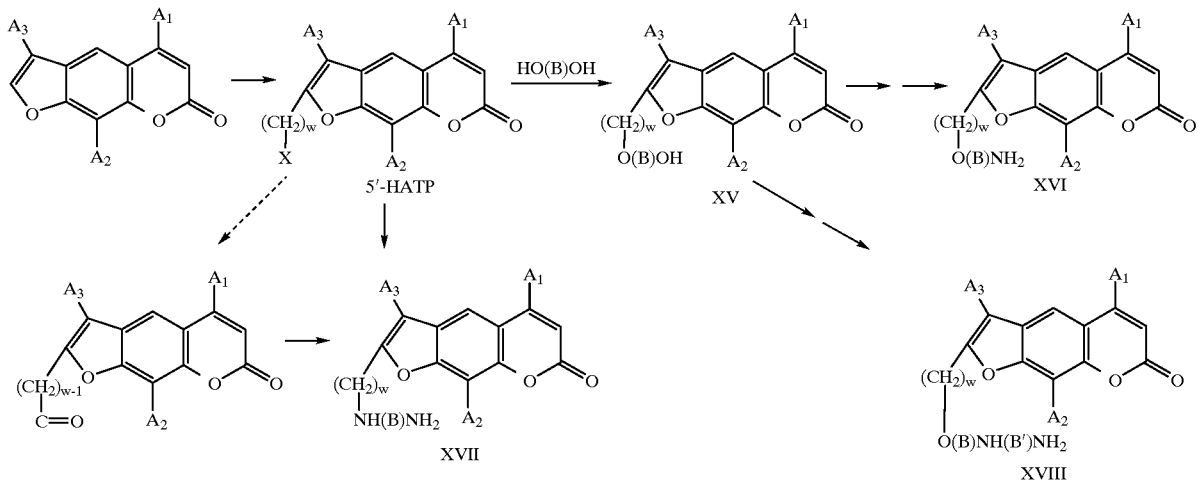

The discussion of the conversion of 4,4',8-trialkylpsoralens to 5'-primaryamino-substituted-4,4',8-trialkylpsorale applies equally well when the 4-, 4'- and/or 8-positions are just substituted with a hydrogen, thus providing 5'-primaryamino-substituted-dialkylpsoralens and 5'-primaryamino-substituted-alkylpsoralens, with the alkyl group(s) at the 4-, 4'- and/or 8- positions.

The discussion above of the syntheses of 4'-primaryamino- and 5'-primaryamino-psoralens can be extended to the non-linear coumarins, specifically the isopthe presence of photoactivating wavelengths of light. The present invention contemplates methods of photobinding with photobinding compounds of the present invention.

One embodiment of the method of the present invention for photobinding involves the steps: a) providing a photobinding compound of the present invention; and b) mixing the photobinding compound with nucleic acid in the presence of photoactivation wavelengths of electromagnetic radiation.

The invention further contemplates a method for modifying nucleic acid, comprising the steps: a) providing photobinding compound of the present invention and nucleic acid; and b) photobinding the photobinding compound to the nucleic acid, so that a compound:nucleic acid complex is formed. Without intending to be limited to any method by which the compounds of the present invention prevent replication, it is believed that the structure of said compound:nucleic acid complex serves to prevent replication of the nucleic acid by preventing the necessary polymerase from acting in the region where the compound has bound.

IV. INACTIVATION OF PATHOGENS

The present invention contemplates treating a blood product with a photoactivation compound and irradiating to inactivate contaminating pathogen nucleic acid sequences before using the blood product

A. Inactivation in General

The term "inactivation" is here defined as the altering of the nucleic acid of a unit of pathogen so as to render the unit of pathogen incapable of replication. This is distinct from "total inactivation", where all pathogen units present in a given sample are rendered incapable of replication, or "substantial inactivation," where most of the pathogen units present are rendered incapable of replication. "Inactivation efficiency" of a compound is defined as the level of inactivation the compound can achieve at a given concentration of compound or dose of irradiation. For example, if 100 $\mu$M of a hypothetical compound X inactivated 5 logs of HIV virus whereas under the same experimental conditions, the same concentration of compound Y inactivated only 1 log of virus, then compound X would have a better "inactivation efficiency" than compound Y.

To appreciate that an "inactivation" method may or may not achieve "total inactivation," it is useful to consider a specific example. A bacterial culture is said to be inactivated if an aliquot of the culture, when transferred to a fresh culture plate and permitted to grow, is undetectable after a certain time period. A minimal number of viable bacteria must be applied to the plate for a signal to be detectable. With the optimum detection method, this minimal number is 1 bacterial cell. With a sub optimal detection method, the minimal number of bacterial cells applied so that a signal is observed may be much greater than 1. The detection method determines a "threshold" below which the "inactivation method" appears to be completely effective (and above which "inactivation" is, in fact, only partially effective).

B. Inactivation of Potential Pathogens

The same considerations of detection method and threshold exist when determining the sensitivity limit of an inactivation method for nucleic acid. Again, "inactivation" means that a unit of pathogen is rendered incapable of replication.

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occurring due to contact with the material. It is recognized that in this practical scenario, it is not essential that the methods of the present invention result in "total inactivation". That is to say, "substantial inactivation" will be adequate as long as the viable portion is insufficient to cause disease. Thus "substantially all" of a pathogen is inactivated when any viable portion of the pathogen which remaining is insufficient to cause disease. The inactivation method of the present invention renders nucleic acid in pathogens substantially inactivated. In one embodiment, the inactivation method renders pathogen nucleic acid in blood preparations substantially inactivated.

Without intending to be limited to any method by which the compounds of the present invention inactivate pathogens, it is believed that inactivation results from light induced binding of psoralens to pathogen nucleic acid. Further, while it is not intended that the inactivation method of the present invention be limited by the nature of the nucleic acid; it is contemplated that the inactivation method render all forms of nucleic acid (whether DNA, mRNA, etc.) substantially inactivated.

When photoactivation compounds are used to modify nucleic acid, the interaction of the pathogen nucleic acid (whether DNA, mRNA, etc.) with the photoactivation compound preferably prevents replication of the pathogen, such that, if a human is exposed to the treated pathogen, infection will not result.

"Synthetic media" is herein defined as an aqueous synthetic blood or blood product storage media. In one embodiment, the present invention contemplates inactivating blood products in synthetic media comprising a buffered saline solution. This method reduces harm to blood products and permits the use of much lower concentrations of photoactivation compounds.

TABLE 3

Viruses Photochemically Inactivated By Psoralens

| Family | Virus |
| --- | --- |
| Adeno | Adenovirus 2 |
|  | Canine Hepatitis |
| Arena | Pichinde |
|  | Lassa |
| Bunya | Turlock |
|  | California Encephalitis |
| Herpes | Herpes Simplex 1 |
|  | Herpes Simplex 2 |
|  | Cytomegalovirus |
|  | Pseudorabies |
| Orothomyxo | Influenza |
| Papova | SV-40 |
| Paramyxo | Measles |
|  | Mumps |
|  | Parainfluenza 2 and 3 |
| Picorna[1] | Poliovirus 1 and 2 |
|  | Coxsackie A-9 |
|  | Echo 11 |
| Pox | Vaccinia |
|  | Fowl Pox |
| Reo | Reovirus 3 |
|  | Blue Tongue |
|  | Colorado Tick Fever |
| Retro | HIV |
|  | Avian Sarcoma |
|  | Murine Sarcoma |
|  | Murine leukemia |
| Rhabdo | Vesticular Stomatitis Virus |
| Toga | Western Equine Encephalitis |
|  | Dengue 2 |
|  | Dengue 4 |
|  | St. Louis Encephalitis |
| Hepadna | Hepatitis B |
| Bacteriophage | Lambda |
|  | T2 |
| (Rickettsia) | R. Akari (Rickettsialpox) |

[1]In the article, it was pointed out that Piconaviruses were photoinactivated only if psoralens were present during virus growth.

The psoralen photoinactivation method inactivates nucleic acid based pathogens present in blood through a single procedure. Thus, it has the potential to eliminate bacteria, protozoa, and viruses as well. Had an effective decontamination method been available prior to the advent of the AIDS pandemic, no transfusion associated HIV transmission would have occurred. Psoralen-based decontamination has the potential to eliminate all infectious agents from the blood supply, regardless of the pathogen involved. Additionally, psoralen-based decontamination has the ability to sterilize blood products after collection and processing, which in the case of platelet concentrates could solve the problem of low level bacterial contamination and result in extended storage life. Morrow J. F., et al., JAMA 266:555–558 (1991); Bertolini F., et al., Transfusion 32:152–156 (1992).

A list of viruses which have been photochemically inactivated by one or more psoralen derivatives appears in Table 3. (From Table 1 of Hanson, C. V., Blood Cells 18:7 (1992)). This list is not exhaustive, and is merely representative of the great variety of pathogens psoralens can inactivate. The present invention contemplates the inactivation of these and other viruses by the compounds described herein. The compounds of the present invention are particularly well suited for inactivating envelope viruses, such as the HIV virus.

C. Selecting Photoinactivation Compounds for Inactivation of Pathogens

In order to evaluate a compound to decide if it would be useful in the photochemical decontamination (PCD) methods of the present invention, two important properties should be considered: 1) the compound's ability to inactivate pathogens and 2) its mutagenicity. The ability of a compound to inactivate pathogens may be determined by several methods. One technique is to perform a bacteriophage screen; an assay which determines nucleic acid binding of test compounds. A screen of this type, an r-17 screen, is described in detail in EXAMPLE 12, below. If the r-17 screen shows inactivation activity, it is useful to directly test the compound's ability to inactivate a virus. One method of performing a direct viral inactivation screen is described in detail in EXAMPLE 13 for cell free HIV.

The R17 bacteriophage screen is believed to be predictive of HIV inactivation efficiency, as well as the efficiency of compounds against many other viruses. R17 was chosen because it was expected to be a very difficult pathogen to inactivate. It is a small, single stranded RNA phage. Without intending to be limited to any means by which the present invention operates, it is expected that shorter pieces of nucleic acid are harder to inactivate because they require a higher frequency of formation of psoralen adducts than do longer pieces of nucleic acid. Further, single stranded RNA pathogens are more difficult to inactivate because psoralens can neither intercalate between base pairs, as with double-stranded nucleic acids, nor form diadducts which function as interstrand crosslinks. Thus it is expected that when inactivation of R17 is achieved, these same conditions will cause the inactivation of many viruses and bacteria.

The cell free HIV screen complements the r-17 screen by affirming that a given compound which has tested positive in r-17 will actually work effectively to inactivate viruses. Thus, if a compound shows activity in the r-17 screen, it is next tested in the viral inactivation screen.

The second property that is important in testing a compound for use in methods of the present invention is mutagenicity. The most widely used mutagen/carcinogen screening assay is the Ames test. This assay is described by D. M. Maron and B. N. Ames in Mutation Research 113:173 (1983) and a specific screen is described in detail in Example 17, below. The Ames test utilizes several unique strains of *Salmonella typhimurium* that are histidine- dependent for growth and that lack the usual DNA repair enzymes. The frequency of normal mutations that render the bacteria independent of histidine (i.e., the frequency of spontaneous revertants) is low. The test allows one to evaluate the impact of a compound on this revertant frequency.

Because some substances are not mutagenic by themselves, but are converted to a mutagen by metabolic action, the compound to be tested is mixed with the bacteria on agar plates along with the liver extract. The liver extract serves to mimic metabolic action in an animal. Control plates have only the bacteria and the extract.

The mixtures are allowed to incubate. Growth of bacteria (if any) is checked by counting colonies. A positive Ames test is one where the number of colonies on the plates with mixtures containing the compound significantly exceeds the number on the corresponding control plates.

When known carcinogens are screened in this manner with the Ames test, approximately ninety percent are positive. When known noncarcinogens are similarly tested, approximately ninety percent are negative.

A new compound (X) can be evaluated as a potential blood photodecontamination compound, as shown in Table 4, below. X is initially evaluated in Step I. X is screened in the r-17 assay at several different concentrations between 4 and 320 μM, as explained in EXAMPLE 12. If the compound shows inactivation activity greater than 1 log inactivation of r-17 (log kill) in the r-17 screen at any concentration, the compound is then screened in the cell free HIV assay, as explained in EXAMPLE 13. If the compound shows inactivation activity greater than 1 log inactivation of HIV (log kill) in the cell free HIV assay, the compound and AMT are then screened in the Ames assay. Finally, if the compound shows lower mutagenicity in the Ames assay than does AMT, the new compound is identified as a useful agent for inactivation of pathogens.

TABLE 4

| Step | Screen | Result | Interpretation |
|---|---|---|---|
| 1 | r-17 | >1 Log Kill By Any Concentration | Potential PCD Compound, Go To Step 2 |
|   |   | <1 Log Kill | Compound Is Ineffective As An Inactivation Treatment |
| 2 | Viral Inactivation | >1 Log Kill By Any Concentration | Potential PCD Compound, Go To Step 3 |
|   |   | <1 log kill | Compound Is Ineffective As An Inactivation Treatment |
| 3 | Ames | Less Mutagenic Than AMT | Useful Agent For PCD |

By following these instructions, a person can quickly determine which compounds would be appropriate for use in methods of the present invention.

D. Delivery of Compounds for Photoinactivation

The present invention contemplates several different formulations and routes by which the compounds described herein can be delivered in an inactivation method. This section is merely illustrative, and not intended to limit the invention to any form or method of introducing the compound.

The compounds of the present invention may be introduced in an inactivation method in several forms. The compounds may be introduced as an aqueous solution in water, saline, a synthetic media such as "Sterilyte™3.0" (contents set forth at the beginning of the Experimental section, below) or a variety of other solvents. The compounds can further be provided as dry formulations, with or without adjuvants.

The new compounds may also be provided by many different routes. For example, the compound may be introduced to the reaction vessel, such as a blood bag, at the point of manufacture. Alternatively, the compound may be added to the material to be sterilized after the material has been placed in the reaction vessel. Further, the compounds may be introduced alone, or in a "cocktail" or mixture of several different compounds.

V. PRESERVATION OF BIOCHEMICAL PROPERTIES OF MATERIAL TREATED

When treating blood products to be used in vivo, two factors are of paramount importance in developing methods and compounds to be used. First, one must ask whether the process or the compounds used alter the in vivo activity of the treated material. For example, platelet transfusion is a well established efficacious treatment for patients with thrombocytopenic bleeding. However, if the decontamination treatment used greatly reduces the platelets clotting activity, then the treatment has no practical value. Psoralens are useful in inactivation procedures, because the reaction can be carried out at temperatures compatible with retaining biochemical properties of blood and blood products. Hanson, C. V., Blood Cells 18:7 (1992). But not all psoralens or methods will decontaminate without significantly lowering the biological activity of the decontaminated material. Previous compounds and protocols have necessitated the removal of molecular oxygen from the reaction before exposure to light, to prevent damage to blood products from oxygen radicals produced during irradiation. See L. Lin et al., Blood 74:517 (1989); U.S. Pat. No. 4,727,027, to Wiesehahn. The present invention may be used to decontaminate blood products, in the presence of oxygen, without destroying the in vivo activity for which the products are prepared. The present invention contemplates that in vivo activity of a blood product is not destroyed or significantly lowered if a sample of blood product which is decontaminated by methods of the present invention tests as would a normally functioning sample of blood product in known assays for blood product function. For example, where platelets are concerned, in vivo activity is not destroyed or significantly lowered if aggregation and pH of the platelets are substantially the same in platelets treated by the methods of the present invention and stored 5 days as they are in untreated samples stored for 5 days. "Substantially the same" pH and aggregation means that the values fall within the range of error surrounding that particular data point.

The second factor is whether the compounds used are toxic or mutagenic to the patient treated. A "compound displaying low mutagenicity" is defined as a compound which is less mutagenic than AMT when it is tested at concentrations below 250 μM in the Ames assay, described in the Experimental section, below. The inactivation compounds and methods of the present invention are especially useful because they display the unlinking of pathogen inactivation efficiency from mutagenicity. The compounds exhibit powerful pathogenic inactivation without a concomitant rise in mutagenicity. The commonly known compounds tested in photoinactivation protocols, such as AMT, appear to exhibit a link between pathogen inactivation efficiency and mutagenetic action that until now seemed indivisible.

While it is not intended that the present invention be limited to any theory by which pathogen inactivation efficiency is unlinked from mutagenicity, it is postulated that unlinking occurs as a result of the length of the groups substituted on the psoralen, and the location of charges on the compounds. It is postulated that positive charges on one or both ends of mutagenic compounds have non-covalent interactions with the phosphate backbone of DNA. These interactions are presumed to occur independent of the presence of light (called "dark binding"). In theory, the psoralen thereby sterically blocks polymerase from opening up the DNA, causing mutagenicity. In contrast, compounds of the present invention carry a positive or neutral charge on a long substitute group. These substituted groups form a steric barrier during dark binding that is much easier to free from the DNA, permitting polymerase to pass. Thus no mutagenicity results.

VI. DEVICES AND METHODS FOR REMOVING PSORALENS AND PSORALEN PHOTOPRODUCTS

Subsequent to photochemical decontamination (PCD), the psoralen photoproducts formed, as well as residual psoralens can be removed from the treated blood product. In essence, removal is a safety precaution. If the psoralens and psoralen photoproducts are not removed from the treated blood product prior to infusion into a recipient, there is the remote possibility that they could form conjugates with the recipient's nucleic acids.

An extensive body of research exists regarding the removal of substances from blood products. The bulk of this research is directed at white cell reduction. [See, e.g., M. N. Boomgaard et al., Transfusion 34:311 (1994); F. Bertolini et al., Vox Sang 62:82 (1992); and A. M. Joustra-Dijkhuis et al., Vox Sang 67:22 (1994)]. White cell reduction is important because patients receiving transfusions of blood components with a large number of white blood cells may experience several adverse reactions, including non-hemolytic febrile transfusion reactions, human leukocyte antigens (HLA) alloimmunization, graft versus host reactions, and refractoriness to random-donor platelet transfusions. [T. Shimizu et al., Transfusion 33:730 (1993); and H. Wadenvik, supra]. Filtration of platelets is the most common method used in white cell reduction of PCs. Numerous filters have been successfully employed to reduce the number of WBCs in PCs to a level that will not cause the above mentioned adverse reactions. [See, e.g., K. J. Kao, supra (PL-100 filters, Pall Corp., Glen Cove, N.Y.); M. Böck et al., Transfusion 31:333 (1991) (Sepacell PL-5A, Asahi, Tokyo, Japan); J. D. Sweeney et al., Transfusion 35:131 (1995) (Leukotrap PL, Miles Inc., Covina, Calif.); and M. van Marwijk et al., Transfusion 30:34 (1990) (Cellselect, NPBI, Emmer-Compascuum, The Netherlands; Immugard Ig-500, Terumo, Tokyo, Japan)]. Unfortunately, these filters are unable to remove either the psoralen photoaddition products or the psoralens themselves, as these relatively low molecular weight compounds are not amenable to removal by current filtration mechanisms.

Adsorption is also a viable method of removing unwanted products from PCs. PCs stored for several days may generate anaphylatoxins that can cause adverse effects, like vascular endothelial injury and peripheral circulatory failure, upon platelet infusion. [T. Shimizu et al., Vox Sang 66:161 (1994)]. Anaphylatoxins such as C3a are positively charged and are believed to be adsorbed onto negatively charged filter membranes by electrostatic forces; most plasma proteins are negatively charged and thus are not adsorbed, allowing isolation and retention of the anaphylatoxins. T. Shimizu et al. found that certain commercially available filters for PCs made of polyester fiber reduced C3a anaphylatoxin levels to about 12% of their prefiltration levels. In theory, psoralens could be developed that are charged molecules capable of binding to filters as do certain anaphylatoxins. However, based on the percentage of anaphylatoxins that escape filter adsorption, psoralen photoproducts and residual psoralens would likely remain in the PCs with such a method because of the limited surface area/adsorptive capacity of such filters.

The process of adsorption has also been used to isolate selective blood components onto phospholipid polymers. For example, several copolymers with various electrical charges have been evaluated for their interactions with blood components, including platelet adhesion and protein adsorption. [K. Ishihara et al, J. Biomed. Mat. Res. 28:1347 (1994)]. However, such polymers are not designed for the adsorption of low molecular weight compounds like psoralens and psoralen photoproducts.

Various dialysis means are able to remove low molecular weight compounds from plasma and whole blood. For example, dialysis can successfully remove low molecular weight toxins and pharmaceutical compounds. Thus, dialysis might be used to remove psoralens and psoralen photoproducts from blood products. Unfortunately, current dialysis procedures involve very complicated and expensive devices. As such, the use of dialysis machines would not be practical for the decontamination of a large volume of blood products. Simpler and more economical means need to be developed to be used in conjunction with PCD.

As presented above, current methods of, and devices for, isolating undesired products from PCs are not suitable for use with PCD and psoralen technology; thus, another approach must be found. An important consideration in the development of a suitable device is the need to avoid deleterious alterations to the blood product itself when it is being processed by the device. [J. M. Courtney et al., Artificial Organs 17(4):260 (1993)]. of particular importance when platelets are involved is the retention of platelet function and platelet integrity. To that end, platelet count and indicators of platelet function such as pH, ATP content, and activation by GMP-140 should not be adversely altered by the device. Furthermore, an acceptable device must not significantly affect the clotting cascade. Finally, the psoralen must be compatible with the device used to remove the psoralens and must have a large enough adsorptive capacity to achieve the desired psoralen removable with a reasonably-sized device.

This aspect of the present invention relates to devices used to remove substances from blood products and particularly to devices used to adsorb psoralens and psoralen photoproducts from platelet mixtures without adversely affecting the platelets. Hereafter, such devices may be interchangeably called "scrub devices" or "capture devices," while the process of removal may be referred to as "the scrub process" or "the capture process."

The description of the devices that follows is divided into the following parts: A) Partitioning of Psoralen in Platelet Concentrate; B) Description and Selection of Adsorbents; C) Adsorption Studies; D) Psoralen Removal Devices; and E) Adsorption of Psoralen from Plasma.

A. Partitioning of Psoralen in Platelet Concentrate

The new psoralen S-59 is a good candidate for use in the process of photochemical treatment (PCT). S-59, 4'-(4-amino-2-oxa)butyl-4,5',8-trimethylpsoralen, has the following chemical structure:

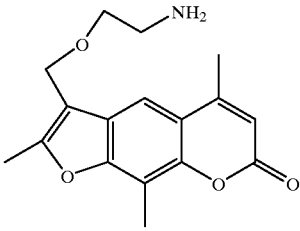

S-59

The process set forth in the description that follows involves the addition of S-59 (final concentration of 150 $\mu$M) to platelets suspended in 35% plasma/65% synthetic media (PAS III) followed by illumination with UVA. Hereafter, reference to 35% PC refers to platelets suspended in 35% plasma/65% PAS III. Analogous partitioning may result with structurally similar psoralens and different platelet formulations. When designing a "capture" or "scrub" device for psoralen removal, an important consideration is the identification and quantification of the residual levels of low molecular weight photoproducts. Several properties of the platelet mixture (e.g., lipid content, platelet content, hemoglobin/RBC content) can affect the final partitioning of psoralen and the amount of each photoproduct that must be removed during the capture or scrub process.

"Photoproduct" is defined as a product of the reaction of a compound and activating wavelengths of electromagnetic radiation. "Photoproduct" is best understood by considering the possible reactions of a photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

C→C*

What happens next is largely a function of what potential reactants are available to the excited species. Since it is short-lived, a reaction of this species with nucleic acid ("NA") is believed to only be possible if nucleic acid is present at the time the excited species is generated. The reaction can be depicted as follows:

C*+NA→NA:C

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

C*→C

On the other hand, the excited species may react with itself (i.e., a ground state or excited species) to create a ground state complex ("C:C"). The product of these self-reactions where two compounds react is referred to as "photodimer" or simply "dimer." The self-reactions, however, are not limited to two compounds; a variety of multimers may be formed (trimers, etc.).

The excited species is not limited to reacting with itself It may react with its environment, such as elements of the solvent ("E") (e.g. ions, gases, etc.) to produce other products:

C*+E→E:C

Furthermore, it may simply internally rearrange ("isomerize") to a ground state derivative ("["):

Finally, the excited species may undergo other reactions than described here.

The present invention and the understanding of "photoproduct" does not depend on which one (if any) of these reactions actually occurs. The present invention simply describes methods and devices for removal of photoproducts following photoactivation of blood products.

Upon addition of S-59 to platelets, the S-59 rapidly partitions, establishing an equilibrium between S-59 in the plasma and S-59 within the platelets. Approximately 25% of the initial S-59 partitions into the platelets, the percentage depending on the platelet count and the viability of the platelets (i.e., dead platelets do not take up psoralen). In addition, higher percentages of S-59 will partition to the platelets if long incubation periods (e.g., greater than 60 minutes) occur between the addition of S-59 and illumination with UVA. The amount of S-59 which partitions to the platelets ultimately determines how much S-59 remains associated with platelets, how much is associated with plasma macromolecules, and how much remains as free photoproduct.

During the UVA illumination process, S-59 undergoes a photochemical reaction to form several low molecular weight photoproducts in addition to associating with macromolecules in both the platelet and the plasma fractions. Approximately 20% of the original 150 $\mu$M of S-59 is associated with the platelets: 8–9% as S-59 and low molecular weight photoproducts and 11–12% as S-59 associated with macromolecules. The remaining approximately 80% of S-59 remains in the plasma, approximately 65% as S-59 and low molecular weight photoproducts and approximately 15% associated with plasma macromolecules. The low molecular weight photoproducts which remain in the platelets and plasma total approximately 73% of the original 150 $\mu$M S-59. This fraction of low molecular weight photoproducts is removed during the scrub process, and their removal can be monitored both by HPLC and by radioactivity measurement using $^3$H-labeled S-59. Schematic A diagrammatically depicts the distribution of S-59 in platelets suspended in 35% plasma/65% PAS III following illumination with UVA.

The S-59 which is not amenable to removal by the scrub/capture process can also be monitored using $^3$H-labeled S-59. This non-removable fraction, which represents 27% of the original 150 $\mu$M S-59, is covalently associated with macromolecules (e.g., lipids) in the platelet and plasma fractions.

B. Description and Selection of Adsorbents

The removal of psoralen and its associated low molecular weight photoproducts from platelet mixtures can be viewed as a situation which is similar to the treatment of patients suffering from drug overdoses. Patients suffering from drug intoxication have been successfully treated utilizing columns containing solid adsorbents to remove low molecular weight drugs from the blood. Treatment is achieved by removing blood from the patient via an extra-corporeal circuit and passing either plasma (plasma perfusion) or whole blood (hemoperfusion) through the adsorbent column before returning the blood to the patient. The majority of the literature relating to hemoperfusion has focussed on two groups of adsorption resins: (i) amberlites, which are polymeric resins [J. L. Rosenbaum et al., Archives of Internal Medicine 136:263–66 (1976); R Hughes et al., Artificial Organs 3(11):23–26 (1979)] and (ii) activated charcoal, which is usually coated with a hemocompatible polymer [D. Webb, British J. of Hospital Medicine 49(7):493–96 (1993)].

The adsorbent resins appropriate for removal of psoralen photoproducts from platelet mixtures should possess several important properties. The adsorbent should be of suitable quality for pharmaceutical applications, including complete characterization of chemical and physical stability, leachables, particle size, and surface area. The adsorbent should also be capable of being sterilized by either autoclave or gamma-irradiation. Finally, the adsorbent should be hemocompatible with respect to platelet function and/or plasma clotting factors. It should also be noted that the adsorbent resins contemplated for use in the present invention may be effective in the removal of cholesterol, lipids and fatty acids, cytokines, and endotoxins.

Table A summarizes some of the resins chosen for the initial screening procedure. Besides the description of the resin as presented in Table A, low-cost resins were specifically chosen. This list is not inclusive, other resins may also be effective. Of note, traditional chromatography resins have recently been examined as potential hemoperfusion adsorbents for several different medical indications. The CA4, C-8, and C-18 adsorbents were included in the screen because of previous utility. [D. J. Hei et al., "Removal of Cytokines from HSA-Containing Solutions by Adsorption onto Silica," Biotechnology and Bioengineering 44:1023–30 (1994); S. Murugavel, "In Vitro Studies of the Efficacy of Reversed Phase Silica Gel as a Sorbent for Hemo- and Plasmaperfusion," Clinical Toxicology 30(1) 69–82 (1992)].

TABLE A

| Adsorbent | Manufacturer | Description |
| --- | --- | --- |
| Amberlite XAD-2 | Rohm and Haas | Polystyrene beads, 250–850 $\mu$m diameter, 300 m$^2$/g |
| Amberlite XAD-4 | Rohm and Haas | Polystyrene beads, 250–850 $\mu$m diameter, 725 m$^2$/g |
| Amberlite XAD-7 | Rohm and Haas | Polyacrylated beads, 250–850 $\mu$m diameter, 450 m$^2$/g |
| Amberlite XAD-16 | Rohm and Haas | Polystyrene beads, 250–850 $\mu$m diameter, 800 m$^2$/g |
| Amberchrom | Rohm and Haas | Polyacrylated beads (pharmaceutical grade resin) |
| Amberchrom | Rohm and Haas | Polystyrene beads (pharmaceutical grade resin) |
| Hemosorba | Asahi | HEMA-coated activated charcoal, 600 $\mu$m diameter |
| Amberlite 200 | Rohm and Haas | Strong cation exchange (sulfonic acid) |
| Amberlite DP1 | Rohm and Haas | Weak cation exchange (carboxylic acid) |
| Macro-Prep | BioRad | Rigid polyacrylic beads modified with |
| Bio-Beads SM-2 | BioRad | Polystyrene divinylbenzene, 300–1180 $\mu$m diameter beads |

TABLE A-continued

| Adsorbent | Manufacturer | Description |
|---|---|---|
| Bio-Beads SM-4 | BioRad | Polystyrene divinylbenzene, 63–150 μm or 300–1180 μm diameter |
| Bio-Beads SM-7 | BioRad | Polyacrylic ester, 63–150 μm or 300–1180 μm diameter |
| Grace-Davison Silica | Grace-Davison | Unmodified silica |
| Grace-Davison Silica | Grace-Davison | Unmodified silica |
| Whatman Silica | Whatman | Unmodified silica, 40 μm diameter, 150 Å pore |
| Waters SPE Silica | Waters | Unmodified silica |
| Baker SPB C4 | Baker | Silica modified with C4 ligand |
| Baker SPE C8 | Baker | Silica modified with C8 ligand |
| Baker SPB C18 | Baker | Silica modified with C18 ligand |
| Waters SPE C18 | Water | Silica modified with C18 ligand |

As will be discussed in detail below, the following resins gave superior results based on the initial screening procedure: Amberlite XAD-4™, Amberlite XAD-16™, Amberchrom CG-161cd™, Hemosorba CH-350™, and Bio-Beads SM-4™ (300–1180 μm diameter).

Amberlite Resins

The amberlite adsorbents have been used to treat patients with both acute drug intoxication [J. L. Rosenbaum et al., Archives of Internal Medicine 136:263–66 (1976)] and liver failure [R Hughes et al., Artificial Organs 3(1):23–26 (1979)]. In addition, amberlite adsorbents are currently used in a variety of applications in the pharmaceutical industry. Supelco, Inc. (Bellefonte, Pa.) currently processes Amberlite XAD-4™ and XAD-16™ resins manufactured by Rohm and Haas (Chauny, France) specifically for pharmaceutical applications. Supelco, Inc. treats the adsorbents to remove potential leachables (e.g., divinyl benzene, DVB) and to restrict the particles to a minimum diameter. The final adsorbent is certified sterile (USP XXI), pyrogen-free (LAL), and free of detectable leachables (DVB and total organics).

Charcoal Resins

Hemoperfusion devices using charcoal resins are currently manufactured by several Japanese companies and are marketed in the United States and Europe. Two hemoperfusion devices manufactured by Asahi Medical Co. (Tokyo, Japan) which contain activated charcoal currently have a 510(k) filing with the FDA for treatment of drug overdose and hepatic coma The adsorbent from the Hemosorba CH-350 hemoperfusion device is a very durable, large diameter particle which is designed specifically for removal of low molecular weight drugs and toxins from cell-containing fluids such as PCs. Charcoal adsorbents for hemoperfiusion are typically manufactured from petroleum pitch and coated with a hemocompatible polymer such as poly(HEMA) (hydroxyethyl methacrylate); the polymer coating increases hemocompatibility and reduces the risk of small particle generation due to mechanical breakdown.

Hemoperfusion devices using charcoal resins are not used very frequently in the United States for several reasons. First, in many circumstances there are better alternative treatment methods such as hemodialysis. Second, some forms of drug intoxication and poisoning are not amenable to hemoperfusion due to strong partitioning of the toxins to particular body compartments (e.g., tissue, lungs, etc.). However, hemoperfusion is still recommended in certain clinical situations such as theophylline overdose. [D. Webb, British J. Of Hospital Medicine 49(7):493–96 (1993)].

C. Adsorption Studies

Equilibrium Adsorption

The easiest method to screen the potential adsorbents for S-59 removal involves examining equilibrium adsorption of S-59 from PC. The use of radiolabeled S-59 in adsorption experiments allowed measurements of residual radioactivity to be used as an indicator of S-59 remaining following adsorption. To compare the various adsorbent candidates, approximately 0.1 g of each adsorbent was added to 3.0 mL of PC containing 150 μM $^3$H-S-59 (non-illuminated). Samples were incubated in sealed tubes on a platelet rotator for 24 hours at room temperature. Kinetic measurements indicated that complete equilibrium was achieved after approximately 6 hours of batch incubation. Following incubation, a sample of PC was removed from each tube and the level of remaining radioactivity was determined for each adsorbent.

Table B displays, among other things, the residual levels of S-59 and thus provides a good indicator of the relative effectiveness of each adsorbent. In order to assure that equilibrium had been achieved, these residual levels were determined after a 24-hour incubation period.

Adsorption isotherms were constructed for each adsorbent, and the equilibrium adsorption constants (K) were determined from the slope of the isotherm (adsorption constants are listed in the third column of Table B). In the fourth column of Table B, the total cost of the resin ($/device) was determined for the reduction of S-59 levels from 30 μM (20% of 150 μM to 5 μM. In the fifth (last) column of Table B, the total cost of certain resins ($/device) was determined for the reduction of S-59 levels from 30 μM to 1 μM. It should be noted that illumination of the platelet mixture will reduce the level of S-59 from 150 μM to 30 μM due to photodegradation. The cost for Hemosorba CH-350 was estimated ($350 for a single adsorption device containing 140 g of adsorbent). Finally, The "ND" indicates that those values were not determined.

TABLE B

| Adsorbent | Residual S-59 (%) | K (L/g) | Cost ($/g) | Total Cost Of Resin ($/Device) Reduction To 5 μM | Total Cost Of Resin ($/Device) Reduction To 1 μM |
|---|---|---|---|---|---|
| Amberlite XAD-2 | 1.3 | 1.84 | 0.06 | 0.05 | 0.28 |
| Amberlite XAD-4 | 0.24 | 12.10 | 0.12 | 0.01 | 0.09 |
| Amberlite XAD-7 | 7.6 | 0.36 | 0.06 | 0.25 | 1.44 |
| Amberlite XAD-16 | 0.40 | 7.33 | 0.13 | 0.03 | 0.15 |
| Amberchrom CG-71cd | ND | ND | 1.40 | ND | ND |
| Amberchrom CG-161cd | ND | ND | 1.40 | ND | ND |
| Amberlite 200 | 6.0 | 0.34 | 0.06 | 10.17 | 1.55 |
| Amberlite DP1 | 74.9 | 0.01 | 0.06 | ND | 58.99 |
| Hemosorba CH-350 | <0.1 | 33.04 | 0.50 | 0.02 | 0.13 |
| Macro-Prep t-butyl HIC | 3.3 | 0.87 | 0.645 | 1.11 | 6.44 |

TABLE B-continued

| Adsorbent | Residual S-59 (%) | K (L/g) | Cost ($/g) | Total Cost Of Resin ($/Device) Reduction To 5 $\mu$M | Total Cost Of Resin ($/Device) Reduction To 1 $\mu$M |
|---|---|---|---|---|---|
| Bio-Beads SM-2 | 0.88 | 3.20 | 1.10 | 0.52 | 2.99 |
| Bio-Beads SM-4 | 0.15 | 19.83 | 1.10 | 0.08 | 0.48 |
| Grace-Davison Silica, Grade 15 | 39.2 | 0.04 | 0.003 | 0.13 | 0.74 |
| Grace-Davison Silica, Grade 636 | 67.8 | 0.01 | 0.003 | 0.41 | 2.40 |
| Whatman Silica | 77.8 | 0.01 | 0.10 | 23.05 | 133.69 |
| Waters SPE Silica | 80.0 | 0.01 | 0.08 | 19.65 | 113.96 |
| Baker SPE C-4 | 9.1 | 0.30 | 0.60 | 3.01 | 17.47 |
| Baker SPE C-8 | 5.3 | 0.51 | 0.60 | 1.77 | 10.24 |
| Baker SPE C-18 | 1.1 | 2.29 | 0.60 | 0.39 | 2.28 |
| Waters SPE C-18 | 2.8 | 0.97 | 0.60 | 0.93 | 5.38 |

The tests performed included analysis of several reversed-phase resins (i.e., C18 from several manufacturers and C-4 and C-8 from Baker) which are typically used in Solid Phase Extraction (SPE) of drugs from blood. Though several reversed phase resins showed good adsorption, these resins suffer from problems related to wetting of the resins with aqueous solution. The reversed phase adsorbents must be pre-wet with ethanol by suspending in ethanol, centrifuging, and decanting the ethanol before adding aqueous solutions. Reversed phase adsorbents that were not pre-wet in ethanol tended to clump together and stick to the side of the tubes, resulting in uneven distribution and contacting. In addition to problems with wetting, reversed phase media tend to be more expensive than other media and are usually supplied only in small particle sizes (ie., diameters less than 50 $\mu$m). As a result, reversed phase resins including C-4, C-8, and C-18, and other resins which do not readily wet with aqueous solutions, such as the Amberchrom resins (Table B) and Waters Porapak RDX™ (Waters, Milford, Mass.) (not listed in Table B), are not preferred.

Examination of the data relating to the amberlites in Table B reveals that Amberlite XAD-4™ and Amberlite XAD-16™ are preferred. In particular, the residual levels of S-59 are much less (more than a three-fold difference) for those two amberlites than for the other amberlites (i.e., Amberlite XAD-2™ and Amberlite XAD-7™).

Several activated charcoals (not listed in Table B) were also tested. The standard activated charcoals were not mechanically stable and tended to break down into very fine particles. Samples taken during adsorption studies often contained high levels of charcoal fines (fine particles of adsorbent) which were impossible to separate from the platelets. The activated charcoals produced specifically for hemoperfusion (e.g., Hemosorba CH-350; Asahi; listed in Table B) are made of petroleum pitch which yields very hard, durable charcoal beads. In addition, as previously noted, activated charcoals that are developed for hemoperfusion are typically coated with a polymer which increases hemocompatibility and reduces the risk of small particle generation due to mechanical breakdown.

Table B summarizes other equilibrium adsorption data besides data relating to residual levels of S-59 for each of the resins. This data can be used to estimate the equilibrium capacity of the resin at the desired final concentration of residual S-59. If the initial concentration of S-59 is 150 $\mu$M and a goal of greater than 99% removal of the initial S-59 is established, the final concentration of S-59 is approximately 1 $\mu$M. The capacity of each resin can be estimated by assuming a linear isotherm (Langmuir, low concentration) and by using the following equation:

$$q = KC_f \quad \text{(Equation 1)}$$

where q ($\mu$mole S-59/ g resin) is the resin capacity, $C_f$ ($\mu$M) is the final equilibrium solution concentration of S-59, and K (L/g) is the adsorption constant which is a property of the resin. Data similar to that displayed in the second column of Table B can be used to estimate a value for K. The resin capacity (q) can then be estimated using the calculated value for K and the final concentration goal of 1 $\mu$M S-59 for $C_f$.

Subsequent to calculation of a resin's capacity, the amount of resin required to treat a given volume of PC can be estimated from the following equation:

$$M = V(C_o - C_f)/q \quad \text{(Equation 2)}$$

where M (g) is the mass of adsorbent, V (L) is the volume of solution, $C_o$ is the initial S-59 concentration, $C_f$ ($\mu$M) is the final concentration of S-59 (1 $\mu$M for purposes of this calculation), and q ($\mu$mole S-59/ g resin) is the resin capacity defined by Equation 1.

For a typical 35% PC (i.e., 35% plasma/65% PAS III), approximately 20% of the original 150 $\mu$M S-59 remains following illumination; therefore, $C_o$ can be estimated at approximately 30 $\mu$M. The volume of PC (V) that is treated is 300 mL. Therefore, one can calculate the mass of adsorbent, M, which is required to reduce the S-59 concentration from $C_o$ to $C_f$ for each resin having capacity q.

The final equilibrium solution concentration, $C_f$, is an important parameter since it determines both the resin capacity, q, and the total amount of S-59 which must be removed. Combining Equation 1 and Equation 2 yields the following relationship:

$$M = (V/K)[(C_o/C_f) - 1] \quad \text{(Equation 3)}$$

Of note, for low values of $C_f$, the required mass of resin, M, is inversely proportional to $C_f$. The asymptotic behavior of adsorbent mass with respect to $C_f$ is set forth in Schematic B. Equation 3 was used to derive the curves presented in FIG. 4, and calculations were based on an initial concentration, $C_o$, of 30 $\mu$M and a volume, V, of 300 mL.

Adsorption Kinetics

As will be discussed in detail below, two potential methods of contacting the selected adsorbent with the PC involve the use of a flow device and the use of a batch device. The kinetics for adsorption of psoralen from PC or plasma is potentially one of the most important factors in determining the effectiveness of a flow scrub device (discussed in detail below). Incomplete equilibrium between the free psoralen and the solid adsorbent during the use of a flow device could result in substantial increases in the amount of adsorbent required to achieve a given level of residual psoralen.

The rates of adsorption processes are often limited by mass transfer processes which involve diffusion of the adsorbate to the surface of the adsorbent. Adsorption of a low molecular weight compound such as S-59 is typically a rapid process because of the relatively high diffusiveness of small molecules. However, interaction of S-59 with cells and/or plasma molecules could result in slower adsorption kinetics if adsorption rates are limited by a process other than diffusion.

D. Psoralen Removal Devices

Overview

The present invention contemplates the use of two distinctly different types of devices for psoralen removal: flow devices and batch devices. Flow devices involve the removal of psoralen by perfusing the PC through an adsorbent column either postillumination or pre-transfusion at bedside. Conversely, batch devices entail either adding an adsorbent directly to the platelet bag following illumination or transferring the platelets to a bag containing the adsorbent following illumination; the platelets are then agitated for a specified period of time.

As set forth above, approximately 73% of the original 150 $\mu$M S-59 is present as S-59 and low molecular weight photoproducts. Approximately 20–30% of the original S-59 remains while the other 40–50% represents the photo-reaction products of S-59. Studies using batch devices have indicated that greater than 99% of the S-59 and low molecular weight photoproducts can be adsorbed from PCs using appropriate adsorbents. Selection of an appropriate flow or batch removal device should allow similar levels of removal to be achieved.

Flow Devices

As set forth above, the present invention contemplates that a platelet preparation can be perfused through a flow device either after illumination of the platelets with UVA or prior to transfusion of the preparation into the recipient. Typically, the flow device entails an in-line column of 5–10 mL capacity that is packed with adsorbent. The body of the device must be manufactured from a hemocompatible plastic (polycarbonate, polypropylene) that is durable enough to protect the resin from being crushed during handling. The device has a flow adapter, preferably a 50–100 $\mu$m opening nylon mesh filter, that should prevent fines (fine particles of adsorbent) from passing through while allowing cells to pass through with minimal pressure drop. In most embodiments, the device also entails an additional bag for storing the platelet preparation after it has perfused through the column and an in-line filter for protecting against transfusion of fine adsorbent particles.

In terms of operation, the flow device should operate under gravity flow; the removal process should be completed within a window of time defined by the minimum amount of time allowed for treating a platelet preparation, 30 minutes to 3 hours and preferably 1 to 2 hours, and the minimum amount of time required for virus testing of the platelet preparation, approximately 12 hours. Both loss of platelets and loss of volume should be negligible.

Several considerations are relevant to the manufacturing process. First, the bed volume should be considered in view of the expected amount of drug to be removed. A greater bed volume is required for removal of larger amounts of drug. Second, the bed diameter is dictated by the pressure drop for a given bed volume; the diameter may also have an effect on psoralen removal at a constant bed volume. Third, the devices should be packed with a wet adsorbent column and primed in an acceptable solution (e.g., synthetic media such as PAS III) before assembly and sterilization. Fourth, the device should be connected to bags for platelet collection/treatment and storage, and this final assembly should then be sterilized and packaged. Priming the device between the platelet bag and the column needs to be performed with care; the introduction of a large air bubble could cause channeling in the device and incomplete psoralen removal.

Supelco, Inc., currently manufactures both large scale (250–1500 mL, Porozorb Cartridges™) and small scale (5 mL, Rezorian Cartridges™) devices containing Amberlite™ and Amberchrom™ resins. These devices are marketed for removal of small molecules such as ethidium bromide, detergents, antibiotics, etc., from protein solutions. Moreover, Waters (Milford, Mass.) currently manufactures small-scale (1 mL) adsorption devices that are classified as Type I Medical Devices.

To this point, the experiments and design considerations that have been discussed are based on equilibrium (batch) adsorption data. In a flow adsorption device, several factors can influence the amount of adsorbent required, and thus the overall design of the device. First, as previously alluded to, kinetic limitations in adsorption can result in increased requirements for adsorbent due to incomplete equilibrium between the fluid and adsorbent. However, the kinetic limitations can typically be counteracted by decreasing the flow rate through the adsorption device to allow sufficient contact time. Second, dispersions resulting from imperfections in flow through the device can also result in a requirement for a larger mass of adsorbent in flow devices. Proper design and manufacturing of the device will minimize dispersion effects.

The effect of adsorbent and column geometry on residual levels of psoralen in flow devices has been examined. The results for several flow configurations, summarized in Table C, indicate several key points. First, increasing the diameter of the flow device at a constant mass of resin resulted in an increase in the level of residual S-59 in the treated platelet unit. Second, longer columns with a narrow diameter will result in lower levels of residual S-59, but may also result in unacceptably high pressure drops for gravity flow. Third, Amberlite XAD-4™ was not as effective as Amberlite XAD-16™ at removing S-59; the smaller pore diameter in Amberlite XAD-4™ may result in substantially slower adsorption kinetics.

TABLE C

| Adsorbent | Mass (g) | Flow Rate (mL/min) | Column Diameter (cm) | Residual S-59 (%) |
| --- | --- | --- | --- | --- |
| Amberlite XAD-16 | 5 | 1.0 | 1.0 | 6.0 |
| Amberlite XAD-16 | 5 | 1.0 | 1.6 | 8.4 |
| Amberlite XAD-4 | 5 | 1.0 | 1.6 | 11.2 |
| Amberlite XAD-4 | 10 | 1.0 | 1.6 | 9.2 |

Table C indicates that doubling the mass of Amberlite XAD-4™ resulted in a disproportionately small gain in S-59 removal in a flow device. Moreover, the data suggests that the limiting factor in S-59 removal from platelet-containing solutions is the transport of S-59 from the platelet's interior. Possible solutions to kinetic limitations of flow devices involve increasing the residence time of the platelets by using a larger flow device and decreasing the flow rate.

Batch Devices

As alluded to above, an alternative to a flow device is batch adsorption. Batch adsorption involves either placing the adsorbent directly in the platelet bag following illumination or transferring the platelets to a bag containing the adsorbent following illumination. The platelets are then agitated for a specified period of time. Thereafter, as an added safety precaution, the platelets may be transferred to another bag through an in-line filter/sieve to remove any solid resin particles.

In certain embodiments, the platelets are treated directly with adsorbent (i.e., the adsorbent is not contained within any type of packaging). In such embodiments, the batch device contains a removal device, such as a flow adapter or other filtration device, with a 50–100 $\mu$m opening nylon mesh filter for removing the adsorbent from the platelets following treatment. In other embodiments, the adsorbent is contained within a mesh enclosure/pouch that is disposed within the platelet bag itself. For experimental purposes, the mesh enclosure was placed inside the platelet bag by cutting a slit along the side of the platelet bag, inserting the mesh enclosure through the slit, then heat sealing the platelet bag. However, in large-scale manufacturing the mesh enclosure may either be fixed or not fixed to the platelet bag. This complete assembly can be sterilized by heat or gamma-irradiation.

As was the case with flow devices, in most embodiments the batch device also entails an in-line filter for protecting against transfusion of fine adsorbent particles and an additional bag for storing the treated platelets. In another embodiment, the adsorbent is packaged in an external compartment that offers protection of the resin during handling. This external compartment could serve as a package for the sterile adsorbent and a device for removing the adsorbent following treatment. The external compartment could resemble a drip chamber with a frangible closure between the bag and compartment and a suitable filter mesh for retaining the adsorbent on the outlet. Following illumination, the frangible would be broken and the adsorbent would be transferred into the bag containing the treated platelets. After removal is complete, the blood product is passed through the external chamber where the adsorbent is removed. There are several manufacturers of mesh materials suitable for use with the present invention. For example, Saati Corp. (Stamford, Conn.) and Tetko, Inc. (Buffalo, N.Y.) manufacturer a variety of medical-grade mesh materials.

Figure 47:
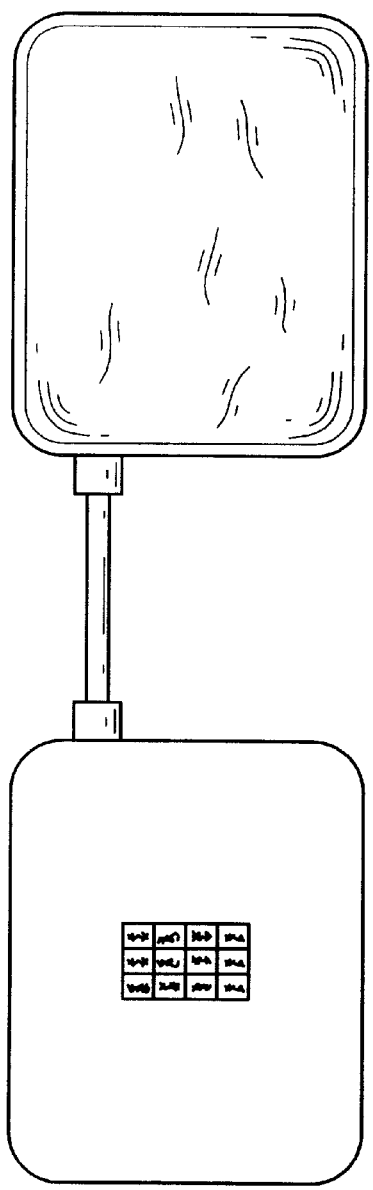
FIG. 47 depicts two possible configurations for a batch RD. Configuration A illustrates a two-bag design, whereas configuration B illustrates a single-bag design.
Figure 47:
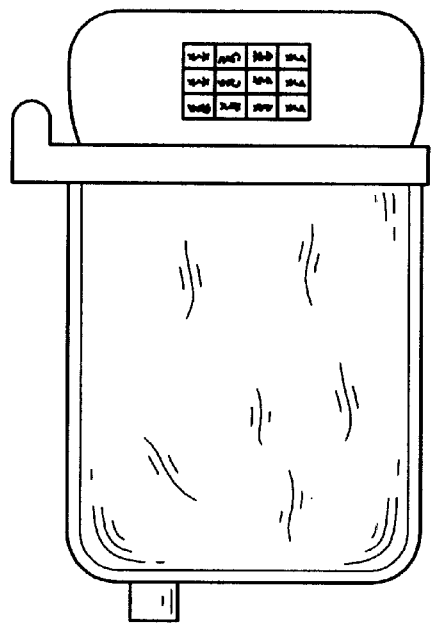
Figure 48:
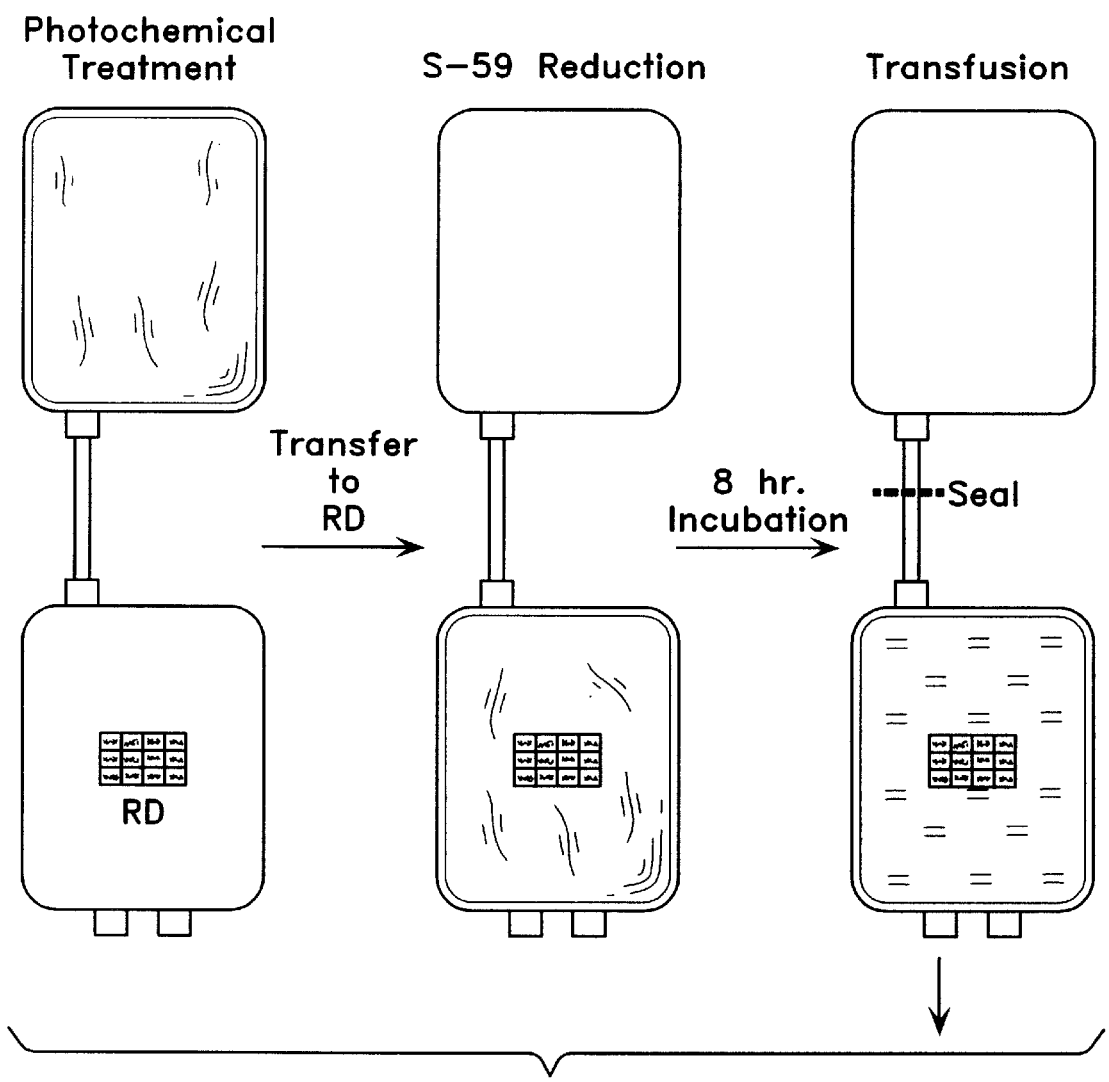
FIG. 48 diagrammatically depicts the S-59 reduction process. Following illumination of the PC containing S-59, the PC is transferred to a container housing the RD, incubated with agitation to allow a time-dependent reduction in the amount of residual S-59 and unbound photoproducts, and then transferred to a storage container.

FIG. 47 depicts two possible configurations for a batch RD. In configuration A (i.e., a two-bag design), platelets are transferred to a second bag following illumination, the second bag containing the adsorbent in a mesh enclosure/pouch. The platelets could be transferred back to the original bag if a limited contact time is desirable. In configuration B (i.e., a single-bag design), the external partition is broken away following illumination, thereby allowing the platelets to freely mix with the adsorbent bag/pouch. Of course, other configurations are possible for a batch RD.

Several factors must be considered when choosing a batch RD. First, extended contact time with the adsorbent could increase the levels of leachables from the adsorbent present in the final PC. Second, batch RDs generally have a longer contact time with the blood product than flow devices. As a result, it is especially important to monitor hemocompatibility (i.e., platelet function and excessive loss of clotting factors). Third, batch RDs involve an additional device for agitation (i.e., a shaker) of the platelets/plasma during the adsorption process. The device used should have safeguards to ensure that the adsorption time is not shortened by malfunction of the device.

Hemocompatibility Studies

Platelet function studies were conducted with both batch and flow devices (Example 25 and Example 29, respectively). The results indicated good retention of platelet function for several particular adsorbents. Problems associated with flow devices mainly entail removal of platelet clumps that may form in the device; however, the removal of clumps likely does not create a significant problem because the clumps would typically be removed by aggregate filters prior to transfusion. Platelet function studies involving batch devices suggested that Amberlite XAD-4™ and Amberlite XAD-16™ have satisfactory hemocompatibility characteristics.

It should be noted that using a flow device will not necessarily produce results analogous to those obtained by using a batch device even when using the same adsorbent. Though contact times between platelets and adsorbent would be lower in a flow device, other factors such as mechanical stress and contact with other column components could adversely affect the platelets.

Coagulation studies were performed on 100% plasma. The best results (Example 30, infra) were obtained with Amberlite XAD-4™ and Hemosorba CH-350™ both of which had little effect on any of the tested parameters. The experiments relating to clotting factor assays were carried out in a batch mode at a higher ratio of adsorbent to plasma than is typically used in adsorption experiments. In addition, a flow device should result in shorter contact times with concomitantly higher recovery of the proteins involved in blood clot formation.

Comparison of Batch and Flow Designs

The flow and batch formats discussed above are similar in that direct contact between the blood product and adsorbent occurs during psoralen removal. However, the two types of devices do possess several significant differences. First, while batch adsorption is capable of reducing residual levels of psoralen and photoproducts to <1%, levels of approximately 5% are more likely with flow adsorption. As previously noted, kinetic limitations due to decreased contact time for psoralen transport from platelets may prevent complete removal of residual psoralen using a flow format; conversely, the extended contact time of batch adsorption is more effective at removal.

Second, the extended contact time of batch formats could increase the levels of leachables present in the final platelet mixture. However, Supelco, Inc., currently processes Amberlite™ adsorbents that effectively reduce the levels of leachables to undetectable levels. Third, with both types of devices there is the possibility that fine particles of adsorbent could ultimately be transfused into the recipient of the blood product. Though a flow device provides a more stable configuration for the resin, the flow adapters for a flow format would require a mesh with minimum approximately 60 $\mu$m opening to prevent clogging by platelet clumps. However, a batch device could use a smaller mesh size (e.g., approximately 10 $\mu$m opening) because the platelets do not need to flow through the mesh itself. The ability to use a smaller mesh may thus reduce the possibility of transfusing fine particles in a batch format.

Based on all of the factors discussed above, a batch approach is preferable to a flow design. In the studies conducted relating to batch adsorption, Amberlite XAD-4™, Amberlite XAD-16™, and Hemosorba CH-350™ were the adsorbents that exhibited high S-59 adsorption capacities and good hemocompatibility characteristics. Of those resins, Amberlite XAD-4™ and Amberlite XAD-16™ processed by Supelco, Inc., are preferable, and Amberlite XAD-4™ is most preferred because it has less of an adverse effect on clotting factors.

E. Adsorption of Psoralen from Plasma

Overview

To this point, the discussion of RDs has focussed on the removal of psoralen from PCs, specifically platelets in 35% plasma/65% PAS III. However, the present invention also contemplates the removal of psoralen from other blood products, such as plasma and serum. This section will discuss the removal of psoralen from plasma.

In general, the same principles apply to removal of psoralen from plasma that apply to removal of psoralen from PCs. Thus, both batch and flow formats can be used to remove psoralen from photo-treated plasma. Residence time is not an important factor with plasma (or serum) because there are no platelets from which the psoralen must be removed. The main limitation in removal of S-59 from plasma is competition by plasma proteins, mainly serum albumin, for binding of free S-59 and photoproduct.

As was the case above for PCs, potential adsorbents were screened to determine their effectiveness. Table D lists the cost and S-59 capacity for several adsorbents. The cost of Amberlite XAD-1600 (fourth column) was not determined.

VII. PERFORMANCE AND MANUFACTURING OF A BATCH REMOVAL DEVICE

One of the preferred embodiments of the present invention entails a batch removal device. A batch removal device is preferable to a flow device for certain blood products. For example, the use of a batch device with platelet concentrates overcomes the kinetic limitations of removing psoralen photoproducts from the platelets. Similarly, fresh frozen plasma (FFP) also has kinetic limitations, e.g., competition by serum albumin and other plasma proteins for binding of free S-59 and photoproducts, which are overcome with a batch device.

The terms "removal device" and "RD" refer to a known mass of medical/pharmaceutical grade adsorbent (e.g., polymeric adsorbent beads) retained in a mesh pouch/bag (e.g., polyester mesh), a pouch constructed from a permeable

TABLE D

| Adsorbent | Manufacturer | Description | Cost ($/g) | S-59 Capacity ($\mu$mole/g) at 1 $\mu$M |
|---|---|---|---|---|
| Amberlite XAD-4 | Rohm & Haas | Polystyrene, 250–850 $\mu$m | 0.12 | 3.4 |
| Amberlite XAD-16 | Rohm & Haas | Polystyrene, 250–850 $\mu$m | 0.13 | 2.0 |
| BioBeads SM-4 | BioRad | Polystyrene, 300–1180 $\mu$m | 1.10 | 7.7 |
| Macro-Prep t-butyl HIC | BioRad | Rigid polyacrylic, t-butyl HEMA-coated | 0.65 | 0.6 |
| Hemosorba CH-350 | Asahi | activated-charcoal | 0.50 | 19.7 |
| Amberchrom CG-71 md | Rohm & Haas | 75 $\mu$m polyacrylic, 200–300 Åpores | 1.40 | 3.8 |
| Amberchrom CG-161 md | Rohm & Haas | 75 $\mu$m polystyrene, 110–175 Åpores | 1.40 | 11.3 |
| Amberchrom CG-300 md | Rohm & Haas | 75 $\mu$m polystyrene, 1000–1400 Åpores | 1.40 | 12.1 |
| Amberlite XAD-1180 | Rohm & Haas | 20–60 mesh polystyrene, 300 Å, 600 m$^2$/g | 0.29 | 0.3 |
| Amberlite XAD-1600 | Rohm & Haas | polystyrene, monodisperse | ND | 2.2 |
| Amberlite XAD-2000 | Rohm & Haas | 20–60 mesh polystyrene, 42 Å, 580 m$^2$/g | 0.17 | 0.3 |
| Amberlite XAD-2010 | Rohm & Haas | 20–60 mesh polystyrene, 280 Å, 660 m$^2$/g | 0.29 | 1.2 |
| Ambersorb 563 | Rohm & Haas | Synthetic charcoal, most hydrophobic, 500 m$^2$/g | 0.85 | 1.7 |
| Diaion HP-2MG | Mitsubishi Kasei | 25–45 mesh polyacrylic, 200–800 Å, 500 m$^2$/g | 0.12 | 0.4 |
| Diaion HP-20 | Mitsubishi Kasei | 30–50 mesh polystyrene, 300–600 Å, 500 m$^2$/g | 0.18 | 1.6 |

In addition, adsorption data using a flow device at two different flow rates was also generated and is presented in Example 30.

Clotting Factor Assays

The adsorbent used for plasma products must be capable of removing S-59 without significantly depleting the levels of proteins important in the clotting cascade. The selectivity of various resins for S-59 was analyzed by performing batch adsorption experiments (See Example 31, infra) and submitting the treated plasma to assays for clotting time and factor levels. The adsorbents used were Amberlite XAD-4™, Amberlite XAD-16™, Hemosorba CH-350™, BioRad t-butyl HIC™ (Macro-Prep), and Davision Silica (Grade 15).

The experiments relating to clotting factor assays were carried out in a batch mode at a higher ratio of adsorbent to plasma than is typically used in adsorption experiments. A flow adsorption device should result in shorter contact times with concomitantly higher recovery of the proteins involved in blood clot formation.

membrane, a cartridge (e.g., an in-line column), or other suitable means; the present invention contemplates the use of a RD for the removal of psoralen and psoralen photoproducts. Generally speaking, the longer the contact time with the RD, the greater is the removal of psoralen and psoralen photoproducts; however, practical limitations imposed by blood banking procedures limit the available contact time.

In a preferred embodiment, the RD (i.e., the adsorbent-containing pouch) is contained in a blood product storage container (e.g., a platelet storage bag). The present invention also contemplates other embodiments, described in detail below, utilizing adsorbent for the removal of S-59 and photoproducts. This section describes the performance requirements for a batch RD, the adsorbents particularly suited for such a RD, and the overall RD-manufacturing process.

A. Requirements for a Batch Removal Device

In one embodiment of the present invention, the blood product is first treated with psoralen and UVA in an illumination container. For example, S-59 (15.2 mg) may be added to approximately $4.0 \times 10^{11}$ platelets suspended in 300 mL of 35% plasma/65% PAS III and illuminated with 3 J/cm² long wavelength UVA (320–400 nm). Following illumination there is residual S-59; moreover, it is believed there are low molecular weight photoproducts. Thereafter, the blood product is transferred to e.g, a modified PL 2410 Plastic container (Baxter) containing the RD and incubated for a specified period of time (e.g., >8 hours on a platelet shaker); this incubation allows the residual psoralen and psoralen photoproducts to be removed (i.e. S-59 reduction) to sufficiently low levels so that the blood product may be released for transfusion to humans. Following the incubation period, the blood product may be transferred to another storage container (e.g., a PL 2410 Plastic container; Baxter) for, e.g., up to 5 days for platelets, pending transfusion. Schematic D diagrammatically depicts the S-59 reduction process described above.

In an alternative embodiment, UVA illumination and RD treatment occur in a single blood product bag. In this embodiment, a removable, external partition separates the blood product bag into two compartments (see FIG. 47, configuration B). Referring to Schematic C, configuration B, the blood product is illuminated in the lower compartment. Following illumination, the partition is removed and the illuminated blood product contacts the RD that is fixed within the upper compartment. After incubation, the blood product bag may be hung up and the partition replaced, thereby isolating the blood product from the RD. Alternatively, the bag may be welded (e.g., heat sealed or impulse welded) to isolate the blood product from the RD. The entire blood product bag (ie., the bag including the illuminated and RD-treated blood product and the RD itself) may then be stored pending transfusion.

In addition to effectively removing S-59 and photoproducts, the RD should not adversely effect the in vivo performance of the transfused blood product. For PCs, several in vitro platelet function tests have been reported to correlate with in vivo post-transfusion recovery and survival, including pH, morphology score, platelet shape change, and hypotonic shock response. [S. Murphy et al., "In Vitro Assessment of the Quality of Stored Platelet Concentrates," Transfusion Med. Rev. VIII(1):29–36 (1994)]. It is preferred that the RD not have a material adverse effect on platelet function.

In Table AA that follows, certain suggested minimum requirements for a batch RD are listed. It should be emphasized that these requirements are merely preferred; as such, it is to be understood that modifications to the requirements are within the scope of the present invention. Though these requirements are specifically geared to a RD for removal of S-59, many of the requirements are applicable regardless of the psoralen being used.

TABLE AA

| Parameter | Requirements |
|---|---|
| Platelet Unit | $3.0–4.4 \times 10^{11}$ Platelets In 300 mL 35% Plasma/65% PAS III |
| Photochemical Treatment | 150 μM S-59, 3 J/cm² UVA |
| Contact Time Of PC with Adsorbent | 4–10 Hours |
| Residual S-59 Following Incubation with the RD | ≦ 0.5 μM S-59 After 8 Hour Contact Time |
| Platelet Function | pH > 6.5, 5 Day Storage After 8 Hour Contact Time, Yield > 90% |

TABLE AA-continued

| Parameter | Requirements |
|---|---|
| Toxicology | Passes Testing For ISO Short Term (24 hrs–30 days), Indirect Blood Contact |
| Particulate Matter | Meets USP LVI Guidelines |
| Sterilization | Terminal Sterilization By γ-Irradiation; Sterility Assurance Level Of $10^{-6}$ |
| Pyrogen Levels | Fluid Path Flush Procedure Using LAL Test Method For Endotoxin Determination, LAL < 0.5 EU/mL |

B. Adsorbents Particularly Suited for a Removal Device

Previous sections have presented an overview of certain adsorbents contemplated for use in the removal of psoralen photoproducts from blood products (see, e.g., Table A). There are a number of polymeric adsorbents suitable for use in a batch RD, including those manufactured by Dow Chemical Company (e.g., Dowex® XUS-40323, XUS-43493, and XUS-40285), Mitsubishi Chemical (e.g., Diaion® HP20), Purolite (e.g., Hypersol-Macronet® Sorbent Resins MN-150 and MN-400) and Rohm and Haas (e.g., Amberlite® XAD-2, XAD-4, and XAD-16). The most preferred adsorbent is Dowex® XUS-43493, an inert polymer manufactured by Dow Chemical Company; Dowex XUS®-43493 is known commercially as Optipore® L493.

The polymeric adsorbents most useful in the present invention are non-ionic macroporous and macroreticular resins. The term "macroporous" generally means that greater than or equal to 20% of the resin is cross-linked (cross-linking is discussed in detail below). The term "macroporous" is distinguishable from the term "macropores", which means that the diameter of the pores is greater than 500 Å. Finally, the term "macroreticular" is a relative term that means that the structure has a high physical porosity (i.e., a large number of pores are present).

Non-ionic macroporous and macroreticular resins are especially adept at removal of psoralen photoproducts from platelet concentrates. The primary reason why the non-ionic macroreticular and macroporous Dowex® XUS-43493 is preferable is that in addition to a high affinity for S-59, it possesses superior wetting properties; as discussed in more detail below, the phrase "superior wetting properties" means that dry (i.e. essentially anhydrous) adsorbent does not need to be wet with a wetting agent (e.g., ethanol) prior to being contacted with illuminated PC in order for the adsorbent to effectively remove residual S-59 and photoproducts. The adsorbent beads of that methylene bridged copolymer of styrene and divinylbenzene are in the form of spherical particles with a diameter range of approximately 300 to 850 μm. Dowex® XUS-43493 has an extremely high internal surface area (1100 m²/g) and relatively small pores (46 Å) which make it very effective at removing small hydrophobic molecules like S-59 and photoproducts; while it is not intended that the present invention be limited to the mechanism by which removal takes place, hydrophobic interaction is believed to be the primary mechanism of adsorption. Dowex® XUS-43493 is insoluble in strong acids and bases and in organic solvents. Its porous nature confers selectively on the adsorption process by allowing small molecules to access a greater proportion of the surface area relative to large molecules (i.e., proteins) and cells. Purolite® MN-150 has many similar characteristics to Dowex® XUS-43493, such as high affinity for S-59 and superior wetting properties, and is a preferred adsorbent.

The Amberlite® XAD series of adsorbents, which contain hydrophobic macroreticular resin beads, are also effective.

there are no aromatic stacking interactions between the resin and the psoralen. Finally, it is noteworthy that the adsorbent used in Dowex® XUS-43493 is commercially available in both wet and dry forms (Dowex® XUS-43493.00 and Dowex XUS-43493.01, respectively).

TABLE BB

| Resin | Chemical Nature | Mean Surface Area (m²/g) | Mean Pore Diam. (Å) | Mesh Size | Particle Size (Micron) |
|---|---|---|---|---|---|
| Amberlite ® Adsorbents - Rohm and Haas | | | | | |
| XAD-2 | polyaromatic | 300 | 90 | 20–60 | 250–840 |
| XAD-4 | polyaromatic | 725 | 40 | 20–60 | 250–840 |
| XAD-7 | polymethacrylate | 450 | 90 | 20–60 | 250–840 |
| XAD-16 | polyaromatic | 800 | 100 | 20–60 | 250–840 |
| XAD-1180 | polyaromatic | 600 | 300 | 20–60 | 250–840 |
| XAD-2000 | polyaromatic | 580 | 42 | 20–60 | 250–840 |
| XAD-2010 | polyaromatic | 660 | 280 | 20–60 | 250–840 |
| Amberchrom ® Adsorbents - Toso Hass | | | | | |
| CG-71m | polymethacrylate | 450–550 | 200–300 | — | 50–100 |
| CG-71c | polymethacrylate | 450–550 | 200–300 | — | 80–160 |
| CG-161m | polyaromatic | 800–950 | 110–175 | — | 50–100 |
| CG-161c | polyaromatic | 800–950 | 110–175 | — | 80–160 |
| Diaion ®//Sepabeads ® Adsorbents - Mitsubishi Chemical | | | | | |
| HP20 | polyaromatic | 500 | 300–600 | 20–60 | 250–840 |
| SP206 | brominated styrenic | 550 | 200–800 | 20–60 | 250–840 |
| SP207 | brominated styrenic | 650 | 100–300 | 20–60 | 250–840 |
| SP850 | polyaromatic | 1000 | 50–100 | 20–60 | 250–840 |
| HP2MG | polymethacrylate | 500 | 200–800 | 25–50 | 297–710 |
| HP20SS | polyaromatic | 500 | 300–600 | — | 75–150 |
| SP20MS | polyaromatic | 500 | 300–600 | — | 50–100 |
| Dowex ® Adsorbents - Dow Chemical Company | | | | | |
| XUS-40285 | functionalized | 800 | 25 | 20–50 | 297–840 |
| XUS-40323 | polyaromatic | 650 | 100 | 16–50 | 297-about 1180 |
| XUS-43493 | polyaromatic | 1100 | 46 | 20–50 | 300–850 |

Moreover, different variations of the Amberlites, such as the Amberchrom® CG series of adsorbents (the small-particle version of the Amberlites), are also suitable for use in a RD. The Amberchrom® adsorbents have shown good results for psoralen removal in conjunction with FFP (Fresh Frozen Plasma) (data not shown). In addition, Rohm and Haas also manufactures the carbonaceous (ie. rich in carbon) Amber-sorb adsorbents, each of which possesses a broad range of pore sizes.

Some of the structurally-related characteristics of the above-described adsorbents are summarized in Table BB. Besides their structurally-related properties, the adsorbents listed in Table BB possess other characteristics which make them appropriate for use in a batch RD. Those characteristics, many of which have been mentioned previously, include high affinity for psoralens (particularly S-59), good selectivity for psoralens, good hemocompatability, and low cost. Because the adsorbents supplied by the manufacturers are generally not acceptable for pharmaceutical and medical applications, the adsorbents must be treated (described below) to produce a high purity state acceptable for those applications. The ability of the adsorbent to achieve such a high purity state represents another desirable characteristic.

Referring to Table BB, the polyaromatics are all polystyrene-divinylbenzene copolymers. In terms of effectiveness in a RD, it should be noted that, generally speaking, the polymethacrylates were not as useful; this may be a result of the fact that they are not as hydrophobic or because Though not limited to the use of adsorbents with any particular composition or obtained by any particular procedure, the preferred adsorbents of the present invention are polystyrene networks. The term "polystyrene network" refers broadly to polymers containing styrene ($C_6H_5CH=CH_2$) monomers; the polymers may be linear, consisting of a single covalent alkane chain with phenyl substituents, or cross-linked, generally with m- or p-phenylene residues, to form a two-dimensional polymer backbone. The polystyrene networks can be further classified, based on their mechanism of synthesis and physical and functional characteristics, as i) conventional networks and ii) hypercrosslinked networks; each of these classes is described further below. The most preferred adsorbents of the present invention are within the hypercrosslinked network class.

The conventional networks are primarily styrene-divinylbenzene copolymers in which divinylbenzene (DVB) serves as the crosslinking agent (ie., the agent that links linear polystyrene chains together). These polymeric networks include the "gel-type" polymers. The gel-type polymers are homogeneous, non-porous styrene-DVB copolymers obtained by copolymerization of monomers; such polymers are frequently used in the preparation of ion exchange resins. The macroporous adsorbents represent a second class of conventional networks. They are obtained by copolymerization of monomers in the presence of diluents that precipitate the growing polystyrene chains. The polystyrene network formed by this procedure possess a relatively large internal surface area (up to hundreds of square meters per gram of polymer); Amberlite® XAD-4 is produced by such a procedure. [See, e.g., Davankov and Tsyurupa, "Structure And Properties of Hypercrosslinked Polystyrene—The First Representative of A New Class of Polymer Networks," Reactive Polymers 13:27–42 (1990); Tsyurupa et al., "Sorption of organic compounds from aqueous media by hypercrosslinked polystyrene sorbents 'Styrosorb', Reactive Polymers 25:69–78 (1995)].

In contrast to the conventional networks described above, the preferred adsorbents of the present invention (e.g., Dowex® XUS-43494) are hypercrosslinked networks. These networks are produced by crosslinking linear polystyrene chains either in solution or in a swollen state with bifunctional agents; the preferred bifunctional agents produce conformationally-restricted crosslinking bridges, discussed further below, that are thought to prevent the pores from collapsing when the adsorbent is in an essentially anhydrous (i.e., "dry") state.

The hypercrosslinked networks are believed to possess three primary characteristics that distinguish them from the conventional networks. First, there is a low density of polymer chains because of the bridges that hold the polystyrene chains apart. As a result, the adsorbents generally have a relatively large porous surface area and pore diameter. Second, the networks are able to swell; that is, the volume of the polymer phase increases when it contacts organic molecules. Finally, the hypercrosslinked polymers are "strained" when in the dry state; that is, the rigidity of the network in the dry state prevents chain-to-chain attractions. However, the strains relax when the adsorbent is wetted, which increases the network's ability to swell in liquid media. [Davankov and Tsyurupa, "Structure And Properties of Hypercrosslinked Polystyrene—The First Representative of A New Class of Polymer Networks," Reactive Polymers 13:27–42 (1990); Tsyurupa et al., "Sorption of organic compounds from aqueous media by hypercrosslinked polystyrene sorbents 'Styrosorb', Reactive Polymers 25:69–78 (1995)].

Several cross-linking agents have been successfully employed to produce the bridges between polystyrene chains, including p-xylene dichloride (XDC), monochlorodimethyl ether (MCDE), 1,4-bis-chloromethyldiphenyl (CMDP), 4,4'-bis-(chloromethyl)biphenyl (CMB), dimethylformal (DMF), p,p'-bis-chloromethyl-1,4diphenylbutane (DPB), and tris-(chloromethyl)-mesitylene (CMM). The bridges are formed between polystyrene chains by reacting one of these cross-linking agents with the styrene phenyl rings by means of a Friedel-Crafts reaction. Thus, the resulting bridges link styrene phenol rings present on two different polystyrene chains. [See, e.g., U.S. Pat. No. 3,729,457, hereby incorporated by reference].

As previously introduced, the bridges are especially important when the adsorbent is to be used in a RD because the bridges generally eliminate the need for a "wetting" agent. That is, the bridges prevent the pores from collapsing when the adsorbent is in an essentially anhydrous (ie., "dry") state, and thus they do not have to be "reopened" with a wetting agent prior to the adsorbent being contacted with illuminated PC. In order to prevent the pores from collapsing, conformationally-restricted bridges should be formed. Some bifunctional agents like DPB do not result in generally limited conformation; for example, DPB contains four successive methylene units that are susceptible to conformation rearrangements. Thus, DPB is not a preferred bifunctional agent for use with the present invention.

C. Removal Device Manufacturing Process

Processing the Adsorbent

The adsorbents that are described above are typically available in bulk quantities and are relatively inexpensive. As noted above, the adsorbents are not acceptable for medical/pharmaceutical applications. In addition to having to be sterilized, the adsorbents typically must be further processed to remove fine particles, salts, potential extractables, and endotoxin. The removal of these extractable components is typically performed by treatment with either organic solvents, steam, or supercritical fluids.

Several companies currently sell "cleaned" (i.e., processed) versions of the polymeric adsorbents. In addition to processing the resins, these companies test the adsorbents, and the final adsorbent is certified sterile (USP XXI), pyrogen-free (LAL), and free of detectable extractables (DVB and total organics). As described in further detail below, Dowex® XUS-43493 may be thermally processed; similarly, the Amberlite resins may be thermally processed or processed with organic solvents. Cleaning with supercritical fluids is not routinely used due to its expense.

Regarding the use of organic solvents, one of the primary disadvantages relates to potential problems associated with residual levels of organic solvent. Residual solvent may interfere with adsorption and may leach into the blood product during the adsorption process, potentially causing adverse effects to the transfusion recipient; this is especially true with methanol, the most commonly used solvent. In addition, organic solvents generally cost more to use than steam, largely due to the cost of solvent disposal.

Thermal processing (e.g., steam) is an effective method for processing adsorbent resins. Indeed, standard references on polymer processing indicate that extraction with steam is a typical process for cleaning polystyrene. [F. Rodriguez, Principles of Polymer Systems, (Hemisphere Publishing Corp.), pp. 449–53 (3rd. Ed., 1989)]. Supelco, Inc. (Bellefonte, Pa.) uses a non-solvent, thermal proprietary process to clean the Dowex® XUS-43493 and Amberlite adsorbents. The main advantage of using steam is that it does not add any potential extractables to the adsorbent. One big disadvantage, however, is that this process can strip water from the pores of the resin beads; effective performance of some adsorbents requires that the beads be re-wet prior to contacting the illuminated blood product. Indeed, as described in detail in the Experimental section, some adsorbents lose the majority of their adsorption capacity if they are dry.

Importantly, different adsorbents have unique wetting requirements. Contrary to the uncleaned Amberlite resin, the cleaned Amberlites have difficulty wetting and tend to float on the surface of aqueous solutions. It was discovered that re-wetting the adsorbent with ethanol (15–30%) in distilled water for a minimum of 10 minutes results in the release of trapped gas from the internal pores of the beads. The beads regain their adsorption capacity once they have been rinsed with distilled water to remove residual ethanol. In fact, a 10-minute exposure to a minimum of 15% ethanol in distilled water restored adsorption capacities to near maximal levels for both Amberlite® XAD-4 and XAD-16 (see Example 32, infra). The adsorption capacities were shown to be a strong function of water content, with optimum adsorption capacities occurring at 50–65% water for Amberlite® XAD-16 and at 40–55% water for Amberlite XAD-4; adsorption capacities decreased with decreasing water content.

To the contrary, it was found that Dowex® XUS-43493 eliminated many of the wetting problems associated with the Amberlite adsorbents because it did not need to be rewet prior to contacting a blood product for effective performance. Indeed, the "wetability" of Dowex® XUS-43493 (and other "bridged" adsorbents which have highly cross-linked structures and thus do not collapse when dried) is one of its most favorable characteristics.

Finally, one of the key features of the cleaned/processed adsorbent is an extremely low level of particles with diameters less than 30 µm. Preliminary testing on adsorbents (Dowex® XUS-43493 and Amberlite® XAD-16) processed by Supelco was performed to determine particle counts. The results of these tests indicated that foreign particles (e.g., dust, fibers, non-adsorbent particles, and unidentified particles) were absent and that fine particles (<30 µm) were essentially absent. After processing, the adsorbent may be packed in bulk quantities and, if necessary, shipped to an assembly site to be introduced into the mesh pouch.

Construction of The Mesh Pouch

The present invention contemplates a batch RD (i.e., adsorbent retained in a mesh bag/pouch) housed in a blood product storage container (e.g., a platelet storage container). The present invention contemplates that mesh pouches will be constructed of a woven, medical-grade polyester mesh. Polyester mesh is a standard material used in manufacturing blood filtration devices; thus, it is particularly well-suited for use in a batch RD. Though not limited to mesh materials manufactured by any particular company, Tetko, Inc. (Depew, N.Y.) and Saati (Stamford, Conn.) currently manufacture mesh materials suitable for use with the present invention.

Of course, other suitable materials (e.g., nylon) may also be used and are within the scope of the present invention. Indeed, studies performed by the inventor indicated that both polyester and nylon functioned equally well for use in a RD (data not shown). However, the preferred embodiment uses polyester because it may possess superior hemocompatability properties to nylon. In addition, the present invention contemplates the use of a pouch constructed from a membrane, e.g., Supor® 200, 800, 1200 (Gelman Sciences, Ann Arbor, Mich.) and Durapore® hydrophilic modified polyvinylidene difluoride (Millipore, Milford, Mass.).

In a preferred embodiment, the mesh pouches are assembled as pocket-like containers with four edges and two surfaces. These containers may be manufactured in one of several ways. For example, the pouch may be created by welding (i.e., uniting to create a seal) two pieces of material (of approximately equal dimensions) together on three edges. The fourth edge is left open to allow filling of the pouch with adsorbent; as discussed further below, the fourth edge is also sealed subsequent to filling. Alternatively, the pouch may be made out of one piece of material by first folding that piece of material back onto itself. The region where the material overlaps itself may then be welded (described below), resulting in the formation of a cylindrical tube. Thereafter, a pocket can be formed by welding closed one of the open ends of the cylinder, leaving the other end open for filling with adsorbent; this pouch design has the advantage of requiring one less weld. The present invention is not limited to pouches assembled as four-edged pockets nor is the invention limited to the techniques of constructing the mesh pouch that are discussed above. For example, circular pouches may also be used in the present invention. Though circular pouches are generally more difficult to manufacture, they have the advantage of being stronger because the weld is not parallel to the mesh's weave.

For the assembly of the pouches, ultrasonic welds are preferable to heat welds because of the superior strength of ultrasonic welds. The technique of ultrasonic welding is well-known in the art of manufacturing filtration devices for the medical industry. [See, e.g., U.S Pat. Nos. 4,576,715 and 5,269,917]. The present invention is not limited to a particular welding/sealing technique; indeed, any suitable sealing technique may be used with the present invention, including but not limited to ultrasonic, radiofrequency (RF), heat and impulse sealing. Regardless of the sealing technique used, the edges of the mesh materials, such as on the open end of the pouch (i.e., the slit), are heat sealed to prevent the shedding of the polyester fibers during manufacturing and handling. The present invention also contemplates rinsing the mesh material with a solvent or detergent solution to remove endotoxin, a technique that is standard in the manufacturing of medical devices.

The present invention contemplates using a mesh material with approximately 30 µm openings when platelet units are involved. This size was chosen, in part, because of particle transfusion limits. There was not a significant difference in the number of particles transfusion between mesh with 10 µm and 30 µm openings (data not shown). It should be noted that the Association for the Advancement of Medical Instruments (AAMI) Guidelines stipulate that fewer than 3000 particles be transfused with 10–25 µm diameter. While it is believed that a mesh material with 30 µm openings will prevent escape of fine particles into the platelet unit, material with openings of other sizes are within the scope of the present invention. However, material with exceedingly small openings (e.g., 5 µm) can inhibit movement of fluid into and out of the RD (i.e., the adsorbent-containing pouch), thereby having a detrimental effect on the adsorption process. The preferred range is therefore between approximately 10 µm and 50 µm.

Assembly of Removal Device

Following construction of the mesh pouch, a defined amount of adsorbent is dispensed into the pouch to form the RD. The mesh pouches can be filled with adsorbent at the same site where the pouch was constructed or shipped to another site for addition of adsorbent and further processing by a medical device assembler (e.g., Baxter Healthcare Corp., Round Lake, Ill.).

After filling of the pouch with adsorbent, an ultrasonic weld is used to seal the open end (ie., the slit). If desired, adsorbent in the sealed pouch may then be re-wet. Though Dowex® XUS-43493 does not require rewetting for effective performance, it may be rewet at this stage, if desired, to prevent or minimize "off-gassing" (discussed below) when the platelets first contact the adsorbent. The wetting step is performed at this stage of manufacturing for several reasons. First, automated filling of the mesh bags with adsorbent requires the adsorbent to be free-flowing. While the cleaned adsorbent is relatively dry and free-flowing, some adsorbents tend to clump like wet sand when they have been re-wet. Thus, re-wetting the adsorbent subsequent to filling preferred. Second, a rinse step following filling of the mesh bag allows fine particles to be washed from the external surface of the bag, helping to reduce fine particle contamination in the final RD. Finally, the rinsing process serves to remove residual ethanol from the adsorbent. Of course, the present invention is not limited to adsorbent rewetting at this stage. Again, while re-wetting of the processed adsorbent has been found necessary for satisfactory performance of many adsorbents, some adsorbents (e.g., Dowex® XUS-43493) do not need to be wet to perform effectively.

The RD can then be inserted into a blood product storage container (this process is described in detail in the Experimental section). The RD contained in a blood product storage container can then be packaged within a moisture-proof barrier to prevent drying during storage. As used herein, the term "moisture-proof barrier" is meant to encompass any container, packaging, overwrap, or the like that is able to maintain the moisture content of the RD during storage. For example, the blood product containing the RD can be sealed in a foil overwrap. Thereafter, the pouches should be terminally sterilized (e.g., γ-irradiation, electron-beam, ie., E-beam, or autoclave) to prevent microbial growth during storage. It should be noted that the preferred platelet storage container, the PL 2410 Plastic container (Baxter), is not autoclavable. Thus, when the PL 2410 Plastic container is used to house the RD, it must be sterilized by either γ-irradiation or E-beam.

Finally, as described in detail in the Experimental section, the "drying kinetics" of both Amberlite® XAD-4 and Amberlite XAD-16 were determined under standard laboratory conditions at room temperature. Gamma sterilization at doses of 5 and 10 MRad had no effect on adsorption kinetics for Amberlite® XAD-16 and only a very minimal effect for Amberlite® XAD-4. Gamma sterilization had small effects on the adsorption capacities for both adsorbents, but adsorption capacities remained acceptable. Data for E-beam sterilization to 5 MRad also indicates acceptable function for both adsorbents following sterilization. Finally, gamma-sterilized devices containing Dowex® XUS-43493 have been tested and shown to be effective.

D. Modifications to the Removal Device to Enhance Performance

While Dowex® XUS-43493 represents the preferred embodiment, its use in a RD is associated with several drawbacks. It should be noted that these problems are not specific to Dowex® XUS-43493 and may be associated with other adsorbents as well. This section describes the nature of such drawbacks and sets forth potential solutions.

Off-Gassing/Foaming

Air which is contained in the pores of the dry adsorbent is released during the initial adsorbent wetting. This "off-gassing" process results in foaming in the platelet concentrate during the first approximately 4 hours of storage. Though the appearance of foam in the during treatment is not desirable, its effect on S-59 removal kinetics, platelet yield, and in-vitro platelet function is not significant.

The problem of off-gassing may be alleviated by one of several potential solutions. First, the RD may be wet with saline or PAS. Results with Dowex® XUS-43493 have shown only minimal increased yield and platelet function when RDs were prewet in an isotonic solution. The main drawbacks to this approach are the increased complexity in the manufacturing process, sterility concerns, and a potential decrease in the shelf-life of the RD due to extractables.

Second, the RD may be stored in an inert gas with a high solubility in aqueous solutions. Previous studies with $CO_2$ (solubility=170 mL/mL) have demonstrated that storing the RD in a gas with high solubility in aqueous solutions can also minimize foaming (data not shown). However, using $CO_2$ results in a large drop in pH during the initial contacting with platelets (pH<6.5). The only other commonly used gas with a high solubility in aqueous solutions is nitrous oxide (solubility=130 mL/mL).

Finally, the RD may be stored under vacuum. For example, a syringe can be used to place a vacuum on a PL 2410 Plastic container (Baxter) containing the RD, thereby minimizing off-gassing during the initial contact with the platelets. Storing under vacuum requires that the PL 2410 Plastic container containing the RD be packaged in a vacuum-sealed foil overwrap since the PL 2410 Plastic container is gas permeable. Indeed, this is the solution for the preferred embodiment of the present invention.

Platelet Yield and Platelet Function

As set forth in Table AA, it is desirable to achieve less than 10% loss of platelets. Studies with transfer of platelets to an empty PL 2410 Plastic container (Baxter) after 8 hours of contact have demonstrated a platelet loss of <10%. Current studies have indicated a wide variability among platelet units with a 10–30% loss in platelets following 5 days of contact with the RD. Though not firmly established, adhesion of platelets to adsorbent and/or mesh is probably the main source of platelet loss.

Studies have indicated that shape change is the most sensitive assay for monitoring effects of the RD of the present invention on platelet function, though the significance of the shape change assay is not clearly understood. Platelets are able to regain their ability to change shape following transfer from the RD and incubation in a PL 2410 Plastic container (Baxter) in an equal volume of autologous plasma. Other assays (pH, hypotonic shock response, morphology score, p-selectin expression (GMP-140), secretable ATP and aggregation) do not appear to be adversely affected by the RD, while assays for lactate, glucose, and $pO_2/pCO_2$ suggest that platelet metabolism may be slightly suppressed during contact with the RD of the present invention.

There are several potential solutions to overcome adverse effects on platelet yield and platelet function. First, the polyester mesh material used in the pouch could be replaced with a membrane material. A RD utilizing a membrane material with a 5 μm or less cutoff may effectively exclude platelets from contact with the adsorbent; removal kinetics for S-59 and photoproducts may be adversely affected since transport to the adsorbent would be by diffusion rather than bulk flow. Potential commercially-available membranes that may prove effective in meeting requirements for S-59 removal include Supor® 200, 800, 1200 (Gelman Sciences, Ann Arbor, Mich.) and Durapore® hydrophilic modified polyvinylidene difluoride (Millipore, Milford, Mass.). These membranes have low protein binding characteristics.

Second, the adsorbent may be coated with a hemocompatible polymer such as poly-(2-hydroxyethyl methacrylate) (pHEMA) and cellulose-based polymers to improve hemocompatibility. These polymers are hydrogels which prevent cells from interacting with the surface of the adsorbent while allowing low molecular weight compounds such as S-59 to pass through to the adsorbent. Studies with Dowex® XUS-43493 coated with pHEMA demonstrated an increase in platelet yield as well as a dramatic effect on platelet shape change; there was only a slight decrease in S-59 adsorption kinetics (data not shown). Samples with increasing coatings of pHEMA (0–15%) can be generated using a Wurster coating process (performed by International Processing Corp., Winchester, Ky.). Any hydrogel which decreases protein binding may also be considered for coating of the adsorbents of the present invention.

Third, the adsorbent surface may be modified with immobilized heparin. In addition, strong anion exchange polystyrene divinylbenzene adsorbents may be modified via heparin adsorption. Heparin, a polyanion, will adsorb very strongly to the surfaces of adsorbents which have strong anion exchange characteristics. A variety of quaternary amine-modified polystyrene divinyl benzene adsorbents are commercially available. The main problem with this approach is that strong anion exchange resins have a positive charge which will also result in a low affinity for S-59. However, XUS-40285 (Dow) and MN-400 (Purolite) have about a 10-fold lower charge density than standard ion exchange resins. These adsorbents have about half the capacity for S-59 as their unmodified counterparts (XUS-43493 and MN-150, respectively), which have high affinities for S-59.

VIII. EFFECT OF PSORALEN STRUCTURAL CHARACTERISTICS ON ADSORPTION

The previous section was directed at the removal of the psoralen S-59 [4'-(4-amino-2-oxa)-butyl-4,5',8-trimethylpsoralen] and S-59 photoproducts from blood products. However, the present invention is not limited to the use and removal of S-59 or structurally-related psoralens. Indeed, the removal of psoralens with distinct structural characteristics is contemplated by the present invention.

This section entails an examination of the removal of several structurally different psoralens from blood products. The psoralens tested were chosen to reflect a variety of structural variations that could be used in a photo-decontamination process. Uncharged and positively charged psoralens would be expected to be the main variations that would be effective since nucleic acid is negatively charged; the chemical structures of the psoralens tested were chosen accordingly. Specifically, a strongly basic (quaternary amine) psoralen was tested, as well as two brominated psoralens with different side groups, one positively charged and one uncharged. For the adsorption studies, these psoralens were combined with Amberlite ionic and non-ionic adsorbents. The experimental procedures are discussed in detail in Example 39.

Though the present invention is not limited to any particular mechanism, the primary mechanism of psoralen removal is thought to entail hydrophobic interactions between the aromatic ring of the psoralen and the side chains (e.g., polystyrene) of the adsorbent. Thus, psoralens which are very polar may be difficult to remove since they have decreased affinity for hydrophobic adsorbents. As described in detail in the Experimental section, HPLC retention time can be used as a rough estimate of hydrophobicity. In addition, other factors besides hydrophobicity affect psoralen adsorption. For example, psoralens may interact with cells or plasma proteins (e.g., serum albumin) which are present in the blood product; these competing interactions can in theory interfere with resin binding and psoralen removal.

As demonstrated in the Experimental section, psoralens having a wide range of structural characteristics are capable of being removed from blood products. It should be understood that the present invention is limited to neither those psoralens specifically tested nor to the adsorbent resins used in the experiments.

IX. INCORPORATION OF A BATCH REMOVAL DEVICE INTO A PLATELET COLLECTION PROCESS

The separation of whole blood into two or more specific components (e.g., red blood cells and platelets) is routine in modem medicine. The separated components can be utilized alone or in conjunction with additives in therapeutic, research, and other related applications. Some blood separation procedures involve withdrawing whole blood from a subject, subjecting the whole blood to a separation procedure, and reinfusing one or more components back into the subject. The component or components that are not reinfused may be used to prepare blood products, such as Factor VIII-containing fractions; conversely, those components may be subjected to pharmacological, radiological, or similar treatments and subsequently returned to the donor or another subject.

A. Apheresis

The term "apheresis" refers broadly to procedures in which blood is removed from a donor and separated into various components, the component(s) of interest being collected and retained and the other components being returned to the donor. The donor receives replacement fluids during the reinfusion process to help compensate for the volume and pressure loss caused by component removal. Apheresis can be performed in most in-patient and out-patient settings, including dialysis centers and blood banks.

There are several specific types of apheresis, including leukapheresis (leukocytes being the collected component of interest), plateletpheresis or thrombocytapheresis (platelets being the collected component of interest), or plasmapheresis (plasma being the collected component of interest). Other types of apheresis include therapeutic plasma exchange, wherein part of the donor's plasma is replaced, and therapeutic plasma processing, wherein the collected blood component is subjected to some type of processing (e.g., the removal of a toxin) and then returned to the donor. [See, e.g., U.S. Pat. No. 5,112,298 to Prince et al., hereby incorporated by reference].

One of the most common uses of apheresis is the collection of a blood component from one or more donors for transfusion to one or more recipients. Apheresis is advantageous in that it requires fewer donors than the random donor procedure to obtain a therapeutic dose of a component. For example, the collection of one unit of platelets generally requires approximately six people with the random donor method, but only one person using apheresis.

Prior to the advent of automated apheresis machines, apheresis was performed manually; that is, withdrawn blood was manually separated (e.g., through centrifugation) and the components that were not going to be retained were manually reinfused into the donor. In contrast, modern automated methods allow the rapid and accurate collection of the desired component(s) without being nearly as labor-intensive as the manual methods. Automated apheresis utilizes devices typically referred to as apheresis units or apheresis systems, but also known as a hemapheresis or plasmapheresis units, cell separators, or blood cell processors; hereafter, these machines will be called "apheresis systems."

B. The Operation of Apheresis Systems

The method of operation of apheresis systems is known in the art. For example, U.S. Pat. No. 5,112,298 to Prince et al. initially describes the major components of apheresis systems and their method of use, then describes a system for simplified fluid separation. Similarly, U.S. Pat. No. 5,147,290 to Jonsson, hereby incorporated by reference, is directed at a method and apparatus for cytapheresis, e.g., plateletpheresis, and sets forth the general principles of apheresis. A brief overview of the operation of apheresis systems will assist in understanding certain aspects of the present invention and is provided below.

Automated apheresis systems generally comprise a blood separation device, an intricate network of tubing and filters, collection bags, an anticoagulant, and a computerized means of controlling all of the components. The blood separation device is most commonly a centrifuge that separates the blood into different components based on density. At least one pump is used to move the blood, separated blood components, and fluid additives through the apheresis system and ultimately back to either the donor or to a collection bag(s). A sterile tubing set (pheresis set) is connected by the operator (generally a nurse or a trained technician) to the apheresis system and to the donor or person to be treated.

While blood is being pumped from the donor into the apheresis system, an anticoagulant, such as acid citrate dextrose (ACD) or heparin, is automatically added to the blood. The blood then enters the centrifuge chamber, where it is separated into its various components. Following separation, the layer(s) containing the desired component(s) is then siphoned into one or more collection bags, while the remaining components are returned to the donor. During this process, the donor is administered replacement fluids to help compensate for the decrease in pressure and volume resulting from the extracorporeal circuit; replacement fluids, the nature of which differs depending on the type and goal of apheresis, include saline, normal serum albumin, and plasma protein fraction.

Apheresis systems possess sensors that are able to monitor and control several important parameters. For example, some sensors are able to detect contaminants and help to minimize contamination. In addition, sensors are able to detect when dangerous conditions, eg., the presence of air bubbles, are eminent or present and emit a signal which prompts the operator of the conditions. Finally, many systems utilize sensors and other mechanisms that determine, control, or establish the required amount of a component like the anticoagulant (see U.S. Pat. No. 5,421,812 to Langley et al., hereby incorporated by reference). Similarly, such mechanisms can be used to calculate the volume of replacement fluids to be reinfused to compensate for the component removed. The more sophisticated apheresis systems are programmable; thus, the operator is able to enter patient-specific variables, like weight and volume to be reinfused, and the system then automatically performs the desired separation.

The present invention especially contemplates the use of apheresis systems for plateletpheresis; the collected platelets are then subjected to photochemical treatment, followed by treatment with a RD. It is noteworthy that certain apheresis systems are able to derive the quantity of platelets in the platelet collection bag(s) through monitoring of the platelet concentration in the collection line tubing with an optical sensor. Moreover, the present invention envisions the use of newly-described techniques for increasing the purity and yield of platelets (see U.S. Pat. No. 5,494,592 to Latham, Jr. et al., hereby incorporated by reference).

Apheresis systems may perform intermittent or continuous centrifugation. Briefly, intermittent centrifugation involves performing all of the steps described above (drawing blood, separating it into components and collecting the desired component(s), and reinfusing the remaining components) by utilizing a single intravenous line. In contrast, continuous centrifugation continually performs all of the above-mentioned steps with small aliquots of blood, returning the blood to the donor through a separate line. Thus, continuous centrifigation requires two venipunctures, while intermittent centrifugation only requires one.

As indicated above, the network of tubing and other components makes up a pheresis set. There are two major types of pheresis sets, closed and open. Closed pheresis sets are self-contained. That is, the set is purchased with all of the components of the set (collection bags, needles, and anticoagulant- and saline-containing bags) already attached to one another. Open pheresis sets usually include all or most of the above-mentioned components, but the components are unattached. Though open pheresis sets are less expensive than closed sets, closed pheresis sets have the advantage of increased storage duration of the blood product, as there is decreased chance of contamination because the closed sets are self-contained. To illustrate, transfusable blood products like platelets may generally be stored for five days with a closed system, while they can only be stored for up to 24 hours with an open set.

Figure 49:
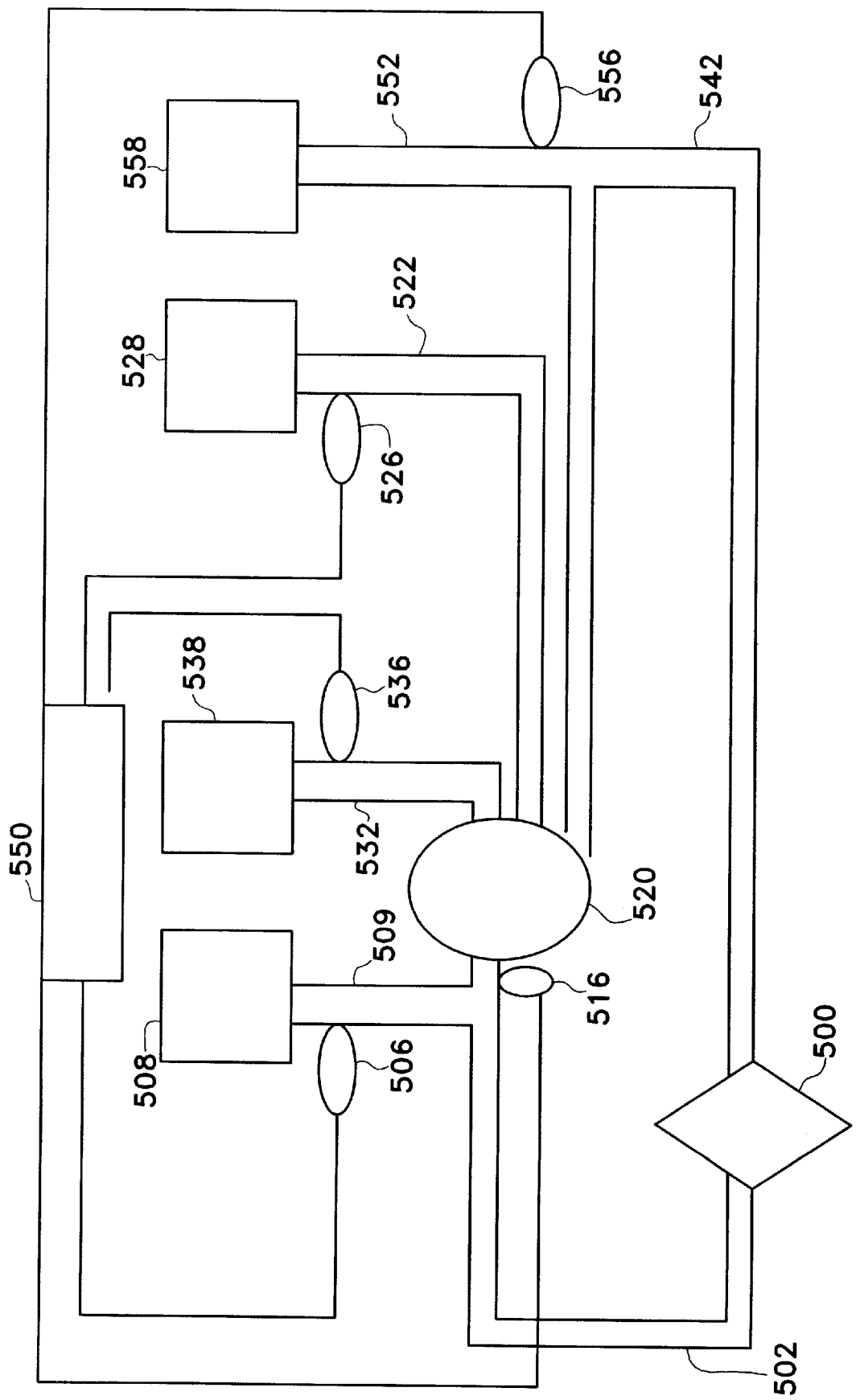
FIG. 49 depicts a flow diagram summarizing the operation of a hypothetical apheresis system in which one embodiment of the RD of the present invention may be employed.

C. The Use of Psoralen Decontamination and a Psoralen Removal Device in Conjunction with Apheresis Systems The present invention contemplates the use of a psoralen decontamination and a batch RD with an apheresis system. Though several procedures are summarized below, the present invention is not limited to any particular means of incorporating the batch RD into the operation of an apheresis system. In order to assist in understanding the discussion that follows, a flow diagram summarizing the operation of a hypothetical apheresis system is depicted in FIG. 49. It should be emphasized that the diagram in FIG. 49 is meant to depict the possible flow of fluids through an illustrative design for an apheresis system and is not intended to depict any actual apheresis procedure. Those skilled in the art will appreciate that apheresis procedures might include different fluid flow pathways and different components or arrangement of components than those shown in FIG. 49.

Referring to FIG. 49, whole blood is withdrawn from a donor 500 and into an inlet line 502. An anticoagulant pump 506 pumps an anticoagulant from an anticoagulant container 508 through an anticoagulant line 509 that exits into the inlet line 502. The anticoagulant-containing whole blood is then pumped by an inlet pump 516 into a centrifuge 520. It should be noted that some apheresis machines utilize a single pump instead of separate anticoagulant and inlet pumps. The centrifuge 520 separates the blood into its various components, such as white blood cells, red blood cells, platelets, and plasma.

Next, a cell component to be collected (e.g., platelets) may be withdrawn from the centrifuge by a cell pump 536 through a cell collection line 532 and into a collection container 538 (e.g., a platelet storage container). In an analogous manner, the plasma may be withdrawn from the centrifuge by a plasma pump 526 through a plasma collection line 522 and into a plasma collection container 528. The remaining components are returned to the donor trough a return line 542. Replacement fluids may be withdrawn from a replacement fluid container 558 through a replacement fluid line 552 that is in fluidic contact with the return line 542 via a replacement fluid pump 556. A computerized controller 550 monitors and controls the pumps and may also be connected to various sensors that monitor fluid volumes, contaminants, and the like.

Though not limited to the use of any particular apheresis system, the preferred embodiment of the present invention utilizes a commercially-available Baxter Biotech CS-3000™ (Baxter Healthcare Corp., Fenwal Division). Those skilled in the art are familiar with the specific features of this system and its mechanism of operation (summarized below); it should be noted, however, that the basic mechanism and components described above for the illustrative design for an apheresis system are applicable with this system as well.

Briefly, the Baxter Biotech CS-300™ may be used in conjunction with Baxter's Closed System Apheresis Kit™, which has preattached bags of normal saline for injection and ACD. The Kit is primed automatically with the normal saline solution. Anticoagulant is added, at a rate indicated by the operator, to whole blood withdrawn from the donor by a combination whole blood-ACD pump. Thereafter, the ACD-containing blood is pumped through one lumen of multiple lumen tubing into a separation container, one of two containers within the centrifuge chamber. The blood progressing through the separation container is separated into platelet-rich plasma and red blood cells. The term "multiple lumen tubing" refers to tubing containing more than one separate and distinct fluid passages.

After the separation, the red blood cells are returned to the donor through a separate lumen of the multiple lumen tubing, and the platelet-rich plasma is pumped into the collection container (the second of the two containers within the centrifuge chamber). When the platelet-rich plasma progresses through the collection container, the platelets are concentrated and retained while the plasma may be returned to the donor; however, there is generally a concurrent collection of a portion of plasma from the donor for platelet resuspension and storage. Finally, the platelets are transferred to a pre-attached storage container, from which they can be further processed prior to being infused into a donor.

In one embodiment of the present invention, the platelets are first collected (i.e., in the pre-attached storage container) and then processed in preparation for illumination. More specifically, an appropriate amount of autologous plasma may first be added to the concentrated platelets, followed by addition of PAS in an amount that will result in the desired composition (e.g., $4.0 \times 10^{11}$ platelets/300 mL in 35% autologous plasma, 65% PAS III). Thereafter, the PC/PAS III solution may be mixed with S-59 and illuminated in an appropriate container. Post-illumination, the PC is added to the container housing the RD, incubated for the requisite period of time for removal of S-59 and photoproducts, and then transferred to a platelet storage container; the resulting PC may then be administered to a recipient from the platelet storage container.

As detailed in the Experimental section, the above-described embodiment involves addition of PAS III only after collection of the plasma-platelet mixture and requires several container transfers before the final platelet product is ready for transfusion to a recipient. However, the present invention is not limited to that particular embodiment. Indeed, the present invention contemplates the use of alternative procedures for reducing the number of overall steps, e.g., solution transfers, when a batch RD is used in conjunction with apheresis.

Figure 50:
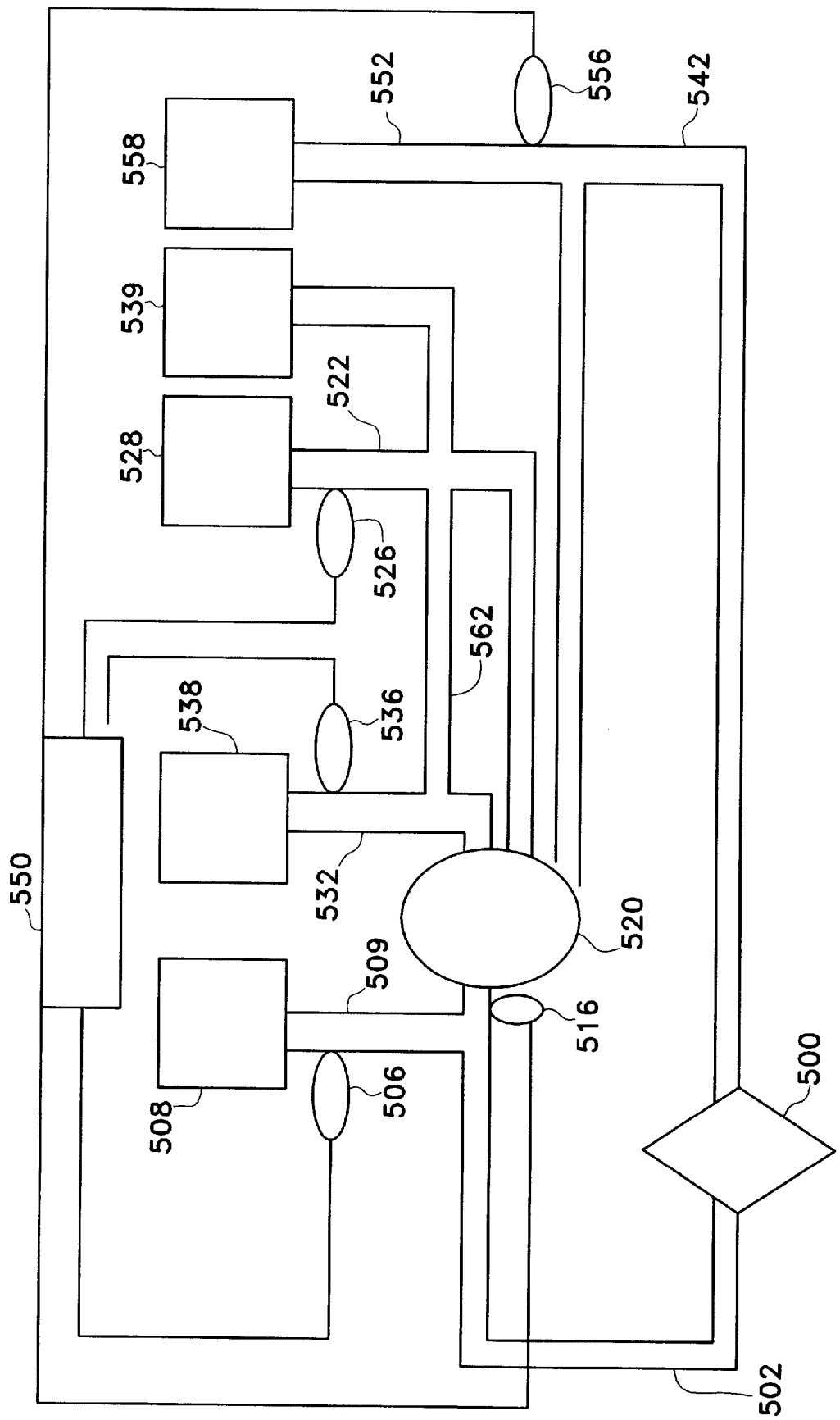
FIG. 50 depicts an alternative embodiment of the present invention in which PAS III is added during the platelet collection procedure.

For example, in one alternative embodiment, the platelets ultimately collected in the platelet collection container already contain the appropriate quantity of platelets and amounts of PAS and plasma. FIG. 50 is a modified version of FIG. 49 depicting the platelet collection procedure in this alternative embodiment. In addition to having the platelet storage container 538 and the autologous plasma container 528, this embodiment contains a bag 539 containing a pre-determined amount of PAS III (or other suitable synthetic media). After or simultaneous with platelet collection, an appropriate amount of collected autologous plasma (e.g., 105 mL) and an appropriate amount of PAS III (e.g., 180 mL) are automatically added to the platelets; this may be performed by adding the PAS III and the plasma through tubing 562 that bypasses the centrifuge 520 and enters the platelet storage container 538. Thus, because the addition of PAS III is integrated into the platelet collection procedure, this embodiment eliminates the sterile docking procedure (see Experimental section) otherwise required to add the PAS III solution.

The appropriate volume of PAS III may be added to the platelet storage container 538 by gravity, by a pump (not shown), or by any other suitable means. In one embodiment, the PAS III bag 539 contains a predetermined volume so that the entire amount may be added to a defined quantity of platelets to be collected in the platelet storage container 538. In addition, the present invention contemplates the use of a microprocessor to add the appropriate amount of PAS III from a reservoir based on the quantity of platelets collected. If added simultaneously, it is preferable that a constant ratio of PAS III to plasma be maintained.

Similar procedures can be applied in the collection and addition of autologous plasma. That is, a predetermined volume of plasma may be concurrently collected from the donor and that entire volume subsequently used in resuspension of the platelets. This eliminates the need for determining how much plasma is associated with the platelets before adding additional plasma to achieve the desired volume. To illustrate, following centrifugation, the platelets in the collection container are generally associated with a small amount of residual plasma (e.g., approximately 30 mL); in addition, there is usually residual plasma in the apheresis system's tubing that must be accounted for (e.g., approximately 18–20 mL). Thus, if a total plasma volume of, e.g., 105 mL is desired, then approximately 55–57 mL of plasma can be concurrently collected from the donor and subsequently added for resuspension of the platelets.

Following collection, the PC/PAS III solution is mixed with S-59, incubated to allow equilibration, and illuminated. Thereafter, the illuminated platelet preparation is transferred to the platelet storage container housing the RD for a defined period of time to allow removal of S-59 and photoproducts. Finally, the treated platelet preparation is transferred to a platelet storage bag from which it can be transfused into a recipient.

Other embodiments of the present invention are also possible. However, it should be pointed out that alternative embodiments are limited by certain practical considerations. For example, S-59 and the synthetic media solution PAS III are not considered to be particularly compatible together for sterilization (e.g., autoclaving) and for storage. Similarly, S-59 should not ordinarily be directly placed in the platelet storage container because, over extended periods of time, uptake of S-59 by platelets could influence microbial inactivation since the amount of available drug is decreased by platelet uptake.

Figure 51:
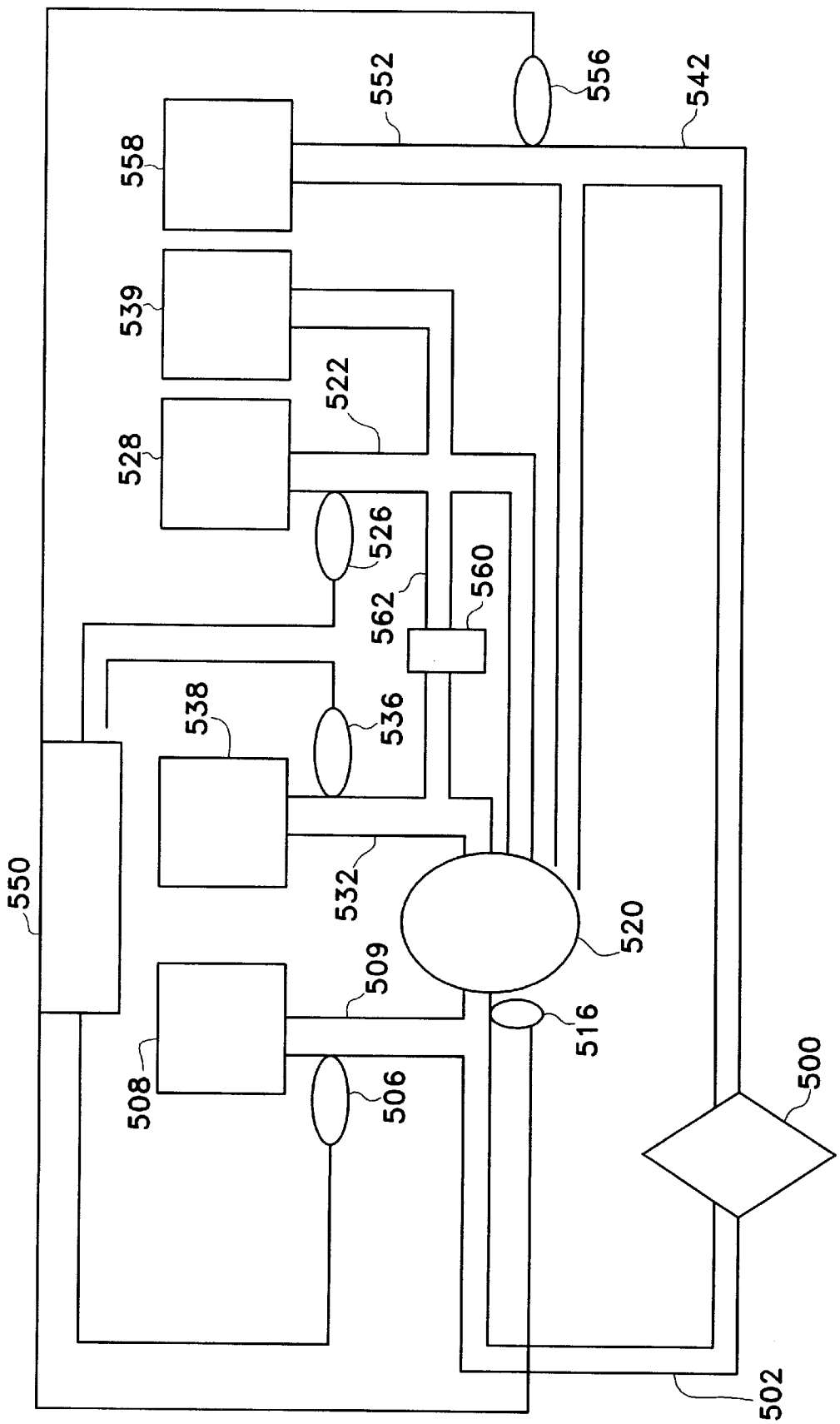
FIG. 51 depicts an alternative embodiment of the present invention in which PAS III combines with S-59 and then is added during the platelet collection procedure.

Another embodiment contemplated by the present invention involves the use of a container 560 containing S-59 positioned between a PAS III-containing bag 539 and the platelet collection container 538. (See FIG. 51) As the PAS III is being added to the PC, it mixes with the S-59 and then immediately enters the platelet collection container. Thus, an additional sterile docking procedure is circumvented with this embodiment.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); μL(microliters); cm (centimeters); mm (millimeters); μm(micrometers); nm (nanometers); min. (minutes); s and sec. (seconds); J (Joules, also watt second, note that in FIGS. 6, 8–17 Joules or J refers to Joules/cm$^2$); °C. (degrees Centigrade); TLC (Thin Layer Chromatography); HPLC (high pressure liquid chromatography); HEMA. (polyhydroxyethyl methacrylate); PC(s) (platelet concentrate(s)); PT (prothrombin time); aPTT (activated partial thromboplastin time); TT (thrombin time); HSR (hypotonic shock response); FDA (United States Food and Drug Administration); GMP (good manufacturing practices); DMF (Drug Masterfiles); SPE (Solid Phase Extraction); Asahi (Asahi Medical Co., Ltd., Tokyo, Japan); Baker (J. T. Baker, Inc., Phillipsburg, N.J.); Barnstead (Barnstead/Termolyne Corp., Dubuque, Iowa); Bio-Rad (Bio-Rad Laboratories, Hercules, Calif.); Eppendorf (Eppendorf North America Inc., Madison, Wis.); Grace Davison (W. R. Grace & Co., Baltimore, Md.); NIS (Nicolet, a Thermo Spectra Co., San Diego, Calif); Rohm and Haas (Chauny, France); Sigma (Sigma Chemical Company, St Louis, Mo.); TosoHaas (TosoHass, Montgomeryville, Pa.); Wallac (Wallac Inc., Gaithersburg, Md.); YMC (YMC Inc., Wilmington, N.C.); DVB (divinyl benzene); LAL (Limulus Amoebocyte Lystate); USP (United States Pharmacopeia); EAA (ethyl-acetoacetate); EtOH (ethanol); HOAc (acetic acid); W (watts); mW (milliwatts); NMR (Nuclear Magnetic Resonance; spectra obtained at room temperature on a Varian Gemini 200 MHz Fourier Transform Spectrometer); m.p. (melting point); UV (ultraviolet light); THF (tetrahydrofuran); DMEM (Dulbecco's Modified Eagles Medium); FBS (fetal bovine serum); LB (Luria Broth); EDTA (ethelene diamine tetracidic acid); Phorbol Myristate Acetate (PMA); phosphate buffered saline (PBS); AAMI (Association for the Advancement of Medical Instruments); ISO (International Standards Organization); EU (endotoxin units); LVI (large volume injectables); GC (gas chromatography); M (mega-); kGy (1000 Gray=0.1 MRad); MΩ (Mohm); PAS III (platelet additive solution III); RD (removal device); SCD (sterile connection device).

For ease of reference, some compounds of the present invention have been assigned a number from 1–18. The reference numbers are assigned in TABLE 2. Their structures appear in FIGS. 5A–5F. The reference numbers are used throughout the experimental section.

When isolating compounds of the present invention in the form of an acid addition salt, the acid is preferably selected so as to contain an anion which is nontoxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed as desired. For example, fumaric, benzoic, ascorbic, succinic, salicylic, bismethylenesalicylic, propionic, gluconic, malic, malonic, mandelic, cinnamic, citraconic, stearic, palnitic, itaconic, glycolic, benzenesulphonic, and sulphamic acids may also be employed as acid addition salt-forming acids.

One of the examples below refers to HEPES buffer. This buffer contains 8.0 g of 137 mM NaCl, 0.2 g of 2.7 mM KCl, 0.203 g of 1 mM MgCl$_2$(6H$_2$0), 1.0 g of 5.6 mM glucose, 1.0 g of 1 mg/ml Bovine Serum Albumin (BSA) (available from Sigma, St. Louis, Mo.), and 4.8 g of 20 mM HEPES (available from Sigma, St. Louis, Mo.).

In one of the examples below, phosphate buffered synthetic media is formulated for platelet treatment. This can be formulated in one step, resulting in a pH balanced solution (e.g. pH 7.2), by combining the following reagents in 2 liters of distilled water:

Preparation of Sterilyte ™ 3.0

| | Formula W. | mMolarity | Grams/2 Liters |
|---|---|---|---|
| NaAcetate*3H$_2$O | 136.08 | 20 | 5.443 |
| Glucose | 180.16 | 2 | 0.721 |
| D-mannitol | 182.17 | 20 | 7.287 |
| KCl | 74.56 | 4 | 0.596 |
| NaCl | 58.44 | 100 | 11.688 |
| Na$_3$ Citrate | 294.10 | 10 | 5.882 |
| Na$_2$HPO$_4$*7H$_2$O | 268.07 | 14.46 | 7.752 |
| NaH$_2$PO$_4$*H$_2$O | 137.99 | 5.54 | 1.529 |
| MgCl$_2$*6H$_2$O | 203.3 | 2 | 0.813 |

The solution is then mixed, sterile filtered (0.2 micron filter) and refrigerated.

The Polymerase Chain Reaction (PCR) is used in one of the examples to measure whether viral inactivation by some compounds was complete. PCR is a method for increasing the concentration of a segment of a target sequence in a mixture of genomic DNA without cloning or purification See K. B. Mullis et al., U.S. Pat. Nos. 4,683,195 and 4,683,202, hereby incorporated by reference. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction". Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g. hybridization with a labelled probe; incorporation of biotinylated primers followed by avidin-enzyme conjugate detection; incorporation of $^{32}P$ labelled deoxynucleotide triphosphates, e.g. dCTP or dATP, into the amplified segment). In addition to genomic DNA, any oligonucleotide sequence can be amplified with the appropriate set of primer molecules.

The PCR amplification process is known to reach a plateau concentration of specific target sequences of approximately $10^{-8}$ M. A typical reaction volume is 100 µl, which corresponds to a yield of $6 \times 10^{11}$ double stranded product molecules.

PCR is a polynucleotide amplification protocol. The amplification factor that is observed is related to the number (n) of cycles of PCR that have occurred and the efficiency of replication at each cycle (E), which in turn is a function of the priming and extension efficiencies during each cycle. Amplification has been observed to follow the form $E^n$, until high concentrations of PCR product are made. At these high concentrations (approximately $10^{-8}$ M/1) the efficiency of replication falls off drastically. This is probably due to the displacement of the short oligonucleotide primers by the longer complementary strands of PCR product. At concentrations in excess of $10^{-8}$ M, the rate of the two complementary PCR amplified product strands finding each other during the priming reactions become sufficiently fast that this occurs before or concomitant with the extension step of the PCR procedure. This ultimately leads to a reduced priming efficiency, and therefore, a reduced cycle efficiency. Continued cycles of PCR lead to declining increases of PCR product molecules. PCR product eventually reaches a plateau concentration.

The sequences of the polynucleotide primers used in this experimental section are as follows:

DCD03: 5' ACT AGA AAA CCT CGT GGA CT 3' (SEQ ID NO:1)

DCD05: 5' GGG AGA GGG GAG CCC GCA CG 3' (SEQ ID NO:2)

DCD06: 5' CAA TTT CGG GAA GGG CAC TC 3' (SEQ ID NO:3)

DCD07: 5' GCT AGT ATT CCC CCG AAG GT 3' (SEQ ID NO:4)

With DCD03 as a common forward primer, the pairs generate amplicons of length 127, 327, and 1072 bp. These oligos were selected from regions that are absolutely conserved between 5 different dHBV isolates (DHBV1, DHBV3, DHBV16, DHBV22, and DHBV26) as well as from heron HBV (HHBV4).

The following examples serve to illustrate certain preferred embodiments and aspects of the present invention and are not to be construed as limiting the scope thereof.

EXAMPLE 1

As noted above, the present invention contemplates devices and methods for the photoactivation of photoreactive nucleic acid binding compounds. In this example, a photoactivation device is described for decontaminating blood products according to the method of the present invention. This device comprises: a) means for providing appropriate wavelengths of electromagnetic radiation to cause photoactivation of at least one photoreactive compound; b) means for supporting a plurality of blood products in a fixed relationship with the radiation providing means during photoactivation; and c) means for maintaining the temperature of the blood products within a desired temperature range during photoactivation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (100) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

Figure 2:
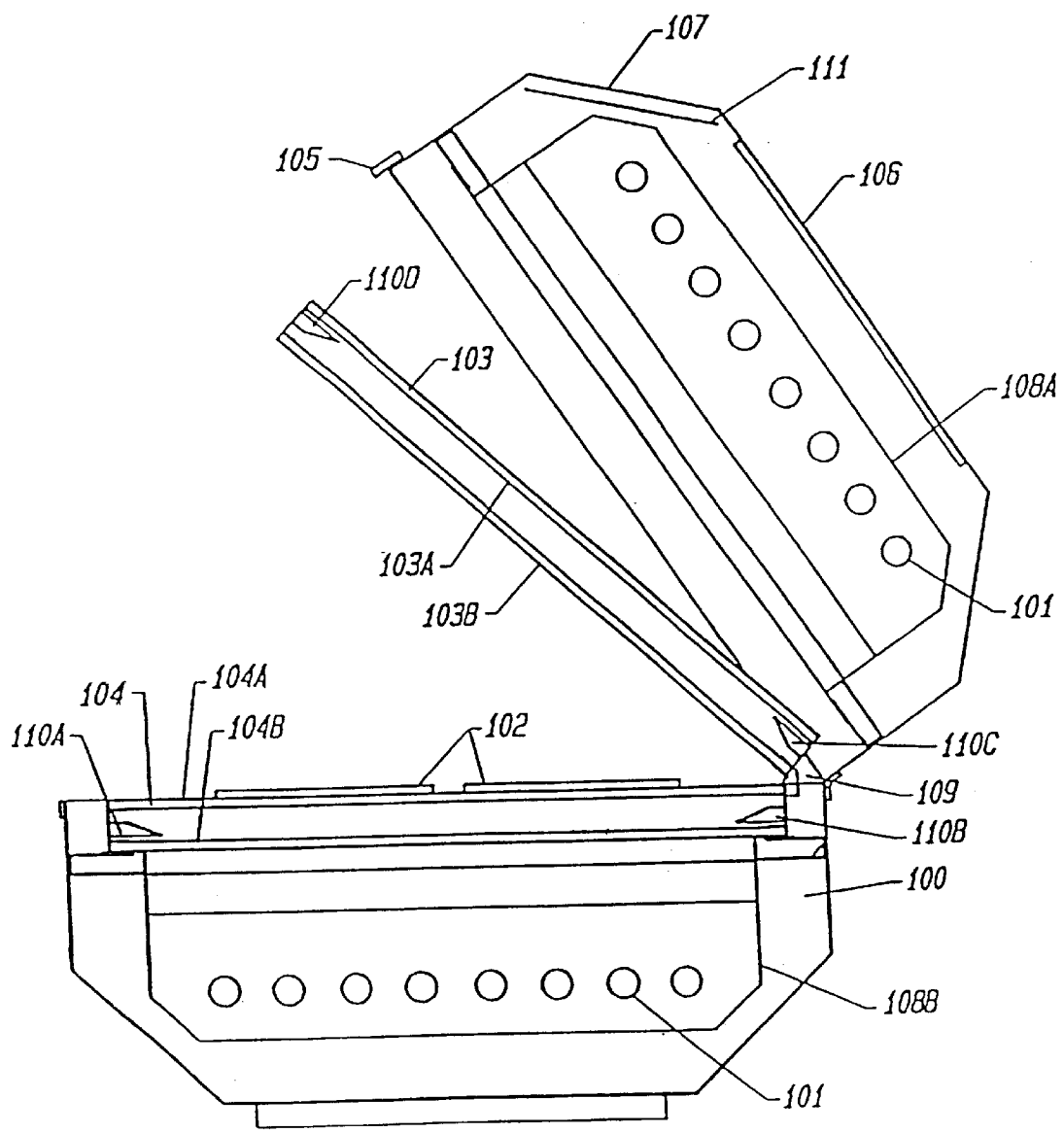
FIG. 2 is a cross-sectional view of the device shown in FIG. 1 along the lines of 2—2.

FIG. 2 is a cross-sectional view of the device shown in FIG. 1 along the lines of 2—2. FIG. 2 shows the arrangement of the bulbs (101) with the housing (100) opened. A reflector (108A, 108B) completely surrounds each array of bulbs (101). Blood product containing means (102) are placed between upper (103) and lower (104) plate assemblies. Each plate assembly is comprised of an upper (103A, 104A) and lower (103B, 104B) plates. The plate assemblies (103, 104) are connected via a hinge (109) which is designed to accommodate the space created by the blood product containing means (102). The upper plate assembly (103) is brought to rest just above the top of the blood product containing means (102) supported by the lower plate (104B) of the lower plate assembly (104).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

Figure 3:
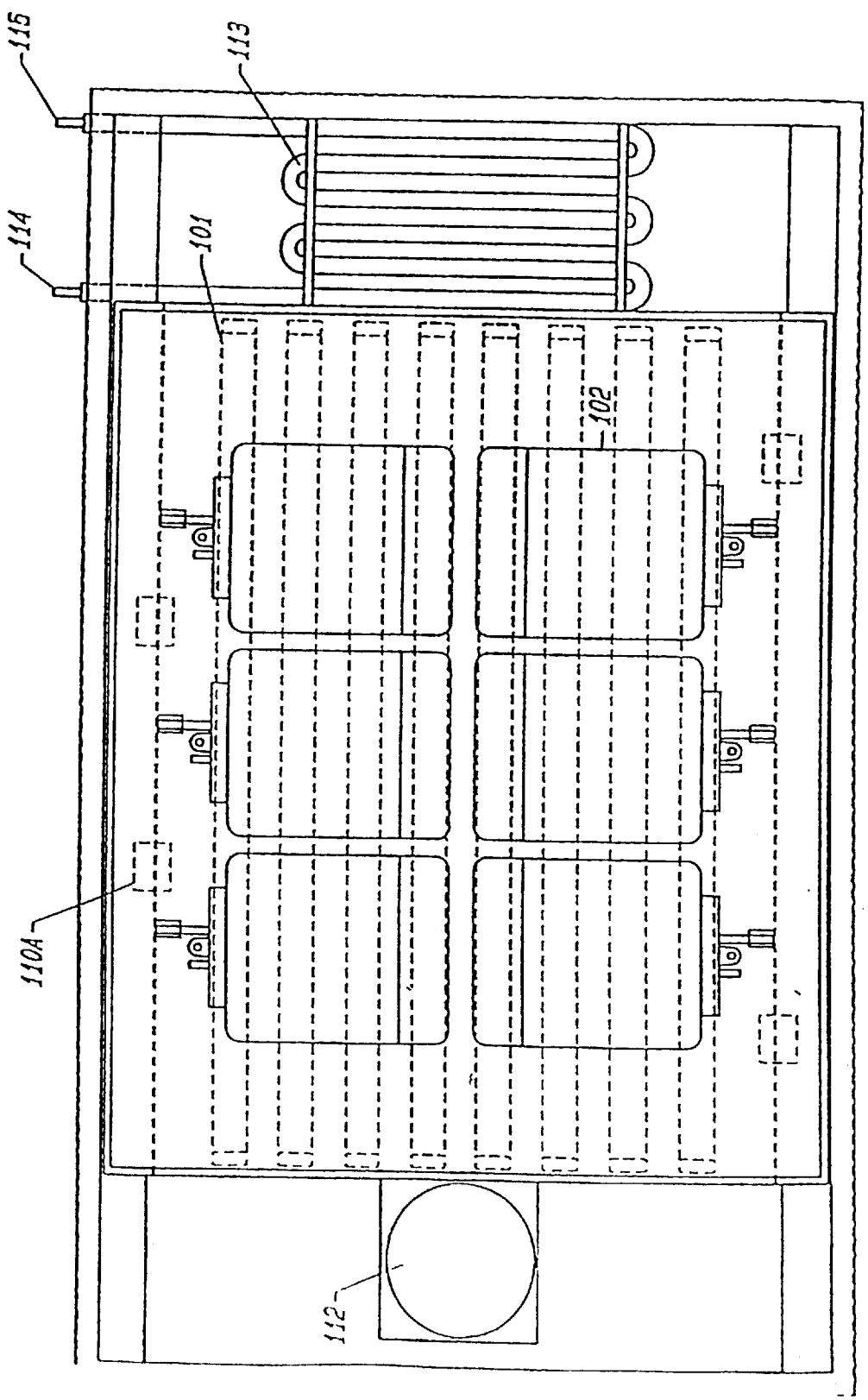
FIG. 3 is a cross-sectional view of the device shown in FIG. 1 along the lines of 3—3.

FIG. 3 is a cross-sectional view of the device shown in FIG. 1 along the lines of 3—3. Six blood product containing means (102) (e.g. Teflon™ platelet unit bags) are placed in a fixed relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

Figure 4:
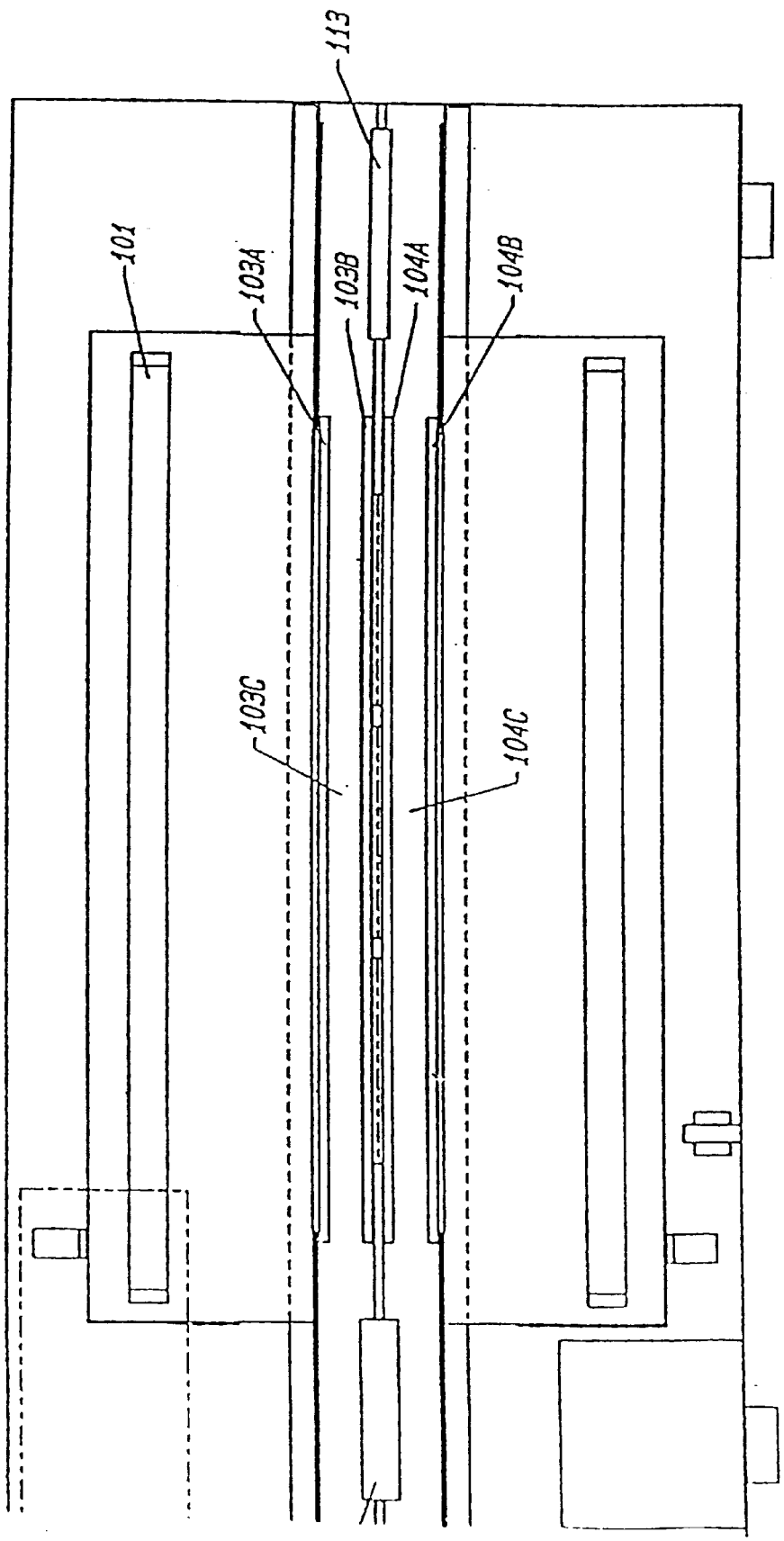
FIG. 4 is a cross-sectional view of the device shown in FIG. 1 along the lines of 4—4.
Figure 5A:
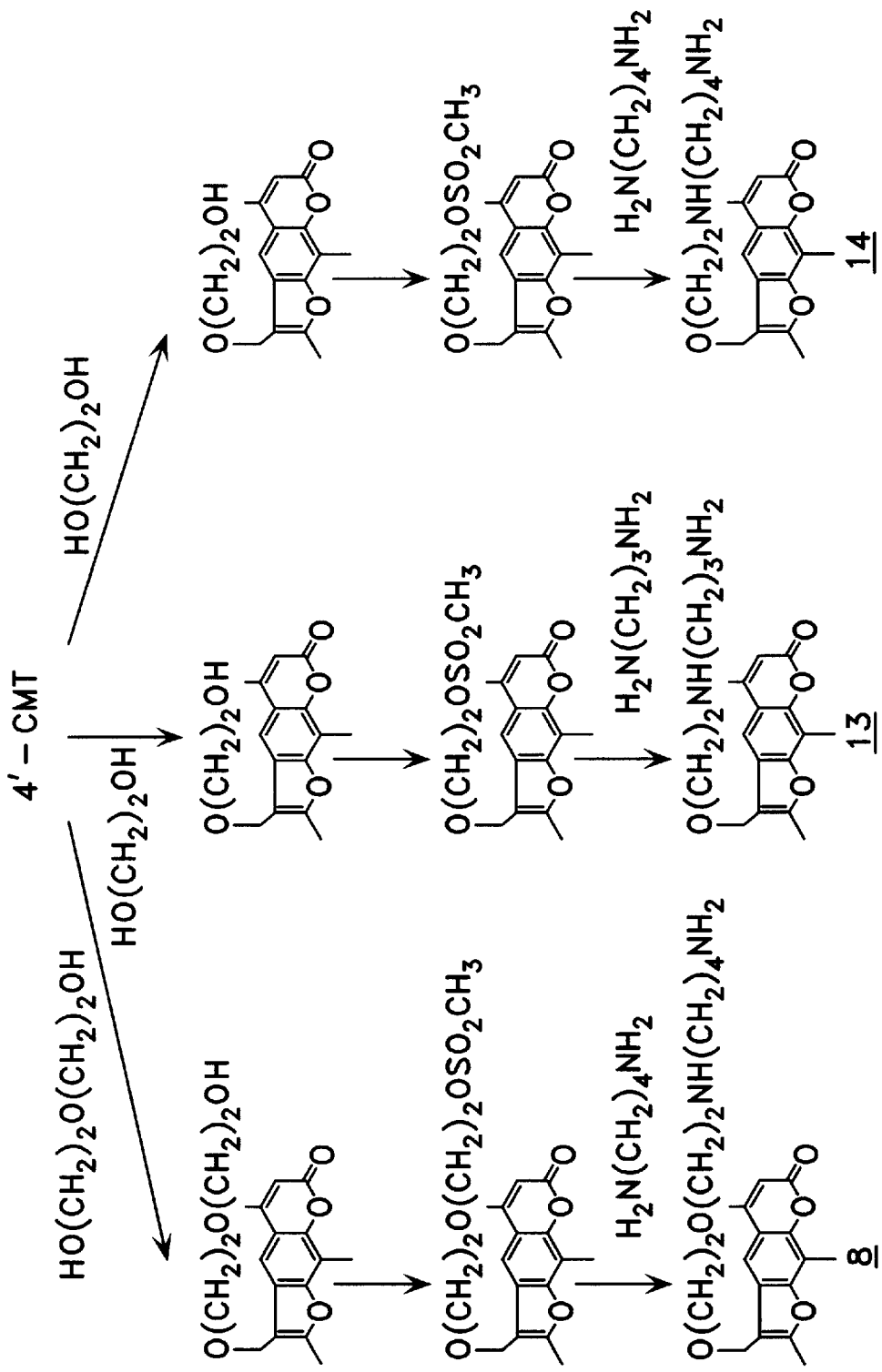
FIG. 5A is a diagram of synthesis pathways and chemical structures of compounds 8, 13, and 14 of the present invention.
Figure 5B:
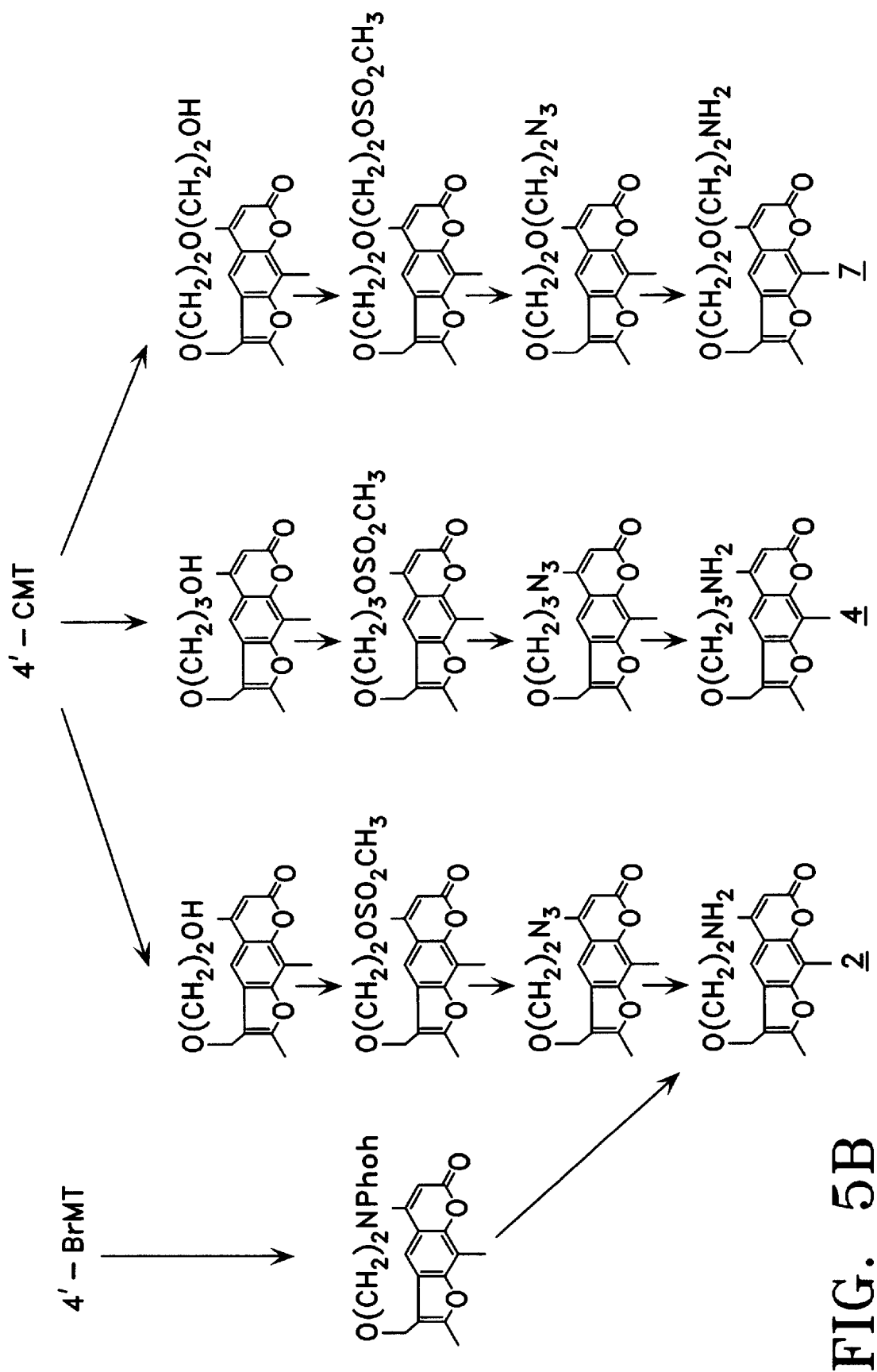
FIG. 5B is a diagram of synthesis pathways and chemical structures of compounds 2, 4, and 7 of the present invention.
Figure 5C:
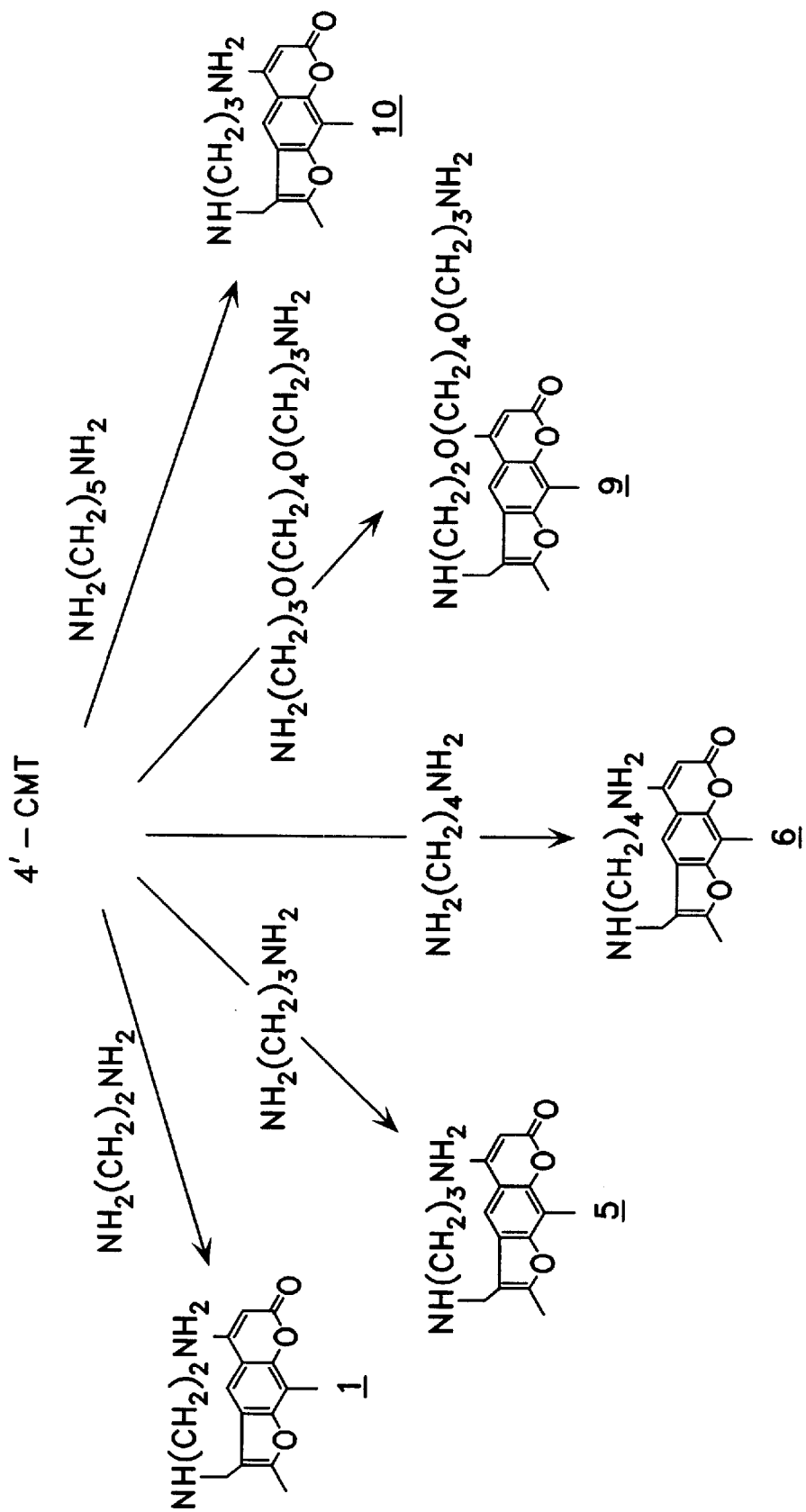
FIG. 5C is a diagram of synthesis pathways and chemical structures of compounds 1, 5, 6, 9, and 10 of the present invention.
Figure 5D:
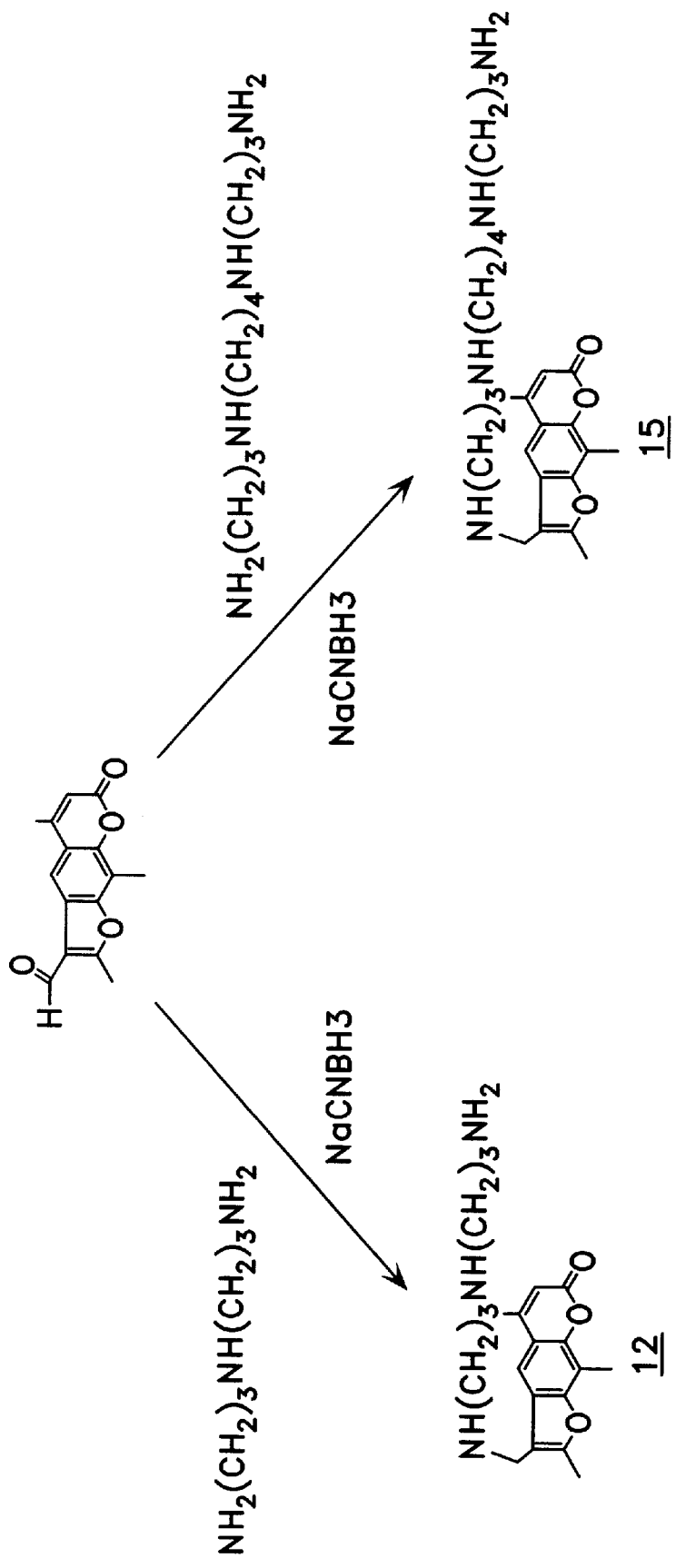
FIG. 5D is a diagram of synthesis pathways and chemical structures of compounds 12 and 15 of the present invention.
Figure 5E:
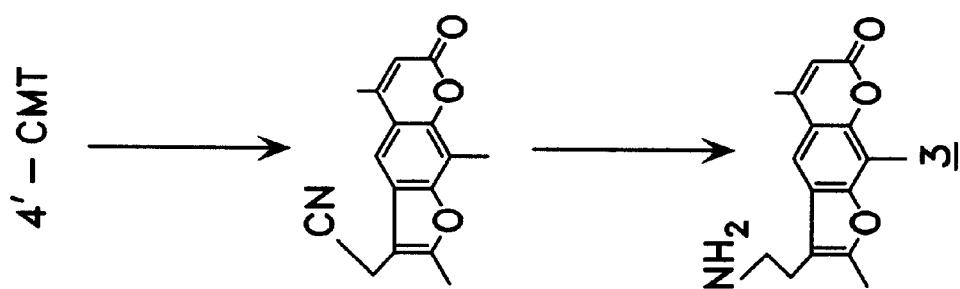
FIG. 5E is a diagram of a synthesis pathway and the chemical structure of compound 3 of the present invention.
Figure 5F:
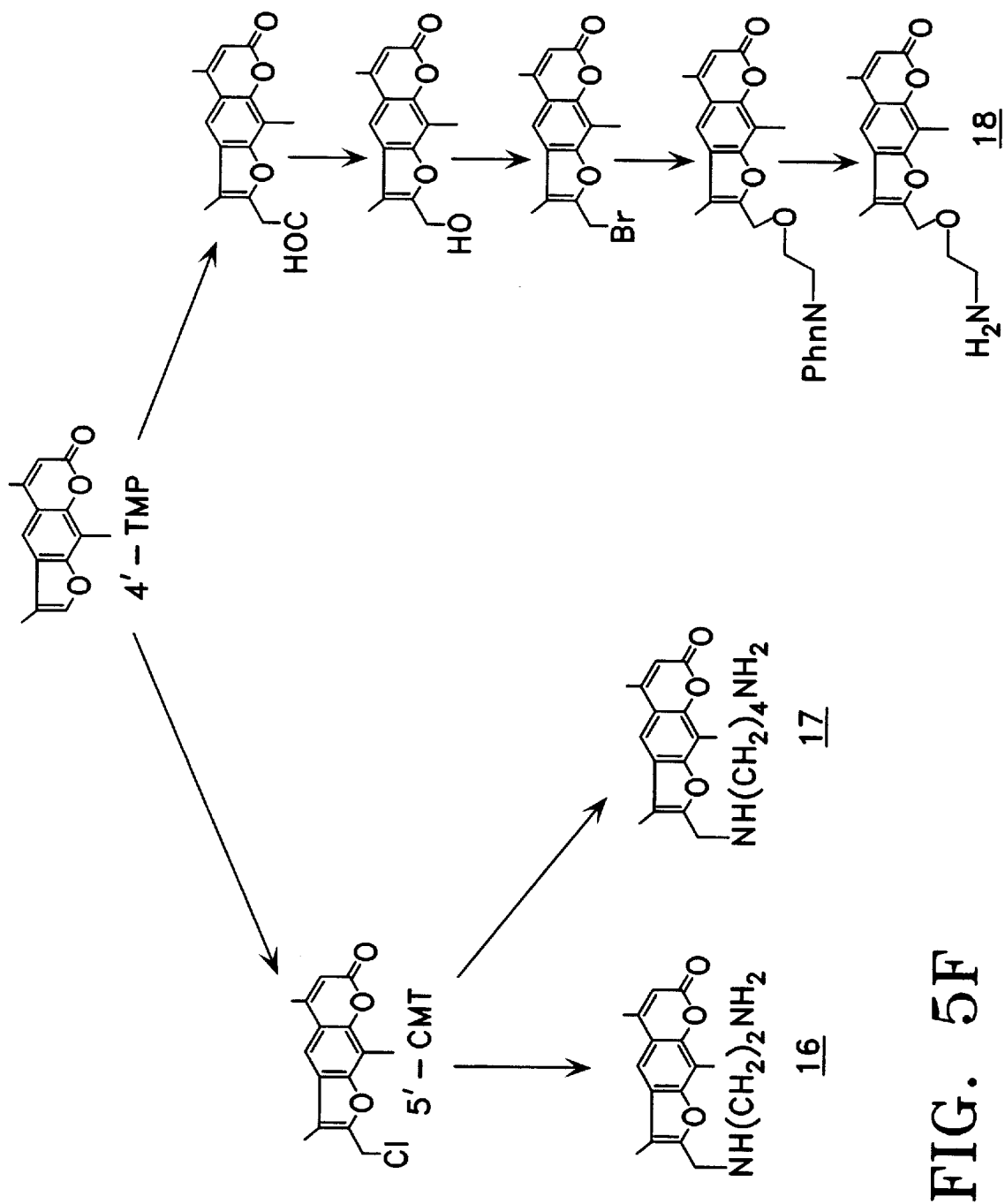
FIG. 5F is a diagram of synthesis pathways and the chemical structure of compounds 16 and 17 of the present invention

FIG. 4 is a cross-sectional view of the device shown in FIG. 1 along the lines of 4—4. FIG. 4 more clearly shows the temperature control approach of a preferred embodiment of the device. Upper plate assembly plates (103A, 103B) and lower plate assembly plates (104A, 104B) each create a temperature control chamber (103C, 104C), respectively. The fan (112) can circulate air within and between the chambers (103C, 104C). When the heat exchanger (113) is employed, the circulating air is cooled and passed between the plates (103A, 103B, 104A, 104B).

EXAMPLE 2

Synthesis of 4'-Bromomethyl-4,5',8-trimethylpsoralen

In this example, the three step synthesis of 4'-Bromomethyl-4,5',8-trimethylpsoralen is described. This synthesis is performed without a bromomethylation step, making it safer than known methods of synthesis.

Step 1: 3-Chloro-2-butanone (29.2 mL, 0.289 mol) was added to a mechanically stirred suspension of 7-hydroxy4,8-dimethylcoumarin (50.00 g, 0.263 mol) and powdered $K_2CO_3$ (54 g, 0.391 mol) in acetone (500 mL). The slurry was refluxed overnight, after which the solvent was stripped off. To remove the salt, the solid was stirred in 1.2 L of water, filtered, and rinsed with water until the pH of the mother liquor was neutral (pH 5–7). The brown filtrate was dissolved in boiling methanol (150 mL), allowed to cool to room temperature to form a thick paste and rinsed with ice cold methanol to remove most of the brown impurity, giving 4,8-dimethyl-7-(1-methyl-2-oxo)propyloxy-coumarin (67.7 g, 99.0% yield) as an off-white solid, melting point 95–96° C. NMR: d 1.57 (d, J=6.7 Hz, 3H), 2.19 (s, 3H), 2.39 (s, 6H), 4,73 (q, J=6.9 Hz, 1H), 6.17 (s, 1H), 6.63 (d, J=8.8 Hz, 1H), 7.38 (d, J=8.9 Hz, 1H)

Step 2: A suspension of 4,8-dimethyl-7-(1-methyl-2-oxo) propyloxy-coumarin (67.5 g, 0.260 mol), 10% aqueous NaOH (114 mL, 0.286 mol) and water (900 mL) was heated for 2–4 hours at 70–85° C. The mixture was then allowed to cool to room temperature. The solid was filtered, and then rinsed with chilled water (1.5 L) until the mother liquor became colorless and pH was neutral (pH 5–7). The product was air and vacuum dried to give 4, 4',5',8-tetramethylpsoralen (56.3 g, 89.5%) as a white solid, mp 197–199° C. NMR: d 2.19 (s, 3H), 2.42 (s, 3H), 2.51 (s, 3H), 2.56 (s, 3H), 623 (s, 1H), 7.40 (s, 1H).

Step 3: Dry 4,4', 5',8-tetramethylpsoralen (10.00 g, 41.3 mmol) was dissolved in methylene chloride (180 mL) at room temperature. N-Bromosuccinimide (8.09 g, 45.3 mmol) was added and the reaction mixture and stirred 4.5 hours. The solvent was completely removed and the resulting solid was stirred with water (200 mL) for 0.5–1 h, filtered and cold triturated with additional water (approximately 500 mL) to remove the succinimide by-product. The crude product (i.e. 4'-bromomethyl-4, 5',8-trimethylpsoralen) was dried in a vacuum dessicator with $P_2O_5$ then recrystallized in a minimum amount of boiling toluene (200–300 mL) to give 4'-bromomethyl-4, 5',8-trimethylpsoralen (10.2 g), a pale yellow solid. The mother liquor was stripped and recrystallized again with toluene (60 mL) to give a second crop of product (1.08 g, combined yield=85.1%, >99% purity by NMR), mp 206–207° C. NMR: d 2.50 (s, 3H), 2.54 (d, J=1.2 Hz, 3H), 2.58 (s, 3H), 4.63 (s, 2H), 6.28 (apparent q, J=1.3 Hz, 1H), 7.59 (s, 1H).

EXAMPLE 3

Synthesis of 5'-bromomethyl-4, 4',8-trimethylpsoralen

In this example, a three step synthesis of 5'-bromomethyl-4, 4',8-trimethylpsoralen is described. Like the synthesis described in Example 2, this method is improved upon previously known synthesis schemes because it does not require bromomethylation.

4, 4',5',8-Tetramethylpsoralen (2.33 g, 9.59 mmol), (synthesis described in Example 2, Steps 1 and 2), was refluxed in carbon tetrachloride (100 mL) until it dissolved. N-Bromosuccinimide (1.88 g, 10.5 mmol) and benzoyl peroxide (80 mg) were then added and the mixture was refluxed for 15 hours. Upon cooling to room temperature methylene chloride (100 mL) was added to dissolve the solid and the solution was washed with water (4×150 mL), then brine, and dried with anhydrous $Na_2SO_4$ The solvent was stripped off to give a mixture of 5'-bromomethyl-4, 4',8-trimethylpsoralen, 4'-bromomethyl-4, 5',8-trimethylpsoralen, and 4', 5'bis(bromomethyl)-4,8-dimethylpsoralen in a ratio of 55/25/20 respectively as determined by $^1H$ NMR (3.0 g, crude product). $^1H$ NMR of 5'-bromomethyl compound: d 2.29 (s, 3H), 2.52 (d, J=1.2 Hz, 3H), 2.60 (s, 3H), 4.64 (s, 2H), 6.27 (apparent d, J=1.2 Hz, 1H), 7.51 (s,1H). $^1H$ NMR of 4', 5'-bis(bromomethyl) compound: d 2.54 (d, J=1.1 Hz, 3H), 2.60 (s, 3H), 4.65 (s, 4H), 6.30 (apparent q, J=1.1 Hz, 1H), 7.67 (s, 1H).

EXAMPLE 4

Synthesis of 4'-(4-amino-2-oxa)butyl-4,5',8-trimethylpsoralen Hydrochloride (Compound 2) and Related Compounds (Compound 4)

In this example, two methods of synthesis of Compound 2 are described. Compound 2 is also known as S-59 and has the chemical structure depicted below and in FIG. 40. The first method was performed as follows:

Step 1: 4'-Bromomethyl4,5',8-trimethylpsoralen (3.09 g, 9.61 mmol), (synthesis described in Example 2), and N-(2-hydroxyethyl)phthalimide (4.05 g, 21.2 mmol) were stirred in dry dimethylformamide (65 mL). Dry $N_2$ gas was bubbled gently into the reaction mixture. The reaction mixture was heated to 100° C. for 4.5 hours then allowed to cool to room temperature and put in the freezer for several hours. The crystalline product was filtered and washed with MeOH followed by $H_2O$. The solid was further triturated with MeOH (100 mL) to remove the impurities. The crude product was air dried and dissolved in $CHCl_3$ (150 mL). Activated carbon and silica gel were added to decolorize and the $CHCl_3$ was completely removed. The resulting white product, 4'-[4-(N-phthalimido)-2-oxa]butyl-4,5',8-trimethylpsoralen (1.56 g, yield 37.5%) was ≧99% pure both by NMR and HPLC; mp 224–225° C. NMR ($CDCl_3$) d 2.37 (s,3H); 2.47 (s, 3H); 2.48 (s, 3H); 3.78 (s,4H); 4.59 (s,2H); 6.22 (s, 1H);7.42 (s,1H); 7.50 (m, 4H).

Step 2: 4'-[4-(N-phthalimido)-2-oxa]butyl-4,5',8-trimethylpsoralen (1.56 g, 3.61 mmol) was suspended in tetrahydrofuran (75 mL) at room temperature. Methylamine (40% aqueous solution, 25 mL, 290 mmol) was added to the suspension and stirred overnight. The solvent and methylamine were completely removed. The resulting solid was taken up in 0.3 N HCl aqueous solution (25 mL). The acid suspension was rinsed three times with 40 mL $CHCl_3$ then taken to pH 11 with 20% aqueous NaOH. $CHCl_3$ (3×60 mL) was used to extract the product (i.e. 4'-(4-amino-2-oxa) butyl-4,5',8-trimethylpsoralen from the basified layer. The combined $CHCl_3$ layers were washed with $H_2O$ (100 mL) followed by brine (100 mL) then dried over anhydrous $Na_2SO_4$ and concentrated to give 4'-(4-amino-2-oxa)butyl-4,5',8-trimethylpsoralen, mp 139–141° C. Purity was greater than 99% by NMR NMR ($CDCl_3$) d 2.50 (s, 6H); 2.58 (s,3H); 2.90 (t, J=5.27 Hz, 2H); 3.53 (t, J=5.17 Hz, 2H); 4.66 (s, 2H); 6.25 (s,1H); 7.61 (s, 1H). The 4'-(4-amino-2-oxa) butyl-4,5',8-trimethylpsoralen was dissolved in absolute ethanol (150 mL), a 1.0 M solution of HCl in ether (10 mL)

was added and the suspension was cooled in the freezer overnight. After filtration and washing with ether, the solid was vacuum dried to give pale yellow crystals (0.76 g yield 62%), mp 235–236° C.

The first method is a preferred embodiment of the present invention because of its high yield and purity.

The second method starts with the preparation of 4'-chloromethyl-4,5',8-trimethylpsoralen from commercially available 4,5',8-trimethylpsoralen, as described above. The synthesis of 4'-(4-amino-2-oxa)butyl-4,5',8-trimethylpsoralen hydrochloride is achieved in four (4) steps:

STEP 1: 4'-Chloromethyl-4,5',8-trimethylpsoralen (550 mg, 1.99 mmol) and ethylene glycol (6.8 ml, 121.9 mmol) were heated in acetone (6 mL) to 50–60° C. for 3.5 hrs. After 2 hrs heating, the white suspension had turned to a clear light yellow solution. The acetone and ethylene glycol were removed on the rotoevaporator and water (50 mL) was added to the residue. The resultant suspension was filtered, washed with cold water then dried in the vacuum oven to give 574 mg (96%) of 4'-(4-hydroxy-2oxa)butyl-4,5',8-trimethylpsoralen; NMR (CDCl$_3$) d: 2.51 (s, 6H); 2.58 (s, 3H); 3.62 (t, J=4.5 Hz, 2H); 3.78 (t, J=4.9 Hz, 2H); 4.70 (s, 2H); 6.26 (d, J=1.1 Hz, 1H); 7.61 (s, 1H).

STEP 2: 4'-(4-Hydroxy-2-oxa)butyl-4,5',8-trimethylpsoralen (574 mg, 1.9 mmol) was dissolved in CH$_2$Cl$_2$ (6 mL) under N$_2$ at ≦10 C. Triethylamine (359 mg, 3.55 mmol) was added. Methanesulfonyl chloride (305 mg, 266 mmol) was dropped in slowly keeping the temperature below 10° C. After addition was completed the mixture was stirred for 15 more minutes and then it was stirred at room temperature for 10 hours. To the reacted suspension CH$_2$Cl$_2$ (45 mL) was added and the mixture was washed with water (3×20 mL), then dried over anhydrous Na$_2$SO$_4$ Concentration at ≦30° C. followed by vacuum drying gave 4'-[(4-methanesulfonyloxy-2-oxa)butyl-4,5',8-trimethylpsoralen as a yellow solid (706 mg, 98%), mp 138–140° C. NMR d 2.51 (s, 3H); 2.52 (d, 3H); 2.58 (s, 3H); 2.99 (s, 3H); 3.77 (m ,2H); 4.39 (m, 2H); 4.71 (s, 2H); 6.26(s, 1H); 7.62 (s, 1H).

STEP 3: 4'-[(4-Methanesulfonyloxy-2-oxa)butyl-4,5',8-trimethylpsoralen (706 mg, 1.86 mmol) and sodium azide (241 mg, 3.71 mmol) were refluxed in 95% ethyl alcohol (5 mL) for 8 hours. The reaction solution was cooled and cold water (55 mL) was added. The off-white solid was filtered and washed with cold water. Upon vacuum drying, the azide (i.e. 4'-(4-Azido-2-oxa)butyl-4,5',8-trimethylpsoralen) was obtained as a light yellowish solid (575 mg, 95%), mp 105–106° C. NMR: d 2.51 (s, 6H); 2.58 (s, 3H); 3.41 (t, J=4.9 Hz, 2H); 3.67 (apparent t, J=4.9 Hz, 2H); 4.70 (s, 2H); 6.26 (s, 1H); 7.66 (s, 1H).

STEP 4: The 4'-(4-Azido-2-oxa)butyl-4,5',8-trimethylpsoralen (1.65 g, 5.03 mmol) was dissolved in tetrahydrofuran (10 mL). Triphenylphosphine (1.59 g, 6.08 mmol) and six drops of water were added to the foregoing solution. After stirring at room temperature overnight, the light yellow solution was concentrated. The residue was dissolved in CHCl$_3$ (90 mL) and extracted with 0.3 N aqueous HCl (30 mL, then 2×5 mL). Combined HCl layers was carefully treated with K$_2$CO$_3$ until saturated. The base solution was extracted with CHCl$_3$ (3×60 mL). Combined CHCl$_3$ layers were washed with 60 mL of water, 60 mL of brine and dried over anhydrous Na$_2$SO$_4$. Upon concentration and vacuum drying the amine was obtained as a yellow solid (1.25 g, 82%), mp 139–141° C.; NMR d 2.48 (s, 6H); 2.55 (s, 3H); 2.89 (t, J=6 Hz, 2H); 3.52 (t, J=6 Hz, 2H); 4.64 (s, 2H); 6.22 (s, 1H); 7.59 (s, 1H).

The amine was dissolved in absolute ethanol (40 mL) and 20 mL of 1N HCl in ethyl ether was added. After sitting at 5° C. overnight, the precipitate was filtered and rinsed with ether to give 1.25 g of Compound 2, mp 236° C. (decomp). $^{13}$C NMR: 8.54, 12.39, 19.18, 38.75, 62.26, 65.80, 108.01, 112.04, 112.42, 112.97, 116.12, 125.01, 148.76, 153.97, 154.37, 155.76, 160.34.

Anal. Calculated for C$_{17}$H$_{20}$ClNO$_4$: C, 60.45: H,5.97; N, 4.15. Found: C, 60.27; H, 5.88; N, 4.10.

Similarly prepared, by reacting 4'-CMT with 1,3-propanediol comparably to Step 1 and proceeding analogously through Step 4, was 4'-(5-amino-2-oxa)pentyl4,5',8-trimethylpsorale (Compound 4), m.p. 212–214° C. (decomposed). NMR of the free base: d 1.73 (pent, J=6.4 Hz, 2H), 2.45(s, 6H), 2.51 (s, 3H), 2.78 (t,J=6.8 Hz, 2H), 3.54 (t, J=6.2 Hz, 2H), 4.59 (s,2H), 6.18 (s, 1H), 7.54 (s, 1H).

EXAMPLE 5

Synthesis of 5'-(4-Amino-2-oxa)butyl-4,4',8-trimethylpsoralen (Compound 18)

This example describes the synthesis of Compound 18. To a stirred solution of N-methylformanilide (16.0 mL, 0.134 mol) in acetonitrile (130 mL) was added phosphorus oxychloride (12.5 mL, 0.134 mol), then 4,4',8-trimethylpsoralen (5.0 g, 21.9 mmol) (described in McLeod, et al., Tetrahedron Letters No. 3:237 (1972)). The temperature was kept between 0–10° C. during addition of the psoralen by use of an ice/water bath. The slurry was stirred at 50° C. for 2 days protected from moisture with a drierite drying tube. The reaction mix was allowed to cool to room temperature, then chilled in an ice/water bath. The acetonitrile was decanted off, then ice/water (150 mL) was added to the orange slurry and stirred for 1 h. The orange solid was filtered off and rinsed with chilled water, then chilled acetonitrile. The crude product was recrystallized and charcoal decolorized in dichloroethane (600 mL) to give 4,4',8trimethyl-5'-psoralencarboxaldehyde (3.59 g, 64.0%) as a pale yellow-orange solid, sublimes ≧250° C., decomp. >300° C. $^1$H NMR (CDCl$_3$): 2.54 (d, J=1 Hz, 3H), 2.64 (s, 3H), 2.68 (s, 3H), 6.32 (apparent d, J=1 Hz, 1H), 7.75 (s, 1H), 10.07 (s, 1H).

4,4',8-trimethyl-5-psoralencarboxaldehyde (7.50 g, 29.3 mmol) was stirred in 200 proof EtOH (250 mL). Sodium borohydride was added and the slurry was stirred overnight. Ice water (150 mL) and 10% aq NaCO$_3$ (50 mL) were added to quench the reaction. After stirring for 45 min, the precipitate was filtered off and rinsed with water until the filtrate was neutral (pH 5–7). The product was dried in a vacuum dessicator with P$_2$O$_5$ to give 5'-hydroxymethyl-4,4',8-trimethylpsoralen (7.46 g, 98.5%) as a pale yellow solid, mp 244–245° C. $^1$H NMR (CDCl$_3$): 1.97 (t, J=6 Hz, 1H), 2.31 (s, 3H), 2.51 (d, J=1 Hz, 3H), 2.58 (s, 3H), 4.79 (d, J=6 Hz, 2), 6.25 (apparent d, J=1 Hz, 1H), 7.49 (s, 1H).

To a stirred, ice/water chilled slurry of 5'-hydroxymethyl4,4',8-trimethylpsoralen (15.42 g, 59.7 mmol) in dichloroethane (500 mL) was added phosphorus tribromide (6.17 mL, 65.7 mmol) dropwise. The reaction was protected from moisture and allowed to stir overnight at room temperature. The mixture was then stirred with 300 mL ice/water for 1 h. The solid was filtered off, dried, dissolved in hot toluene, filtered through fluted filter paper and stripped to give 5'-bromomethyl4,4',8-trimethylpsoralen (3.43 g). The reaction solvents (dichloroethane and water) were separated and the aqueous layer was extracted three times with dichloroethane. The organic layers were combined, rinsed with brine then dried (anhyd Na$_2$SO$_4$) and stripped under vacuum to give the bulk of the product, 5'-bromomethyl-4,4',8-trimethylpsoralen, (13.13 g, combined yield of 86.4%), as a pale yellow solid, mp 201–202° C. $^1$H NMR (CDCl$_3$): 2.29 (s, 3H), 2.52 (d, J=1 Hz, 3H), 2.60 (s, 2H), 4.64 (s, 2H), 6.27(apparent d, J=1 Hz, 1H), 7.51 (s, 1H)

N-Hydroxyethylphthalimide (3.00 g, 15.5 mmol) was dissolved in DMF (5 mL) at 60–64° C. while N$_2$ was bubbled into the solution. Sodium iodide (0.01 g, 0.067 mmol) and 5'-bromomethyl-4,4',8-trimethylpsoralen (1.00 g, 3.11 mmol) were added and the slurry was stirred under these conditions overnight. The thick yellow reaction mixture was allowed to cool to room temperature, chilled in an ice/water bath, filtered and rinsed with ice cold MeOH to give crude product (1 g). The solid was recrystallized in dichloroethane (100 mL) to give 4,4',8-trimethyl-5'-[2-(N-phthalimido)-2-oxa]butylpsoralen (0.68 g, 50.8%), as an off-white solid, mp 225–228° C. $^1$H NMR (CDCl$_3$): 2.26 (s, 3H), 2.46 (s, 3H), 2.51 (d, J=1 Hz, 3H), 3.87 (m, 4H), 4.64 (s, 2H), 6.26 (apparent d, J=1 Hz, 1H), 7.42 (s, 1H), 7.64 (multiplet, 4H).

4,4',8-Trimethyl-5'-[4'-(N-phthalimido)-2-oxa]butylpsoralen (1.61 g, 3.73 mmol) was stirred with THF (40 mL) and 40 wt % aq methylamine (20 mL, 257 mmol) overnight. The solvent was stripped and the residue was partitioned between dilute aq HCl and dichloromethane. The aqueous layer was rinsed several more times with dichloromethane then made basic with K$_2$CO$_3$. The base layer was extracted three times with dichloromethane. The combined organic extracts from the base were shaken with brine then dried (anhydrous Na$_2$SO$_4$) and stripped to give 5'-(4-amino-2oxa)butyl-4,4',8-trimethylpsoralen (0.71 g, 63.4%), mp 126–129° C. $^1$H NMR (CDCl$_3$): 2.30 (s, 3H), 2.51 (s, 3H), 2.58 (s, 3H), 2.91 (t, J=5 Hz, 2H), 3.59 (t, J=5 Hz, 2H), 4.64 (s, 2H), 6.25 (s, 1H), 7.50 (s, 1H).

The above amine (0.71 g, 2.36 mmol) was dissolved in hot ethanol, converted to the acid with 1M HCl in diethylether (3 mL, 3 mmol), decolorized with charcoal, cooled and collected. The solid was decolorized again with charcoal and stripped to give 5'-(4-amino-2-oxa)butyl-4,4',8-trimethylpsoralen hydrochloride (0.39 g, 49.3% yield) as a white solid, mp 235–236° C. (Note: Other preparations of this material have given a product with a significantly lower melting point, but identical NMR spectra). $^1$H NMR (d6-DMSO): 2.32 (s, 3H), 2.45 (s, 3H), 2.50 (s, 3H), 3.00 (m, 2H), 3.71 (t, J=5 Hz, 2H), 4.71 (s, 2H), 6.33 (s, 1H), 7.79 (s, 1H), 8.15 (br). $^{13}$C NMR (d6-DMSO): 7.93, 8.57, 19.01, 38.74, 62.66, 66.28, 108.22, 112.42, 113.69, 115.34, 116.06, 125.60, 149.38, 150.95, 154.26 (tentatively 2 carbons), 160.26.

EXAMPLE 6

Synthesis of 4'-(7-amino-2,5-oxa)heptyl-4,5',8-trimethylpsoralen Hydrochloride (Compound 7)

In this example, the synthesis of Compound 7 is described. The synthesis of 4'-(7amino-2,5-oxa)heptyl-4,5',8-trimethylpsoralen hydrochloride proceeds in four (4) steps:

STEP 1: 4'-Chloromethyl-4,5',8-trmethylpsoralen (589 mg, 2.13 mmol), diethylene glycol (15.4 g, 145 mmol) and acetone (13 mL) were refluxed for 11.5 hours. The reaction solution was concentrated to remove acetone and part of the diethylene glycol. To the resulting light brown solution was added CHCl$_3$ (40 mL), then washed with water several times. The CHCl$_3$ layer was dried over anhydrous Na$_2$SO$_4$ and concentrated to give 781 mg of product, 4'-(7-Hydroxy-2,5-oxa)heptyl-4,5',8trimethylpsoralen, (~100%). NMR d 2.46 (d, 3H), 2.47 (s, 3H ), 2.51 (s, 3H), 3.58–3.67 (m, 8H), 4.67 (s, 2H), 6.18 (s, 1H), 7.57 (s, 1H).

STEP 2: 4'-(7-Hydroxy-2,5-oxa)heptyl4,5',8-trimethylpsoralen (781 mg, 2.25 mmol) was dissolved in CH$_2$Cl$_2$ (2.5 mL) under a N$_2$ stream at <10° C. Triethylamine (363 mg, 3.59 mmol) was added. Methanesulfonyl chloride (362 mg, 3.16 mmol) was slowly dropped in to keep the temperature below 10° C. After addition was completed, the mixture was kept below 10° C. for 15 more minutes. The mixture was stirred at room temperature overnight then CH$_2$Cl$_2$ (50 mL) was added. The solution was washed with water (3×60 mL), dried over anhydrous Na$_2$SO$_4$ and concentrated at <30° C. Upon vacuum drying, a light brown syrup was obtained [4'-(7-Methanesulfonyloxy-2,5-oxa)heptyl4,5',8-trimethylpsoralen]; 437 mg (76%). NMR d 2.50 (s, 3H), 2.51 (s, 3H), 2.58 (s, 3H), 3.01 (s, 3H), 3.66 (m, 4H), 3.77 (t,J=4.6 Hz, 2H), 4.37 (t, J=6 Hz, 2H), 4.69 (s, 2H), 6.25 (s, 1H), 7.61 (s, 1H).

STEP 3: 4'-(7-Methanesulfonyloxy-2,5-oxa)heptyl-4,5',8-trimethylpsoralen (288 mg, 0.678 mmol) and sodium azide (88.2 mg, 1.36 mmol) were refluxed in 3 mL of 95% ethyl alcohol for 8 hours. The reaction solution was let cool and cold water (50 mL) was added. The water layer was poured away. The crude material was purified by chromatography on (Silica gel with chloroform eluent) a Chromatotron (Harrison Research, Inc., Palo Alto, Calif.) and vacuum dried to give a light yellow syrup, 4'-(7-Azido-2,5-oxa)heptyl-4,5',8-trimethylpsoralen, (123 mg, 49%). NMR d 2.50 (s, 6H), 2.57 (s, 3H), 3.39 (t, J=5.2 Hz, 2H), 3.68 (m, 6H), 4.70 (s, 2H), 6.24 (s, 1H), 7.62 (s, 1H).

STEP 4: 4'-(7-Azido-2,5-oxa)heptyl-4,5',8-trimethylpsoralen (122 mg, 0.33 mmol), triphenylphosphine (129 mg, 0.49 mmol) and several drops of water were dissolved in tetrahydrofuran (2 mL). The light yellow clear solution was stirred at room temperature over a weekend; no starting material was detected by TLC. The reaction solution was concentrated and the residue was dissolved in CHCl$_3$ (20 mL). The solution was extracted with 0.15 N aqueous HCl solution (10 mL then 2×5 mL) and the HCl layers was taken to pH 13 by addition of 20% aqueous NaOH solution. The basic solution was extracted with CHCl$_3$ (3×15 mL). The combined CHCl$_3$ layers were washed with water, dried over anhydrous Na$_2$SO$_4$, concentrated, and vacuum dried to give 63.9 mg of product, 4'-(7-amino-2,5-oxa)heptyl-4,5',8-trimethylpsoralen, (56%). TLC showed only one spot. NMR d 2.50 (s, 3H); 2.50 (s, 3H); 2.57 (s, 3H); 2.86 (t, J=5.3 Hz, 2H); 3.50 (t, J=5.3 Hz, 2H); 3.63 (s, 4H); 4.70 (s, 2H); 6.24 (s, 1H); 7.62 (s, 1H). m.p. 170–173° C.

The solid was dissolved in absolute ethanol, then 1M HCl in ethyl ether was added, the suspension was filtered and the product rinsed with ether and dried.

EXAMPLE 7

Synthesis of 4'-(12-amino-8-aza-2,5dioxa)dodecyl-4,5',8-trimethylpsoralen Dihydrochloride (Compound 8)

The synthesis of 4'-(12-amino-8-aza-2,5-dioxa)dodecyl4,5',8-trimethylpsoralen dihydrochloride proceeds in one (1) step from the product of Example 5, method 2, step 2: A solution of 4'-(7-methanesulfonyloxy-2,5-oxa)heptyl-4,5', 8trimethylpsoralen (108 mg, 0.253 mmol) in 8 mL of acetonitrile was slowly added to a solution of 1, 4-diaminobutane (132 mg, 1.49 mmol) in 2.8 mL of acetonitrile. After refluxing for 8 hours, no starting material remained by TLC. The reaction mixture was cooled to room temperature and CHCl$_3$ (25 mL) and 1 N aqueous NaOH (25 mL) solution were added. The layers were separated and CHCl$_3$ (2×10 mL) was used to wash the aqueous layer. Aqueous HCl (0.3 N, 3×10 mL) was used to extract the product from the combined organics layers. The HCl layers was treated with 20% aqueous NaOH solution until pH 13. The combined basic layers were then extracted with CHCl$_3$ (3×20 mL). The CHCl$_3$ layer was washed with saturated NaCl aqueous solution (10 mL) then dried over anhydrous Na$_2$SO$_4$. After concentration and vacuum drying, 63 mg of product, 4'-(12-amino-8-aza-2,5-dioxa)dodecyl-4,5', 8trimethylpsoralen dihydrochloride, was obtained (60%). NMR d 1.45 (m, 2H), 2.49 (s, 6H), 2.55 (s, 3H), 2.58 (t, 2H), 2.66 (t, J=5.6 Hz, 2H), 2.76 (m, 4H), 3.55–3.61 (m, 6H), 4.68 (s, 2H), 6.22 (s, 1H), 7.61 (s, 1H).

EXAMPLE 8

Synthesis of 4'-(2-aminoethyl)-4,5',8-trimethylpsoralen Hydrochloride (Compound 3)

The synthesis of 4'-(2-aminoethyl)-4,5',8-trimethylpsoralen proceeds in one (1) step: sodium trifluoroacetoxyborohydride was made by adding trifluoroacetic acid (296 mg, 2.60 mmol) in 2 mL of THF to a stirred suspension of sodium borohydride (175 mg, 4.63 mmol) in 2 mL of THF over a period of 10 minutes at room temperature. The resultant suspension was added to a suspension of 4'-cyanomethyl4,5',8-trimethylpsoralen (Kaufman et al., J Heterocyclic Chem. 19:1051(1982)) (188 mg, 0.703 mmol) in 2 mL of THF. The mixture was stirred overnight at room temperature. Several drops of water were added to the reacted light yellow clear solution to decompose the excess reagent under 10° C. The resulting mixture was concentrated and 1 N aqueous NaOH solution (30 mL) was added. Chloroform (30 mL then 10 mL, 5 mL)) was used to extract the resultant amine. Combined CHCl$_3$ layers were washed with saturated NaCl solution. The amine was then extracted into aqueous 0.3 N HCl (10, 5, 5 mL) and the acid layers were taken to pH 13 with 20% aqueous NaOH. CHCl$_3$ (3×10 mL) was used to extract the amine from the combined base layers then washed with water (2 mL) and dried over anhydrous Na$_2$SO$_4$. Upon concentration and vacuum drying the amine was obtained as a solid, >95% pure by NMR. NMR d 2.45 (s, 3H); 2.47 (s, 3H); 2.53 (s, 3H); 2.78 (t, J=6.6 Hz, 2H); 3.00 (t, J=6.5 Hz, 2H); 6.20 (s, 1H); 7.44 (s, 1H). The solid was dissolved in absolute ethanol. A solution of hydrogen chloride in diethyl ether (1 N, 1 mL) was added. The suspension was filtered to obtain compound 3, a light purple solid (32.7 mg, yield 15%), m.p. >237° C. (decomp.)

EXAMPLE 9

4'-(6-Amino-2-aza)hexyl-4,5',8-trimethylpsoralen Dihydrochloride (Compound 6)

The synthesis of 4'-(6-amino-2-aza)hexyl4,5',8-trimethylpsoralen dihydrochloride proceeds in one (1) step, as follows: a solution of 4'-chloromethyl4,5',8-trimethylpsoralen (188 mg, 0.68 mmol) in 30 mL of acetonitrile was added to a solution of 1,4-diaminobutane (120 mg, 1.4 mmol) in 7 mL of acetonitrile. After stirring overnight the solvent was removed under reduced pressure. Chloroform (10 mL) and 1N NaOH (10 mL) were added to the residue and the mixture was shaken and separated. The aqueous solution was extracted with a further 2×10 mL of CHCl$_3$ and the combined extracts were rinsed with water. The product was then extracted from the CHCl$_3$ solution with 0.3 N aqueous HCl and the acidic layer was then taken to pH 12 with concentrated NaOH solution. The base suspension was extracted with CHCl$_3$ which was then rinsed with water, dried over Na$_2$SO$_4$ and concentrated under reduced pressure to give the amine as the free base; NMR (CDCl$_3$); d 1.33 (m, 3H), 1.52 (m, 4H), 2.47 (s, 3H), 2.49 (d, J=1.1 Hz, 3H), 2.54 (s, 3H), 2.68 (q, J=6.5 Hz, 4H), 3.86 (s, 2H), 6.21 (apparent d, J=1.1 Hz, 1 H), 7.60 (s, 1H).

The free base, dissolved in about 6 mL of absolute EtOH, was treated with a solution of HCl in ether (1.0M, 3 mL). The resultant HCl salt was filtered, rinsed with absolute EtOH and dried under vacuum to yield 150 mg of compound 6, (55%), m.p. 290° C. (decomposed). Analysis calculated for C$_{19}$H$_{26}$C$_{12}$N$_2$O$_3$.H$_2$O: C,54.42; H, 6.73; N, 6.68. Found: C, 54.08; H. 6.45; N, 6.65.

The following compounds were prepared in a similar manner, with the differences in synthesis noted:

a) 4'-(4-amino-2-aza)butyl-4,5',8-trimethylpsoralen dihydrochloride (Compound 1), mp 320–322° C. (decomp). In this synthesis ethylene diamine was used as the diamine.

b) 4'-(5-amino-2-aza)pentyl-4,5',8-trimethylpsoralen dihydrochloride (Compound 5), mp 288° C. (decomp). NMR of free base: d 1.33 (br s, 3H), 1.66 (pent, J=6.8 Hz, 2H), 2.47 (s, 3H), 2.50 (d, J=1 Hz, 3H), 2.55 (s, 3H), 2.6–2.8 (m, 4H), 3.89 (s, 2H), 6.22 (apparent d, J=1 Hz, 1H), 7.62 (s, 1H). For this synthesis, 1,3-diaminopropane was used as the diamine.

c) 4'-(7-amino-2-aza)heptyl4,5',8-trimethylpsoralen dihydrochloride (Compound 10), mp 300° C. (decomp). NMR of free base: d 1.22 (br s,), 1.3–1.6 (m) total 9 H, 2.44 (s), 2.50 (s), total 9H, 2.63 (m, 4H), 6.17 (s, 1H), 7.56 (s, 1H). Here, 1,5-diaminopentane was used as the diamine.

EXAMPLE 10

5'-(6-Amino-2-aza)hexyl4,4',8-trimethylpsoralen Dihydrochloride (Compound 17)

The synthesis of 5'-(6-amino-2-aza)hexyl-4,4',8-trimethylpsoralen dihydrochloride proceeds in one (1) step, as follows: a suspension of 5'-chloromethyl4,4',8-trimethylpsoralen (190 mg, 0.68 mmol) in 30 mL of acetonitrile was added to a solution of 1,4-diaminobutane (120 mg, 1.4 mmol) in 7 mL of acetonitrile. After stirring at room temperature overnight, the solvent was removed under reduced pressure. Chloroform (10 mL) and 1N NaOH (10 mL) were added to the residue and the mixture was shaken and separated. The aqueous layer was extracted with a further 2×10 mL of CHCl$_3$ and the combined extracts were rinsed with water. The product was then extracted from the CHCl$_3$ solution with 0.3 N aqueous HCl and the acidic layer was then taken to approximately pH 12 with concentrated NaOH solution. The base suspension was extracted with CHCl$_3$ which was then rinsed with water, dried over Na$_2$SO$_4$ and concentrated under reduced pressure.

The residue was purified by column chromatography on silica gel with CHCl$_3$: EtOH : Et$_3$N (9:1:0.25). The fractions containing the product were combined and stripped of the solvent to give the free amine. NMR (CDCl$_3$): d 1.35 (m, 3H); 1.49 (m, 4H); 2.22 (s, 3H); 2.46 (d, J=1.1 Hz, 3H); 2.51 (S, 3H); 2.65 (m, 4H); 3.88 (s, 2H); 6.17 (apparent d, 1 Hz); 7.40 (s, 1H).

The free base, dissolved in absolute EtOH (~6 mL) was treated with a solution of HCl in ether (1.0 M,~3 mL). The resultant HCl salt was filtered, rinsed with absolute EtOH and dried under vacuum to yield 100 mg (36.3%) of product, 5'-(6Amino-2-aza)hexyl-4,4',8trimethylpsoralen dihydrochloride, m.p. 288° C. (decomposed).

5'-(4-Amino-2-aza)butyl4,4',8-trimethylpsoralen dihydrochloride (Compound 16) was prepared in the same manner, except that ethylene diamine was used as the diamine. NMR of free base: d 1.83 (br s, 3H), 2.27 (s, 3H), 2.51 (s, 3H), 2.58 (s, 3H), 2.74 (m, 2H), 2.87 (m, 2H), 3.95 (s, 2H), 6.24 (s, 1H), 7.46 (s, 1H).

EXAMPLE 11

4'-(14-Amino-2,6,11-triaza)tetradecyl-4,5',8-trimethylpsoralen Tetrahydrochloride (Compound 15)

The synthesis of 4'-(14-amino-2,6,11-triaza)tetradecyl-4,5',8-trimethylpsoralen tetrahydrochloride proceeds in one (1) step, as follows. To a solution of 0.5 g (2.5 mmol) of spermine (Aldrich, Milwaukee, Wis.) in 10 ml of methanol was added a 5N methanolic solution of HCl (concentrated HCl diluted with MeOH to 5N) to adjust to pH 5–6, followed by 0.128 g (0.5 mmol) of 4,5',8-trimethylpsoralen-4' carboxaldehyde, 20 mg (0.3 mmol) of $NaBH_3CN$ and 3 mL of MeOH. The reaction mixture was stirred at room temperature overnight. A solution of 5N methanolic HCl was added until pH<2 and methanol was removed under reduced pressure. The residue was taken up in about 100 mL of water and rinsed with three 25 mL portions of $CHCl_3$. The aqueous solution was brought to pH>10 with concentrated NaOH and extracted with three 25 mL portions of $CHCl_3$. These final extracts were combined and washed with water, dried ($Na_2SO_4$) and evaporated to give the free base of the amine, ≧95% pure by NMR. NMR ($CDCl_3$): d 1.31 (m, 5H), 1.45 (pent, J=3.41 Hz, 4H), 1.65 (m, 4 H), 2.46 (s, 3H), 2.49 (d, J=1.14 Hz, 3H), 2.66 (m, 15 H), 3.85 (s, 2H), 6.21 (s, 1H)m 7.60 (s, 1H).

The free amine was dissolved in absolute ethanol and HCl (anhydrous, 1N in ethyl ether) was added. The hydrochloride salt was filtered and washed with absolute ethanol and dried under vacuum at room temperature giving 80.2 mg of product, 4'-(14-amino-2,6,11-triaza)tetradecyl4,5',8-trimethylpsoralen tetrahydrochloride, as a light yellow solid.

EXAMPLE 12

An r-17 bacteriophage assay was used in this example to predict pathogen inactivation efficiency and to determine nucleic acid binding of the photoreactive binding compounds of the present invention. In the r-17 assay, the bacteriophage was placed in a solution with each compound tested and was then irradiated. The ability of the phage to subsequently infect bacteria and inhibit their growth was measured. The bacteriophage was selected for its relatively accessible nucleic acid such that the culture growth inhibition would accurately reflect nucleic acid damage by the test compounds. The bacteriophage assay for nucleic acid binding to test compounds offers a safe and inexpensive procedure to identify compounds likely to display efficient pathogen inactivation. Previous experiments support that the r-17 assay accurately measures HIV-1 sensitivity to similar compounds.

The R17 was grown up in Hfr 3000 bacteria, approximate titer $5 \times 10^{11}$. (R17 and Hfr 3000 were obtained from American Tissue Culture Collection (ATCC), Washington, D.C.) The R17 phage stock was added to a solution of 15% fetal bovine serum in Dulbecco's Modified Eagles Medium (DMEM) to a final phage concentration of $10^9$/mL. An aliquot (0.5 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at concentrations between 4 μM and 320 μM. (AMT is commercially available from HRI, Inc., Concord, Calif.; 8-MOP is commercially available from Sigma, St. Louis, Mo.). The tubes were placed in a light device as described in EXAMPLE 1 and irradiated for between 1 and 10 minutes. Sterile 13 mL dilution tubes were prepared; each test compound required one tube with 0.4 mL of Luria broth (LB) and five tubes containing 0.5 mL of LB broth. To make the dilutions, a 0.100 mL aliquot of the irradiated solution of phage and test compound was added to the first dilution tube of 0.4 mL of media then 0.020 mL of this solution was added to the second tube of 0.5 mL medium (1:25). The second solution was then diluted serially (1:25) into the remaining tubes. To each diluted sample was added 0.050 mL of Hfr 3000 bacteria cultured overnight and 3 mL of molten LB top agar and the mixed materials were poured onto LB broth plates. After the top agar hardened, the plates were incubated at 37° C. overnight. The plaque forming units were then counted the following morning and the titer of the phage remaining after phototreatment was calculated based on the dilution factors.

The following controls were run: the "phage only" in which phage was not treated with test compound and not irradiated (listed as "starting titer" in the tables below); the "UV only" in which the phage was irradiated in the absence of test compound; and the "dark" control in which the phage/test compound solution was not irradiated before it was diluted and plated.

TABLE 5, below, shows three different experiments which tested Compound 1 according to the R17 protocol just described. A comparison of values for the control samples in runs 1–3 (values in bold) shows that neither the "UV only" nor the "dark" controls result in significant bacterial kill (at most, .3 logs killed in the "UV only" control and 0.1 logs killed in the "dark" control).

The "UV only" control was repeated in many similar experiments with other compounds of the present invention and consistently showed no significant kill. (Data not shown). Thus, the "UV only" control is not shown in the tables and figures that follow, although it was performed in every experiment in this example. As for the "dark" control, after many trials with various compounds of the present invention, it became apparent that regardless of the type of substitution on the 4' position of the psoralen, no experimentally significant bacterial inactivation was observed in the dark. (Data not shown). For example, in Table 5, experiment 1 shows 0.1 logs kill with compound 1 in the dark. In contrast, when Compound 1 is irradiated for just 1 minute, the resulting drop in titer is >6.7 logs. Therefore, "dark" controls were not run for the later tested compounds and where run, are not shown in the tables and figures that follow.

TABLE 5

| Experiment # | Treatment | Log Titer | Logs Killed |
| --- | --- | --- | --- |
| 1 | phage only | 7.7 | — |
|  | uva only (10') | 7.4 | 0.3 |
|  | compound only (32 μM) | 7.6 | 0.1 |
|  | 32 μM compound 1' uva | <1 | >6.7 |
|  | 32 μM compound 10' uva | <1 | >6.7 |
| 2 | phage only | 7.8 | — |
|  | uva only (10') | 7.6 | 0.2 |
|  | compound only (3.2 μM) | 7.7 | 0.1 |
|  | 3.2 μM compound 1' uva | 6.9 | 0.9 |
|  | 3.2 μM compound 10' uva | 6.1 | 1.7 |

TABLE 5-continued

| Experiment # | Treatment | Log Titer | Logs Killed |
|---|---|---|---|
| 3 | phage only | 7.3 | — |
| | uva only (1') | 7.3 | 0 |
| | compound only (16 μM) | 7.3 | 0 |
| | 4 μM compound 1' uva | 6.3 | 1.0 |
| | 8 μM compound 1' uva | 5.6 | 1.7 |
| | 16 μM compound 1' uva | 3.9 | 3.4 |

Figure 6:
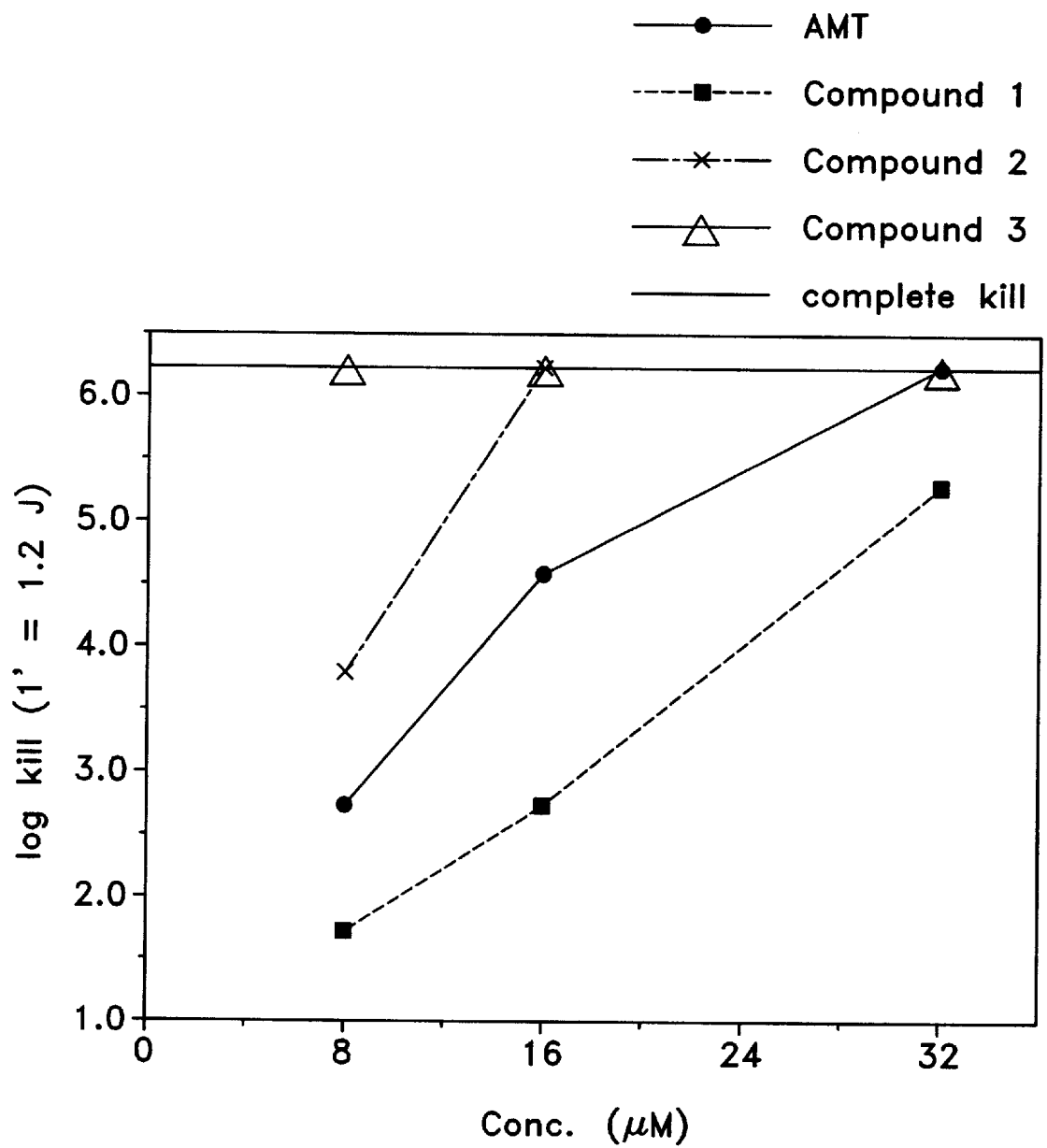
FIG. 6 shows the impact of concentration on the log kill of R17 when Compounds 1–3 of the present invention are photoactivated.
Figure 7:
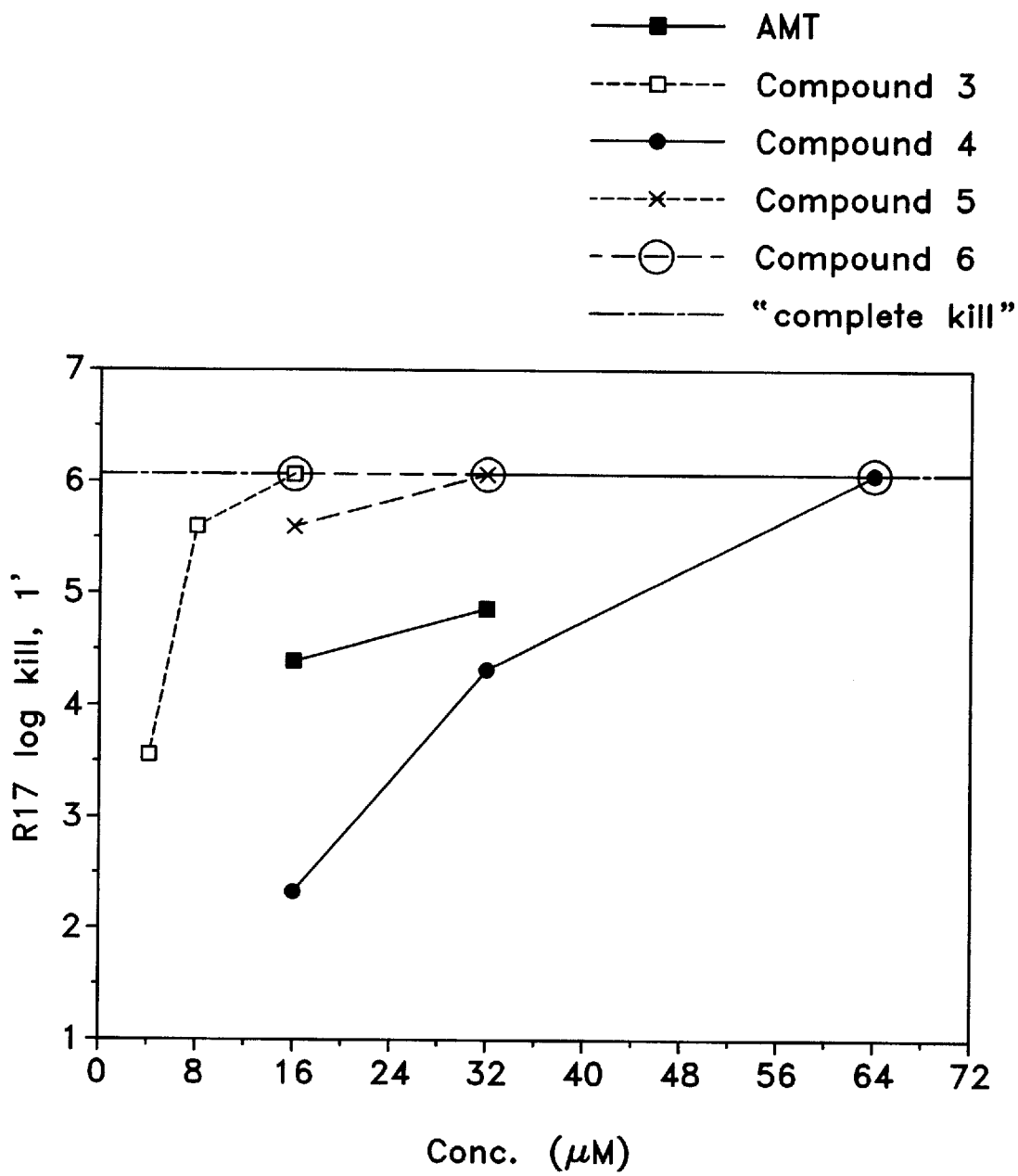
FIG. 7 shows the impact of concentration on the log kill of R17 when Compounds 3–6 of the present invention are photoactivated.
Figure 8:
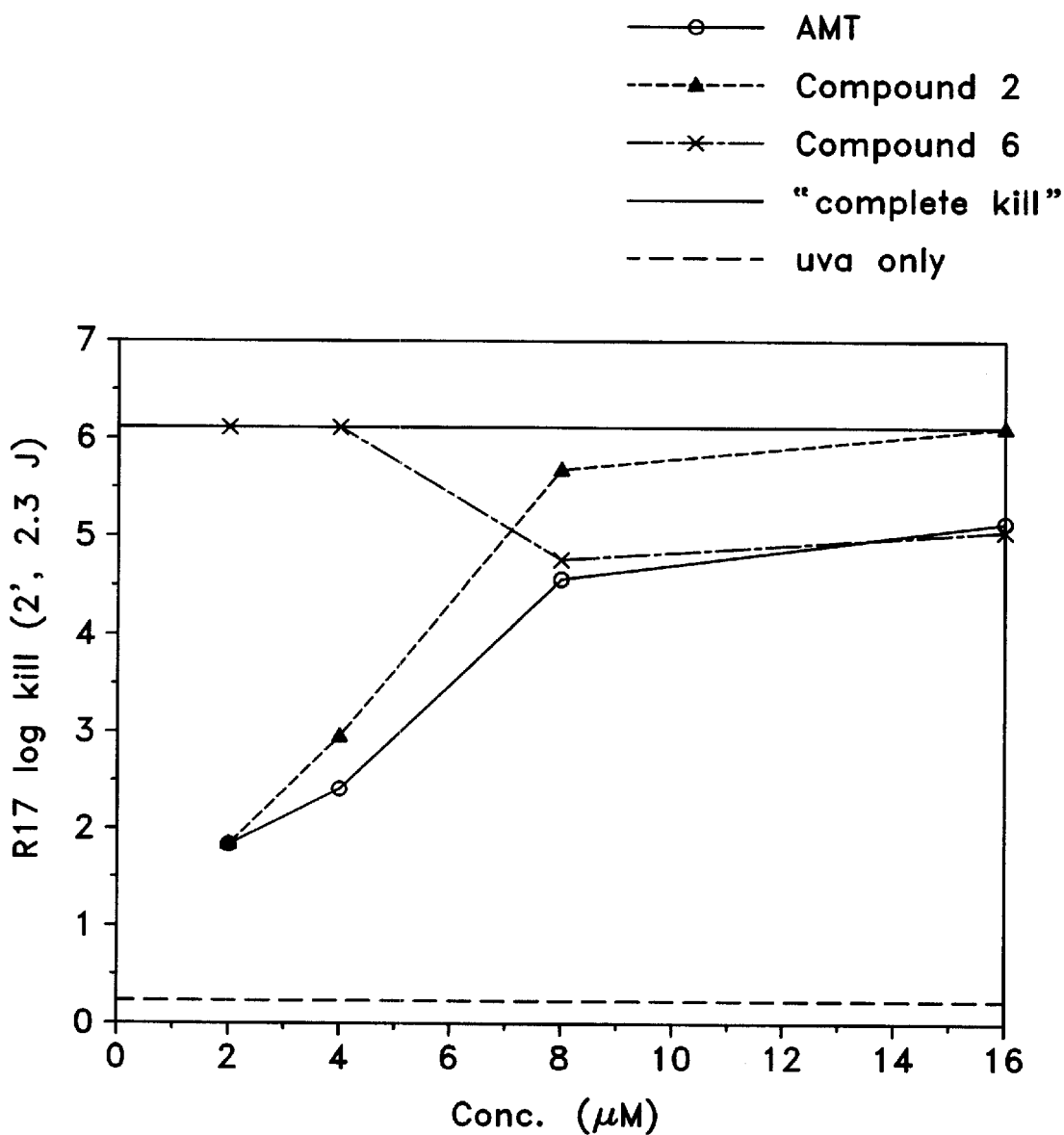
FIG. 8 shows the impact of concentration on the log kill of R17 when Compounds 2 and 6 of the present invention are photoactivated.
Figure 9:
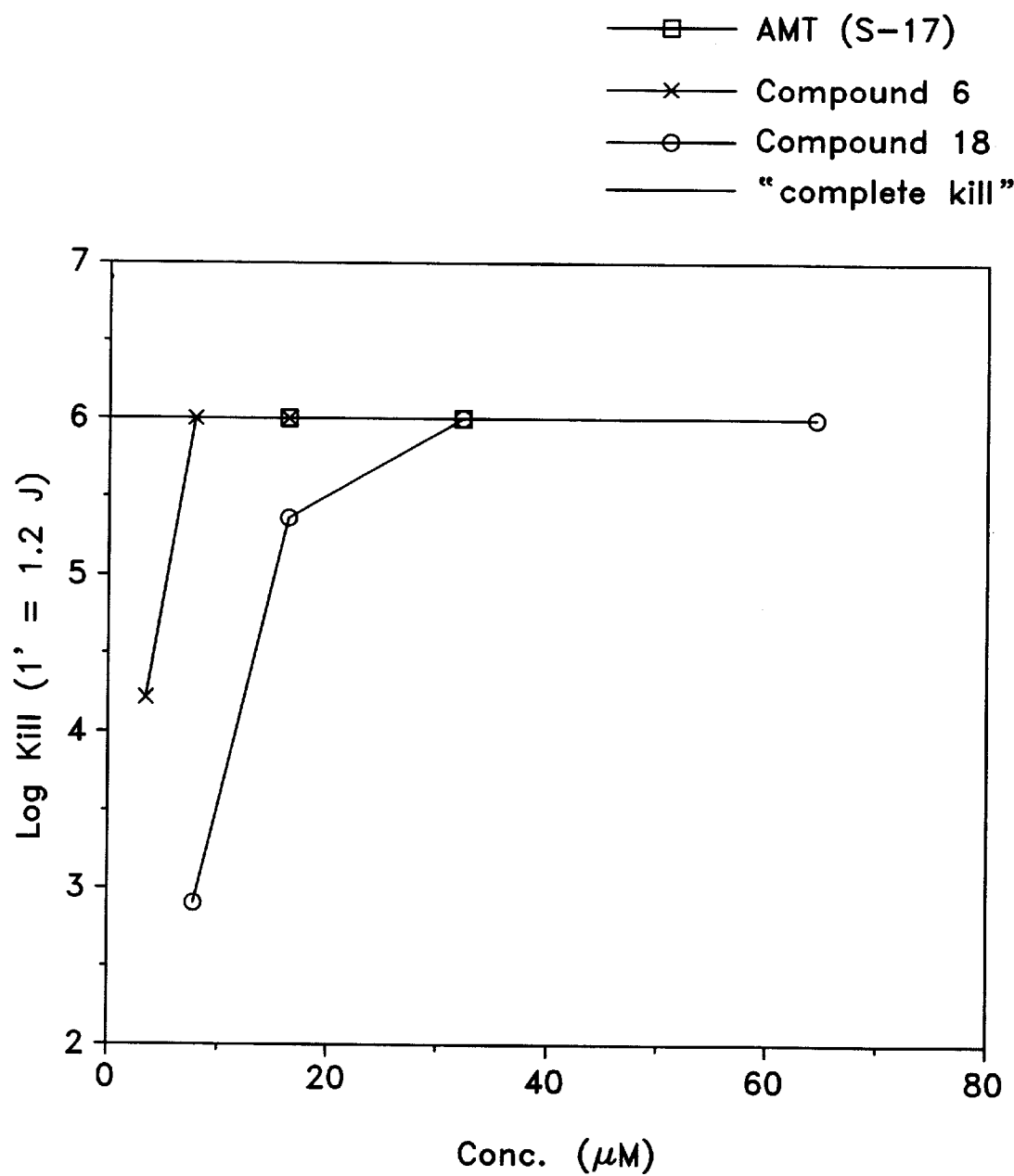
FIG. 9 shows the impact of concentration on the log kill of R17 when Compounds 6 and 18 of the present invention are photoactivated.
Figure 10:
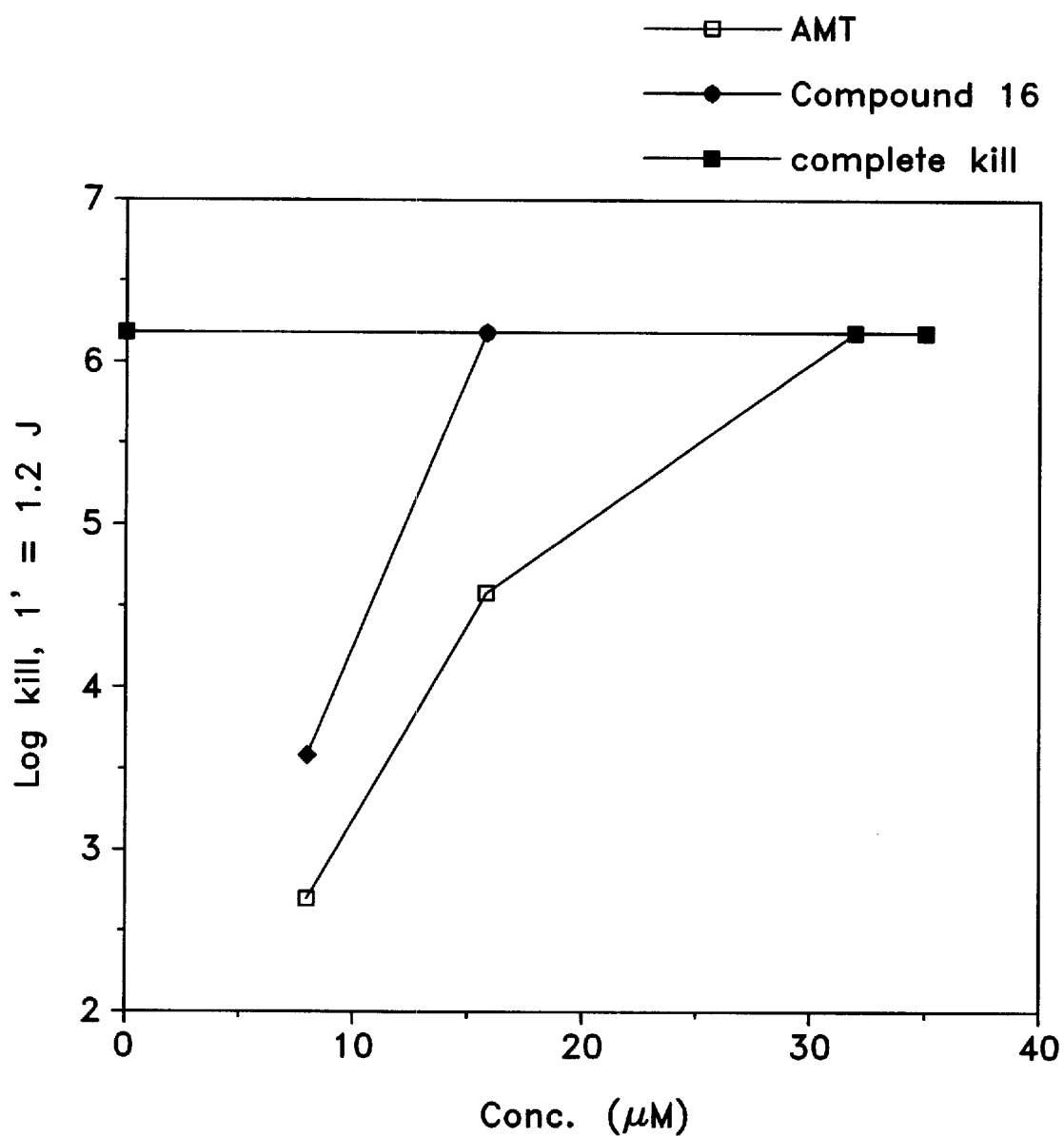
FIG. 10 shows the impact of concentration on the log kill of R17 when Compound 16 of the present invention is photoactivated.
Figure 11:
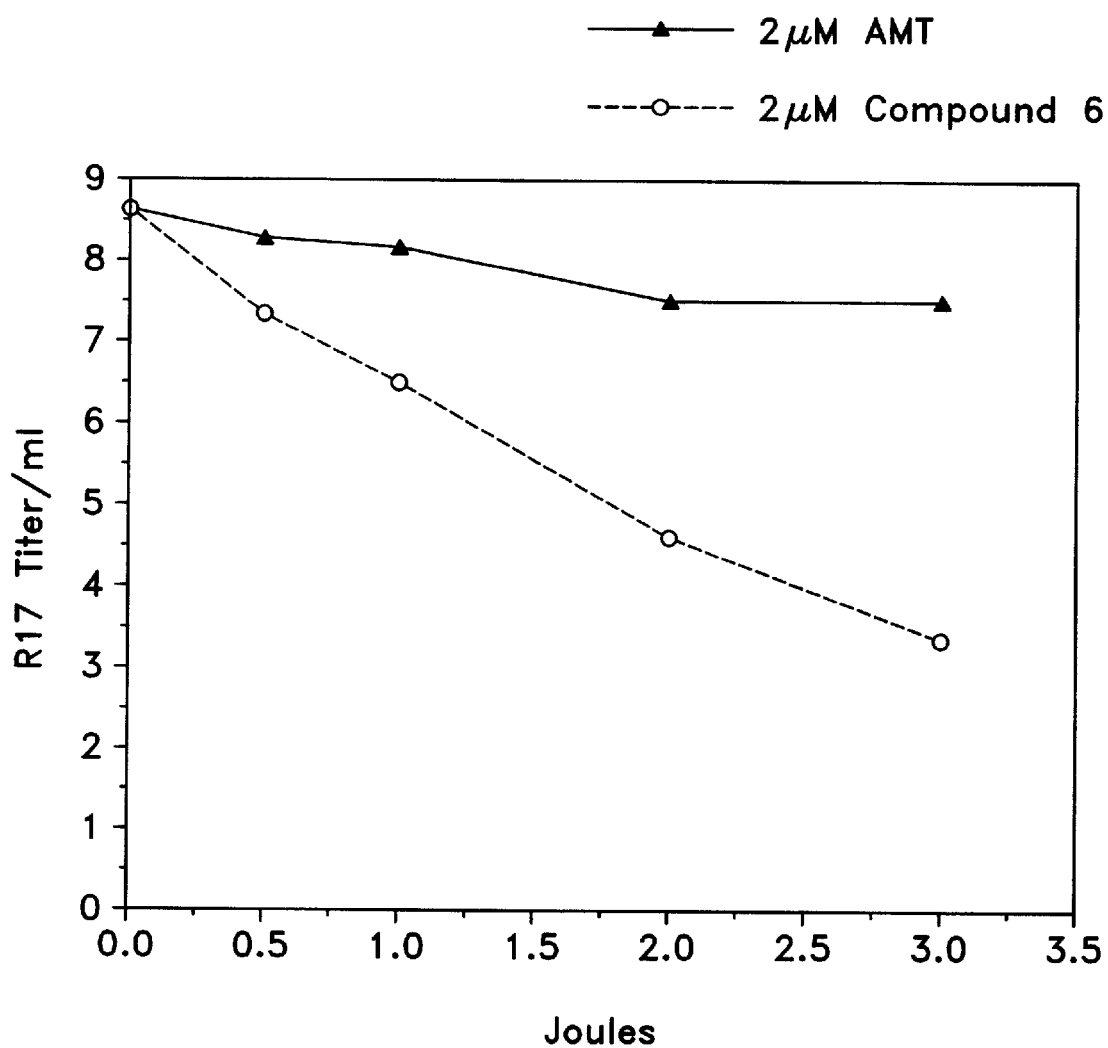
FIG. 11 shows the impact of varying Joules/$cm^2$ (Watt second/$cm^2$) of irradiation on the log titer of R17 for Compound 6 of the present invention.
Figure 12:
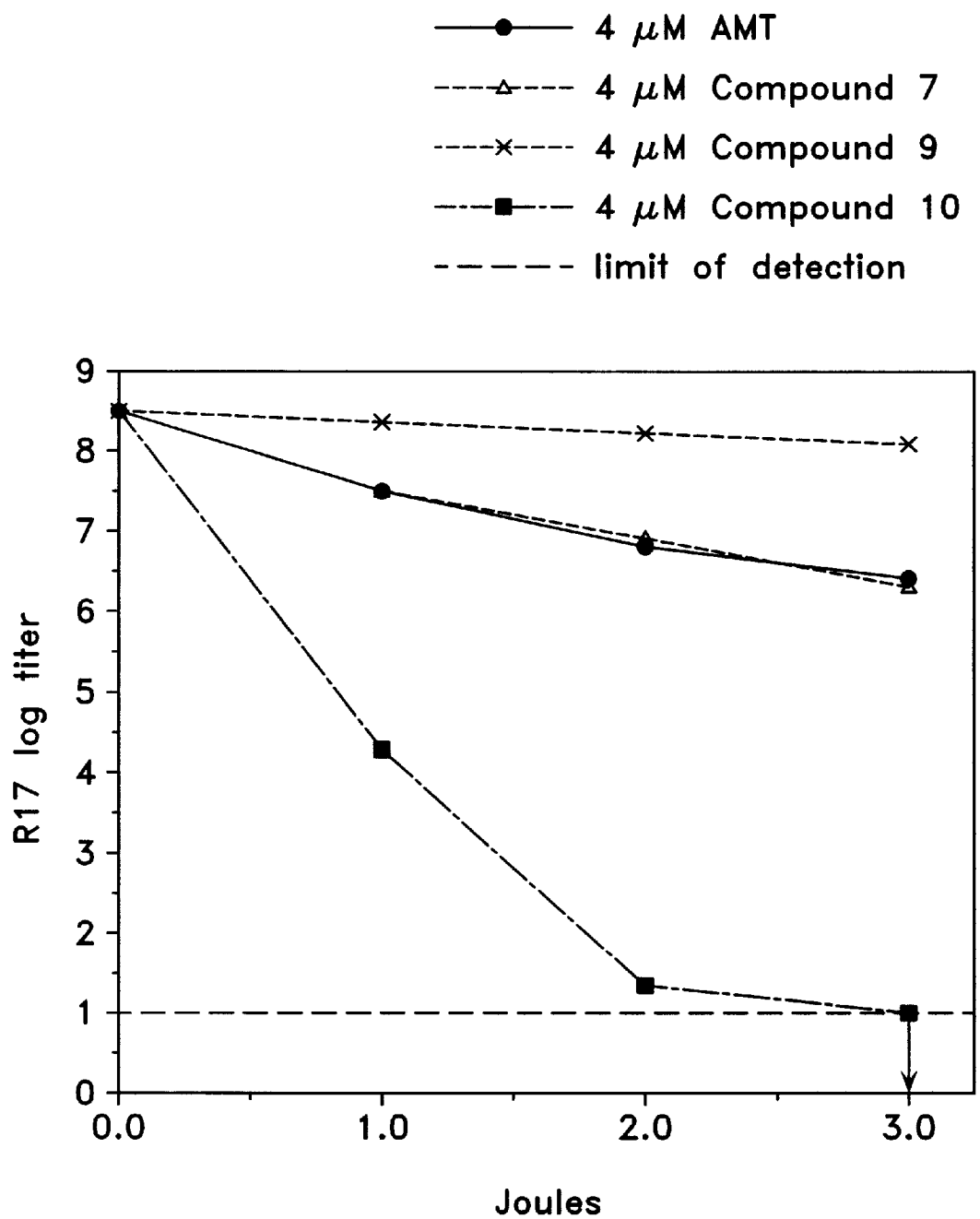
FIG. 12 shows the impact of varying Joules/$cm^2$ of irradiation on the log titer of R17 for Compounds 7, 9 and 10 of the present invention.
Figure 13:
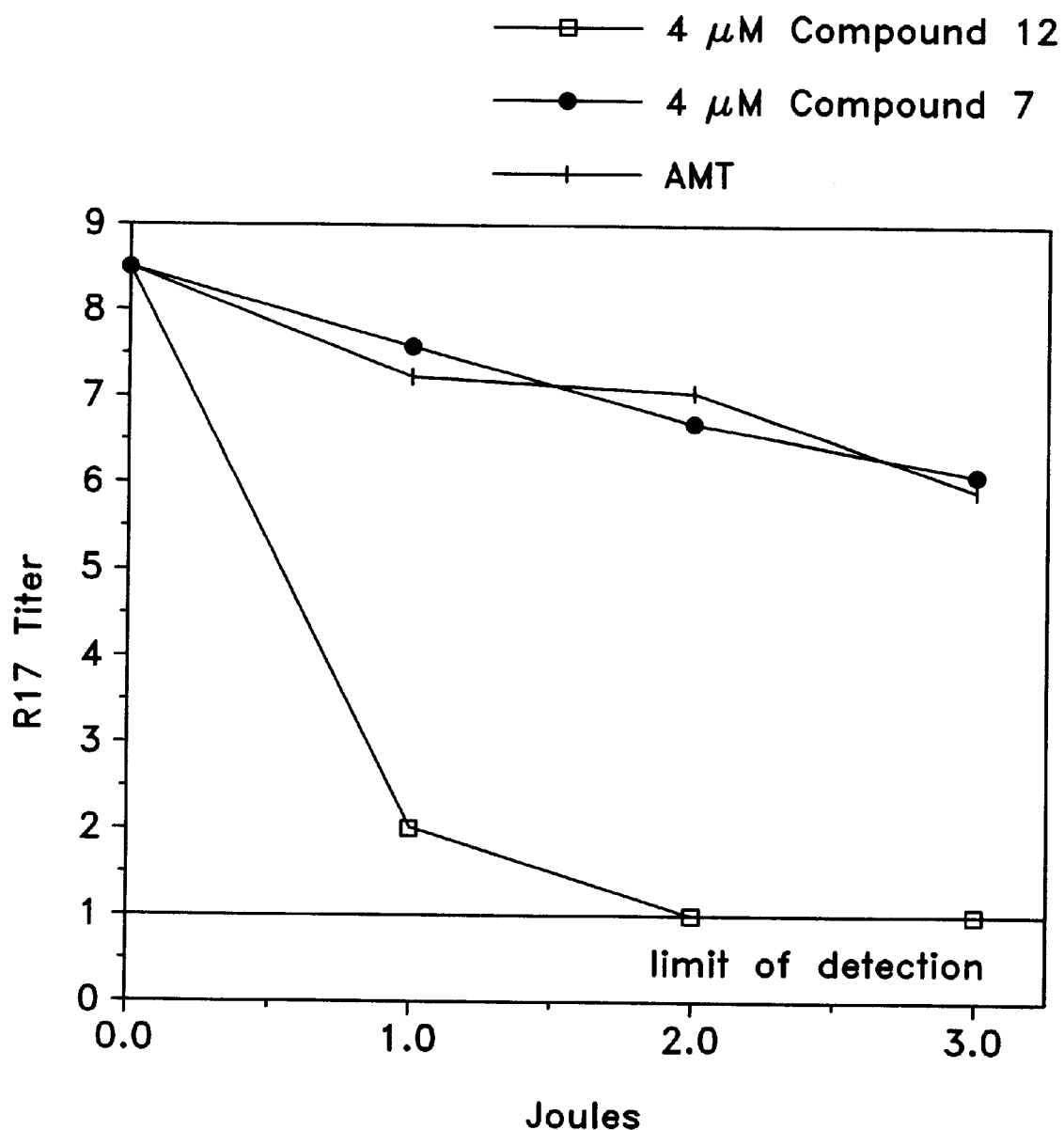
FIG. 13 shows the impact of varying Joules/$cm^2$ of irradiation on the log titer of R17 for Compounds 7 and 12 of the present invention.
Figure 14:
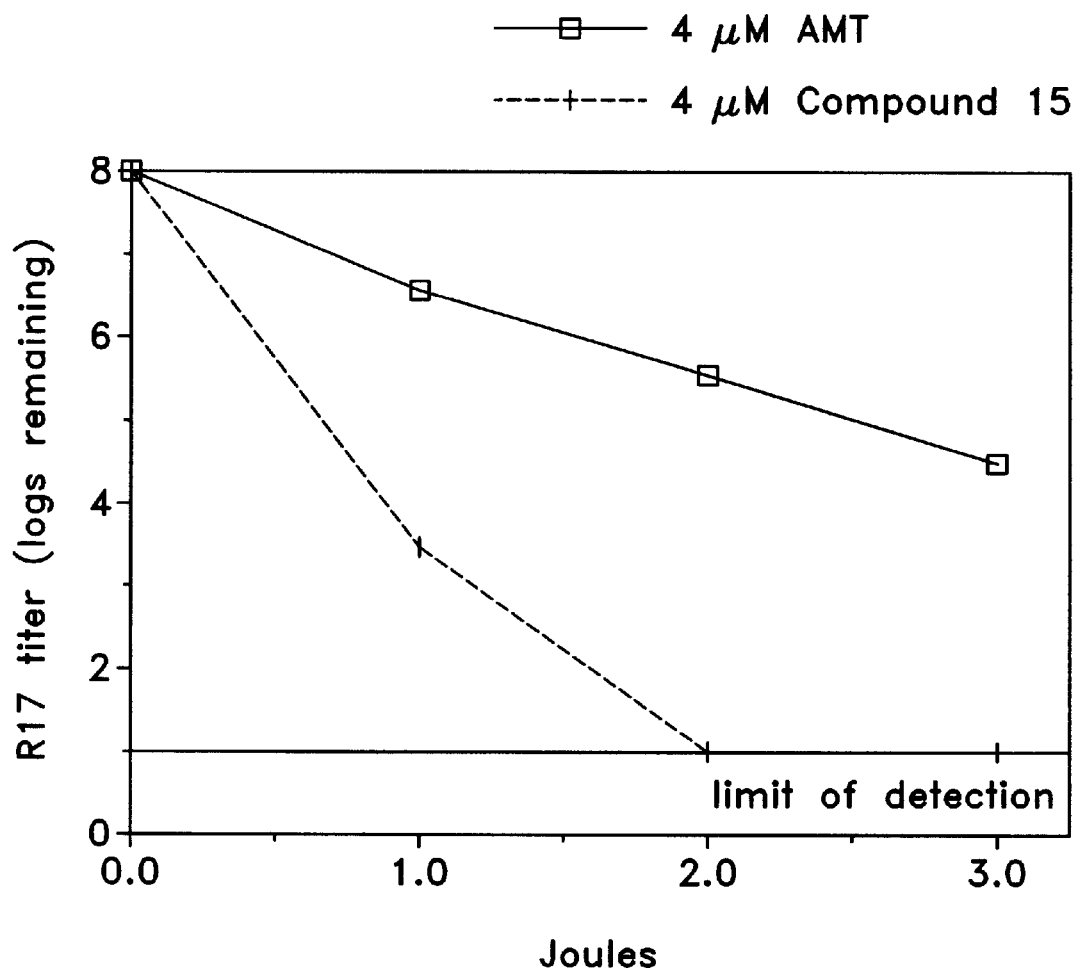
FIG. 14 shows the impact of varying Joules/$cm^2$ of irradiation on the log titer of R17 for Compound 15 of the present invention.
Figure 15:
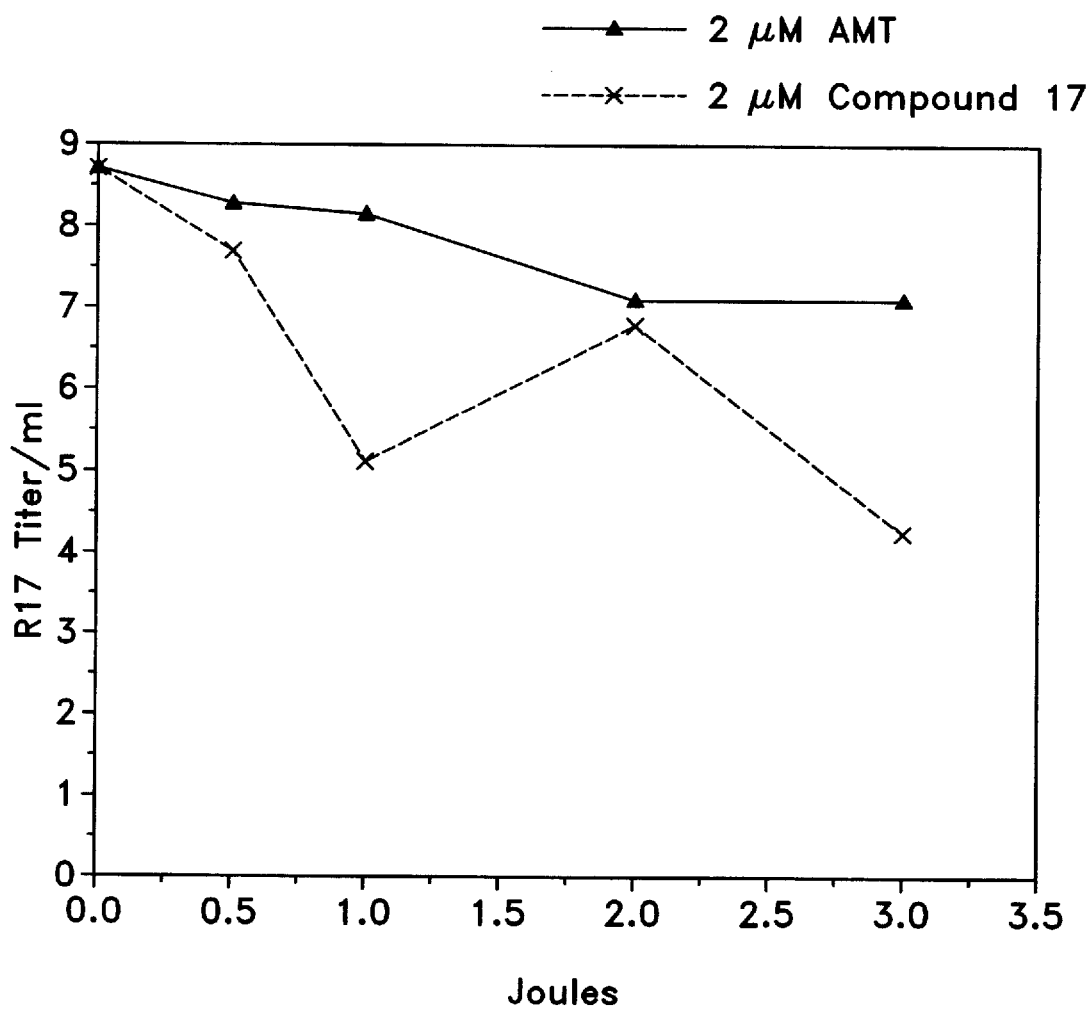
FIG. 15 shows the impact of varying Joules/$cm^2$ of irradiation on the log titer of R17 for Compound 17 of the present invention.
Figure 16:
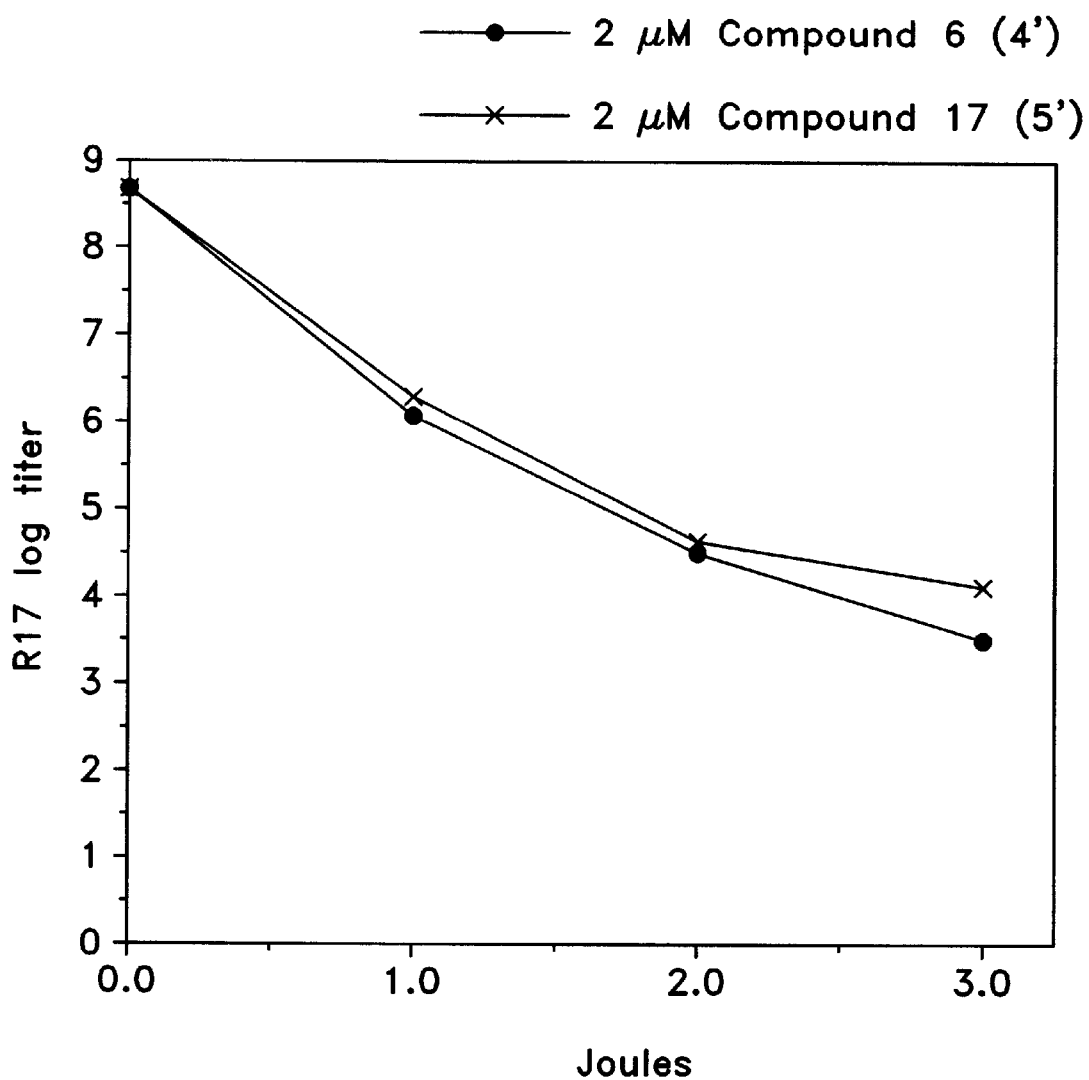
FIG. 16 shows the impact of varying Joules/$cm^2$ of irradiation on the log titer of R17 for Compounds 6 and 17 of the present invention.
Figure 17:
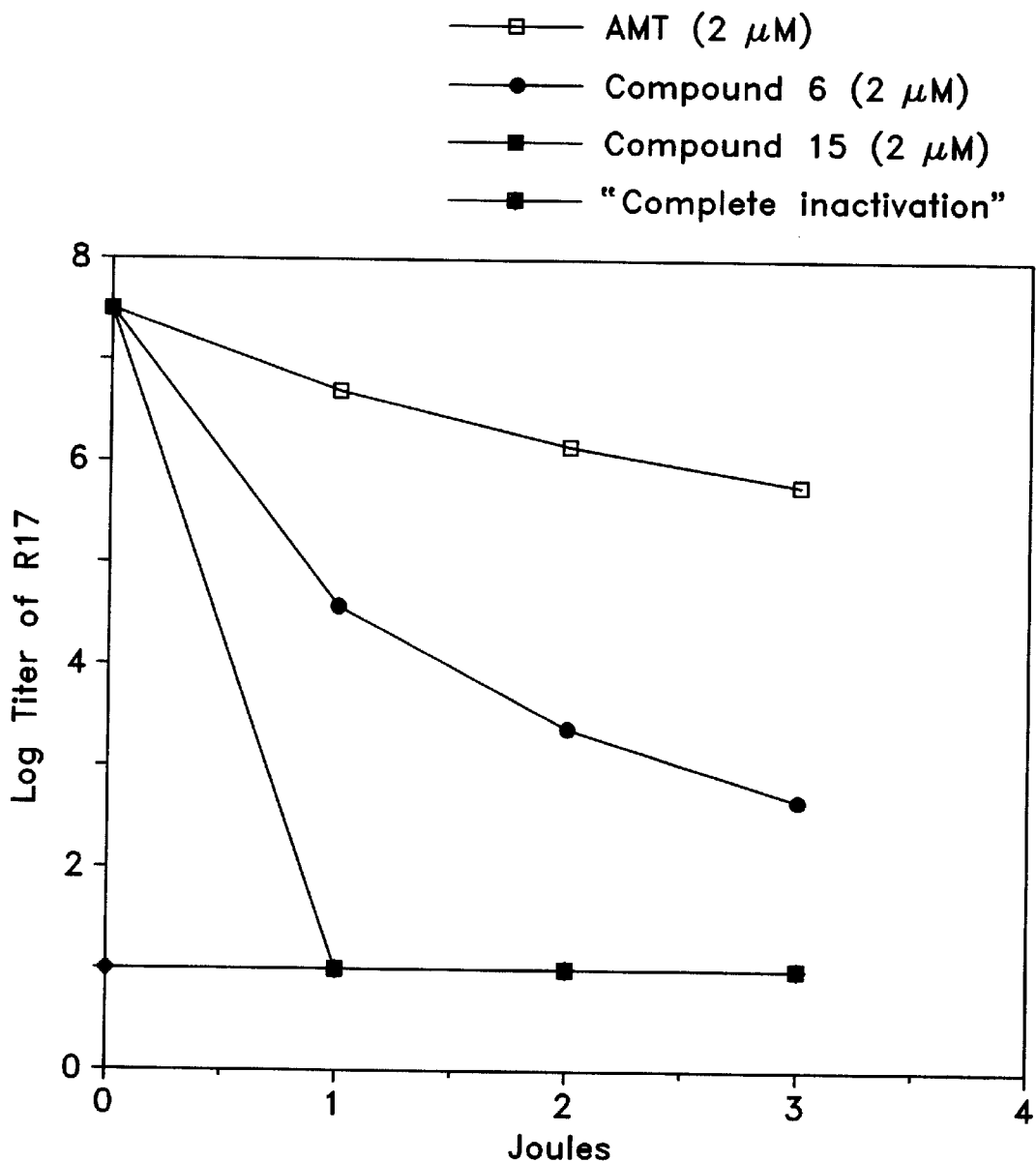
FIG. 17 shows the impact of varying Joules/$cm^2$ of irradiation on the log titer of R17 for Compounds 6 and 15 of the present invention.

Tables 6–9, below, and FIGS. 6–8 show the results of the R17 assay for several of the 4'-primaryamino-substituted psoralen compounds of the present invention. The data in Tables 7 and 8 appears in FIGS. 6 and 7, respectively. 5'-rimaryamino-substituted psoralen compounds of the present invention, which have substitutions on the 5' position similar to the 4'-primaryamino-substituted psoralen compounds, were also tested at varying concentration, as described above in this example, and are shown to exhibit comparable inactivation efficiency. The results for these compounds are shown in FIGS. 9 and 10, below.

TABLE 6

Starting Titer Of R17: Approx. 7.5 Logs 1 Minute Irradiation

| Compound | R17 log kill (32 μM) |
|---|---|
| AMT | >6.7 |
| 8-MOP | 0 |
| 1 | >6.6 |

TABLE 7

Starting Titer Approx. 7.2 Logs R17 1 Minute Irradiation

| | R17 Log Kill | | |
|---|---|---|---|
| Compound | 8 μM | 16 μM | 32 μM |
| AMT | 2.7 | 4.6 | >6.2 |
| 1 | 1.7 | 2.8 | 5.3 |
| 2 | 3.8 | >6.2 | >6.2 |
| 3 | >6.2 | >6.2 | >6.2 |

TABLE 8

Starting Titer Approx. 7.1 Logs 1 Minute Irradiation = 1.2 J/cm$^2$

| | R17 Log Kill | | | |
|---|---|---|---|---|
| Compound | 8 μM | 16 μM | 32 μM | 64 μM |
| AMT | — | 4.5 | 4.8 | — |
| 3 | 5.6 | >6.1 | — | — |
| 4 | — | 2.3 | 4.3 | >6.1 |
| 5 | — | 5.6 | >6.1 | >6.1 |
| 6 | — | >6.1 | >6.1 | >6.1 |

TABLE 9

Starting Titer Approx. 7.1 Logs R17.1 Minute Irradiation

| | R17 Log Kill | | | |
|---|---|---|---|---|
| Compound | 8 μM | 16 μM | 32 μM | 64 μM |
| AMT | — | >6 | >6 | — |
| 6 | >6 | >6 | — | — |
| 7 | — | >6 | >6 | >6 |

The compounds of the present invention having substitutions on the 4' position of the psoralen ring proved to be active in killing R17, as shown in the tables above. In Table 7, it is apparent that compound 1 of the present invention exhibits much higher R17 inactivation efficiency than does 8-MOP. As shown in Table 7 and FIG. 6, Compound 1 is one of the less active compounds of the present invention. Both Compounds 2 and 3 show higher log inactivation than Compound 1 at each concentration point. These results support that the compounds of the present invention are generally much more active than 8-MOP.

The compounds of the present invention also have similar or better R17 inactivation efficiency than AMT. In Tables 7 and 8, and FIGS. 6–10, all compounds of the present invention achieve R17 log inactivation at levels comparable to AMT. Compounds 2 and 3 (Table 6, FIG. 6), Compounds 5 and 6 (Table 8, FIG. 7), and Compound 16 (FIG. 10) exhibit significantly higher inactivation efficiency than does AMT.

Compounds of the present invention were also tested at a constant concentration for varying doses of UV light. Three sets of 1.5 mL tubes were prepared containing 0.6mL aliquots of R17 in DMEM (prepared as described above). The compound tested was added at the desired concentration and the samples were vortexed. The samples were then irradiated at intervals of 1.0 J/cm$^2$, until 3.0 J/cm$^2$ was reached. Between each 1.0 J/cm$^2$ interval, 100 μL was removed from each sample and placed in the first corresponding dilution tube, then five sequential dilutions were performed for each compound tested, at all 3 irradiation doses, as described above in this example.

Then 50 μL of Hfr 3000 bacteria was added to each tube, 3 mL of top agar was added and the tube contents were vortexed The contents of each tube was poured into its own LB plate and the plates were incubated overnight at 37° C. Plaques were counted by visual inspection the following morning.

The results of the assay for several 4' and 5'-primaryamino-substituted psoralen compounds are shown in FIGS. 11–17. This data further supports that the compounds of the present invention are comparable to AMT in their ability to inactivate R17. Further, Compounds 6 (FIG. 11), 10 (FIG. 12), 12 (FIG. 13), 15 (FIG. 14 and 17), and Compound 17 (FIG. 15), all were more efficient at inactivating R17 than was AMT.

EXAMPLE 13

Pathogen inactivation efficiency of several compounds of the present invention was evaluated by examining the ability of the compounds to inactivate cell-free virus (HIV). Inactivation of cell-free HIV was performed as follows.

As in the R17 assay, small aliquots of the compounds listed in TABLES 10 and 11, below, at the concentrations listed in the table, were added to stock HIV-1 to a total of 0.5 mL. The stock HIV ($10^5$–$10^7$ plaque forming units/mL) was in DMEM15% FBS. The 0.5 mL test aliquots were placed in 24-well polystyrene tissue culture plates and irradiated with 320–400 nm (20 mW/cm$^2$) for 1 min on a device similar to the device of Example 1. The photoactivation device used here was previously tested and found to result in light exposure comparable to the Device of Example 1. (Data not shown). Controls included HIV-1 stock only, HIV-1 plus UVA only, and HIV-1 plus the highest concentration of each psoralen tested, with no UVA. Post irradiation, all samples were store frozen at −70° C. until assayed for infectivity by a microtiter plaque assay. Aliquots for measurement of residual HIV infectivity in the samples treated with a compound of the present invention were withdrawn and cultured.

Residual HIV infectivity was assayed using an MT-2 infectivity assay. (Previously described in Hanson, C. V., Crowford-Miksza, L. and Sheppard, H. W., J. Clin. Micro 28:2030 (1990)). The assay medium was 85% DMEM (with a high glucose concentration) containing 100 µg of streptomycin, 100 U of penicillin, 50 µg of gentamicin, and 1 µg of amphotericin B per mL, 15% FBS and 2 µg of Polybrene (Sigma Chemical Co., St. Louis, Mo.) per mL. Test and control samples from the inactivation procedure were diluted in 50% assay medium and 50% normal human pooled plasma The samples were serially diluted directly in 96-well plates (Corning Glass Works, Corning, N.Y.). The plates were mixed on an oscillatory shaker for 30 seconds and incubated at 37° C. in a 5% $CO_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.) and prewarmed to 38.5° C. was added to each well. The plates were kept at 37° C. for a few minutes until several plates had accumulated and then centrifuged in plate carriers at 600×g for 20 minutes in a centrifuge precooled to 10° C. In the centrifuge, cell monolayers formed prior to gelling of the agarose layer. The plates were incubated for 5 days at 37° C. in 5% $CO_2$ and stained by the addition of 0.05 mL of 50 µg/mL propidium iodide (Sigma Chemical Co.) in phosphate-buffered saline (pH 7.4) to each well. After 24 to 48 hours, the red fluorescence-stained microplaques were visualized by placing the plates on an 8,000 µW/$cm^2$304 nm UV light box (Fotodyne, Inc., New Berlin, Wis.). The plaques were counted at a magnification of x20 to x25 through a stereomicroscope. The results are shown in TABLES 10 and 11, below. "n" represents the number of runs for which the data point is an average.

The results support that the compounds of the present invention are effective in inactivating HIV. In fact, the data for concentrations of 64 µM of compound or higher suggests that compounds 2 and 3 are significantly more active than AMT, which was previously thought to be one of the most active anti-viral psoralens. At lower concentrations, Compound 6 is able to kill a higher log of HIV (3.1 logs at 32 µM) than is AMT (2.5 logs at 32 µM). The other compounds listed in TABLE 9 display inactivation efficiency in the same range as AMT.

TABLE 10

1 Minute Irradiation HIV Starting Titer: Approximately 5 Logs

| | HIV Log Kill | | | |
|---|---|---|---|---|
| Compound | 16 µM | 32 µM | 64 µM | 128 µM |
| AMT | 1.4 | 1.9->3.6 | 3.9->3.6 | >4.1 |
| 1 | — | — | 2.1 | >2.8 |
| 2 | 1.4 | 3.8 | >4.5 | >4.5 |
| 3 | — | 2.7 | >3.8 | >3.8 |
| 4 | — | 2.2 | >3.6 | >3.6 |
| 5 | 0.9 | 1.3 | >2.6 | — |
| 6 | 2.0 | 3.1 | >3.8 | — |
| 7 | 0.8 | 2.1 | 3.5 | — |
| 8 | 1.1 | 1.9 | 3.7 | >3.7 |

TABLE 11

HIV Starting Titer: Approximately 5.4 Logs 1 Minute Irradiation

| | HIV Log Kill | | |
|---|---|---|---|
| Compound | 16 µM | 32 µM | 64 µM |
| 6 | 2.1 | 3.2 | >2.8 |
| 9 | 0.8 | 1.4 | 2.7 |
| 10 | 2.0 | >3.5 | >3.5 |
| 12 | 0.4 | 0.8 | 1.3 |
| 17 | 1.2 | 2.9 | 3.4 |
| 18 | 1.0 | 1.0 | 3.1 |

EXAMPLE 14

This example describes the protocol for inactivation of Duck Hepatitis B Virus (DHBV), a model for Hepatitis B Virus, using compounds of the present invention.

DHBV in duck yolk was added to platelet concentrate (PC) to a final concentration of $2 \times 10^7$ particles per mL and mixed by gentle rocking for $\geq 15$ min. Psoralens S-70, S-59 and AMT were added to 3 mL aliquots of PC in a Teflon™ mini-bag at concentrations of 35, 70, and 100 mM. Samples, including controls without added psoralen, were irradiated with 5 J/$cm^2$ UVA, with mixing at 1 J/$cm^2$ increments. After irradiation, leukocytes and platelets were separated from virus by centrifugation. The supernatant containing DHBV was digested overnight with 50 µg/mL proteinase K in a buffer containing 0.5% sodium dodecyl sulphate, 20 mM Tris buffer, pH 8.0, and 5 mM EDTA at 55° C. Samples were extracted with phenol-chloroform and chloroform, followed by ethanol precipitation. Purified DNA was then used in PCR amplification reactions with a starting input of $10^6$ DHBV genomes from each sample. PCR amplicons were generated using primers pairs DCD03/DCD05 (127 bp), DCD03/DCD06 (327 bp) and DCD03/DCD07 (1072 bp). PCR was performed in a standard PCR buffer containing 0.2 mM each deoxyribonucleoside 5'-triphosphates (dATP, dGTP, dCTP, and dTTP), 0.5 mM each primer, and 0.5 units Taq polymerase per 100 ml reaction. 30 cycles of amplification were performed with the following thermal profile: 95° C. 30 sec, 60° C. 30 sec, 72° C. 1 min. The amplification was followed by a 7 min incubation at 72° C. to yield full length products. [lambda-$^{32}$P] dCTP was added at an amount of 10 mCi per 100 ml in order to detect and quantify the resulting products. Products were separated by electrophoresis on denaturing polyacrylamide slab gels and counted. The absence of signal in a given reaction was taken to indicate effective inactivation of DHBV.

The results showed that the smaller amplicons displayed increasing inactivation as a function of psoralen concentration for all psoralens tested. At the same concentrations, S-59 and S-70 inhibited PCR of the smaller amplicons better than did AMT. For the 1072 bp anplicon, complete inhibition of PCR was observed at all concentrations of S-59 and S-70, whereas the sample without psoralen gave a strong signal. AMT inhibited PCR amplification of the 1072 bp amplicon at the 70 and 100 mM levels, but a signal could be detected when AMT was used at 35 mM final concentration.

EXAMPLE 15

In Example 13, the compounds of the present invention were tested for their ability to inactivate virus in DMEM/ 15% FBS. In this example, the compounds are tested in both 100% plasma and predominantly synthetic media, to show that the methods of the present invention are not restricted to any particular type of medium.

For the samples in synthetic media: standard human platelet concentrates were centrifuged to separate plasma. Eighty-five percent of the plasma was then expressed off and replaced with a synthetic medium (referred to as "Sterilyte™3.0") containing 20 mM Na acetate, 2 mM glucose, 4 mM KCl, 100 mM NaCl, 10 mM $Na_3$ Citrate, 20 mM $NaH_2PO_4/Na_2HPO_4$, and 2 mM $MgCl_2$. H9 cells infected with HIV were added to either the 85% Sterilyte™3.0 platelet concentrates or standard human platelet concentrates ($2.5 \times 10^7$ cells per concentrate), final concentration $5 \times 10^5$ cells/mL. The platelet concentrates were placed in Teflon™ modified FL20 or Teflon™ Minibags (American Fluoroseal Co., Silver Springs, Md.), treated with one of the compounds shown in FIGS. 18 and 19, at the concentrations shown, and then irradiated with 320–400 nm (20 mW/cm$^2$) for 5 J/cm$^2$ (for plasma samples) or 2 J/cm$^2$ (for 85% Sterilyte™3.0 samples) on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured.

Figure 18:
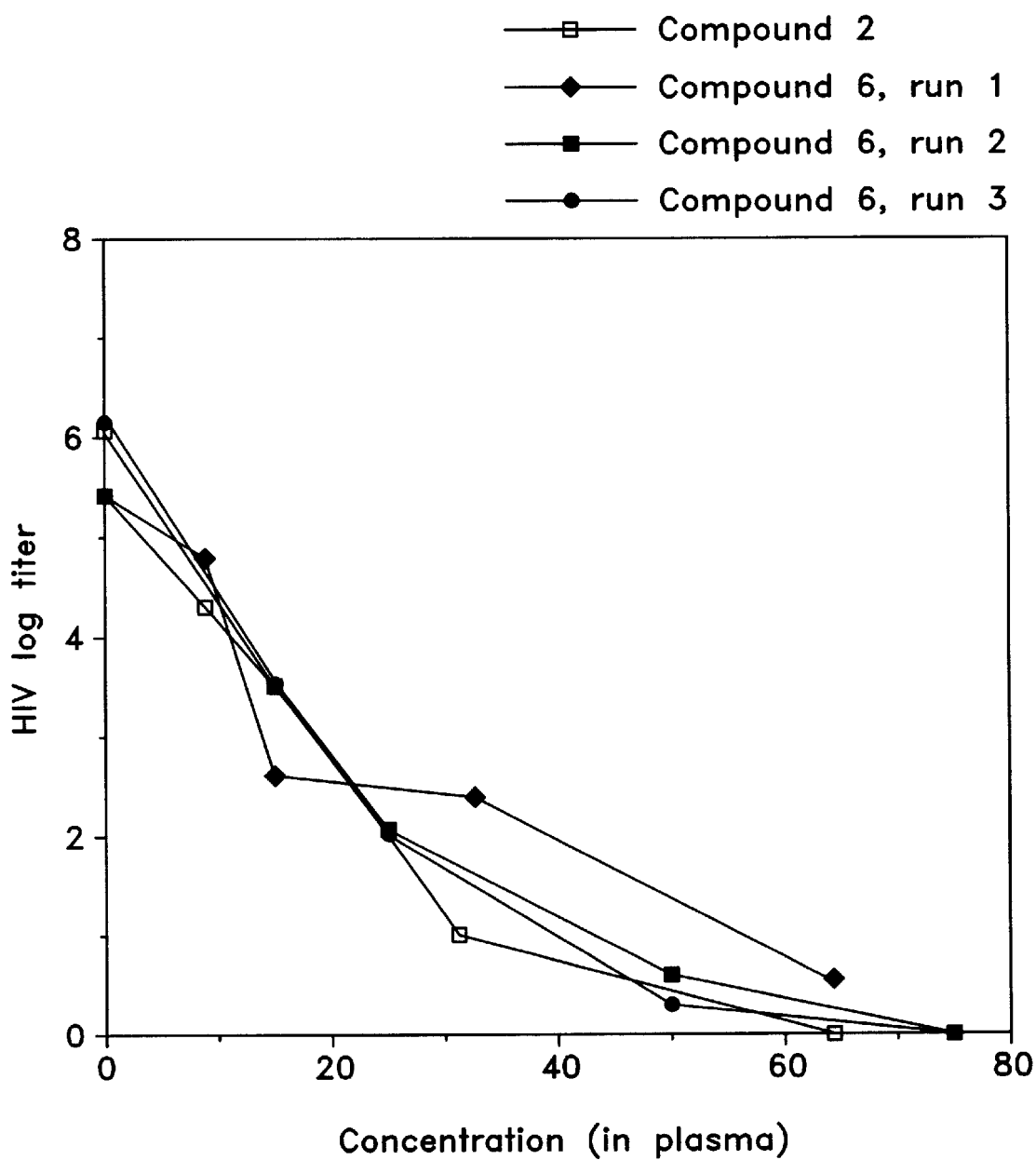
FIG. 18 shows the effect of varying the concentration of Compounds 2 and 6 of the present invention, in plasma.
Figure 19:
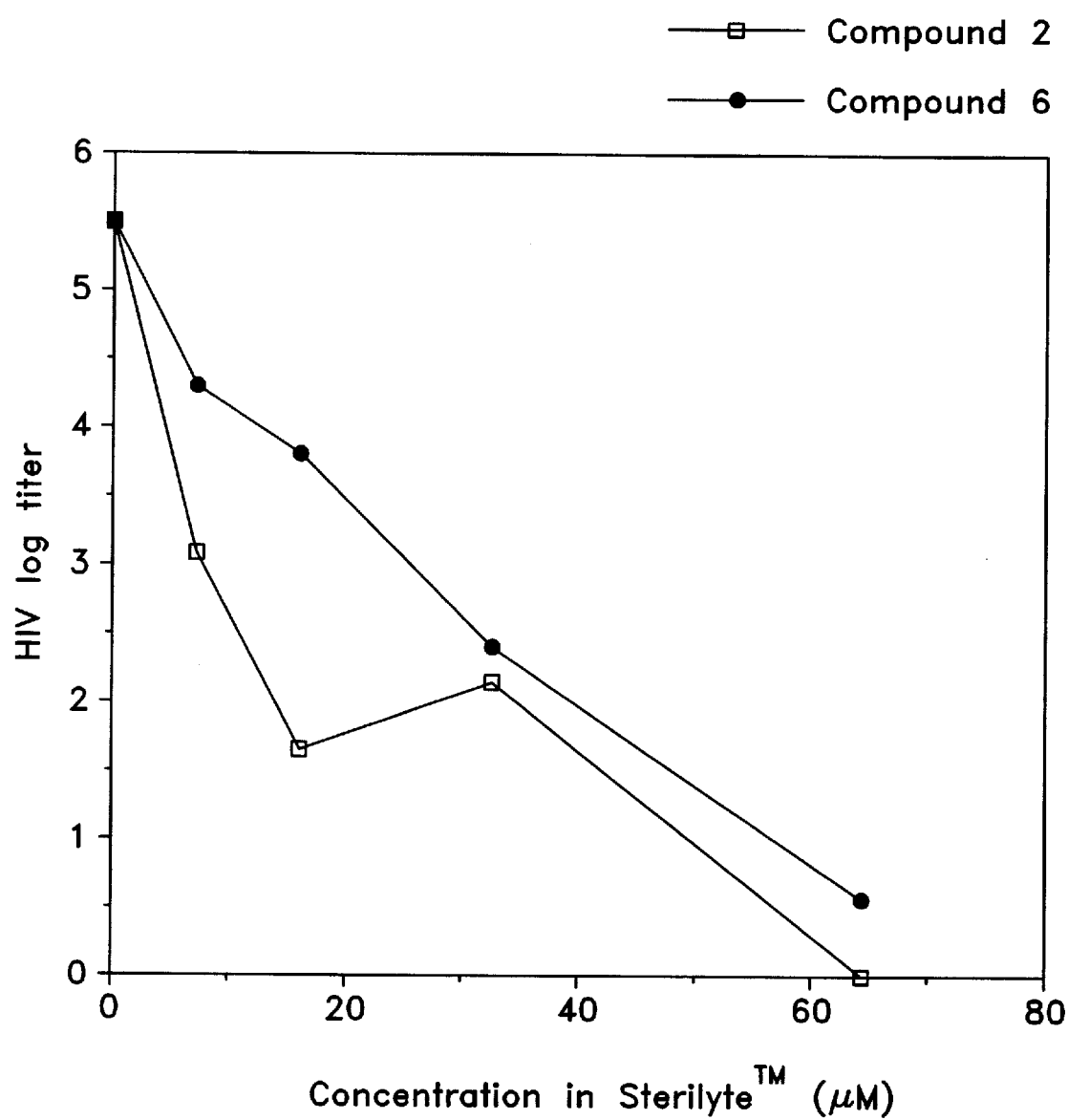
FIG. 19 shows the effect of varying the concentration of Compounds 2 and 6 of the present invention, in synthetic medium.

For samples run in plasma: H9 cells infected with HIV were added to standard human platelet concentrates ($2.5 \times 10^7$ cells per concentrate), final concentration $5 \times 10^5$ cells/mL. Aliquots of HIV contaminated platelet concentrate (5 mL) were placed in water jacketed Pyrex chambers. The chambers had previously been coated on the inside with silicon. The platelet concentrates were treated with one of the compounds listed in TABLES 10 and 11, below, at the concentrations listed in the table, and then irradiated with 320–400 nm (20 mW/cm$^2$) for 1 minute on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured. Residual HIV infectivity was assayed for both the plasma and the 85% Sterilyte™ samples using an MT-2 infectivity assay. (Detailed in Example 13, above, and previously described in Hanson, C. V., et al., J. Clin. Micro 28:2030 (1990)). The results are shown in FIGS. 18 and 19.

The results support that the compounds of the present invention are effective in inactivating HIV in both plasma and synthetic medium. Comparing FIGS. 18 and 19, the inactivation curves appear to be the same, both achieving approximately 5 logs of inactivation at 64 µM concentrations of compound. However, the inactivation in synthetic media was performed with only 2 J/cm$^2$ irradiation, 3 J/cm$^2$ less than that required to achieve the same inactivation in plasma Thus, it appears from the data that synthetic media facilitates the inactivation methods of the present invention.

EXAMPLE 16

In this example bacterial inactivation by the photoreactive nucleic acid binding compounds of the present invention was measured as a function of the ability of the bacteria to subsequently replicate. A gram negative bacteria was chosen as representative of the more difficult bacterial strains to inactivate.

The bacteria, a strain of Pseudomonas, was inoculated into LB with a sterile loop and grown overnight in a shaker at 37° C. Based on the approximation that one OD at 610 mn is equivalent to $5 \times 10^8$ colony forming units (cfu)/mL, a 1:10 dilution of the culture was measured on a spectrophotometer, (manufactured by Shimatsu). The bacterial culture was added to a solution of 15% fetal bovine serum in DMEM to a final bacteria concentration of approximately $10^6$/mL. An aliquot (0.8 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at a concentration of 16 µM. The tubes were placed in a light device as described in EXAMPLE 1 and irradiated with 1.3 J/cm$^2$, 1.2 J/cm$^2$, and finally 2.5 J/cm$^2$, for a total of 5 J/cm$^2$. 150 µL were removed for testing after each pulse period. Sterile 13 mL dilution tubes were prepared; each test compound required one tube with 0.4 mL of LB broth and four tubes containing 0.5 mL of LB broth. To make the dilutions, a 0.050 mL aliquot of the irradiated solution of phage and test compound was added to the first dilution tube of 0.5 mL of media then 0.050 mL of this solution was added to the second tube of 0.5 mL medium (1:10). The second solution was then diluted serially (1:10) into the remaining tubes. 100 µL of the original sample and each dilution are plated separately onto LB agar plates and incubated at 37° C. overnight. The colony forming units were then counted the following morning and the titer of the phage remaining after phototreatment was calculated based on the dilution factors.

The following controls were run: the "bacteria only" in which bacteria was not treated with test compound and not irradiated (listed as "starting titer" in the tables below); the "UV only" in which the bacteria was irradiated in the absence of test compound. Dark controls were not performed here for reasons set forth in Example 12 above.

The results were as follows. The starting titer of bacteria was 6.5 logs. After 5 J/cm$^2$ irradiation, the log kill for the various compounds tested were as follows: 8-MOP—1.9 logs, AMT—5.2 logs, Compound 2—>5.5, Compound 6—>5.5. From these results, it is clear that the compounds of the present invention are more efficient than both AMT and 8-MOP at inactivating a gram negative bacteria.

EXAMPLE 17

In the above examples, psoralens of the present invention have been demonstrated to be effective for inactivating pathogens, such as bacteria (Pseudomonas), bacteriophage (R17) and viruses (HIV and DHBV). Without intending to be limited to any method by which the compounds of the present invention inactivate pathogens, it is believed that inactivation results from light induced binding of the psoralens to the nucleic acid of the pathogens. As discussed above, AMT is known both for its pathogen inactivation efficiency and its accompanying mutagenic action in the dark at low concentrations. In contrast, the less active psoralens, such as 8-MOP, that have been examined previously, show significantly less mutagenicity. This example establishes that photobinding and mutagenicity are not linked phenomenon in the compounds of the present invention. The psoralens of the present invention have exceptional pathogen inactivation efficiency while displaying only minimal mutagenicity.

In this example the compounds of the present invention are tested for their dark mutagenicity using an Ames assay. The procedures used for the Salmonella mutagenicity test as described in detail by Maron and Ames were followed exactly. Maron, D. M. and B. N. Ames, Mutation Research 113: 173 (1983). A brief description for each procedure is given here. The tester strains TA97a, TA98, TA100, TA102, TA1537 and TA1538 were obtained from Dr. Ames. TA97a, TA98, TA1537 and TA1538 are frameshift tester strains. TA100 and TA102 are base-substitution tester strains. Upon receipt each strain was cultured under a variety of conditions to confirm the genotypes specific to the strains.

The standard Salmonella tester strains used in this study require histidine for growth since each tester strain contains a different type of mutation in the histidine operon. In addition to the histidine mutation, these tester strains contain other mutations, described below, that greatly increase their ability to detect mutagen.

Histidine Dependence: The requirement for histidine was tested by streaking each strain first on a minimal glucose plate supplemented only with biotin and then on a minimal glucose plate supplemented with biotin and histidine. All strains grew the lack of growth of the strains in the absence of histidine.

rfa Mutation: A mutation which causes partial loss of the lipopolysaccharide barrier that coats the surface of the bacteria thus increasing permeability to large molecules was confirmed by exposing a streaked nutrient agar plate coated with the tester strain to crystal violet. First, 100 µL of each culture was added to 2 mL of molten minimal top agar and poured onto a nutrient agar plate. Then a sterile filter paper disc saturated with crystal violet was placed at the center of each plate. After 16 hours of incubation at 37° C. the plates were scored and a clear zone of no bacterial growth was found around the disc, confirming the rfa mutation.

uvrB Mutation: Three strains used in this study contain a deficient UV repair system (TA97a, TA98, TA100, TA1537 and TA1538). This trait was tested for by streaking the strains on a nutrient agar plate, covering half of the plate, and irradiating the exposed side of the plate with germicidal lamps. After incubation growth was only seen on the side of the plate shielded from UV irradiation.

R-factor: The tester strains (TA97a, TA98, TA100, and TA102) contain the pKM101 plasmid that increases their sensitivity to mutagens. The plasmid also confers resistance to ampicillin to the bacteria This was confirmed by growing the strains in the presence of ampicillin.

pAQ1: Strain TA102 also contains the pAQ1 plasmid that further enhances its sensitivity to mutagens. This plasmid also codes for tetracycline resistance. To test for the presence of this plasmid TA102 was streaked on a minimal glucose plate containing histidine, biotin, and tetracycline. The plate was incubated for 16 hours at 37° C. The strain showed normal growth indicating the presence of the pAQ1 plasmid.

The same cultures used for the genotype testing were again cultured and aliquots were frozen under controlled conditions. The cultures were again tested for genotype to confirm the fidelity of the genotype upon manipulation in preparing the frozen permanents.

The first tests done with the strains were to determine the range of spontaneous reversion for each of the strains. With each mutagenicity experiment the spontaneous reversion of the tester strains to histidine independence was measured and expressed as the number of spontaneous revertants per plate. This served as the background controls. A positive mutagenesis control was included for each tester strain by using a diagnostic mutagen suitable for that strain (2-aminofluorene at 5mg/plate for TA98 and sodium azide at 1.5 mg/plate for TA100).

For all experiments, the pre-incubation procedure was used. In this procedure one vial of each tester strain was thawed and 20 µL of this culture was added to 6 mL of Oxoid Nutrient Broth #2. This solution was allowed to shake for 10 hours at 37° C. In the pre-incubation procedure, 0.1 mL of this overnight culture was added to each of the required number of sterile test tubes. To half of the tubes 0.5 mL of a 10% S-9 solution containing Aroclor 1254 induced rat liver extract (Molecular Toxicology Inc., Annapolis, Md.), and $MgCl_2$, KCl, glucose-6-phosphate, NADP, and sodium phosphate buffer (Sigma, St. Louis, Mo.) were added. To the other half of the tubes 0.5 mL of 0.2M sodium phospate buffer, pH 7.4, was used in place of the S-9 mixture (the—S9samples). Finally 0.1 mL of the test solution containing either 0, 0.1, 0.5, 1, 5, 10, 50, 100, 250, or 500 µg/mL of the test compound was added. The 0.7 mL mixture was vortexed and then pre-incubated while shaking for 20 minutes at 37° C. After shaking, 2 mL of molten top agar supplemented with histidine and biotin were added to the 0.7 mL mixture and immediately poured onto a minimal glucose agar plate (volume of base agar was 20 mL). The top agar was allowed 30 minutes to solidify and then the plates were inverted and incubated for 44 hours at 37° C. After incubation the number of revertant colonies on each plate were counted. The results appear in TABLES 12 (A)–18 (B), below. ("n" represents the number of replicates performed for each data point.)

TABLE 12 (A)

| | AMT | | | | | |
|---|---|---|---|---|---|---|
| Dose | Strain | | | | | |
| µg/plate | TA97a − S9 | TA97a + S9 | TA98 − S9 | TA98 + S9 | TA100 − S9 | TA100 + S9 |
| 0 | 109 | 158 | 20 | 25 | 126 | 123 |
| | n = 23 | n = 39 | n = 38 | n = 53 | n = 41 | n = 56 |
| 0.1 | 14 | −23 | 3 | 1 | −10 | −16 |
| | n = 3 | n = 6 | n = 3 | n = 6 | n = 3 | n = 6 |
| 0.5 | 9 | 32 | 5 | 3 | 13 | −12 |
| | n = 3 | n = 6 | n = 3 | n = 6 | n = 3 | n = 6 |
| 1 | 54 | 32 | 5 | 21 | 17 | −19 |
| | n = 3 | n = 6 | n = 3 | n = 6 | n = 3 | n = 6 |
| 5 | 73 | 149 | 16 | 232 | 59 | −6 |
| | n = 3 | n = 6 | n = 6 | n = 9 | n = 9 | n = 12 |
| 10 | | | 20 | 403 | 105 | 17 |
| | | | n = 9 | n = 9 | n = 15 | n = 15 |
| 50 | | | 69 | 620 | 73 | 52 |
| | | | n = 9 | n = 9 | n = 9 | n = 9 |

TABLE 12 (A)-continued

AMT

| Dose μg/plate | TA97a − S9 | TA97a + S9 | TA98 − S9 | TA98 + S9 | TA100 − S9 | TA100 + S9 |
|---|---|---|---|---|---|---|
| 100 | | | 114<br>n = 9 | 745<br>n = 9 | 75<br>n = 9 | 85<br>n = 9 |
| 250 | | | 112<br>n = 6 | 933<br>n = 6 | 24<br>n = 6 | 89<br>n = 6 |
| Positive Control | | 5 μg/plate<br>2-Amino<br>fluorene<br>808<br>n = 21 | | 5 μg/plate<br>2-Amino-<br>fluorene<br>1154<br>n = 35 | 1.5 μg/plt<br>sodium<br>azide<br>965<br>n = 38 | |

TABLE 12 (B)

AMT

| Dose μg/plate | TA102 − S9 | TA102 + S9 | TA1537 − S9 | TA1537 + S9 | TA1538 − S9 | TA1538 + S9 |
|---|---|---|---|---|---|---|
| 0 | 346<br>n = 26 | 404<br>n = 41 | 9<br>n = 30 | 9<br>n = 45 | 15<br>n = 30 | 19<br>n = 42 |
| 0.1 | 27<br>n = 3 | −20<br>n = 6 | 0<br>n = 3 | 2<br>n = 6 | 3<br>n = 3 | 3<br>n = 6 |
| 0.5 | 47<br>n = 3 | 5<br>n = 6 | 3<br>n = 9 | 2<br>n = 12 | 4<br>n = 9 | 13<br>n = 12 |
| 1 | 88<br>n = 3 | −17<br>n = 6 | 5<br>n = 9 | 3<br>n = 12 | 4<br>n = 9 | 37<br>n = 12 |
| 5 | 266<br>n = 3 | 51<br>n = 6 | 44<br>n = 9 | 22<br>n = 12 | 13<br>n = 18 | 177<br>n = 21 |
| 10 | | | 52<br>n = 9 | 30<br>n = 9 | 14<br>n = 9 | 255<br>n = 9 |
| 50 | | | 2688<br>n = 9 | 94<br>n = 9 | | |
| 100 | | | 2058<br>n = 9 | 686<br>n = 9 | | |
| 250 | | | 434<br>n = 9 | 3738<br>n = 12 | | |
| Positive Control | 100 μg/pl<br>hydrogen<br>peroxide<br>660<br>n = 23 | | 10 μg/plt<br>9-Amino<br>acridine<br>284<br>n = 6 | 10 μg/plt<br>2-Amino-<br>fluorene<br>73<br>n = 24 | | 5 μg/plate<br>2-Amino-<br>fluorene<br>1064<br>n = 30 |

TABLE 13 (A)

8-MOP

| Dose μg/plate | TA102 − S9 | TA102 + S9 | TA1537 − S9 | TA1537 + S9 |
|---|---|---|---|---|
| 0 | 346<br>n = 26 | 404<br>n = 41 | 9<br>n = 30 | 9<br>n = 45 |
| 1 | −55<br>n = 14 | 46<br>n = 17 | | |
| 10 | −57<br>n = 14 | −27<br>n = 17 | | |
| 30 | | | 5<br>n = 3 | 1<br>n = 6 |
| 60 | | | 3<br>n = 3 | 1<br>n = 6 |
| 90 | | | −1<br>n = 3 | −4<br>n = 6 |
| 100 | 217<br>n = 14 | 290<br>n = 17 | | |
| 500 | 781<br>n = 11 | 1179<br>n = 11 | | |

TABLE 13 (A)-continued

8-MOP

| Dose μg/plate | TA102 − S9 | TA102 + S9 | TA1537 − S9 | TA1537 + S9 |
|---|---|---|---|---|
| Positive Control | 100 μg/plt<br>hydrogen<br>peroxide<br>660<br>n = 23 | | 10 μg/plt<br>9-Amino-<br>Acridine<br>284<br>n = 6 | 10 μg/plt<br>2-Amino-fluorene<br>73<br>n = 24 |

TABLE 13 (B)

8-MOP

| Dose μg/plate | TA102 − S9 | TA102 + S9 | TA1537 − S9 | TA1537 + S9 |
|---|---|---|---|---|
| 0 | 346<br>n = 26 | 404<br>n = 41 | 9<br>n = 30 | 9<br>n = 45 |

TABLE 13 (B)-continued

8-MOP

| Dose μg/plate | TA102 − S9 | TA102 + S9 | TA1537 − S9 | TA1537 + S9 |
|---|---|---|---|---|
| 1 | −55<br>n = 14 | −46<br>n = 17 | | |
| 10 | −57<br>n = 14 | −27<br>n = 17 | | |
| 30 | | | 5<br>n = 3 | 1<br>n = 6 |
| 60 | | | 3<br>n = 3 | 1<br>n = 6 |
| 90 | | | −1<br>n = 3 | −4<br>n = 6 |
| 100 | 217<br>n = 14 | 290<br>n = 17 | | |
| 500 | 781<br>n = 11 | 1179<br>n = 11 | | |
| Positive Control | 100 μg/plt<br>hydrogen<br>peroxid<br>660<br>n = 23 | | 10 μg/plt<br>9-Amino-<br>Acridine<br>284 | 10 μg/plt<br>2-Amino-<br>fluorene<br>73<br>n = 24 |

TABLE 14

Compound 1

| Dose μg/plate | TA100 − S9 | TA100 + S9 | TA1538 − S9 | TA1538 + S9 |
|---|---|---|---|---|
| 0 | 126<br>n = 41 | 123<br>n = 56 | 15<br>n = 30 | 19<br>n = 42 |
| 5 | 292<br>n = 3 | −24<br>n = 3 | 10<br>n = 3 | 21<br>n = 3 |
| 10 | 337<br>n = 3 | −22<br>n = 3 | 12<br>n = 3 | 22<br>n = 3 |
| Positive Control | 1.5 μg/plate<br>Sodium Azide<br>965<br>n = 38 | | | 5 μg/plate<br>2-Amino-<br>fluorene<br>1064<br>n = 30 |

TABLE 15 (A)

Compound 2

| Dose μg/plate | TA98 − S9 | TA98 + S9 | TA100 − S9 | TA100 + S9 |
|---|---|---|---|---|
| 0 | 20<br>n = 35 | 25<br>n = 50 | 126<br>n = 41 | 123<br>n = 56 |
| 5 | | | 103<br>n = 3 | −18<br>n = 3 |
| 10 | 28<br>n = 3 | 24<br>n = 3 | 46<br>n = 6 | 1<br>n = 6 |
| 50 | 52<br>n = 3 | 35<br>n = 3 | 182<br>n = 3 | 115<br>n = 3 |
| 100 | 39<br>n = 6 | 53<br>n = 6 | 121<br>n = 3 | 96<br>n = 3 |
| 250 | 29<br>n = 3 | 69<br>n = 3 | | |
| 500 | 6<br>n = 3 | 63<br>n = 3 | | |
| Positive Control | 10 μg/plt<br>9-Amino-<br>acridine<br>284<br>n = 6 | 10 μg/plt<br>2-Amino-<br>fluorene<br>73<br>n = 24 | | 5 μg/plate<br>2-Amino-<br>fluorene<br>1064<br>n = 30 |

TABLE 15 (B)

Compound 2

| Dose μg/plate | TA1537 − S9 | TA1537 + S9 | TA1538 − S9 | TA1538 + S9 |
|---|---|---|---|---|
| 0 | 9<br>n = 30 | 9<br>n = 45 | 15<br>n = 30 | 19<br>n = 42 |
| 5 | | | −8<br>n = 3 | 2<br>n = 3 |
| 10 | 36<br>n = 3 | 5<br>n = 3 | −13<br>n = 3 | 4<br>n = 3 |
| 50 | 282<br>n = 3 | 40<br>n = 3 | | |
| 100 | 258<br>n = 3 | 88<br>n = 3 | | |
| 250 | 176<br>n = 3 | 744<br>n = 3 | | |
| 500 | 114<br>n = 3 | 395<br>n = 3 | | |
| Positive Control | 10 μg/plt<br>9-Amino-<br>acridine<br>284<br>n = 6 | 10 μg/plt<br>2-Amino-<br>fluorene<br>73<br>n = 24 | | 5 μg/plate<br>2-Amino-<br>fluorene<br>1064<br>n = 30 |

TABLE 16

Compound 3

| Dose μg/plate | TA100 − S9 | TA100 +S9 | TA1538 − S9 | TA1538 + S9 |
|---|---|---|---|---|
| 0 | 126<br>n = 41 | 123<br>n = 56 | 15<br>n = 30 | 19<br>n = 42 |
| 5 | 47<br>n = 3 | −19<br>n = 3 | 0<br>n = 3 | 1<br>n = 3 |
| 10 | 47<br>n = 3 | 8<br>n = 3 | −6<br>n = 3 | 9<br>n = 3 |
| Positive Control | 1.5 μg/plt<br>Sodium Azide<br>965<br>n = 38 | | | 5 μg/plt 2-<br>Amino-fluorene<br>1064<br>n = 30 |

TABLE 17

Compound 4

| Dose μg/plate | TA100 − S9 | TA100 + S9 | TA1538 − S9 | TA1538 + S9 |
|---|---|---|---|---|
| 0 | 126<br>n = 41 | 123<br>n = 56 | 15<br>n = 30 | 19<br>n = 42 |
| 5 | −41<br>n = 3 | −10<br>n = 3 | −2<br>n = 3 | 7<br>n = 3 |
| 10 | 3<br>n = 3 | −3<br>n = 3 | −2<br>n = 3 | −2<br>n = 3 |
| Positive Control | 1.5 μg/plate<br>Sodium<br>Azide<br>965<br>n = 38 | | | 5 μg/plate<br>2-Amino-<br>fluorene<br>1064<br>n = 30 |

TABLE 18 (A)

Compound 6

| Dose µg/plate | TA1537 − S9 | TA1537 + S9 | TA1538 − S9 | TA1538 + S9 |
|---|---|---|---|---|
| 0 | 20<br>n = 38 | 25<br>n = 53 | 126<br>n = 41 | 123<br>n = 56 |
| 5 | | | −32<br>n = 3 | 12<br>n = 3 |
| 10 | 12<br>n = 3 | −5<br>n = 3 | 3<br>n = 9 | −5<br>n = 9 |
| 50 | 12<br>n = 3 | 2<br>n = 3 | 2<br>n = 6 | 24<br>n = 6 |
| 100 | 22<br>n = 6 | 20<br>n = 6 | −18<br>n = 6 | −2<br>n = 6 |
| 250 | 12<br>n = 3 | 40<br>n = 3 | | −38<br>n = 3 |
| 500 | 9<br>n = 3 | 52<br>n = 3 | | |
| Positive Control | | 5 µg/plate<br>2-Amino-fluorene<br>1154<br>n = 35 | 1.5 µg/plate<br>Sodium Azide<br>965<br>n = 38 | |

TABLE 18 (B)

Compound 6

| Dose µg/plate | TA1537 − S9 | TA1537 + S9 | TA1538 − S9 | TA1538 + S9 |
|---|---|---|---|---|
| 0 | 9<br>n = 30 | 9<br>n = 45 | 15<br>n = 30 | 19<br>n = 42 |
| 5 | | | −5<br>n = 3 | 0<br>n = 3 |
| 10 | 141<br>n = 6 | −1<br>n = 6 | −2<br>n = 3 | 8<br>n = 3 |
| 50 | 2010<br>n = 6 | 17<br>n = 6 | | |
| 100 | 795<br>n = 6 | 35<br>n = 6 | | |
| 250 | 228<br>n = 6 | 99<br>n = 6 | | |
| 500 | 43<br>n = 3 | 369<br>n = 3 | | |
| Positive Control | 10 µg/plate<br>9-Amino-acridine<br>284<br>n = 6 | 10 µg/plate<br>2-Amino-fluorene<br>73<br>n = 24 | | 5 µg/plate<br>2-Amino-fluorene<br>1064<br>n = 30 |

TABLE 19 (A)

Compound 18

| Dose µg/plate | TA98 − S9 | TA98 + S9 |
|---|---|---|
| 0 | 17<br>n = 3 | 28<br>n = 3 |
| 5 | | |
| 10 | 21<br>n = 3 | 8<br>n = 3 |
| 50 | 303<br>n = 3 | 6<br>n = 3 |
| 100 | 390<br>n = 6 | 26<br>n = 6 |
| 200 | 225<br>n = 3 | 42<br>n = 3 |
| 500 Positive Control | | 5 µg/plate 2-Amino-fluorene<br>2589<br>n = 3 |

TABLE 19 (B)

Compound 18

| Dose µg/plate | TA1537 − S9 | TA1537 + S9 |
|---|---|---|
| 0 | 8<br>n = 3 | 7<br>n = 3 |
| 5 | | |
| 10 | 21<br>n = 3 | 8<br>n = 3 |
| 50 | 303<br>n = 3 | 6<br>n = 3 |
| 100 | 390<br>n = 3 | 26<br>n = 3 |
| 200 | 225<br>n = 3 | 42<br>n = 3 |
| 500 | 100 µg/plate AMT<br>608<br>n = 3 | 100 µg/plate AMT<br>500<br>n = 3 |

Maron and Ames (1983) describe the conflicting views with regard to the statistical treatment of data generated from the test. In light of this, this example adopts the simple model of mutagenicity being characterized by a two-fold or greater increase in the number of revertants above background (in bold in the tables), as well as dose dependent mutagenic response to drug.

With regard to 8-MOP, the only mutagenic response detected was a weak base-substitution mutagen in TA102 at 500 µg/plate (TABLE 13 (B)).

In sharp contrast, AMT (TABLE 12 (A) and 12 (B)) showed frameshift mutagenicity at between 5 and 10 µg/plate in TA97a and TA98, at 5 µg/plate in TA1537 and at 1 µg/plate in TA1538. AMT showed no significant base-substitution mutations.

Looking at Compound 1, the only mutagenic response detected was a weak frameshift mutagen in TA1538 at 5 µg/plate in the presence of S9. Compound 1 also displayed mutation in the TA100 strain, but only in the absence of S9. Compound 2 also showed weak frameshift mutagenicity in the presence of S9 in TA98 and TA1537. Compounds 3 and 4 showed no mutagenicity. Compound 6 had no base substitution mutagenicity, but showed a frameshift response in TA98 in the presence of S9 at concentrations of 250 µg/plate and above. It also showed a response at 50 µg/plate in TA1537 in the presence of S9. Compound 18 showed only a weak response at high concentrations in the presence of S9 in strains TA 9o and TA 1537. The response was higher in the absence of S9, but still was significantly below that of AMT, which displayed mutagenicity at much lower concentrations (5 µg/plate).

From this data it is clear that the compounds of the present invention are less mutagenic than AMT, as defined by the Ames test. At the same time, these compounds show much higher inactivation efficiency than 8-MOP, as shown in Examples 12 and 16. These two factors support that the compounds of the present invention combine the best features of both AMT and 8-MOP, high inactivation efficiency and low mutagenicity.

EXAMPLE 18

Figure 20A:
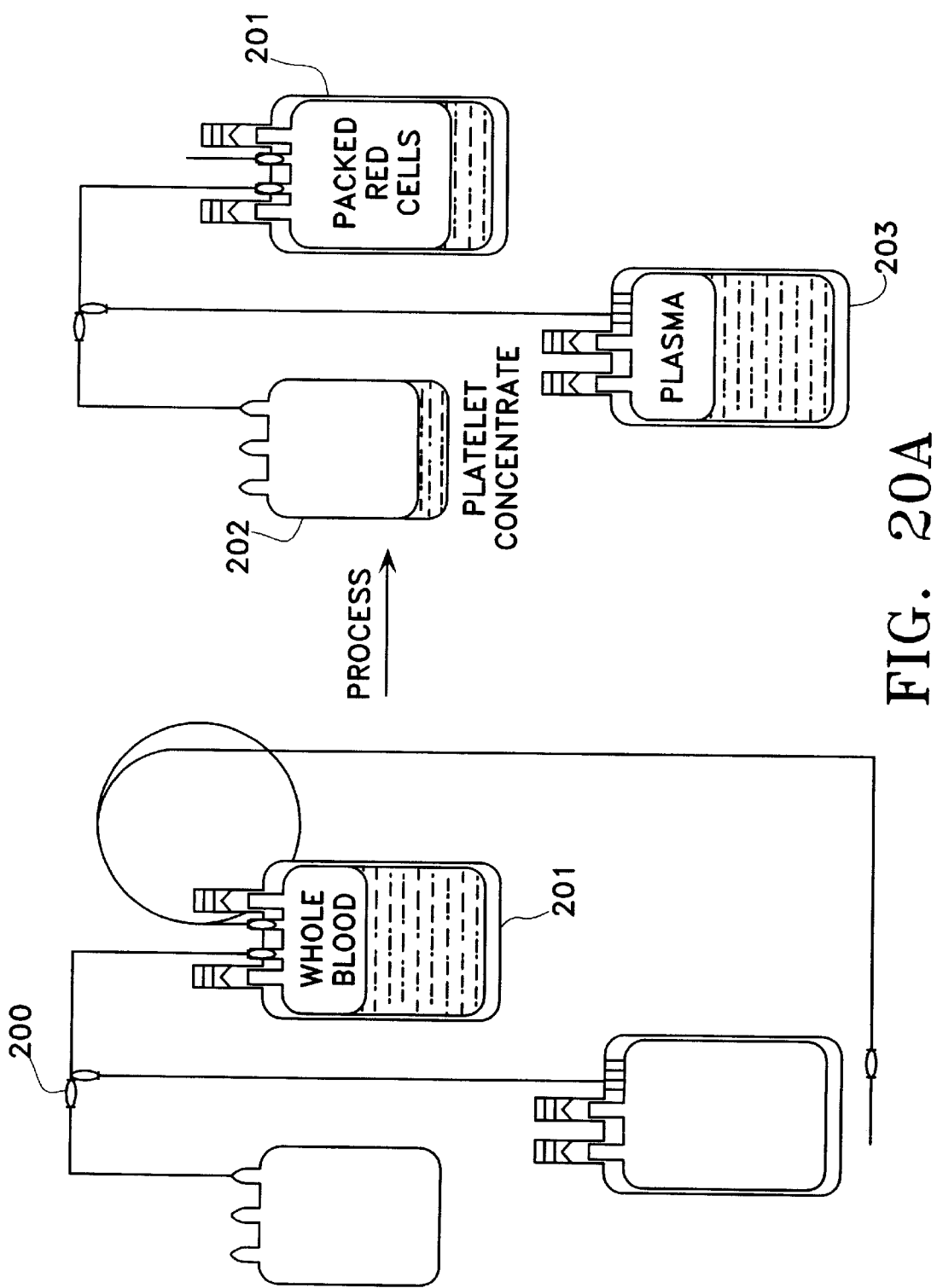
FIG. 20A schematically shows the standard blood product separation approach used presently in blood banks.

In Example 15, the compounds of the present invention exhibited the ability to inactivate pathogens in synthetic media This example describes methods by which synthetic media and compounds of the present invention may be introduced and used for inactivating pathogens in blood. FIG. 20A schematically shows the standard blood product separation approach used presently in blood banks. Three bags are integrated by flexible tubing to create a blood transfer set (200) (e.g., commercially available from Baxter, Deerfield, Ill.). After blood is drawn into the first bag (201), the entire set is processed by centrifugation (e.g., Sorvall™ swing bucket centrifuge, Dupont), resulting in packed red cells and platelet rich plasma in the first bag (201). The plasma is expressed off of the first bag (201) (e.g., using a Fenwalim device for plasma expression), through the tubing and into the second bag (202). The first bag (201) is then detached and the two bag set is centrifuged to create platelet concentrate and platelet-poor plasma; the latter is expressed off of the second bag (202) into the third bag (203).

Figure 20B:
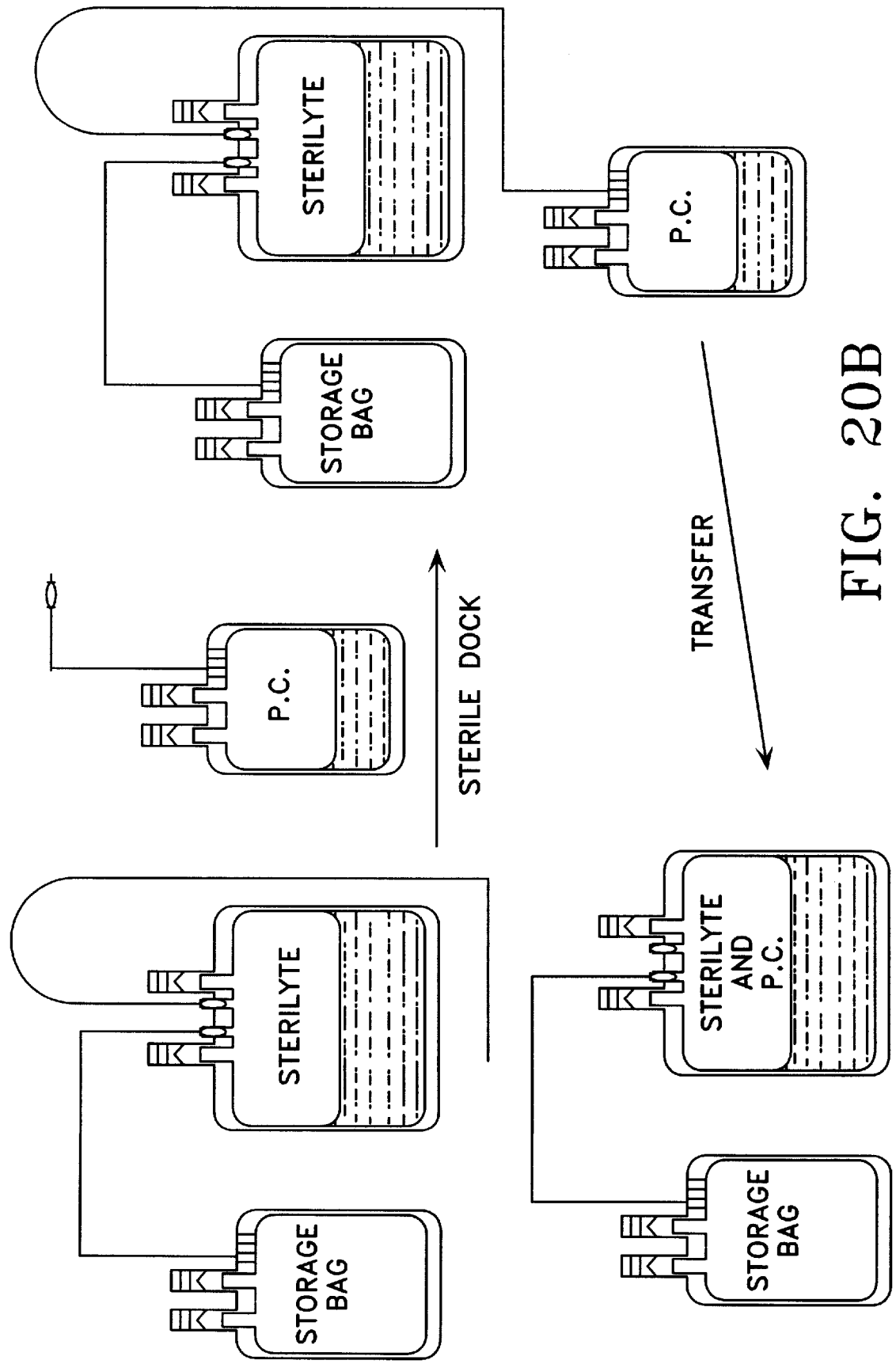
FIG. 20B schematically shows an embodiment of the present invention whereby synthetic media is introduced to platelet concentrate prepared as in FIG. 20A.

FIG. 20B schematically shows an embodiment of the present invention by which synthetic media and photoactivation compound are introduced to platelet concentrate prepared as in FIG. 20A. A two bag set (300) is sterile docked with the platelet concentrate bag (202) (indicated as "P.C."). Sterile docking is well-known in the art. See e.g., U.S. Pat. No. 4,412,835 to D. W. C. Spencer, hereby incorporated by reference. See also U.S. Pat. Nos. 4,157,723 and 4,265,280, hereby incorporated by reference. Sterile docking devices are commercially available (e.g., Terumo, Japan).

One of the bags (301) of the two bag set (300) contains a synthetic media formulation of the present invention (indicated as "STERILYTE"). In the second step shown in FIG. 20B, the platelet concentrate is mixed with the synthetic media by transferring the platelet concentrate to the synthetic media bag (301) by expressing the platelet concentrate from the first blood bag into the second blood bag via a sterile connection means. The photoactivation compound can be in the bag containing synthetic media (301), added at the point of manufacture. Alternatively, the compound can be mixed with the blood at the point of collection, if the compound is added to the blood collection bag (FIG. 20A, 201) at the point of manufacture. The compound may be either in dry form or in a solution compatible with the maintenance of blood.

Figure 20C:
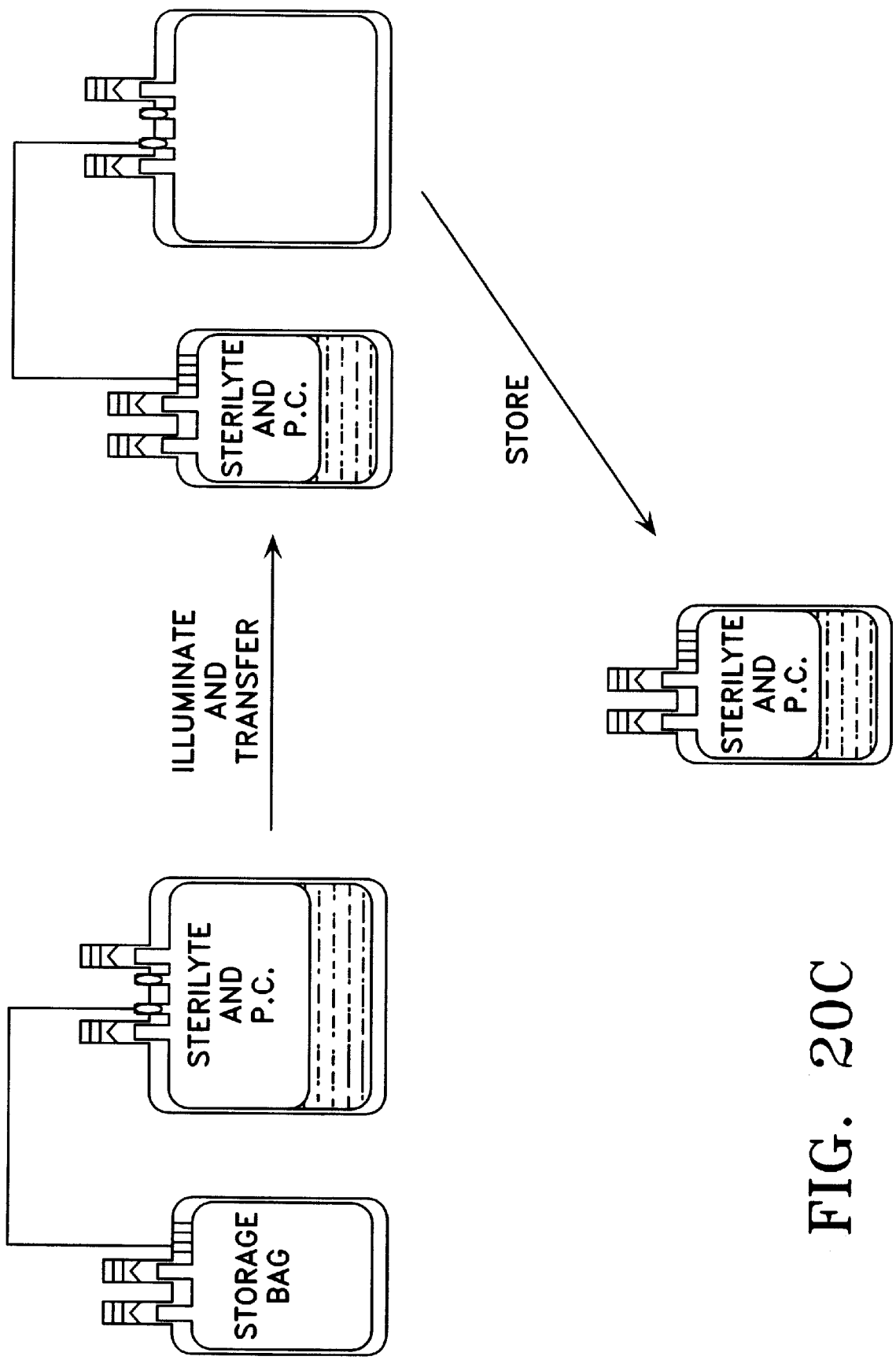
FIG. 20C schematically shows one embodiment of the decontamination approach of the present invention applied specifically to platelet concentrate diluted with synthetic media as in FIG. 20B.
Figure 21A:
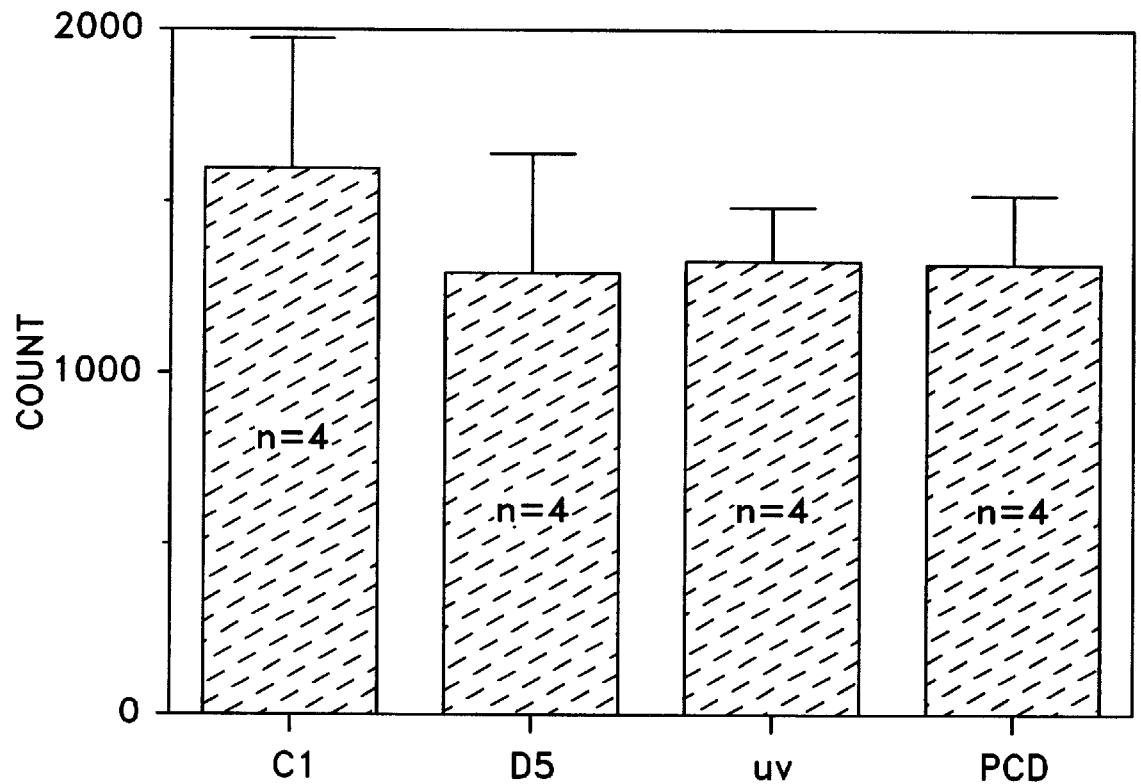
FIG. 21A is a graph comparing the effects of 5-day storage (D5), ultraviolet light (uv) and treatment with Compound 2 at 100 $\mu$M (PCD) on platelet function as measured by platelet count. "n" represents the number of experiments represented by the data point.
Figure 21B:
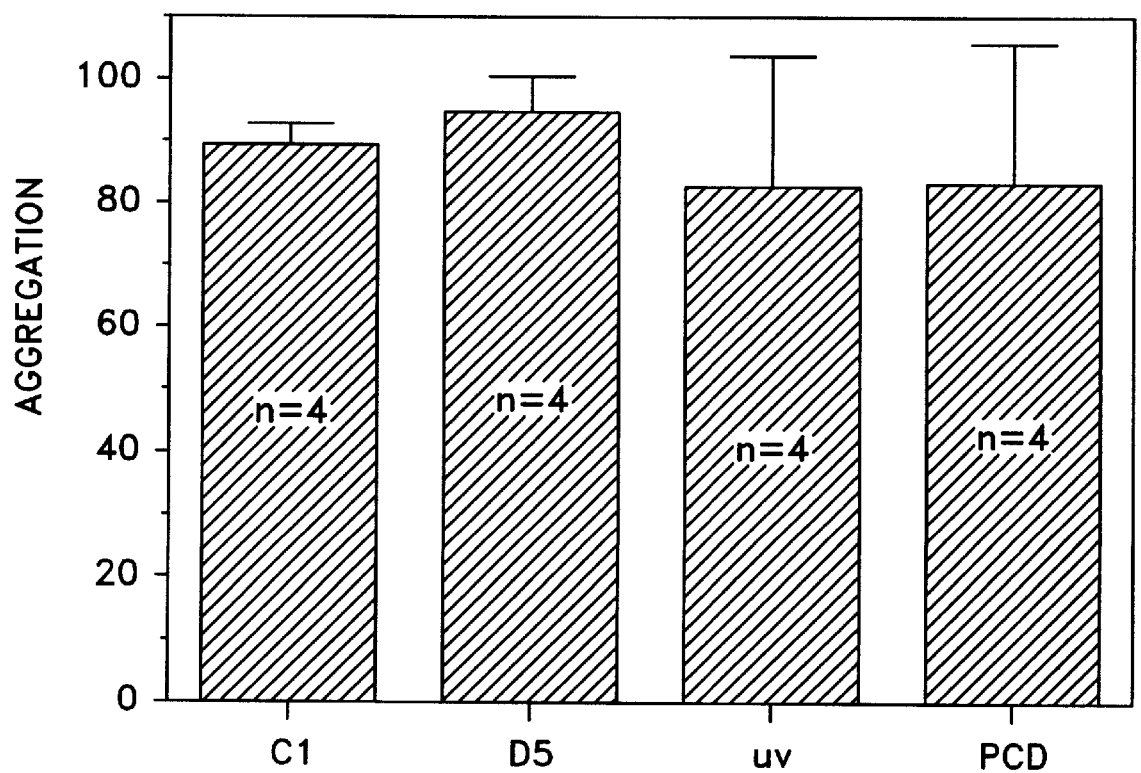
FIG. 21B is a graph comparing the effects of 5-day storage (D5), ultraviolet light (uv) and treatment with Compound 2 at 100 $\mu$M (PCD) on platelet function as measured by platelet aggregation. "n" represents the number of experiments represented by the data point.
Figure 21C:
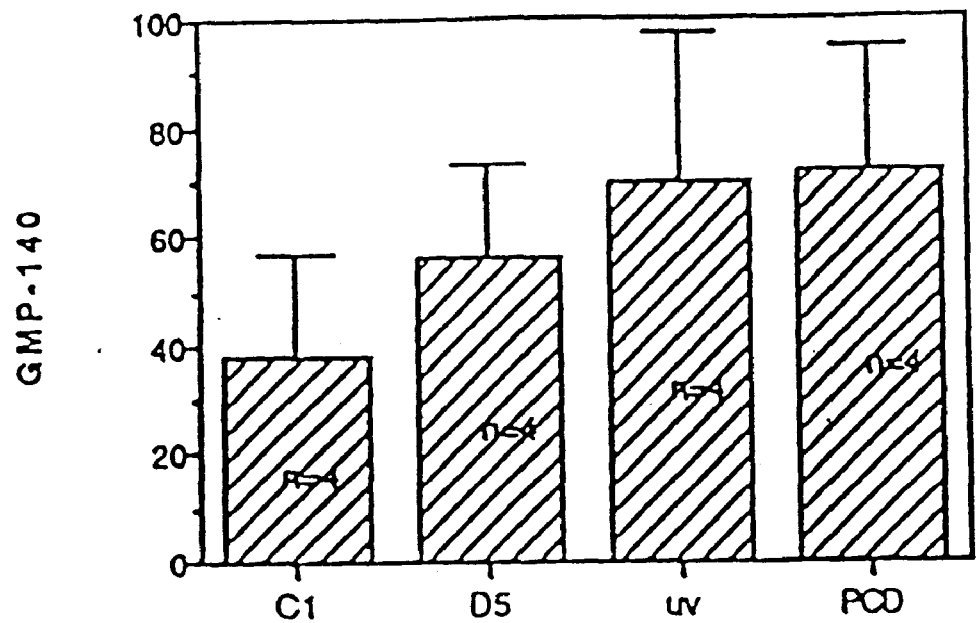
FIG. 21C is a graph comparing the effects of 5-day storage (D5), ultraviolet light (uv) and treatment with Compound 2 at 100 $\mu$M (PCD) on platelet function as measured by GMP-140 expression. "n" represents the number of experiments represented by the data point.
Figure 21D:
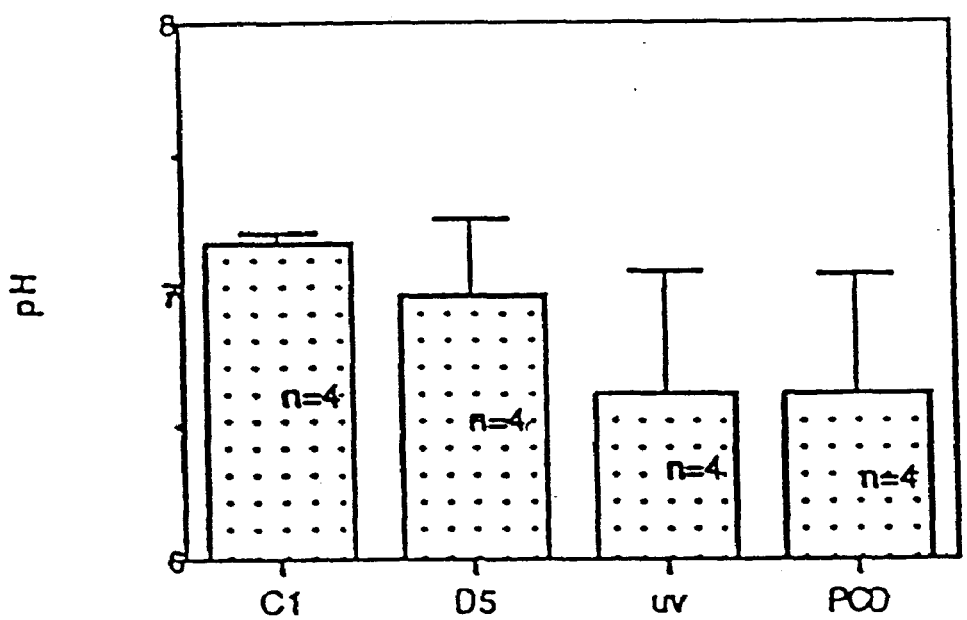
FIG. 21D is a graph comparing the effects of 5-day storage (D5), ultraviolet light (uv) and treatment with Compound 2 at 100 $\mu$M (PCD) on platelet function as measured by pH. "n" represents the number of experiments represented by the data point.
Figure 22A:
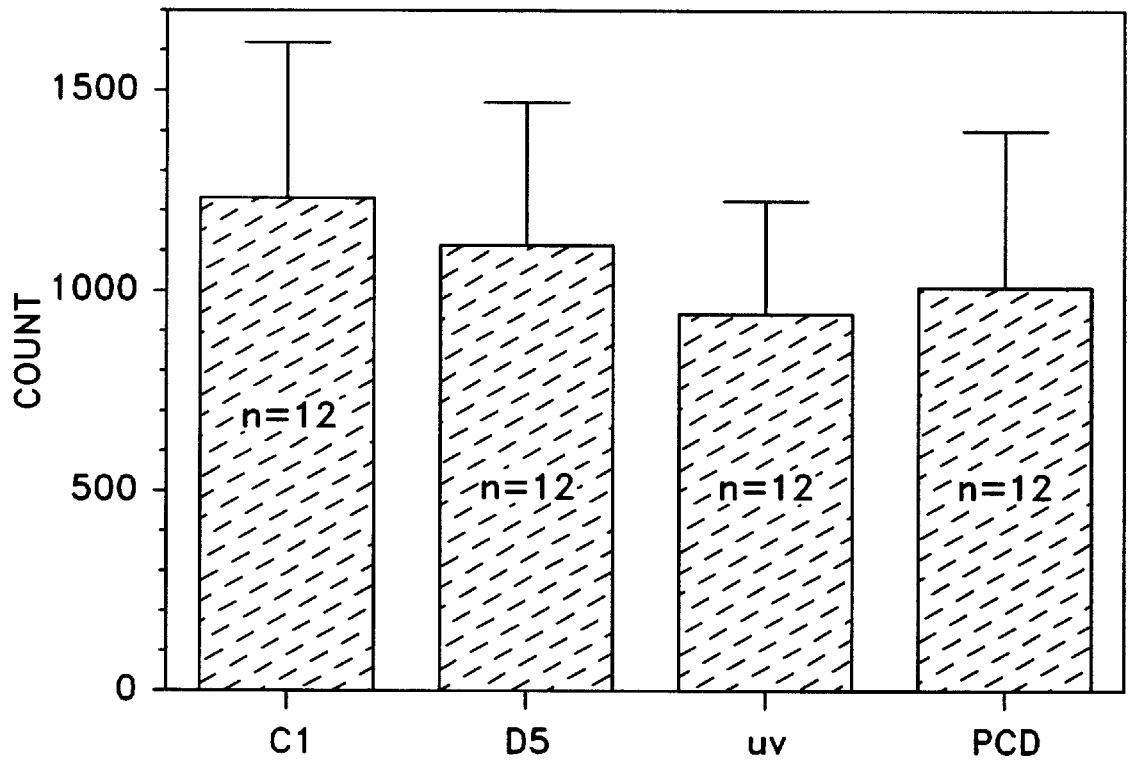
FIG. 22A is a graph comparing the effects of 5-day storage (D5), ultraviolet light (uv) and treatment with Compound 6 at 100 $\mu$M (PCD) on platelet function as measured by platelet count. "n" represents the number of experiments represented by the data point.
Figure 22B:
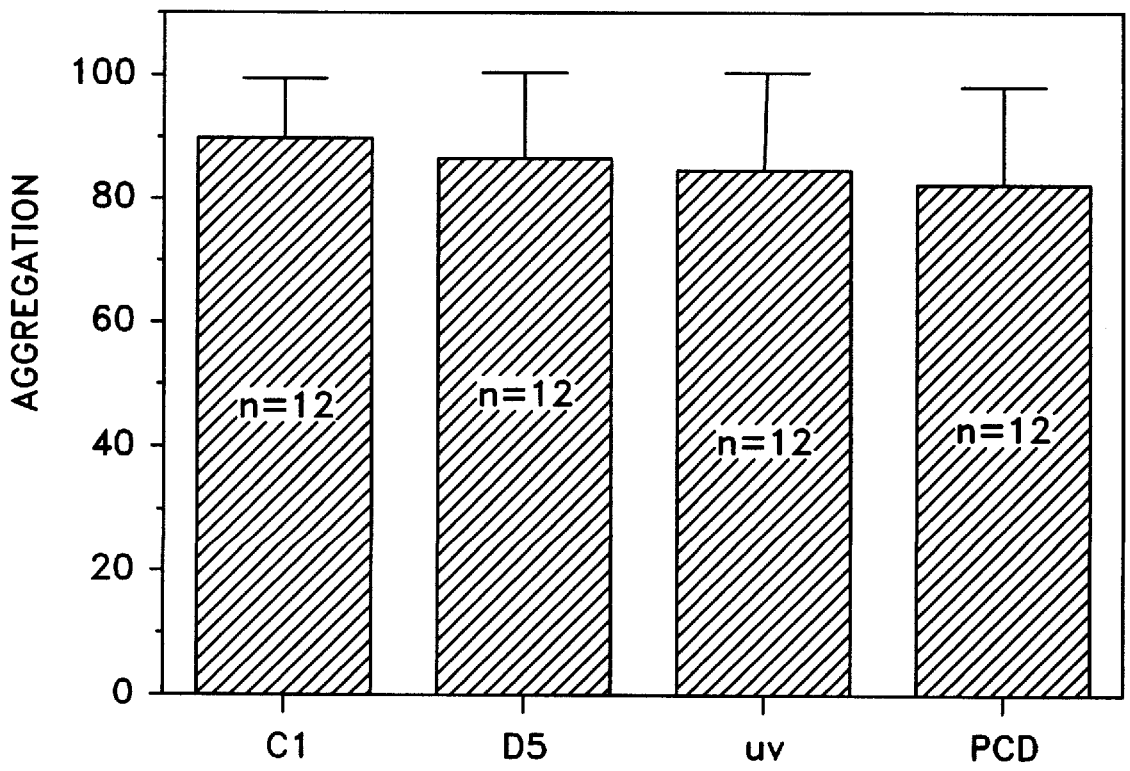
FIG. 22B is a graph comparing the effects of 5-day storage (D5), ultraviolet light (uv) and treatment with Compound 6 at 100 µM (PCD) on platelet function as measured by platelet aggregation. "n" represents the number of experiments represented by the data point.
Figure 22C:
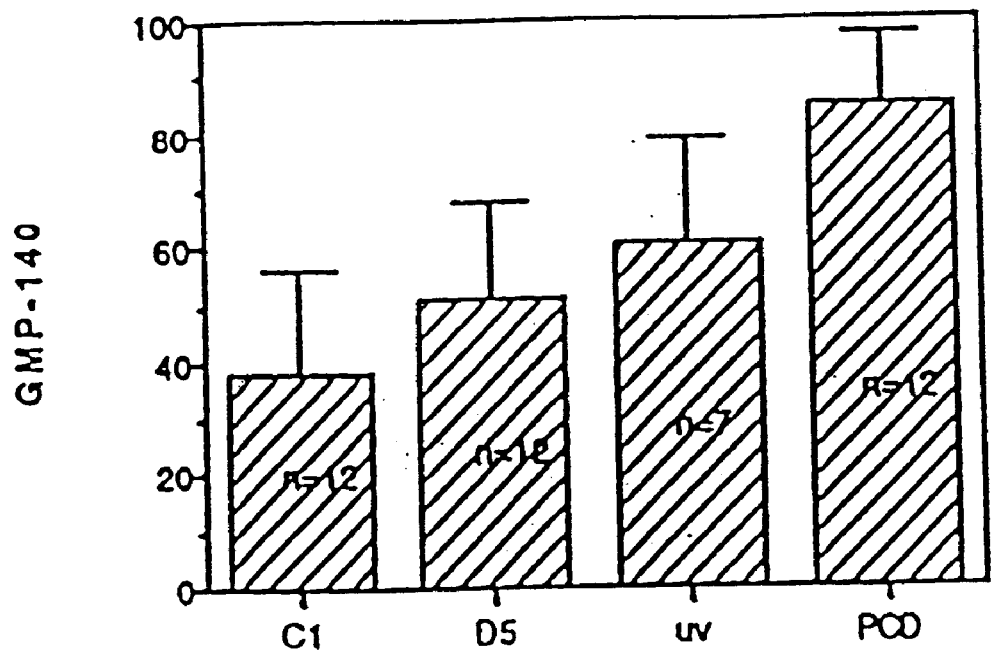
FIG. 22C is a graph comparing the effects of 5-day storage (D5), ultraviolet light (uv) and treatment with Compound 6 at 100 µM (PCD) on platelet function as measured by GMP-140 expression. "n" represents the number of experiments represented by the data point.
Figure 22D:
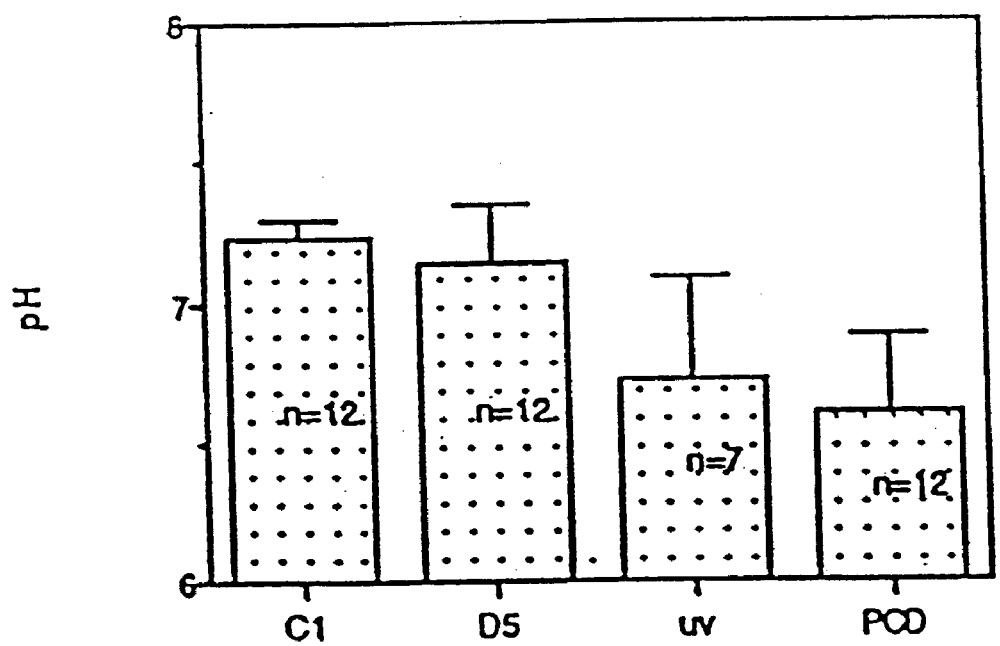
FIG. 22D is a graph comparing the effects of 5-day storage (D5), ultraviolet light (uv) and treatment with Compound 6 at 100 µM (PCD) on platelet function as measured by pH. "n" represents the number of experiments represented by the data point.
Figure 23A:
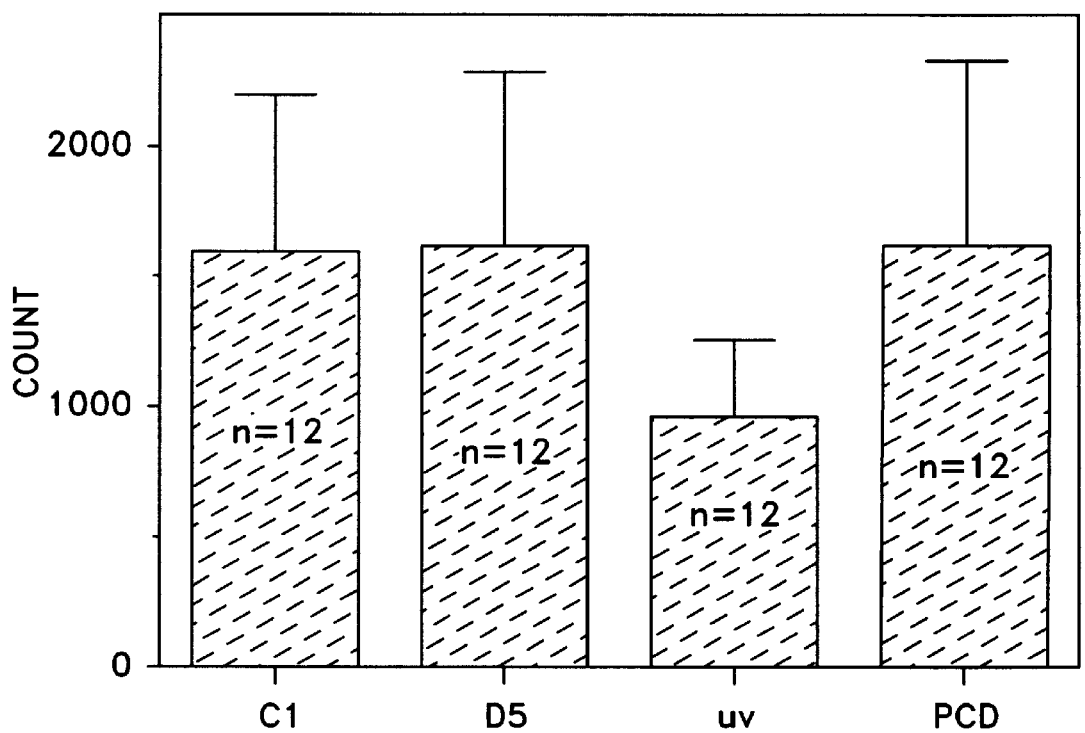
FIG. 23A is a graph comparing the effects of 5-day storage (D5), ultraviolet light (uv) and treatment with Compound 17 at 100 µM (PCD) on platelet function as measured by platelet count. "n" represents the number of experiments represented by the data point.
Figure 23B:
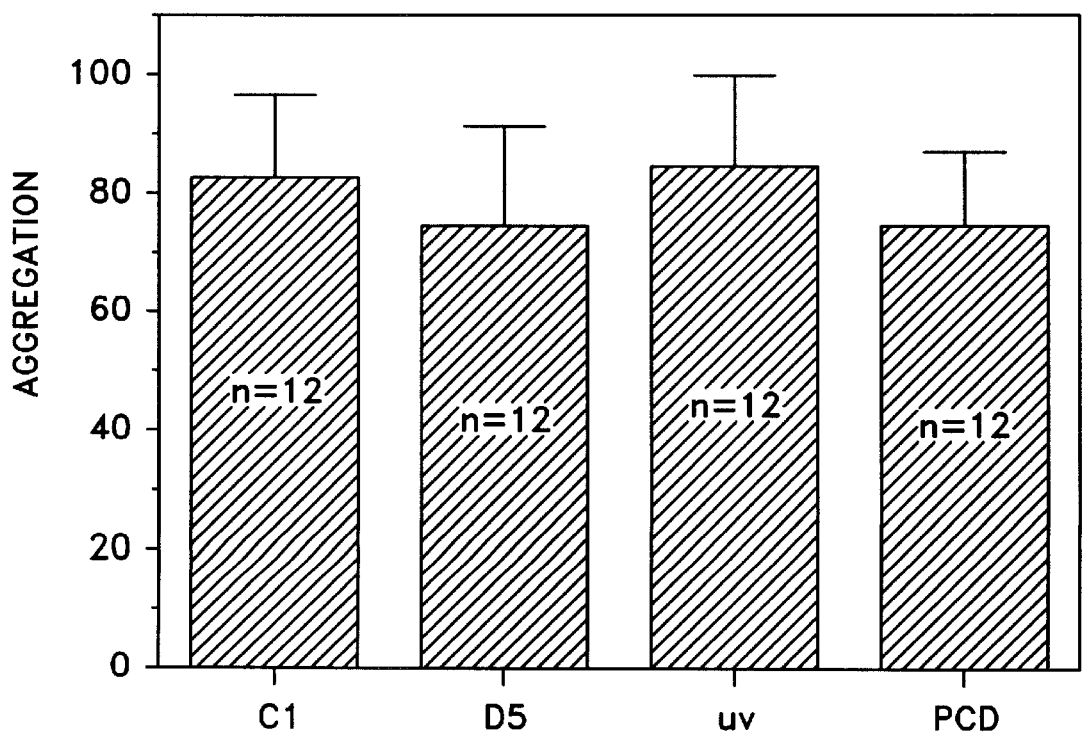
FIG. 23B is a graph comparing the effects of 5-day storage (D5), ultraviolet light (uv) and treatment with Compound 17 at 100 µM (PCD) on platelet function as measured by platelet aggregation. "n" represents the number of experiments represented by the data point.
Figure 23C:
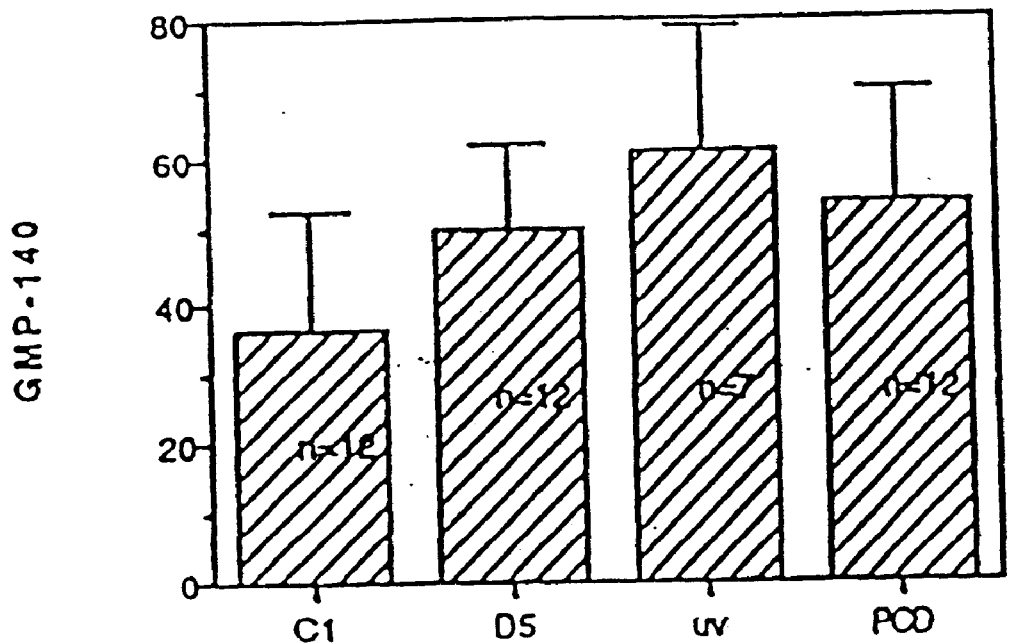
FIG. 23C is a graph comparing the effects of 5-day storage (D5), ultraviolet light (uv) and treatment with Compound 17 at 100 µM (PCD) on platelet function as measured by GMP-140 expression. "n" represents the number of experiments represented by the data point.
Figure 23D:
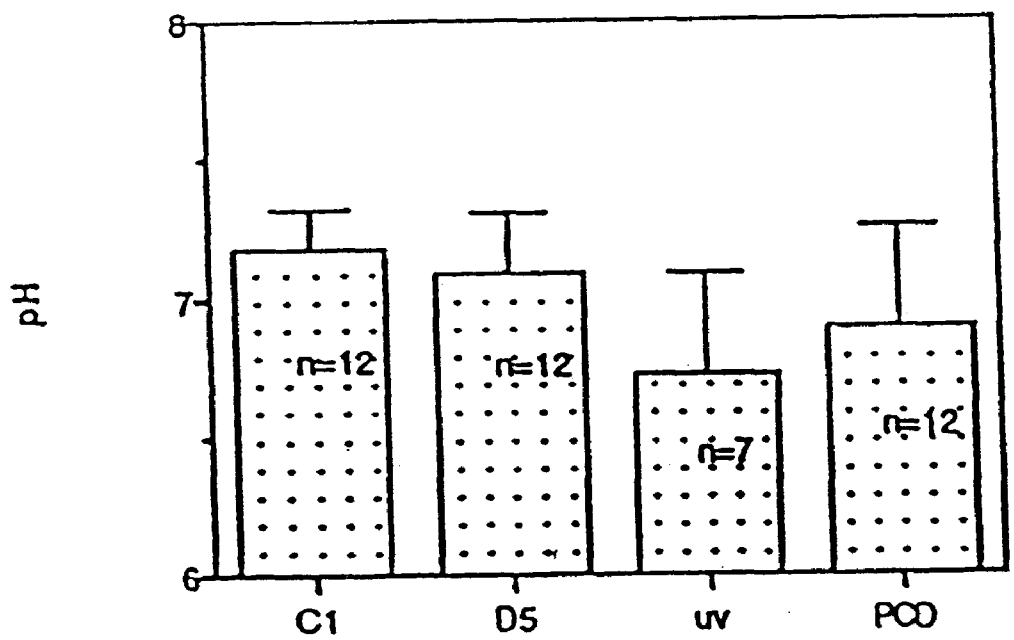
FIG. 23D is a graph comparing the effects of 5-day storage (D5), ultraviolet light (uv) and treatment with Compound 17 at 100 µM (PCD) on platelet function as measured by pH. "n" represents the number of experiments represented by the data point.
Figure 24A:
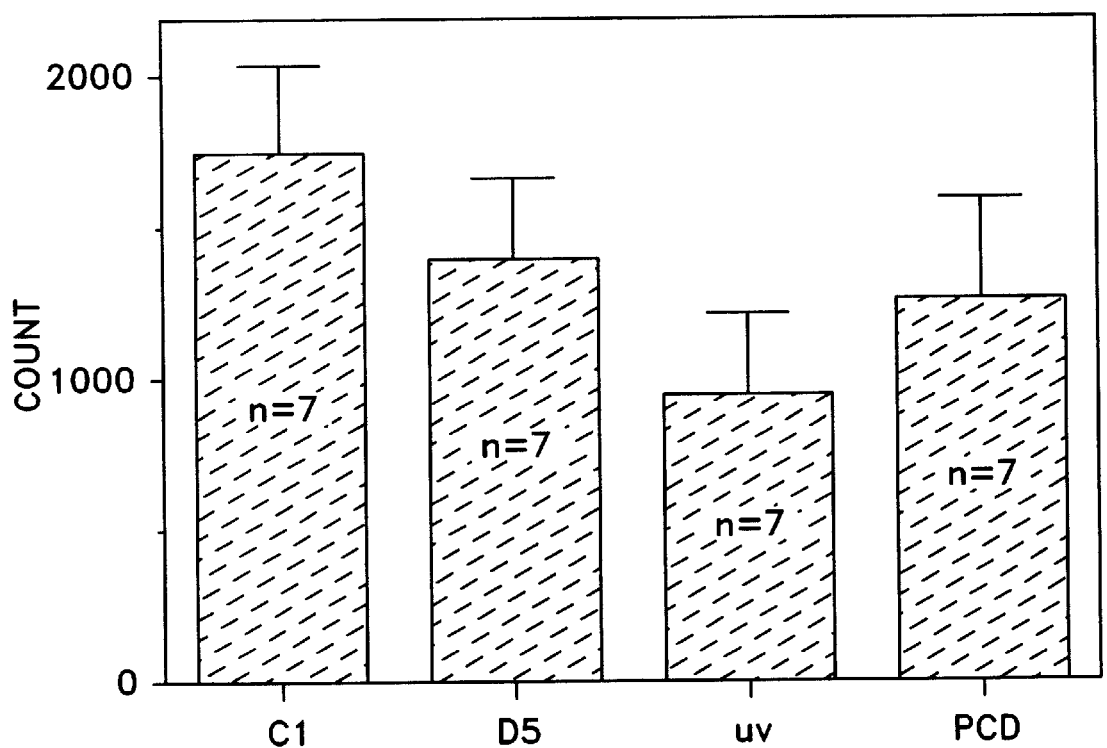
FIG. 24A is a graph comparing the effects of 5-day storage (D5), ultraviolet light (uv) and treatment with Compound 18 at 100 µM (PCD) on platelet function as measured by platelet count. "n" represents the number of experiments represented by the data point.
Figure 24B:
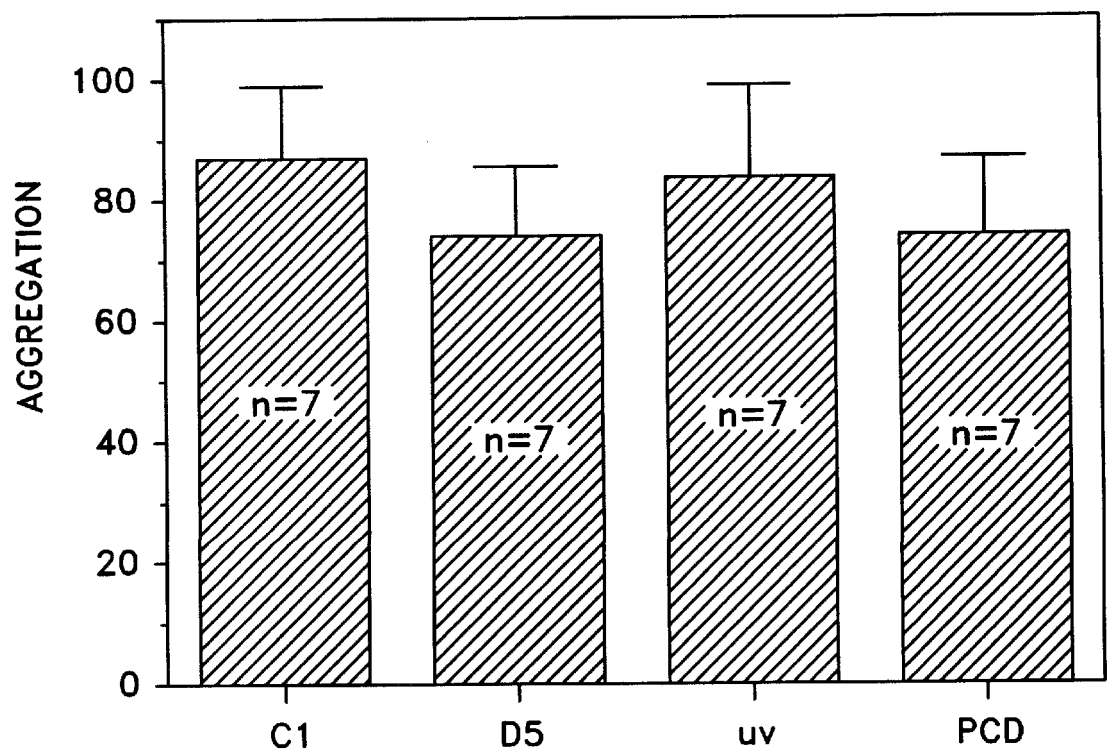
FIG. 24B is a graph comparing the effects of 5-day storage (D5), ultraviolet light (uv) and treatment with Compound 18 at 100 µM (PCD) on platelet function as measured by platelet aggregation. "n" represents the number of experiments represented by the data point.
Figure 24C:
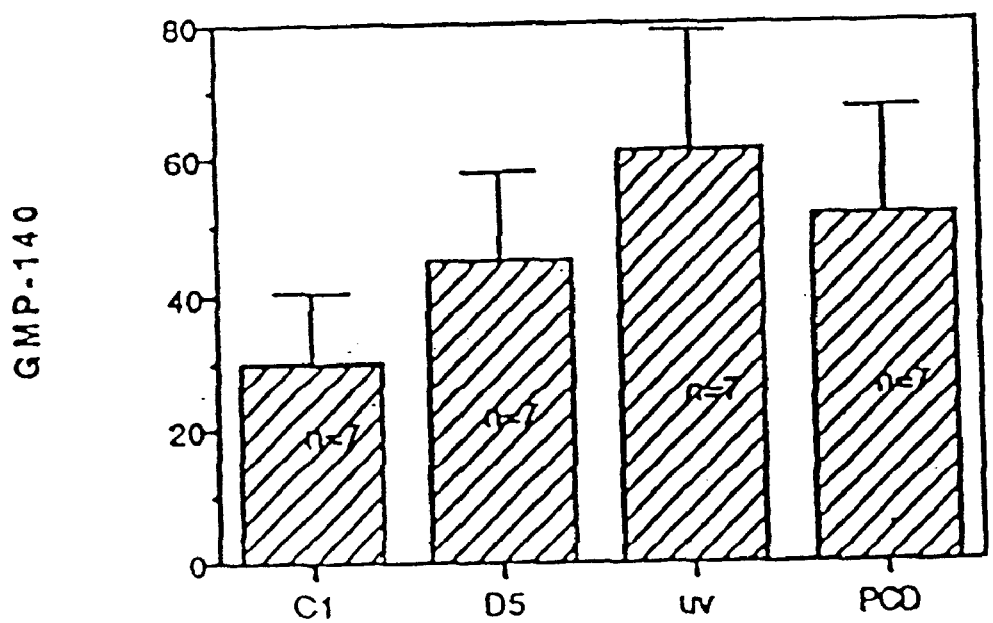
FIG. 24C is a graph comparing the effects of 5-day storage (D5), ultraviolet light (uv) and treatment with Compound 18 at 100 µM (PCD) on platelet function as measured by GMP-140 expression. "n" represents the number of experiments represented by the data point.
Figure 24D:
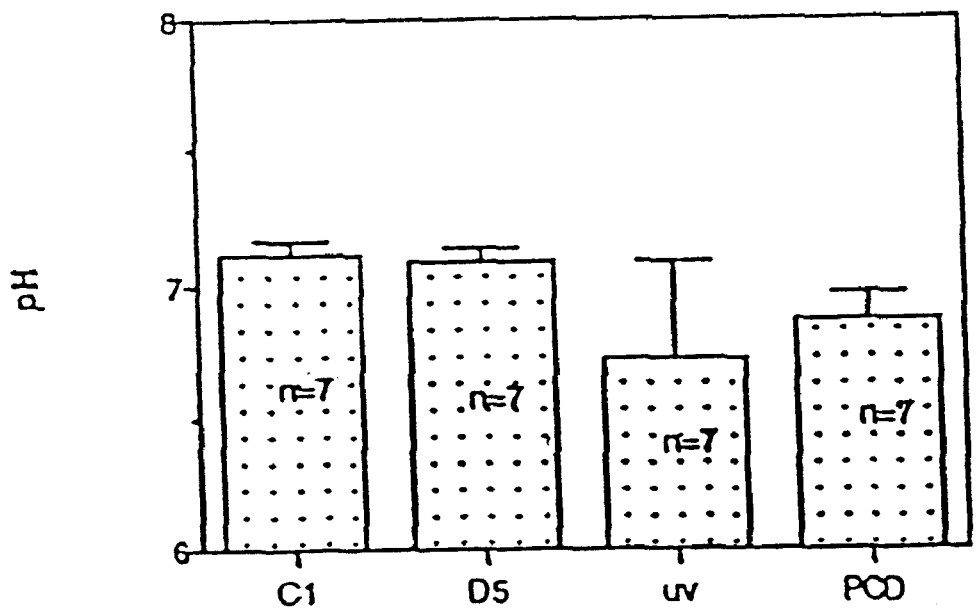
FIG. 24D is a graph comparing the effects of 5-day storage (D5), ultraviolet light (uv) and treatment with Compound 18 at 100 µM (PCD) on platelet function as measured by pH. "n" represents the number of experiments represented by the data point.

FIG. 20C schematically shows one embodiment of the decontamination approach of the present invention applied specifically to platelet concentrate diluted with synthetic media as in FIG. 20B. In this embodiment, platelets have been transferred to a synthetic media bag (301). The photoactivation compound either has already been introduced in the blood collection bag (201) or is present in the synthetic media bag (301). Either the platelets are then expressed into the synthetic media bag via a sterile connection means (as shown) or the synthetic media is expressed into the platelet bag. The bag containing the mixture of platelet concentrate and synthetic media (301), which has UV light transmission properties and other characteristics suited for the present invention, is then placed in a device (such as that described in Example 1, above) and illuminated.

Following phototreatment, the decontaminated platelets are transferred from the synthetic media bag (301) into the storage bag (302) of the two bag set (300). The storage bag can be a commercially available storage bag (e.g., CLX bag from Cutter).

EXAMPLE 19

This example involves an assessment of the impact of the compounds and methods of the present invention on platelet function. Four indicators of platelet viability and function were employed: 1) GMP-140 expression; 2) maintenance of pH; 3) platelet aggregation, and 4) platelet count.

To measure the effects of the present compounds and methods of decontamination on platelet function using these four indicators, four samples were prepared for each compound tested, two control samples and two containing compound. Three units of human platelets were obtained from the Sacramento Blood Center, Sacramento, Calif. These were each transferred under sterile conditions to 50 ml centrifuge tubes, then aliquots of each unit were transferred into a second set of 50 ml sterile centrifuge tubes. To each centrifuge tube containing platelet concentrate (PC), an aliquot of compound stock was added to reach a final concentration of 100 $\mu$M of compound. The compounds tested in this experiment were Compound 2 ( 36 $\mu$L of 10 mM stock added to 4 ml PC), Compound 6 (173.5 $\mu$l of 9.8 mM stock added to 16.8 ml PC), Compound 17 (2.0 ml of 1 mM stock added to 18 ml PC) and Compound 18 (0.842 ml of 2.0 mM stock to 16 ml PC). The samples were pipetted gently up and down to mix. Then aliquots (either 3 ml or 8 ml) of each sample was transferred to two sterile Teflon™ Medi-bags™ (American Fluoroseal Co., Silver Springs, Md.) (presently owned by The West Company, Lionville, Pa.). Samples were treated in one of two different sized bags, having either 3 ml or 8 ml capacity. The bags both have approximately the same surface area to volume ratios, and previous experiments have shown that the two bags exhibit approximately equivalent properties during irradiation of samples. (Data not shown). For each compound tested, two control samples without compound were prepared by again removing aliquots of platelet concentrate (17 ml if using an 8 ml bag, 4 ml if using a 3 ml bag) from the same one of the first set of 50 ml centrifuge tubes from which the compound sample was drawn, and dividing into Medibags, as before. One of each pair of Medibags containing a compound, and one of each pair of control Medibags, were illuminated for 5 Joules/cm$^2$ on the device described in Example 1, above. Then all experimental and control Medibags were placed on a platelet shaker for storage for 5 days. The same experiments were repeated several times to obtain more statistically meaningful data, as represented by "n", the number of data points represented, in the graphs of FIGS. 21–24, discussed below.

To obtain data for control samples at day one, approximately 3 ml were removed from the remaining volume of each of the three units and divided into two 1.5 ml tubes. These samples were tested for pH as described below. A platelet count was also taken, as described below, at a 1:3 dilution. The residual platelet concentrate from each unit was spun for 10 minutes at 3800 rpm (3000 g) in Sorval RC3B (DuPont Company, Wilmington, Del.) to pellet platelets. Plasma was then decanted into 2 sterile 50 ml tubes (one for Day one, and the other stored at 4° C. for Day 5) for use in the aggregation assay.

1) GMP-140 Expression

When platelets become activated, an alpha granule membrane glycoprotein called p-selectin (GMP140) becomes exposed on the platelet surface. Less than (5%) of fresh, normal unstimulated platelets express detectable GMP140 levels by flow cytometry. See generally M. J. Metzelaar, *Studies On The Expression Of Activation-Markers On Human Platelets* (Thesis 1991).

To measure GMP140, a small aliquot of platelet rich plasma is placed in HEPES buffer containing a GMP140-binding antibody or an isotype control mouse IgG. CD62 is a commercially available monoclonal antibody which binds to GMP140 (available from Sanbio, Uden, the Netherlands; Caltag Labs, So. San Francisco, Calif., and Becton Dickinson, Mountain View, Calif.). After a fifteen minute incubation at room temperature, Goat F(ab')$_2$ Anti-Mouse IgG conjugated to FITC (Caltag Laboratories, So. San Francisco, Calif.) is added to the tube in saturating amounts and allowed to incubate at room temperature (RT) for 15 minutes. Finally, the cells are diluted in 1% paraformaldehyde in phosphate buffered saline and analyzed on a FACSCaN™0 (Becton Dickinson, Mountain View, Calif.). The positive control is made by adding Phorbol Myristate Acetate (PMA) to the test system at a fmal concentration of $2 \times 10^{-7}$ M.

In this example, CD62 was employed to measure the impact, if any, of irradiation in the presence of several compounds of the present invention on platelet activation. The antibody was mixed with HEPES buffer (10 μL antibody [0.1 mg/ml]: 2.49 mL buffer) and stored in 50 μL aliquots at −40° C. prior to use. A positive control consisted of: 10 μL CD62, 8 μL PMA and 2.482 mL Hepes buffer. A mouse IgG1 control (0.05 mg/ml) (Becton Dickinson, Mountain View, Calif. #9040) 5× concentrated was also employed. The antibody was diluted in HEPES buffer (20 μL antibody : 2.48 ml buffer) and stored at −40° C. Phorbol Myristate Acetate (PMA) (Sigma, St. Louis, Mo.) was stored at −40° C. At time of use, this was dissolved in DMSO (working concentration was 10 μg/mL).

1% Paraformaldehyde (PFA) (Sigma, St. Louis, Mo.) was prepared by adding 10 grams paraformaldehyde to 1 liter PBS. This was heated to 70° C., whereupon 3 M NaOH was added dropwise until the solution was clear. The solution was cooled and the pH was adjusted to 7.4 with 1 N HCl. This was filtered and stored.

Processing each of the samples of platelet concentrate after treatment involved adding 5 microliters of platelet concentrate, diluted 1:3 in Hepes buffer, to each microcentrifuge tube containing the antibody CD62, and appropriate reagents and mixing very gently by vortex. The samples were then incubated for 15 minutes at room temperature.

The Goat anti-Mouse IgG-FITC (diluted 1:10 in HEPES buffer) was added (5 microliters) to each tube and the solution was mixed by gentle vortex. The samples were incubated for an additional 15 minutes at room temperature. Next, 1 ml of 1% PFA in PBS was added to each tube and mixed gently. The platelets were analyzed on the FACS-CAN™. The results are shown in FIGS. 21C, 22C, 23C, and 24C. (FIGS. 21 correspond to Compound 2, FIGS. 22 correspond to Compound 6, FIGS. 23 correspond to Compound 17 and FIGS. 24 correspond to Compound 18). Clearly, three of the four compounds tested, 2, 6, and 17, exhibited little or no difference between the day 5 untreated control (D5) and the sample treated with both light and psoralen compound (PCD). Only Compound 18 exhibited a notable increase above the control. But the value was still well below the positive control value.

2) Maintenance of pH

Changes in pH of platelets in concentrate can alter their morphological characteristics and their survival post transfusion. Moroff, G., et al., "Factors Influencing Changes in pH during Storage of Platelet Concentrates at 20–24° C.," Vox Sang. 42:33 (1982). The range of pH at which platelets function normally is from approximately 6.0–6.5 to 7.6. Stack, G. and E. L. Snyder, "Storage of Platelet Concentrate," Blood Separation and Platelet Fractionation 99, at 107 (1991). To measure pH of the samples, a CIBA-CORNING 238 pH/Blood Gas analyzer was used (CIBA-CORNING, Norwood, Mass.). A small amount of platelet concentrate from each sample was introduced into the pH/Blood Gas analyzer.

Measurements of pH were taken at time zero and after 5 days of storage for all samples. FIGS. 21D, 22D, 23D and 24D are bar graphs showing pH results for a dark control, a light control and an experimental light plus compound. These graphs indicate that the pH of platelet concentrate samples after illumination in the presence of any one of the compounds remains above a pH of 6.5. Thus platelets remain at a pH acceptable for stored platelets following photoinactivating treatment using compounds of the present invention.

3) Aggregation

Platelet aggregation is measured by the change in optical transmission that a platelet sample exhibits upon stimulation of aggregation. Platelet aggregation was measured using a Whole Blood Aggregometer (Chrono-Log Corp., Havertown, Pa., model 560VS). The number of platelets in each sample was controlled to be constant for every measurement A Model F800 Sysmex cell counter (Toa Medical Electronics, Kobe, Japan) was used to measure platelet count in the platelet samples and autologous plasma was used to adjust platelet counts to 300,000/mL of platelet concentrate.

For the procedure, all the samples were incubated in a capped plastic tube for 30 minutes at 37° C. for activation. The aggregometer was warmed up to 37° C. The optical channel was used for platelet aggregation measurement. The magnetic speed of the aggregometer was set at 600/min. Remaining platelet concentrate, from the units obtained which was not drawn as a sample for treatment, was centrifuged at high speed (14,000 g) with a micro-centrifuge for 5 minutes to obtain containers of platelet poor plasma autologous to the experimental samples.

To begin, 0.45 ml of the autologous platelet poor plasma was added along with 0.5 ml of saline into a glass cuvette and placed in the PPP channel. Then 0.45 ml of the sample platelet concentrate and 0.50 ml of saline were added to a glass cuvette (containing a small magnet) into the sample channel. After one minute, ADP and collagen reagents (10 μl) each were added to the sample cuvette. The final concentration of ADP was 10 μM and the final concentration of collagen was 5 μg/ml. Platelet aggregation was recorded for about 8–10 minutes or until the maximum reading was reached.

The results appear in FIGS. 21B, 22B, 23B, and 24B. The 100% aggregation line is the level at which the recorder was set to zero. The 0% aggregation line is where the platelets transmitted before the ADP and collagen were added. The aggregation value for the sample is determined by taking the maximum aggregation value as a percent of the total range. Three of the four compounds tested showed very little or no difference in aggregation levels between the samples treated with compound and the untreated samples which were stored for 5 days. Compound 2 exhibited a small reduction in aggregation, of approximately 8% from the day 1 control. The aggregation for the sample treated with compound and uv was the same as that for the uv only sample. This is supporting evidence that the decontamination compounds tested do not have a significant effect on platelet aggregation when used in the methods of the present invention.

4) Count

A Sysmex cell counter was used to measure platelet count in the platelet samples. Samples were diluted 1:3 in blood bank saline.

The results of the platelet count measurements appear in FIGS. 21A, 22A, 23A, and 24A. For each of the compounds, the samples show little or no drop in platelet count between the Day 5 control and the Day 5 treated sample. Interestingly, samples treated with Compounds 6, 17 and 18 all display a higher platelet count than samples treated with light alone. For example, samples treated with Compound 6 had counts equivalent to the 5 day control, but samples treated with only ultraviolet light showed approximately a 33% reduction in platelet count. Thus, not only is treatment with compounds of the present invention compatible with the maintenance of platelet count, but it actually appears to prevent the drop in count caused by ultraviolet light exposure.

EXAMPLE 20

A preferred compound for decontaminating blood subsequently used in vivo should not be mutagenic to the recipient of the blood. In the first part of this experiment, some compounds were screened to determine their genotoxicity level in comparison to aminomethyltrimethylpsoralen. In the second part, the in vivo clastogenicity of some compounds of the present invention was measured by looking for micronucleus formation in mouse reticulocytes.

1) Genotoxicity

Mammalian cell cultures are valuable tools for assessing the clastogenic potential of chemicals. In such studies, cells are exposed to chemicals with and/or without rat S-9 metabolic activation system (S-9) and are later examined for either cell survival (for a genotoxicity screen) or for changes in chromosome structure (for a chromosome aberration assay).

Chinese hamster ovary (CHO; ATCC CCL 61 CHO-K1, proline-requiring) cells were used for the in vitro genotoxicity and chromosomal aberration tests. CHO cells are used extensively for cytogenic testing because they have a relatively low number of chromosomes (2n=20) and a rapid rate of multiplication (~12 to 14 hours, depending on culture conditions). The cells were grown in an atmosphere of 5% $CO_2$ at approximately 37° C. in McCoy's 5a medium with 15% fetal bovine serum (FBS), 2 mM L-glutamine, and 1% penicillin-streptomycin solution to maintain exponential growth. This medium was also used during exposure of the cells to the test compound when no S-9 was used. Cell cultures were maintained and cell exposures were performed in T-75 or T-25 flasks.

Each of the sample compounds were tested at seven dilutions, 1, 3, 10, 33, 100, 333, and 1000 µg/ml. The compound was added in complete McCoy's 5a medium. After the compound was added, cells were grown in the dark at approximately 37° C. for approximately 3 hours. The medium containing the test compound was then aspirated, the cells were washed three times with phosphate-buffered saline (PBS) at approximately 37° C., and fresh complete McCoy's 5a medium was added. The positive control was methylmethane sulfonate. The solvent control was dimethylsulfoxide (DMSO) diluted in culture medium. For assays using metabolic activation (see below) the activation mixture was also added to the solvent control. The cultures were then incubated for an additional time of approximately 12 hours before they were harvested. Colchicine (final concentration, 0.4 µg/ml) was added approximately 2.5 hours prior to the harvest.

After approximately 2.5 hours in colchicine, the cells were harvested. Cells were removed from the surface of the flasks using a cell scraper. The resulting cell suspension was centrifuged, the supernatant, aspirated, and 4 ml of a hypotonic solution of 0.075 M KCl added to the cells for 15 minutes at approximately 37° C. The cells were then centrifuged, the supernatant aspirated, and the cells suspended in a fixative of methanol: acetic acid (3:1). After three changes of fixative, air-dried slides were prepared using cells from all flasks. The cell density and metaphase quality on the initial slide from each flask was monitored using a phase-contrast microscope; at least two slides of appropriate cell density were prepared from each flask. The slides were stained in 3% Giemsa for 20 min, rinsed in deionized water, and passed through xylene. Coverslips were mounted with Permount Slides were then examined to determine what concentration of each test compound represented a toxic dose.

An analysis of the results showed that AMT was genotoxic at 30 µg/ml. In contrast, Compounds 2 and 6 were only genotoxic at 100 µg/ml, more than three times the toxic dose of AMT.

A psoralen compound with a structure distinct from compounds of the present invention, 8-aminomethyl4,4',5'-trimethylpsoralen, was also tested in this experiment and proved to be toxic at 10 µg/ml. While the 8- substituted aminomethyl compound and similar structures may not be suited for methods of the present invention, they may be useful for alternative purposes. In light of the ability of the compounds to prevent nucleic acid replication, in combination with their extreme toxicity, the compounds could be used, for example, to treat diseases characterized by uncontrolled cell growth, such as cancer.

2) Micronucleus Assay Protocol

Saline solutions were prepared for Compounds 2, 6, 17 and 18 at various concentrations. Male Balb/c mice were then injected with 0.1 ml of a compound solution via the tail vein. At least 3 mice were injected per dose level. Saline only was used as a negative control. For a positive control, cyclophosphamide (cycloPP) was administered at a dose of 30 mg/kg. In the experimental group, the injections were repeated once per day for four days. In the positive control group, the sample was administered only once, on day three. On day 5, several microliters of blood were withdrawn from each subject and smeared on a glass slide. Cells were fixed in absolute methanol and stored in a slide rack.

For analysis, cells were stained with acridine orange and visualized under a fluorescence microscope by counting: (i) the number of reticulocytes per 5000 erythrocytes; and (ii) the number of micronucleated reticulocytes per 1000 reticulocytes. Reticulocytes were distinguished by their red fluorescence due to the presence of RNA. Micronuclei were distinguished by their green fluorescence due to the presence of DNA. The percentage of reticulocytes (%PCE) was then calculated. A decrease in the frequency of erythrocytes, represented by an increase in the percentage of reticulocytes, is an indication of bone marrow toxicity. The percentage of reticulocytes with micronuclei (%PCE with MN) was also calculated. An increase in %PCE with MN is a measure of clastogenicity.

TABLE 20

| Compound | Dose (mg/kg) | PCE/RBC (%) | PCE + MN (%) | # Duplicates |
|---|---|---|---|---|
| 2 | 40 | 3.08 ± 0.82 | 0.20 ± 0.14 | 4 |
| 2 | 25 | 3.46 ± 0.32 | 0.25 ± 0.11 | 6 |
| CylcoPP | 30 | 1.65 ± 0.64 | 1.98 ± 0.40 | 6 |
| saline | | 3.49 ± 0.55 | 0.18 ± 0.13 | 6 |
| 6 | 45 | 3.79 ± 0.41 | 0.36 ± 0.14 | 3 |
| 6 | 30 | 3.61 ± 0.12 | 0.27 ± 0.38 | 3 |
| 17 | 45 | 5.7 ± 2.14 | 0.31 ± 0.07 | 3 |
| 17 | 30 | 3.47 ± 0.83 | 0.30 ± 0.17 | 3 |
| CylcoPP | 30 | 0.99 ± 0.33 | 1.76 ± 0.64 | 3 |
| saline | | 3.47 ± 0.44 | 0.23 ± 0.15 | 3 |
| 18 | 20 | 3.48 ± 0.79 | 0.17 ± 0.06 | 3 |
| 18 | 7.5 | 3.59 ± 0.33 | 0.43 ± 0.12 | 3 |
| 18 | 3.75 | 3.61 ± 1.14 | 0.17 ± 0.12 | 3 |
| CylcoPP | 30 | 1.39 ± 0.41 | 2.09 ± 0.17 | 3 |
| saline | | 3.31 ± 0.63 | 0.36 ± 0.11 | 3 |

After initial results were determined, the experiment was repeated using increased dose levels, until: (i) Micronucleus formation was seen; or (ii) Bone marrow toxicity was observed; or (iii) The lethal dose was reached; or (iv) A dose of 5 g/kg was administered. For the assays with each of the compounds 2, 6, 17 and 18, the acutely lethal dose was reached before there were any signs of bone marrow toxicity or micronucleus formation. The results of the experiment appear in Table 20, above. As is clear from the table, no bone marrow toxicity was observed for any of the compounds at the doses tested. The percent reticulocyte value for treatment with each compound remained close to the negative control value. This is in contrast with a drop of approximately 2–2.5% PCE/RBC seen in the positive control, representing erythrocyte depletion due to bone marrow toxicity. Nor did any of the compounds display clastogenic action. cl EXAMPLE 21

In EXAMPLE 13, the inactivation of cell-free HIV virus, using compounds and methods of the present invention, is shown. This example shows inactivation of cell-associated HIV also using compounds of the present invention.

H9 cells chronically infected with $HIV_{IIIB}$ were used. (H9/HTLV-III-B NIH 1983 Cat.#400). Cultures of these cells were maintained in high glucose Dulbecco Modified Eagle Medium supplemented with 2 mM L-glutamine, 200 u/mL penicillin, 200 μg/ml streptomycin, and 9% fetal bovine serum (Intergen Company, Purchase, N.Y.) For maintenance, the culture was split once a week, to a density of $3\times10^5$ to $4\times10^5$ cells/ml and about four days after splitting, 3.3% sodium bicarbonate was added as needed. For the inactivation procedure, the cells were used three days after they were split. They were pelleted from their culture medium at 400 g×10 minutes, the supernatant was discarded, and the cells were resuspended in one to five day old human platelet concentrate (PC) (pH 7.5–6.5), to a concentration of $2\times10^6$ cells/ml. Aliquots of the PC-infected cell suspension were made for psoralen free dark controls, for psoralen free UVA only controls, for psoralen dark controls, and for the psoralen plus UVA experimental sample. Concentrated filter-sterilized stock solutions of each psoralen in water were diluted into the appropriate aliquots to yield a final concentration of 150 μM. (A 10 mM stock of Compound 18 was diluted about 67-fold and a 2 mM stock of Compound 2 was diluted about 13-fold). After an equilibration period of thirty minutes at room temperature, 0.5 ml of each of the dark controls was placed in a cryovial and stored in the dark at −80° C. For UVA illumination, 8 ml of the psoralen free aliquot and 8 ml of each psoralen containing aliquot were introduced into a modified Fl 20 Teflon™ bag (modified to be 92 $cm^2$ total surface area, The West Co., Phoenixvill, Pa.) via a plastic disposable 10 ml syringe attached to one of the polypropylne ports on the bag. This gave an average path length of 0.17 cm. The bags were then illuminated for a total exposure of 3 Joules/$cm^2$ in the device described in Example 1, above, attached to a circulating refrigerating water bath set at 4° C., which maintains the temperature in the bag at approximately 22–25° C. During exposure, the device was shaken on a platelet shaker (Helmer Labs, Noblesville, Ind.). After exposure, the contents of the bags were withdrawn by a fresh syringe through the remaining unused port on the bag, and placed in cryovials for storage in the dark at −80° C. until analysis.

The stored samples were thawed at 37° C., then titrated in an HIV microplaque assay, as described in Hanson, C. V., Crawford-Mksza, L. and Sheppard, H. W., J. Clin. Micro 28:2030 (1990), and as described in EXAMPLE 13, above, with the following modifications. Clot removal from each sample was performed before plating. Because plating of a target volume of 4 ml after clot removal was desired, an excess of sample (6 ml) was transferred to a polypropylene tube and diluted to a final volume of 60 ml with Test and control samples from the inactivation procedure were diluted in 50% assay medium and 50% normal human pooled plasma. The samples were serially diluted directly in 96-well plates (Corning Glass Works, Corning, N.Y.). The plates were mixed on an oscillatory shaker for 30 seconds and incubated at 37° C. in a 5% $CO_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.) and prewarmed to 38.5° C. was added to each well. The plates were kept at 37° C. for a few minutes until several plates had accumulated and then centrifuged in plate carriers at 600×g for 20 minutes in a centrifuge precooled to 10° C. In the centrifuge, cell monolayers formed prior to gelling of the agarose layer. The plates were incubated for 5 days at 37° C. in 5% $CO_2$ and stained by the addition of 0.05 mL of 50 μg/mL propidium iodide (Sigma Chemical Co.) in phosphate-buffered saline (pH 7.4) to each well. After 24 to 48 hours, the red fluorescence-stained microplaques were visualized by placing the plates on an 8,000 μW/$cm^2$ 304 nm UV light box (Fotodyne, Inc., New Berlin, Wis.). The plaques were counted at a magnification of ×20 to ×25 through a stereomicroscope.

The results were as follows: Compound 2 (150 μM) inactivated >6.7 logs of HIV after 3 Joules/$cm^2$ irradiation (compared to dark and light controls of 0 log inactivation, starting log titer 6.1 plaque forming units/ml). At the same concentration and irradiation time, Compound 18 inactivated >7.2 logs of HIV (compared to a dark control of 0 logs and a light control of 0.1 logs, starting titer 6.6). This example supports that the compounds of the present invention are effective in inactivating cell associated virus.

EXAMPLE 22

This example involves an assessment of new synthetic media formulations as measured by the following in vitro platelet function assays: 1) maintenance of pH; 2) platelet aggregation ("Agg") and 3) GMP140 expression. The assays for each of these tests have been described above.

Four formulations were prepared: S 2.19, S 2.22, S 3.0 and S.4.0. The composition of these synthetic media formulations are shown in Table 2 below:

TABLE 21*

|  | S 2.19 | S 2.22 | S 3.0 | S 4.0 |
|---|---|---|---|---|
| Na gluconate | 23 | 0 | 0 | 0 |
| Na acetate | 27 | 20 | 20 | 20 |
| glucose | 0 | 2 | 2 | 2 |
| mannitol | 30 | 20 | 0 | 20 |
| KCl | 5 | 4 | 4 | 4 |
| NaCl | 45 | 80 | 100 | 90 |
| Na$_3$ citrate | 15 | 15 | 10 | 10 |
| Na phosphate | 20 | 20 | 20 | 20 |
| MgCl$_2$ | 0 | 3 | 2 | 2 |

*Amounts of mM.

One unit of human platelet rich plasma (PRP) was obtained from the Sacramento Blood Bank. The unit was centrifuged at room temperature for 6 minutes at 4000 rpm and then transferred to a unit press. Using an attached transfer line, plasma was expressed from the unit, leaving approximately 9.4 mL of residual plasma The unit was allowed to rest for 1 hour, after which it was gently kneaded to resuspend the platelets. To 0.6 ml of the suspension, 2.4 ml of plasma was added back and the entire contents transferred to a Teflon™ minibag. The reconstituted unit was assayed for pH and other tests the next day, with the following results:

| pH | 7.19 |
|---|---|
| GMP140 | 62% |
| Agg | 58% |

The remaining unit was then used to evaluate synthetic media for platelet storage with and without photodecontamination. Aliquots (0.8 ml) from the unit were added to each formulation (3.2 mls) in tubes. 3 mls of each mixture was transferred to a Teflon™ minibag (final plasma concentration of 20%).

Five days later, platelet function was assessed using the battery of tests described above. The results for each of the synthetic media formulations are shown in Table 3 below.

TABLE 22

|  | No Light | | Light | |
|---|---|---|---|---|
|  | S 2.19 | S 2.22 | S 2.19 | S 2.22 |
| pH | 6.86 | 6.82 | 6.83 | 6.60 |
| GMP140 | 87% | 74% | 90% | 80% |
| Agg | 30 | 48 | 16 | 31 |

It appeared that the synthetic media containing 2 mM glucose (i.e., S 2.22) maintained platelet function, as measured by GMP140 and Aggregation, better than the synthetic media that did not contain glucose (i.e., S 2.19).

To confirm the above finding, experiments were repeated ("n" being the number of replicate experiments) with these formulations as well as additional glucose-free formations (3.0 and 4.0). Platelet function was evaluated both before and after storage, and in conjunction with photodecontamination. A summary of the results is provided in Tables 4, 5 and 6 below.

TABLE 23*

|  | Plasma n = 17 | S 2.22 n = 22 | S 3.0 n = 4 | S 4.0 n = 4 | S 2.19 n = 23 |
|---|---|---|---|---|---|
| pH | 7.31 | 7.14 | 7.12 | 7.13 | 7.04 |
| Agg | 82 | 83 | 76 | 78 | 81 |
| GMP-140 | 52 | 49 | 46 | 45 | 68 |

*No UVA; Day 1 of storage.

TABLE 24*

|  | Plasma n = 18 | S 2.22 n = 20 | S 3.0 n = 4 | S 4.0 n = 4 | S 2.19 n = 23 |
|---|---|---|---|---|---|
| pH | 7.03 | 6.92 | 6.93 | 6.93 | 6.96 |
| Agg | 75 | 70 | 67 | 70 | 64 |
| GMP-140 | 61 | 63 | 63 | 64 | 74 |

*No UVA; Day 5 of Storage.

TABLE 25*

|  | S 2.22 n = 20 | S 3.0 n = 4 | S 4.0 n = 4 | S 2.19 n = 22 |
|---|---|---|---|---|
| pH | 6.80 | 6.78 | 6.79 | 6.95 |
| Agg | 59 | 54 | 54 | 58 |
| GMP-140 | 73 | 76 | 76 | 83 |

*3 Joules UVA; Day 5 of Storage.

EXAMPLE 23

Effect on Adsorption Kinetics of S-59 Partitioning into Platelets

Figure 25A:
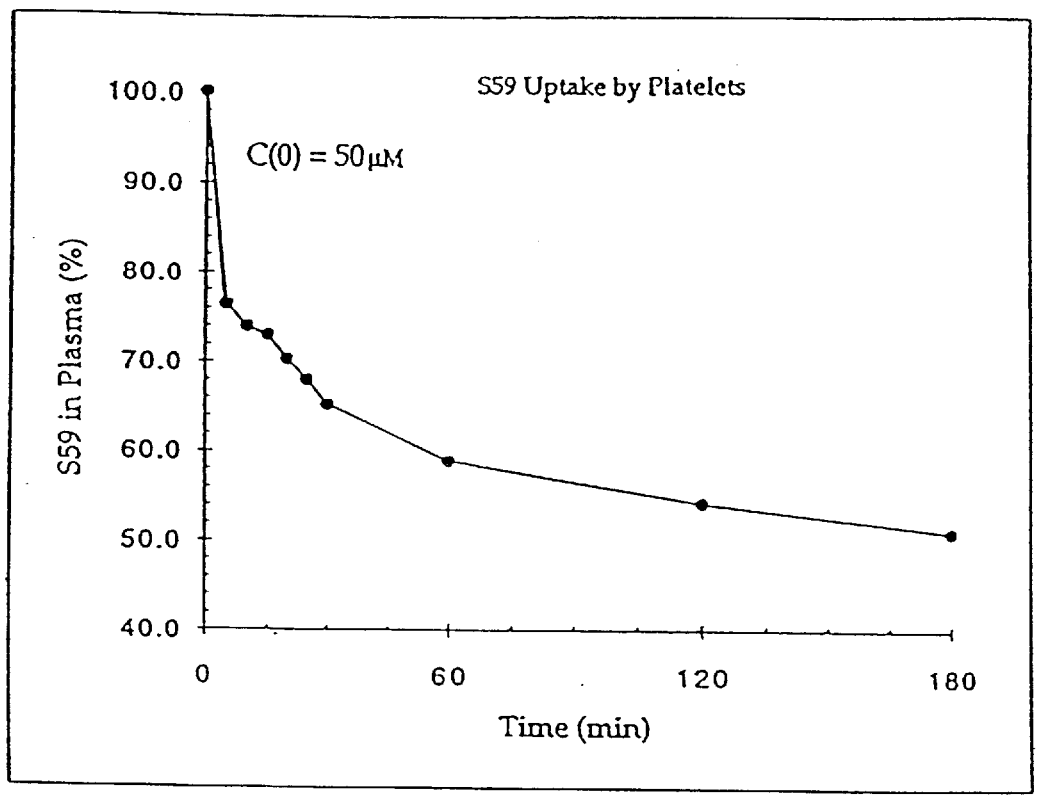
FIGS. 25A and 25B graphically depict S-59 ($C_o$=50 µM) uptake by platelets over time (FIG. 25A) and S-59 release by platelets over time (FIG. 25B).

As discussed previously, S-59 uptake by platelets can occur over a period of several hours before saturation occurs. FIG. 25A graphically depicts S-59 ($C_o$=50 $\mu$M) uptake by platelets over time (top) and S-59 release by platelets over time (bottom). As shown in the top graph, S-59 equilibrium is achieved at approximately two hours.

This example is directed to the question of whether partitioning of S-59 into platelets has a significant effect on adsorption kinetics. The adsorption kinetics of PC pre-incubated with S-59 for 24 hours prior to adsorption were compared to adsorption kinetics in PC without a pre-incubation period. The kinetics of adsorption in both cases (with or without a 24-hour pre-incubation period) were determined by contacting 35% PC (ie., 35% plasma165% PAS III) spiked with 150 $\mu$M ($C_o$) of S-59 with solid adsorbent (Amberlite XAD-4™; 0.1 g/3.0 mL). Samples of PC were removed at various time points and analyzed for levels of residual S-59.

Figure 25B:
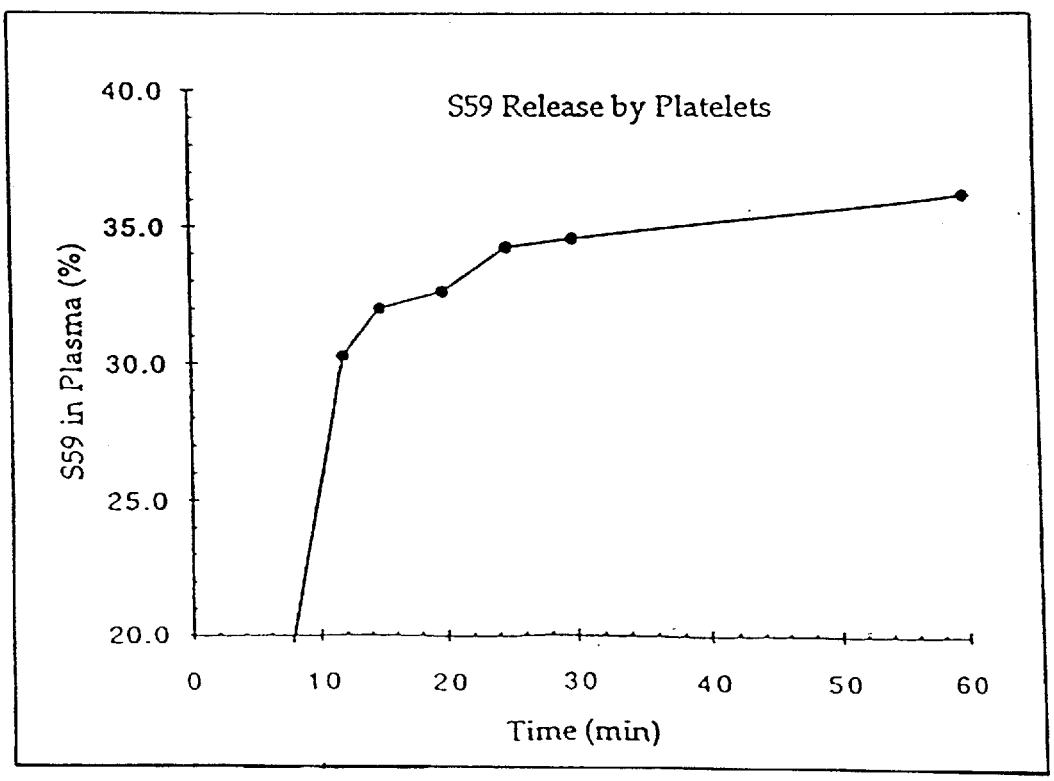
Figure 25C:
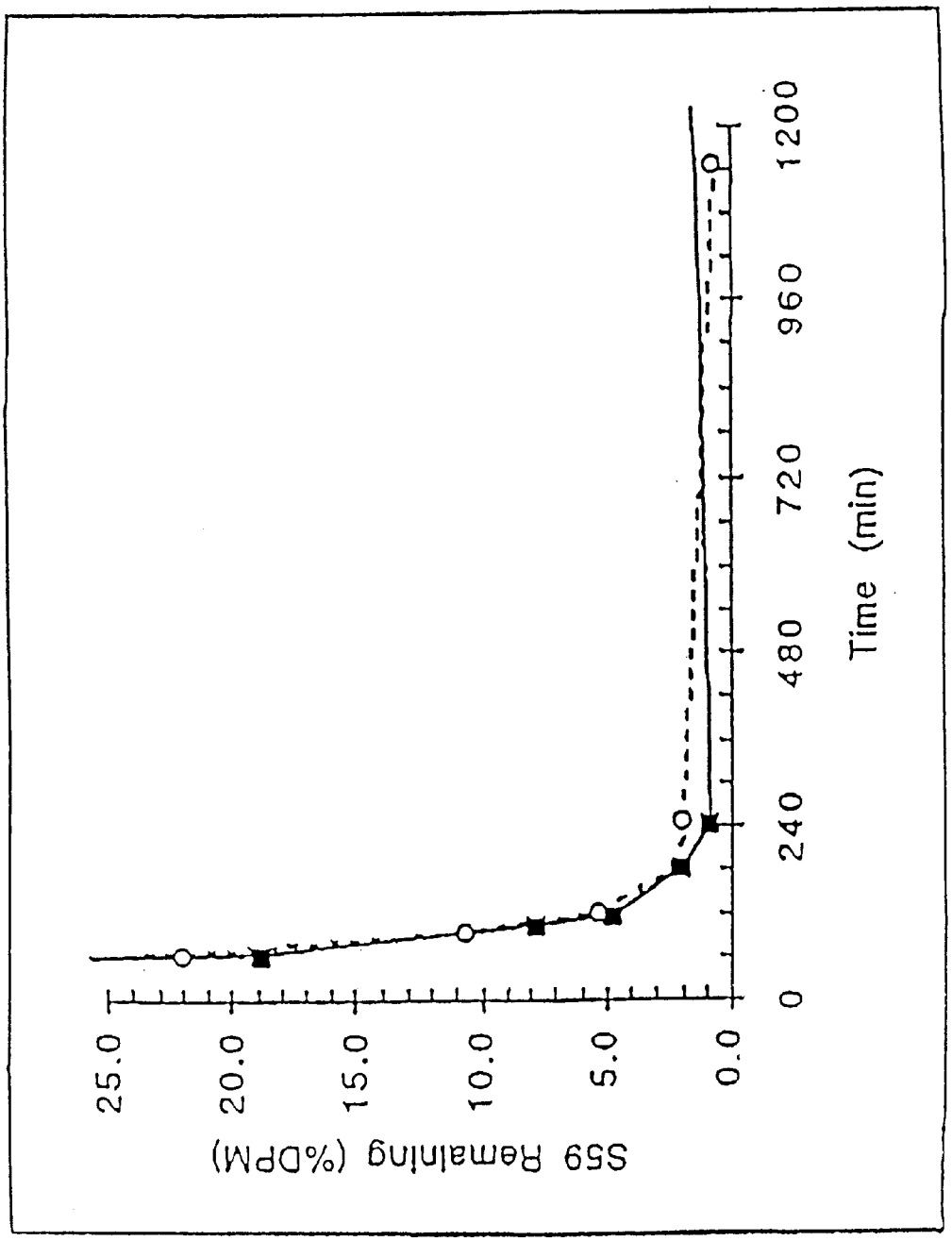
FIG. 25C is a graph showing the kinetics for adsorption of non-illuminated S-59 ($C_o$=50 µM) from 35% plasma/65% PAS III by Amberlite XAD-4™ (0.1 g/3.0 mL) with and without a 24-hour pre-incubation period with S-59 before addition of the adsorbent.

FIG. 25B graphically depicts the results; the data represented by the solid squares/solid line is adsorption data without pre-incubation, and the open circles/dashed line represents adsorption data with incubation. The results indicate that pre-incubation of platelets with S-59 did not result in significantly slower batch adsorption. Batch adsorption kinetics do not appear to be adversely affected by platelet uptake of psoralens. Flow adsorption devices, however, have a much shorter contact time. The data presented in FIG. 25A suggests that transport of S-59 from the platelet interior could be a major limitation for S-59 removal in devices with short residence time.

EXAMPLE 24

Removal of Residual S-59 and S-59 Photoproducts from Illuminated PC and Illuminated Plasma by Flow Adsorption Flow experiments were performed with Pharmacia C columns (borosilicate glass) (Pharmacia Biotech, Inc., Piscataway, N.J.) fit with special nylon mesh flow adapters with mm nylon. Columns were prepared with sterile resin and were rinsed with sterile PAS III before each experiment. Platelets were prepared in 35% plasma/65% PAS III with 150 $\mu$M S-59 and were illumninated to 3.0 J/cm$^2$ in large PL-2410 platelet storage bags. Following illumination, the platelets were allowed to agitate for at least one hour before passing through the S-59 adsorption device. The platelet mixtures were pumped through the column with a peristaltic pump so that the flow rate could be accurately controlled. Sterile connections were used so that platelet units could be transferred from one PL2410 bag, through the sterile adsorption column, to another PL2410 bag without contamination. A sample of the scrubbed platelet mixture was analyzed for residual S-59 and photoproducts using HPLC. In addition, units were stored in PL2410 bags and monitored for platelet function throughout storage.

Figure 26:
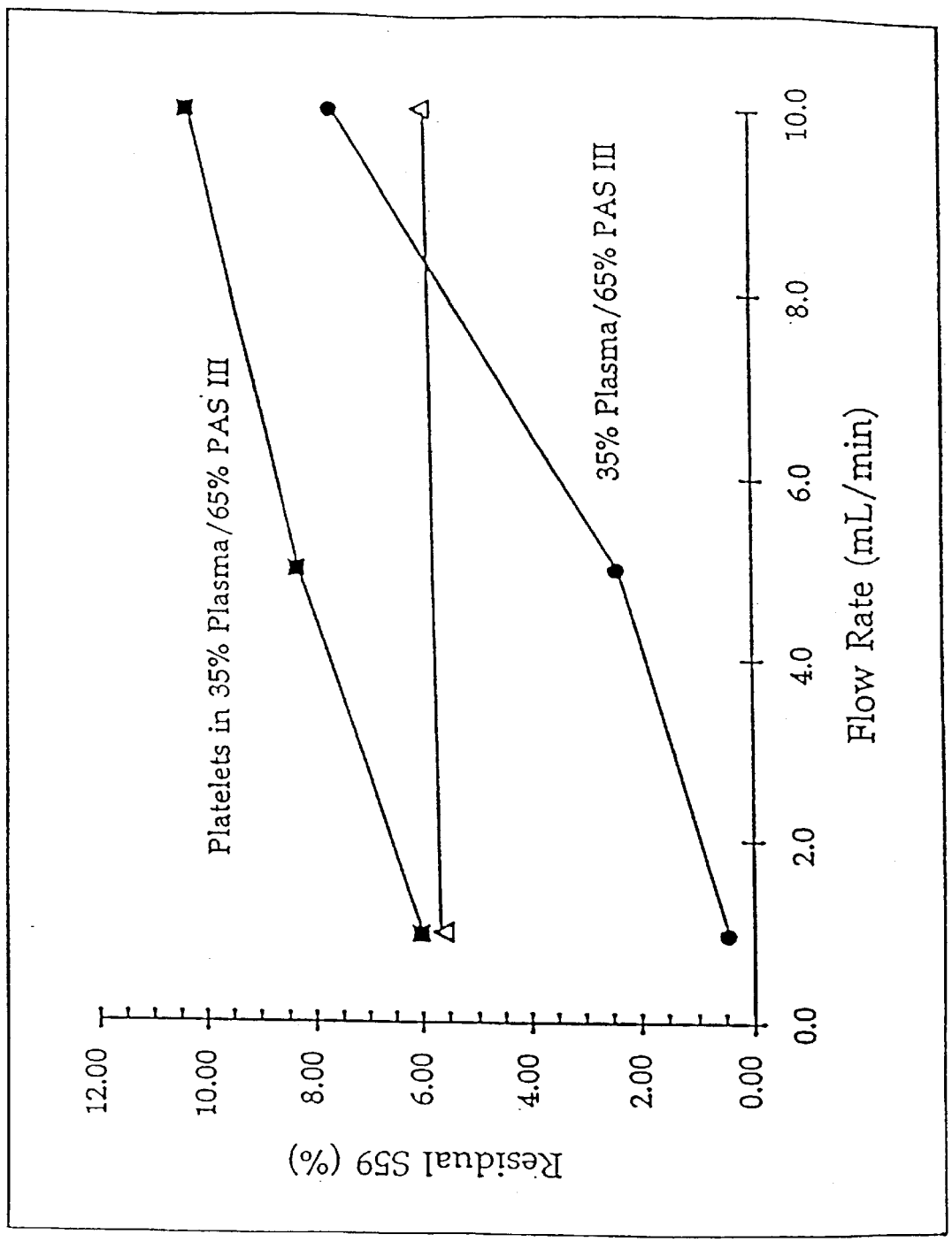
FIG. 26 is a graph illustrating the effect of flow rate on S-59 adsorption with Amberlite XAD-16™ (10 g/300 mL) in a 1 cm diameter column. Data for platelets in 35% plasma/65% PAS III is indicated by squares, whereas data for 35% plasma/65% PAS III is indicated by circles; open triangles indicate residual levels of S-59 adsorption with Amberchrom cg-161™ (120 diameter polystyrene, 5 g/300 mL).

The data shown in FIG. 26 summarizes the effect of flow rate in a 1 cm diameter column, particle size, and platelets on residual levels of S-59 in illuminated platelet units. Decreasing flow rate resulted in increased removal of S-59 for flow adsorption with Amberlite XAD-16™ (10 g/300 mL). Interestingly, the dependence on flow rate was not observed for Amberchrom cg-161™, a small particle (120 $\mu$m diameter) version of the Amberlite XAD-16™ (250–850 $\mu$m diameter). The effect of platelets on removal of S-59 was demonstrated by examining S-59 adsorption from illuminated 35% plasma/65% PAS III. Levels of residual S-59 were much lower in the 35% plasma/65% PAS III samples, suggesting that transport of S-59 and photoproducts from the platelets is the main kinetic resistance to S-59 adsorption. In FIG. 26, data for platelets in 35% plasma/65% PAS III is indicated by squares, whereas data for 35% plasma/65% PAS III is indicated by circles; the open triangles indicate residual levels of S-59 adsorption with Amberchrom cg-161 (120 $\mu$m diameter polystyrene, 5 g/300 mL).

EXAMPLE 25

Platelet Function Following Flow Adsorption

This example involved platelet function studies and clotting factor studies; the clotting factor studies were conducted by the UCSF Hematology Laboratory (San Francisco, Calif.). Platelets were collected in PL2410 platelet storage bags following passage through the flow adsorption device (Pharmacia C column; Pharmacia Biotech, Inc., Piscataway, N.J.). The platelet units were stored under standard conditions (platelets shaken at 22° C.) and were analyzed for platelet function following three days of storage. Platelet function data for platelets treated with adsorbent (10 g/300 mL) and stored for two days in PL2410 bags is summarized in Table E.

TABLE E

| Adsorbent | Flow (mL/min) | Plalelet Count (× 10$^6$/mL) | GMP-140 | Morph. | Aggreg. (%) | Shupe Change | Sec. ATP (nmol/10$^8$) | HSR (%) |
|---|---|---|---|---|---|---|---|---|
| None | 0.0 | 932 | 80.9 | 231 | 67.5 | 0.34 | 0.40 | 18.5 |
| None | 5.0 | 828 | 77.6 | 172 | 75.0 | 0.43 | 0.33 | 20.3 |
| XAD-16 | 5.0 | 816 | 77.8 | 200 | 75.0 | 0.39 | 0.35 | 16.2 |
| XAD-16 | 9.2 | 852 | 79.0 | 204 | 74.0 | 0.26 | 0.38 | 27.3 |
| XAD-4 | 9.2 | 912 | 80.2 | 212 | 65.0 | 0.35 | 0.29 | 19.4 |
| Hcmosorba | 5.0 | 876 | 76.1 | 208 | 73.0 | 0.38 | 0.28 | 31.5 |

In addition to the data summarized in Table E, measurements of pH, pO$_2$, and pCO$_2$ were taken over a five-day storage period. No significant differences between the treated and control units were observed. Finally, it should be noted that these experiments were performed with standard Amberlite™ resins (i.e., resins which were not treated by Supelco, Inc.). The leachables that are removed by the Supelco, Inc., cleaning process do not appear to have a substantial impact on platelet function as indicated by in vitro assays.

EXAMPLE 26

Removal of Residual S-59 and S-59 Photoproducts from Illuminated PC by Batch Adsorption The removal of residual S-59 and S-59 photoproducts from illuminated PC by batch adsorption was investigated. A unit of fresh platelets (i.e., 35% plasma/65% PAS III) was spiked with 150 $\mu$M $^3$H-S-59 and transferred to a PL2410 bag (Baxter). The bag was illuminated to 3.0 J/cm$^2$ and 20 mL aliquots of illuminated PC were transferred to PL2410 bags containig 0.67 g of adsorbent (10 g/300 mL), either Amberlite XAD-4™ or Amberlite XAD-16™. The bags were placed in a platelet incubator. Two separate platelet units were treated for each adsorbent; one unit was agitated for 3 hours before the platelets were separated from the adsorbent and transferred to another bag, and the other platelet unit was left in contact with the adsorbent for 4 days. Samples were removed from the units before treatment, after 3 hours of contact with the adsorbent, and on day 4.

Samples were analyzed for residual S-59 and platelet function. The results for S-59 removal are summarized in Table F.

TABLE F

| Adsorbent | % Residual S-59 Time = 3 Hours | % Residual S-59 Time = 4 Hours |
|---|---|---|
| Amberlite XAD-4 | 40.8 | 37.2 |
| Amberlite XAD-16 | 40.2 | 35.9 |

The data in Table F suggest that S-59 photoproduct adsorption is near completion after 3 hours of contact. The 36–37% of non-adsorbed radioactivity represents counts associated with plasma macromolecules (about 18%), platelet macromolecules (about 15%), and $^3$H exchanged water (about 10%). The residual radioactivity which is typically associated with macromolecules or water (43%) is in good agreement with the residual counts of the samples which were treated for 4 days (36–37%). The lower levels of residual radioactivity which were seen in the PC post-adsorption may be due to either a high estimate for counts associated with water or actual removal of plasma macromolecules covalently associated with S-59.

EXAMPLE 27

Removal of Residual S-59 and S-59 Photoproducts from Illuminated PC by Batch Adsorption This example, which examined the removal of residual S-59 and S-59 photoproducts from illuminated platelet mixtures by batch adsorption, was a continuation of Example 26. A unit of fresh platelets suspended in 35% plasma/65% PAS III was spiked with 150 $\mu$M S-59 and illuminated to 3.0 J/cm$^2$ in a large PL2410 platelet storage bag. The illuminated platelet mixture was contacted with Amberlite XAD-4™ (10 g/300 mL). Samples of the platelet mixture were removed at various time intervals and analyzed for residual S-59 and photoproducts using HPLC.

Figure 27:
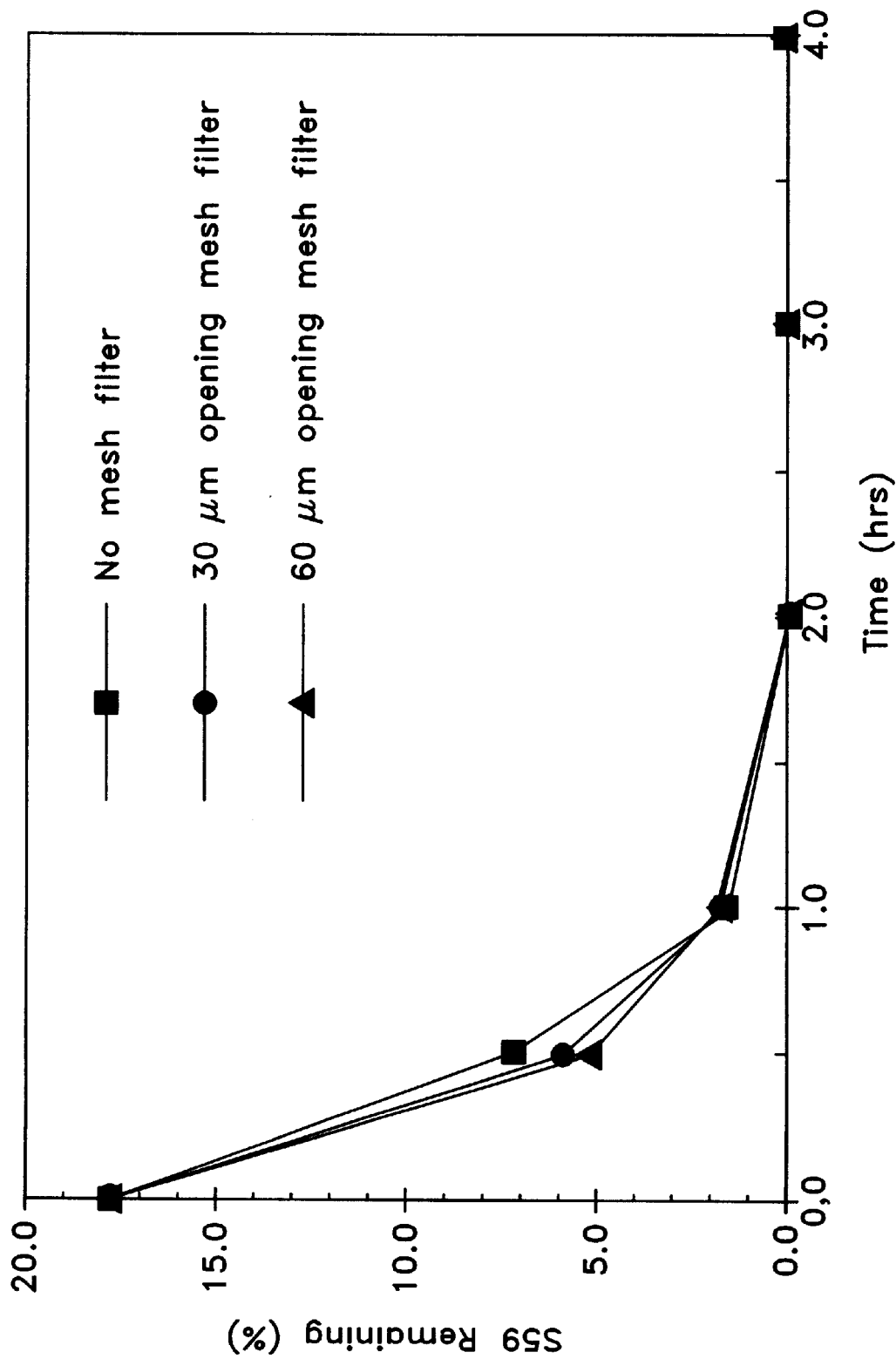
FIG. 27 graphically illustrates the kinetics of adsorption for batch contacting of Amberlite XAD-4™ (10 g/300 mL) with illuminated platelets in 35% plasma/65% PAS III. The percentages are relative to a non-illuminated platelet mixture.

The HPLC profiles (not shown) indicated greater than 99% removal of S-59 at 2 hours with non-detectable levels of S-59. The results are graphically depicted in FIG. 27. In FIG. 27, the squares represent residual levels of S-59 in a unit of platelets containing "free" (i.e., no encompassing mesh enclosure/pouch) Amberlite XAD-4™. Levels of residual S-59 in units containing Amberlite XAD-4™ enclosed in a mesh enclosure/pouch with 30 $\mu$m openings (Spectra/Mesh 30 $\mu$m nylon, open area=21%) and mesh enclosure/pouch with 60 $\mu$m openings (Spectramesh 60 $\mu$m nylon, open area=45%) are represented by circles and triangles, respectively. Percentages are relative to a non-illuminated platelet mixture (150 $\mu$m S-59).

EXAMPLE 28

HPLC Analysis of Illuminated PC

Figure 28A:
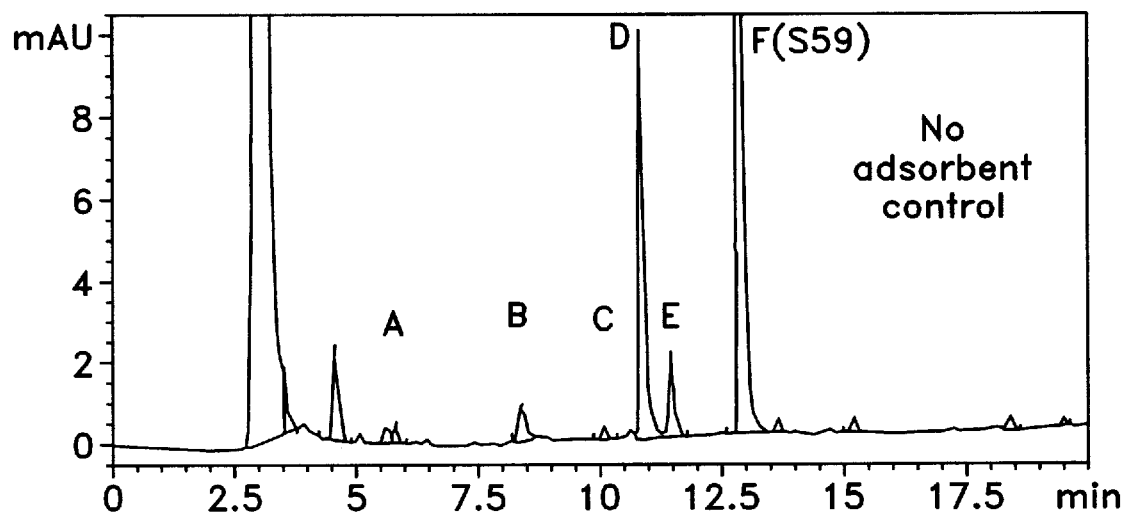
FIGS. 28A, 28B and 28C depict HPLC chromatograms of illuminated 35% plasma/65% PAS III after no treatment (FIG. 28A), adsorption with Amberlite XAD-16™ (FIG. 28B), and adsorption with Hemosorba CH-350™ (FIG. 28C).

A study was performed in which 20 mL samples of illuminated 35% plasma/65% PAS III were contacted with Amberlite XAD-16™ and Hemosorba CH-35™ for 4 days, then submitted to HPLC analysis. FIG. 28A depicts HPLC chromatograms of illuminated 35% plasma/65% PAS III after no treatment (i.e., no adsorbent) (top), adsorption with 0.033 g/mL Amberlite XAD-16™ (middle), and adsorption with 0.033 g/mL Hemosorba CH-350™ (bottom).

The parent S-59 is nearly completely removed in the case of both adsorbents with trace amounts of photoproducts B, D, and E. Photoproduct B appears to be the most difficult to remove, but probably represents less than 1% of the original S-59 on a molar basis. Analysis of FIG. 28A reveals that Hemosorba CH-350 appears to remove compounds in addition to photoproducts, as indicated by the decrease in the injection peak (retention time=3 min); thus, the Hemosorba CH-350 could potentially have an adverse effect on platelet function by removing necessary compounds such as nutrients.

Figure 28B:
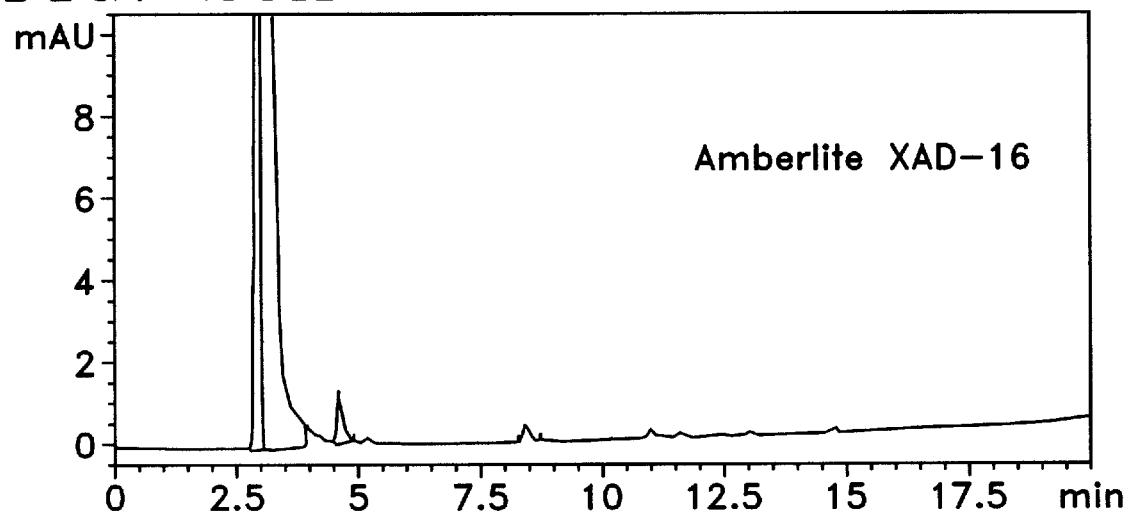
Figure 28C:
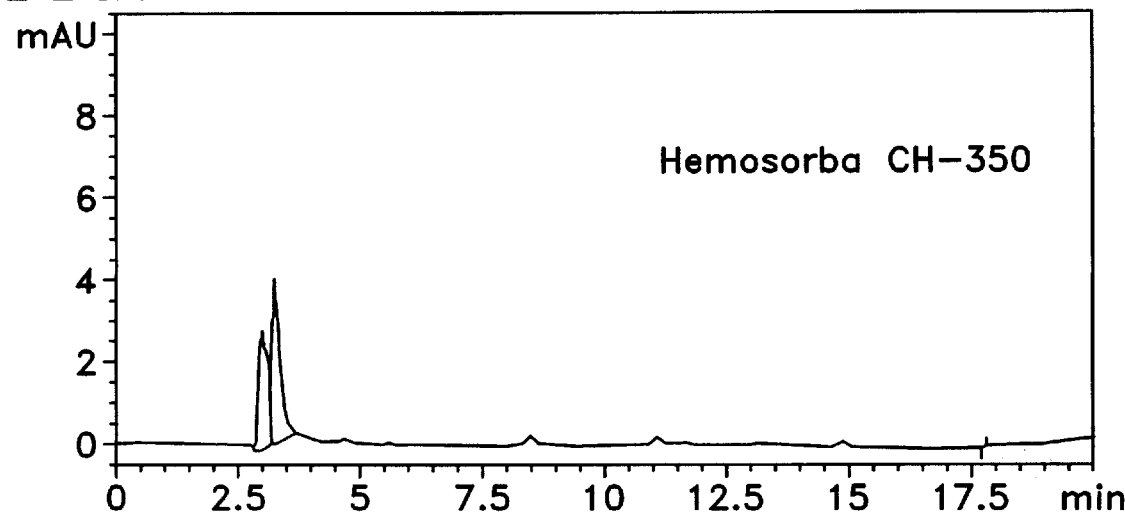
Figure 28D:
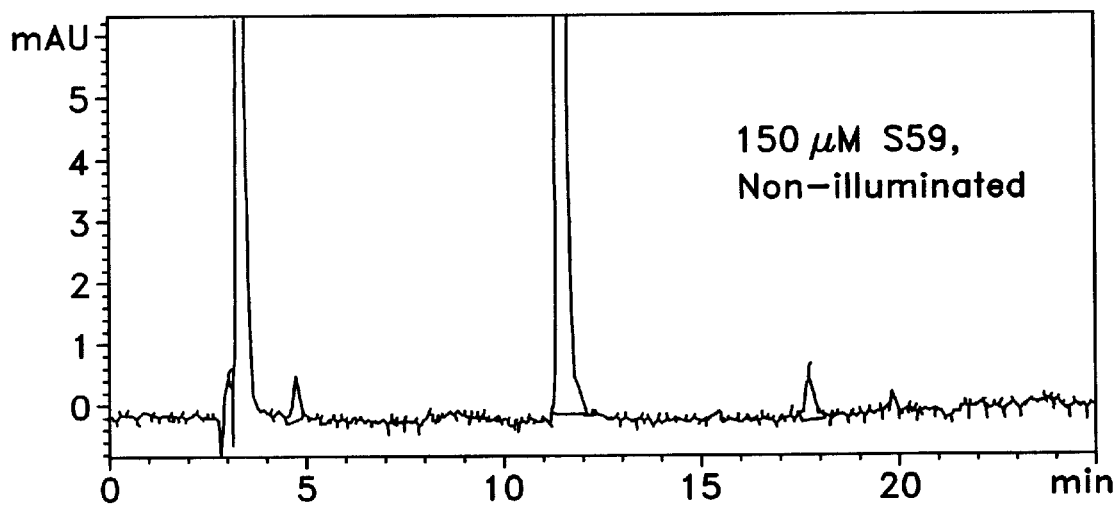
FIGS. 28D, 28E and 28F depict HPLC chromatograms of 35% plasma/65% PAS III containing non-illuminated S-59 (FIG. 28D), illuminated S-59 (FIG. 28E), and illuminated S-59 treated with Amberlite XAD-4™ (FIG. 28F), and adsorption was contained in a 30 µm opening nylon mesh enclosure/pouch, and the contact time was three hours.
Figure 28E:
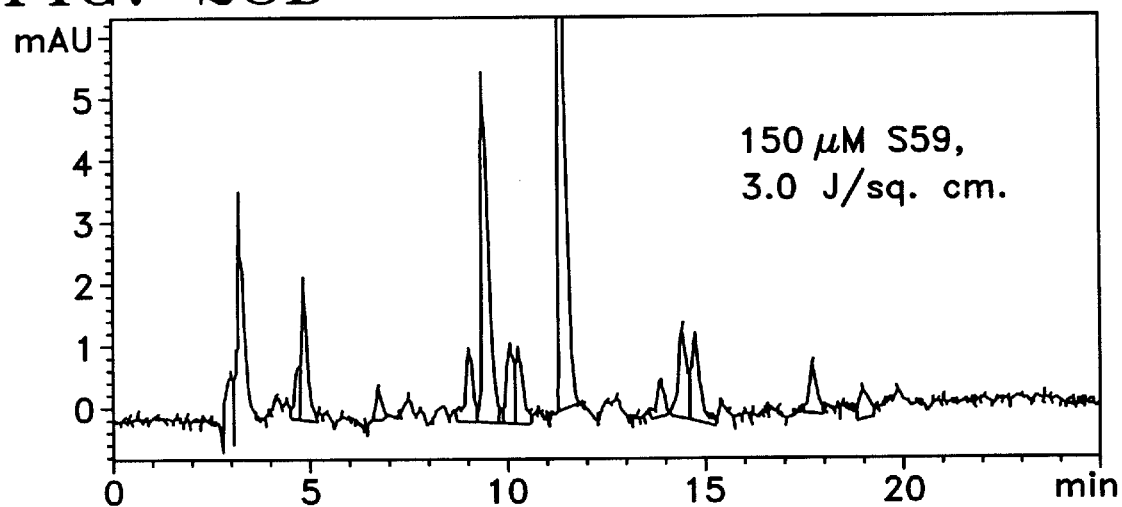
Figure 28F:
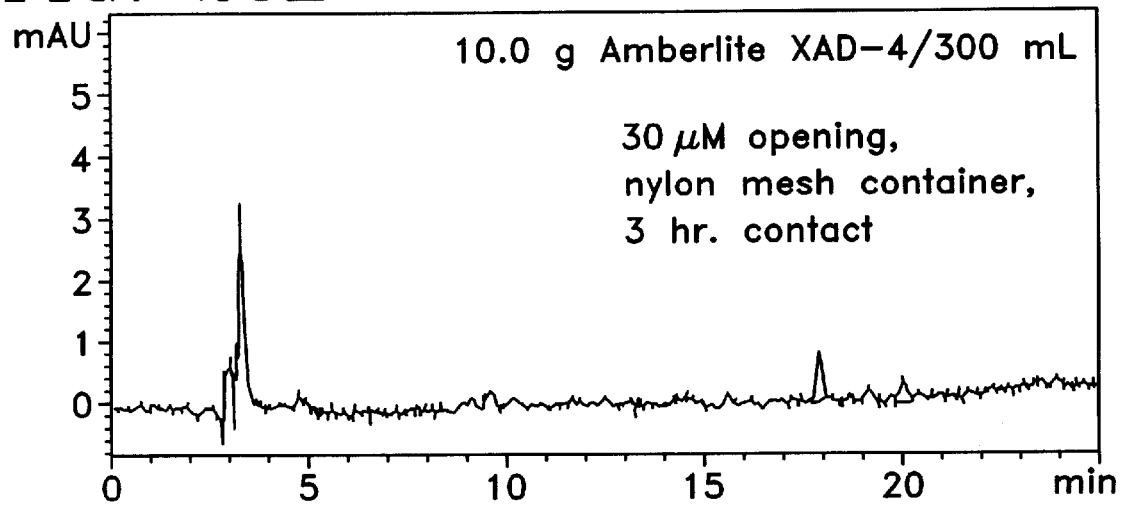

FIG. 28B depicts HPLC chromatograms of 35% PC (i.e., 35% plasma/65% PAS III) containing 150 $\mu$M of non-illuminated S-59 (top), 150 $\mu$M of illuminated S-59 (middle), and 150 $\mu$M of illuminated S-59 treated with 10.0 g of Amberlite XAD-4™ per 300 mL (bottom); the adsorbent was contained in a nylon mesh enclosure/pouch with 30 $\mu$m openings and the contact time was three hours. The peak corresponding to S-59 is present in the chromatograms representing non-illuminated S-59 (top) and illuminated S-59 (middle) at a retention time of approximately 12 minutes. The other peaks in the chromatogram representing illuminated S-59 (middle) (besides the injection peak at about 3 minutes) correspond to S-59 photoproducts formed during illumination. Note that the peaks appear at time (t)=18 minutes and t=20 minutes are plasma species and are not related to S-59. The peaks which remain in the bottom panel are not S-59 photoproducts, so removal of S-59 and photoproducts was essentially complete in this case as indicated by HPLC (i.e., non-detectable by HPLC). Analysis of the chromatogram treated with Amberlite XAD-4™ reveals that most of the S-59 and the S-59 photoproducts have been adsorbed.

EXAMPLE 29

Platelet Function Following Batch Adsorption

A unit of fresh platelets (i.e., 35% plasma/65% PAS III) was spiked with 150 $\mu$M S-59 and transferred to a PL2410 bag. The bag was illuminated to 3.0 J/cm$^2$ and 20 mL aliquots of the illuminated PC were transferred to small PL2410 bags containing 0.67 g of adsorbent (10 g/300 mL); Amberlite XAD-4Tm, Amberlite XAD-16™, Amberlite 200, and standard activated charcoal were the adsorbents used. The small poly PL2410 bags were stored in a platelet shaker at 22° C. Two separate platelet units were treated for each adsorbent. One unit of each pair was contacted with adsorbent for 3 hours before transferring to a platelet bag without adsorbent. The other platelet unit remained in contact with the adsorbent thoughout the 4-day storage period.

Samples were removed from the units after 24 hours and were analyzed for platelet count and pH. After 5 days, samples were taken and also analyzed for platelet count and pH, as well as ATP content and activation by GMP-140. Controls included a sample of PCD-treated PC without adsorbent (no-adsorbent control) and a sample of PC that was not treated. The results for each of the platelet function assays are present in Table G (the "*" In Table G indicates a contact time of three hours only).

TABLE G

| Adsorbent | PH | | Platelet Count (10$^6$/mL) | | ATP Content | GMP-140 |
| --- | --- | --- | --- | --- | --- | --- |
| | Day 1 | Day 5 | Day 1 | Day 5 | Day 5 | Day 5 |
| Original PC | 6.67 | — | 1192 | — | 0.7 (Day 0) | 48 (31) (Day 0) |
| No-Adsorbent Control | 6.81 | 7.03 | 1128 | 940 | 0.2 | 74 (69) |
| Amberlite XAD-4* | 6.81 | 7.05 | 1144 | 1220 | 0.3 | 64 (64) |
| Amberlite XAD-4 | 6.79 | 7.03 | 1132 | 1228 | 0.2 | 61 (62) |
| Amberlite XAD-16* | 6.82 | 7.07 | 1304 | 1352 | 0.3 | 64 (60) |
| Amberlite XAD-16 | 6.81 | 7.06 | 1108 | 988 | 0.2 | 58 (58) |
| Amberlite 200* | 6.79 | 6.93 | 1080 | 1104 | 0.0 | 92 (88) |
| Amberlite 200 | 6.79 | 7.00 | 1112 | 956 | 0.1 | 92 (92) |
| Sigma AC | 7.55 | 7.55 | 940 | 864 | 0.1 | 74 (91) |

The pH measurements and platelet counts summarized in Table G indicate that contact with the Amberlite resins did not drastically affect either the pH or platelet count of the PC. The PC that was treated with activated charcoal had a high pH, suggesting that the charcoal may have had a buffering effect on the PC. In addition, the platelet counts were significantly lower for the PC treated with activated charcoal. The most sensitive assay, GMP-140, indicates that both Amberlite XAD-4 and Amberlite XAD-16 have good hemocompatibility characteristics. The PC treated with Amberlite XAD-4 and Amberlite XAD-16 had lower levels of activation than the PCD-treated no-adsorbent control. Moreover, both the Amberlite XAD-4 and Amberlite XAD-16 samples that remained in contact with the adsorbent for 5 days had lower levels of activation than the corresponding samples that were contacted for only 3 hours. This observation suggests that contact of the PC with Amberlite XAD-4 and Amberlite XAD-16 for extended periods of time does not adversely affect platelet function. Conversely, the Amberlite 200 activated the platelets significantly relative to the no-adsorbent control. The platelet function studies suggested that Amberlite XAD-4 and Amberlite XAD-16 have satisfactory hemocompatibility characteristics.

Table H presents data for additional in vitro assays obtained from a similar batch adsorption experiment with Amberlite XAD-4. Once again, no adverse effects on platelet function were noted.

TABLE H

| Adsorbent | Platelet Count (× $10^6$/ml) | GMP-140 | Aggreg. (%) | Sec. ATP (nmol/$10^8$) | HSR (%) |
|---|---|---|---|---|---|
| No-Scrub Control | 957 | 55 | 105 | 0.58 | 56 |
| Amberlite XAD-4 | 973 | 57 | 113 | 0.58 | 88 |

Once again, it should be noted that these experiments were performed with standard Amberlite resins which were not treated by Supelco, Inc. As indicated by the in vitro assays, the leachables that are removed by the Supelco, Inc., cleaning process do not appear to have a substantial impact on platelet function.

EXAMPLE 30

Flow Adsorption of Plasma

This example describes the removal of psoralen from a sample of plasma using a flow device. In plasma, residence time is not as important as it is with other blood products (e.g, PCs) because adsorption is not dependent on transport of the S-59 from platelets.

As noted above, Supelco, Inc. (Bellefonte, Pa.) sells cartridges containing a hydrophobic adsorbent that can be used for a number of purposes, including adsorption of certain drugs and small proteins. The Rezorian™ A161 Cartridge (5 mL bed volume) sold by Supelco, Inc., is an in-line cartridge (i.e., a type of flow device) suitable for use in the removal of S-59 from plasma The polymer adsorbent beads have a mean pore diameter of 120 Å and a surface area of approximately 800–900 $m^2$/g.

Figure 29:
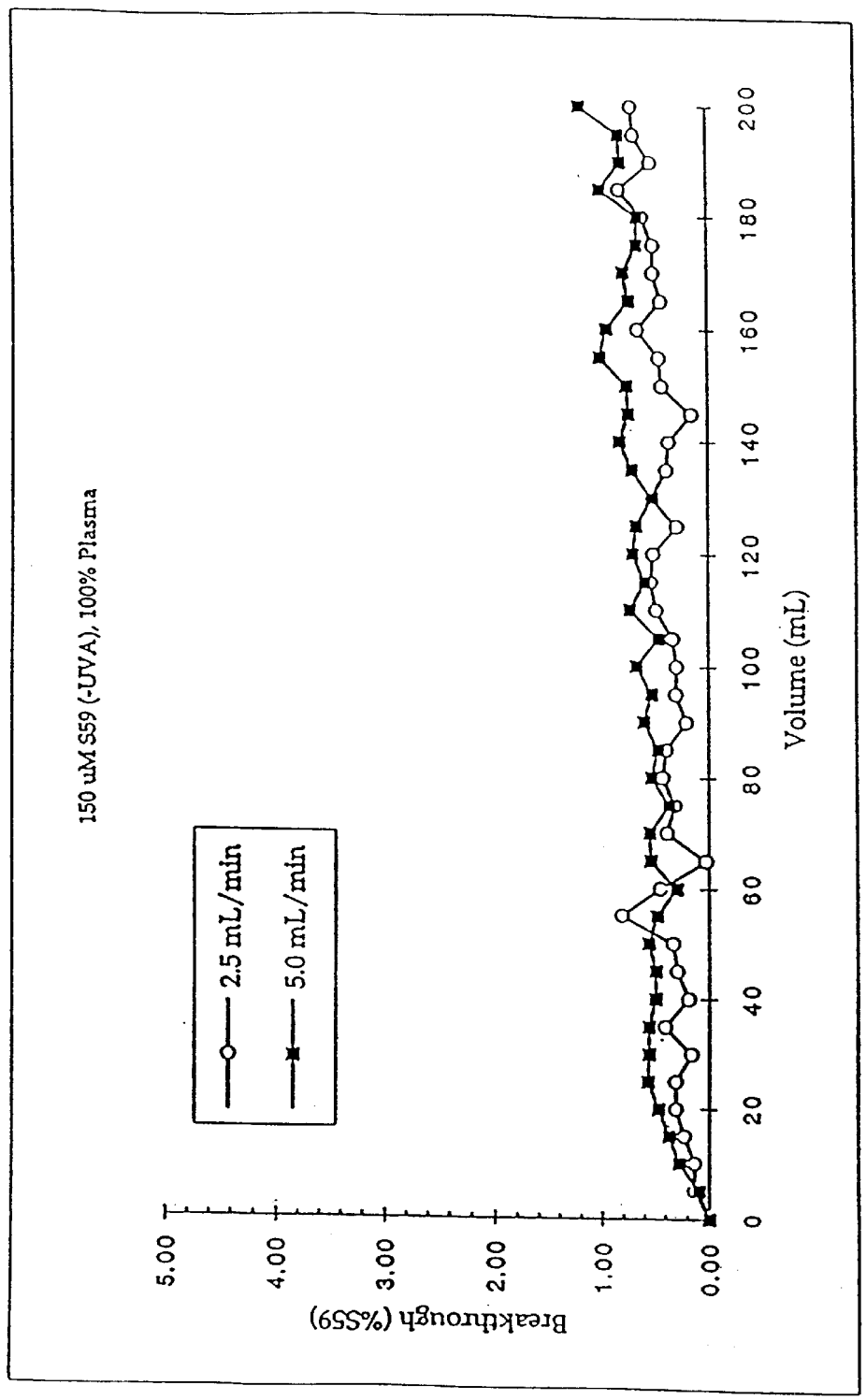
FIG. 29 is a graph that depicts the percentage of S-59 that escapes adsorption (indicated as Breakthrough) as a function of the volume of S-59-spiked plasma that is perfused through the cartridge; non-illuminated S-59 (150 µM) in 100% plasma at two different rates of flow (2.5 mL/min and 5.0 mL/min) is shown.
Figure 30D:
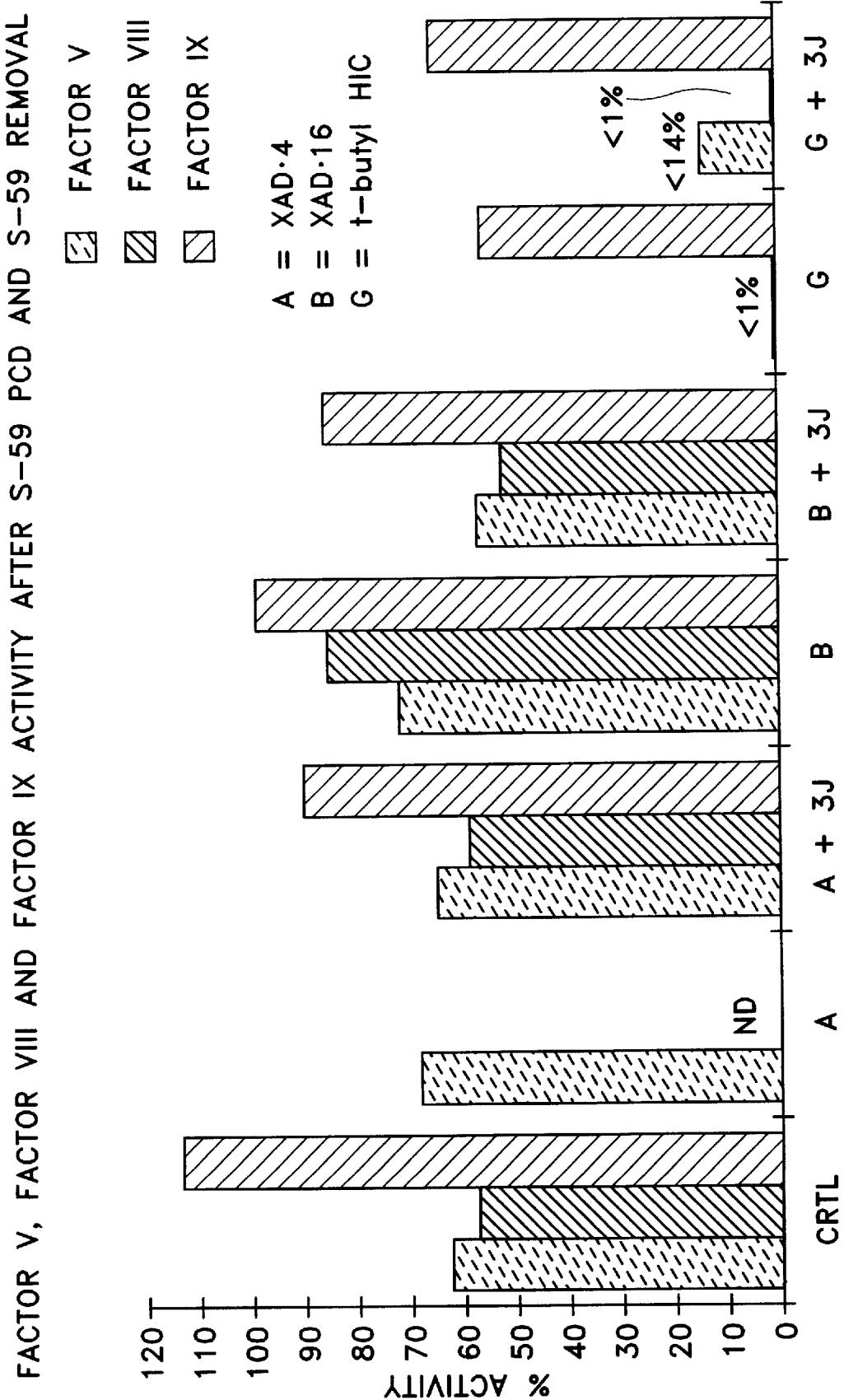
FIG. 30D graphically depicts Factor V, Factor VIII, and Factor IX activity after S-59 PCD and S-59 removal with Amberlite XAD-4™, Amberlite XAD-16™, and Bio-Rad t-butyl HIC™; both non-illuminated and illuminated samples were analyzed.

Studies were conducted with 100% human plasma at two different flow rates: 2.5 mL/min. and 5.0 mL/min. The results are graphically depicted in FIG. 29, which shows the percentage of S-59 that escapes adsorption (indicated as Breakthrough) as a function of the volume of S-59-spiked plasma that is perfused through the cartridge; the studies were conducted with non-illuminated S-59 in 100% plasma (150 $\mu$M). As one would expect, there is less adsorption of S-59 the higher the rate of flow through the cartridge.

It should be noted that if removal from platelet mixtures is being performed, the sintered plastic flow adapters of the Rezorian™ cartridges must be replaced with appropriate flow adapters (e.g., nylon mesh with 80 $\mu$m openings), as the flow adapters may harm the platelets.

EXAMPLE 31

Clotting Factor Assays Following Batch Adsorption of Plasma

The adsorbent used for plasma products must also be capable of removing psoralen without significantly depleting the levels of proteins important in the clotting cascade. In this example, the selectivity of various resins for S-59 was analyzed by performing batch adsorption experiments and analyzing the treated plasma for levels of clotting factors and clotting times.

A 1.0 mL aliquot of 100% plasma was added to 0.1 g of adsorbent and sealed in polypropylene tubes. The tubes were gently agitated at room temperature for 3 hours. Samples of plasma were obtained by either allowing the adsorbent to settle or filtering the sample through a 0.2 $\mu$m filter to remove the adsorbent. Plasma samples were submitted to the UCSF Hematology Laboratory (San Francisco, Calif.) for standard clotting assays. Assays that were performed included fibrinogen level, Factor V level, Factor VIII level, Factor IX level, activated partial thromboplastin time, prothrombin time, thrombin time, and ristoceitin level. Table I summarizes the data from the plasma assays, while FIGS. 30A–30D graphically depict the effect of S-59 PCD and S-59 removal on certain indicators of coagulation function. In Table I, the designation "+S-59/+UVA" refers to data obtained from plasma samples containing 150 $\mu$M S-59 exposed to 3 J/$cm^2$ of ultraviolet radiation; in addition, "PT" designates prothrombin time, "aPTT" designates activated partial thromboplastin time, and "TT" designates thrombin time.

TABLE I

| Absorbent | Fibrinogen (mg/dL) | Factor V (%) | Factor VIII (%) | Factor IX (%) | Ristoceitin (%) | PT* (sec) | aPTT* (sec) | TT* (sec) |
|---|---|---|---|---|---|---|---|---|
| High Normal | 375 | | | | | 13.8 | 36 | |
| Low Normal | 175 | | | | | 10 | 23 | |
| Control (+S-59/+UVA) | 215 | 68 | 57 | 106 | 69 | 12.3 | 34.4 | 37.4 |
| Amberlite XAD-4 | 215 | 65 | 59 | 90 | 67 | 12.3 | 32.8 | 35.3 |
| Amberlite XAD-16 | 158 | 57 | 52 | 86 | 67 | 13.3 | 37.3 | 45.4 |

TABLE I-continued

| Absorbent | Fibrinogen (mg/dL) | Factor V (%) | Factor VIII (%) | Factor IX (%) | Ristoceitin (%) | PT* (sec) | aPTT* (sec) | TT* (sec) |
|---|---|---|---|---|---|---|---|---|
| Control (+S-59/ +UVA) | 199 | 59 | 47 | 108 | 96 | 12.5 | 35.3 | 30.5 |
| Hemosorba CH-350 | 190 | 64 | 41 | 92 | 130 | 12.4 | 35.7 | 30.7 |
| BioRad t-butyl HIC | 240 | 2-14 | <1% | 65 | <10 | 42.9 | 100 | 29.8 |
| Davison Silica (Grade 15) | 233 | 68 | 51 | 88 | 106 | 12.1 | 38.6 | 30.4 |

The samples were submitted to the UCSF Hematology Laboratory in two separate groups (as indicated by the separation of results in Table I). The control plasma samples for each group were treated with S-59 and UVA but were not contacted with adsorbent Levels of Factor V and Factor VIII activity were suppressed in the plasma sample prior to treatment with S-59, indicating that treatment with S-59 was not the cause. Amberlite XAD-4 and Hemosorba CH-350 showed the best results with little effect on any of the tested parameters. Factor IX levels were slightly depressed in both cases.

Amberlite XAD-16 showed a reduction in fibrinogen level, but only slight reductions in Factor V and IX levels, and slight increases in activated partial thromboplastin time and thrombin time. The increased pore size of Amberlite XAD-16 (160 Å) may be the cause of increased adsorption of clotting factor relative to Amberlite XAD-4, which has much smaller pores (40 Å). Reduced pore size may therefore offer specificity for adsorption of small molecules such as S-59 and prevent adsorption of larger molecules such as proteins. Finally, the BioRad t-butyl HIC (Macro-Prep) gave very poor results, with almost complete removal of Factor V and Factor VIII and significant increases in prothrombin time and activated partial thromboplastin time.

The experiments relating to clotting factor assays were carried out in a batch mode at a higher ratio of adsorbent to plasma than is typically used in adsorption experiments. In addition, a flow device should result in shorter contact times with concomitantly higher recovery of the proteins involved in blood clot formation.

EXAMPLE 32

Effect of Water Content on the Function of Amberlite Adsorbents

As previously introduced, the Amberlite® XAD-4 and XAD-16 adsorbents (Rohm and Haas) have properties which make them appropriate for use in removing compounds from transfusable blood products (e.g., platelet concentrates [PC] and fresh frozen plasma [FFP]) following photochemical decontamination. Indeed, the non-ionic, macroporous polystyrene divinyl benzene adsorbents Amberlite® XAD-4 and Amberlite XAD-16 have shown a high capacity for S-59. Early in the development of the RD for PC, the inventors found that steam treatment or drying of the Amberlite adsorbents removed some water from the pores of the adsorbent; as a result, the cleaned adsorbent had a substantially lower adsorption capacity for S-59 than the wet adsorbent. This example is directed at the effect of water on the adsorption capacity of the Amberlite and on conditions for wetting the adsorbent and restoring adsorbent function following treatment.

Initial studies performed by the inventor in developing the RD for platelets used Amberlite adsorbents purchased directly from Rohm & Haas. These adsorbents were obtained in a highly hydrated form with Amberlite® XAD-16 typically having a water content of 50–65% by weight and Amberlite® XAD-4 typically having water content of approximately 40–55% by weight. However, the thermal cleaning process currently performed by Supelco (Bellefonte, Pa.) results in a reduced water content (<5%) and a concomitant significant decrease in adsorption capacity. In addition, the dry adsorbent particles contain air in the bead pores which causes the beads to float in aqueous solution unlike the hydrated adsorbent particles, also reducing adsorptive capacity.

A. Wetting Procedure in the Manufacturing of a RD

Wetting of polymeric adsorbents such as Amberlite® XAD-4 and XAD-16 can be achieved using organic solvents which reduce the surface tension of the wetting solution and increase the wetability of the adsorbent. Ethanol was chosen as the organic solvent for this process. The two variables which can be adjusted for the wetting process include (i) ethanol concentration and (ii) contact time with the wetting solution. A contact time of 10 minutes was chosen based on the desired processing time for wetting of the adsorbent.

A study was performed to determine the ethanol concentration required for wetting in a 10 minute batch procedure. Samples of cleaned Amberlite® XAD-4 (Supelco lot SC-27) and Amberlite® XAD-16 (Supelco lot SC-30) were suspended in ethanol/water solutions containing levels of ethanol from 0–50% by volume. Adsorbent was contacted with the solution at a ratio of 1 g adsorbent to 5 mL of wetting solution. The samples of adsorbent were periodically agitated during the 10 minute incubation. The ethanol solution was removed at the end of 10 minutes and replaced with distilled water. A series of three batch-rinsing steps (10 min. each) in distilled water was performed at a ratio of 1 g adsorbent per 5 mL of water. The water was then removed and the adsorbent particles were allowed to drain dry.

The water content of each adsorbent sample was determined by accurately weighing a sample of adsorbent into a previously dried and pre-weighed container (a scintillation vial). The samples were placed in a drying oven at 120° C. and allowed to dry for 24 hrs. The dried samples were weighed and the mass % water content was calculated. Of note, drying of the samples for longer than 24 hours did not result in additional loss of water.

Figure 31:
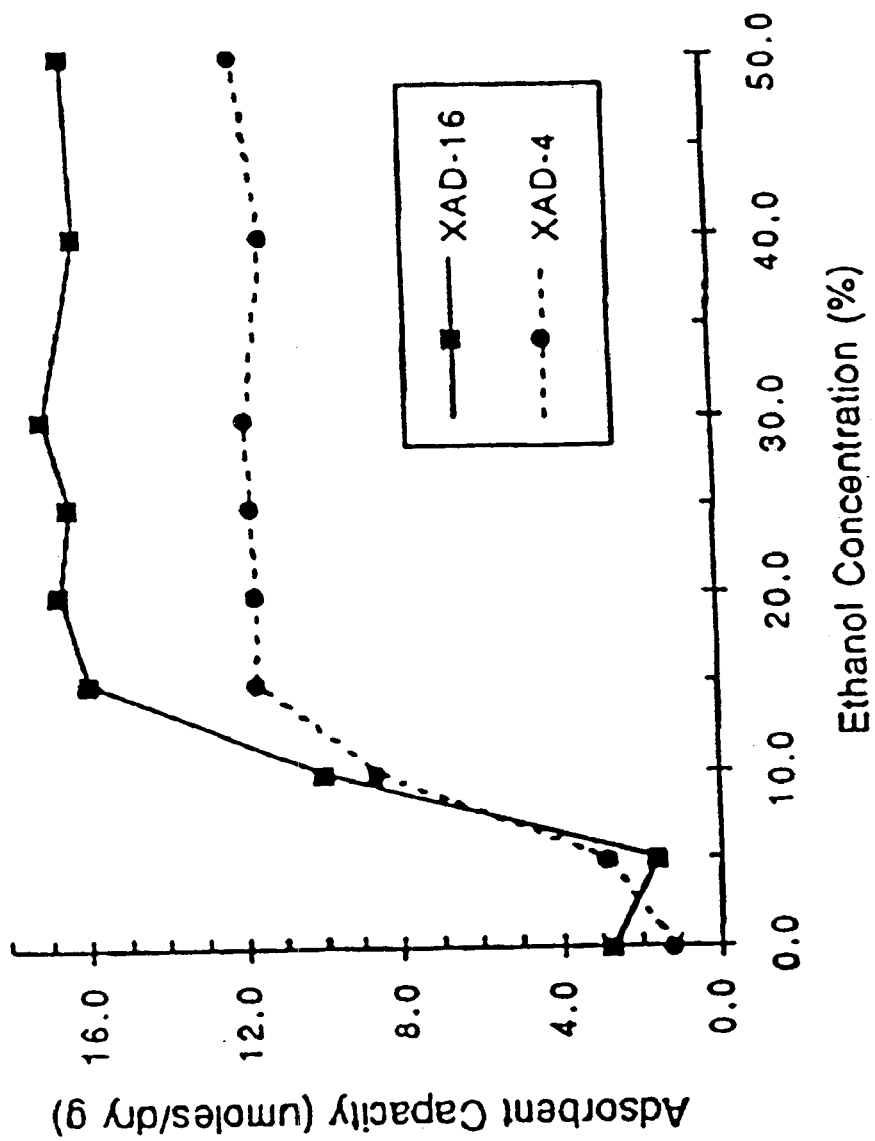
FIG. 31 graphically depicts the relationship between the ethanol content of the wetting solution and the adsorption capacity of the resulting adsorbent for a 10 min. batch wetting process with Amberlite® XAD-4 (circles) and XAD-16 (squares) adsorbents.

Samples of each adsorbent were also tested for equilibrium adsorption capacity. Approximately 0.1 g of adsorbent was weighed and transferred into a 5 mL polypropylene tube. A 3.0 mL aliquot of 35% plasma, 65% PAS III containing 150 µM $^3$H-S-59 was added to each tube. The tubes were placed on rotators and incubated for 24 hours at room temperature. Following incubation, a sample was removed from each tube and transferred into an Eppendorf tube. A 200 µL sample of 35% plasma was removed from each Eppendorf tube and diluted in 5.0 mL of HiSafe LSC cocktail (Wallac). Samples were counted on a Wallac LSC to determine residual levels of S-59 in each sample. Capacities were calculated by determining the total µmoles of S-59 which were removed from each sample per mass of dry adsorbent. FIG. 31 depicts the relationship between the ethanol content of the wetting solution and the adsorption capacity of the resulting adsorbent for a 10 minute batch wetting process. Adsorption capacities are for removal of S-59 from 35% plasma, 65% PAS III. Capacities were estimated from single adsorption measurements with $C_o$=150 µM.

The results summarized in FIG. 31 suggest that wetting the Amberlite adsorbents with aqueous ethanol solutions having ethanol concentrations above 15% (v/v) results in near maximal recovery of adsorbent capacities. It should be noted that this data was collected for a 10 minute batch process. It is possible that lower levels of ethanol could be used if longer contact times were used. In addition, it should be emphasized that a minimum of 20% ethanol may be required to prevent microbial growth in the wetting solution. Excessively high levels of ethanol should obviously be avoided to reduce both ethanol costs and levels of ethanol that must be removed in the subsequent water rinse.

B. Adsorbent Capacity as a Function of Water Content

Figure 32:
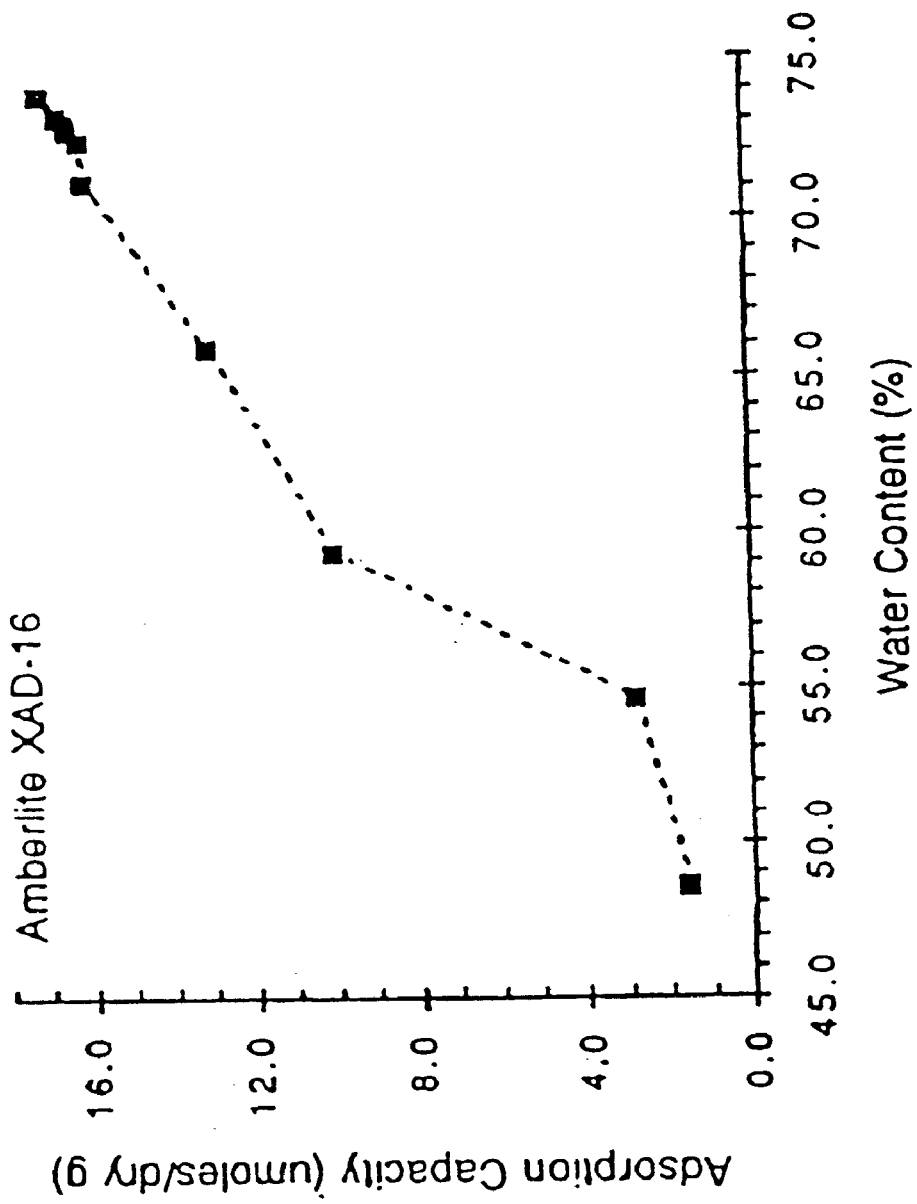
FIG. 32 graphically depicts that removal of S-59 from 35% plasma, 65% PAS III decreases with decreasing water content for Amberlite® XAD-16.

The samples that were prepared in the wetting study described above can also be analyzed to determine the relationship between water content and adsorption capacity. The results for Amberlite® XAD-16 are summarized in FIG. 32. FIG. 32 indicates that the adsorption capacity (i.e., µmoles of S-59 adsorbed/g of dry adsorbent) of Amberlite® XAD-16 for removal of S-59 from 35% plasma, 65% PAS III decreases with decreasing water content. The data presented in FIG. 32 were taken following wetting of the adsorbent with various concentrations of aqueous ethanol solutions. It should be pointed out that the relationship between adsorption capacity and water content may be different for the same adsorbent depending upon the possessing history (i.e., water content achieved by wetting or drying).

Referring to FIG. 32, the adsorption capacity approaches extremely low levels as the water content decreases to below 50% water by mass. Conversely, the adsorption capacity increases steadily to a maximum value at water contents between 70–75% water. The adsorption capacities have been corrected back to a dry mass basis for the adsorbent so that the increasing capacity reflects real changes in adsorbent function.

Although the correlation presented in FIG. 32 is noteworthy, it is important to emphasize that the samples having varying water contents were obtained by wetting the adsorbent under different conditions. Though not confirmed, more relevant data might be obtained by producing adsorbent samples having varying water contents by drying a sample of fully hydrated adsorbent. It is believed that samples obtained by wetting the adsorbent may contain a higher percentage of water on the external surface of the adsorbent bead. Conversely, it is believed that adsorbent prepared by drying will probably lose water covering the external surface of the bead first; this would result in a change in the appearance of the adsorbent but may not affect adsorption capacity if significant water has not been removed from the pores of the adsorbent. Preliminary data indicating the approximate rate of water loss from the Amberlite adsorbents at room temperature is presented in the next section.

C. Drying During Handling of Amberlite Adsorbents

As previously discussed, the polyester mesh pouch may be filled with dry Amberlite adsorbent and sealed by ultrasonic or impulse weld during manufacturing of the RD of the present invention. The sealed pouches will then be subjected to the wetting process in aqueous ethanol followed by a final rinse with distilled water. The final RD will be incorporated into PL 2410 Plastic containers (Baxter) which will be sealed in a foil overwrap. The foil overwrap will serve as a liquid barrier and prevent drying of the adsorbent during storage. The most vulnerable time for potential drying of the Amberlite adsorbents during the manufacturing process is the time between completion of the final rinse step and enclosure of the RD in the foil overwrap. In order to better understand the potential for drying of the adsorbent during manufacturing, a study was performed to assess the rate of drying of the Amberlite adsorbents at room temperature.

In this study, samples of Amberlite® XAD-16 (Supelco Lot SC-30) and Amberlite® XAD-4 (Supelco Lot SC-27) were prepared by wetting the adsorbent in a 30% aqueous ethanol solution. Following a 10 minute incubation in the aqueous ethanol, the adsorbent was rinsed thoroughly with distilled water. Approximately 50 g of each adsorbent were allowed to drain dry and were then placed in a plastic container. The container was left at room temperature and was not subjected to increased air flow (e.g., laminar flow hood). Samples were removed from the container at time intervals and placed in air-tight polypropylene vials. The water content of each sample was determined as discussed above.

Figure 33:
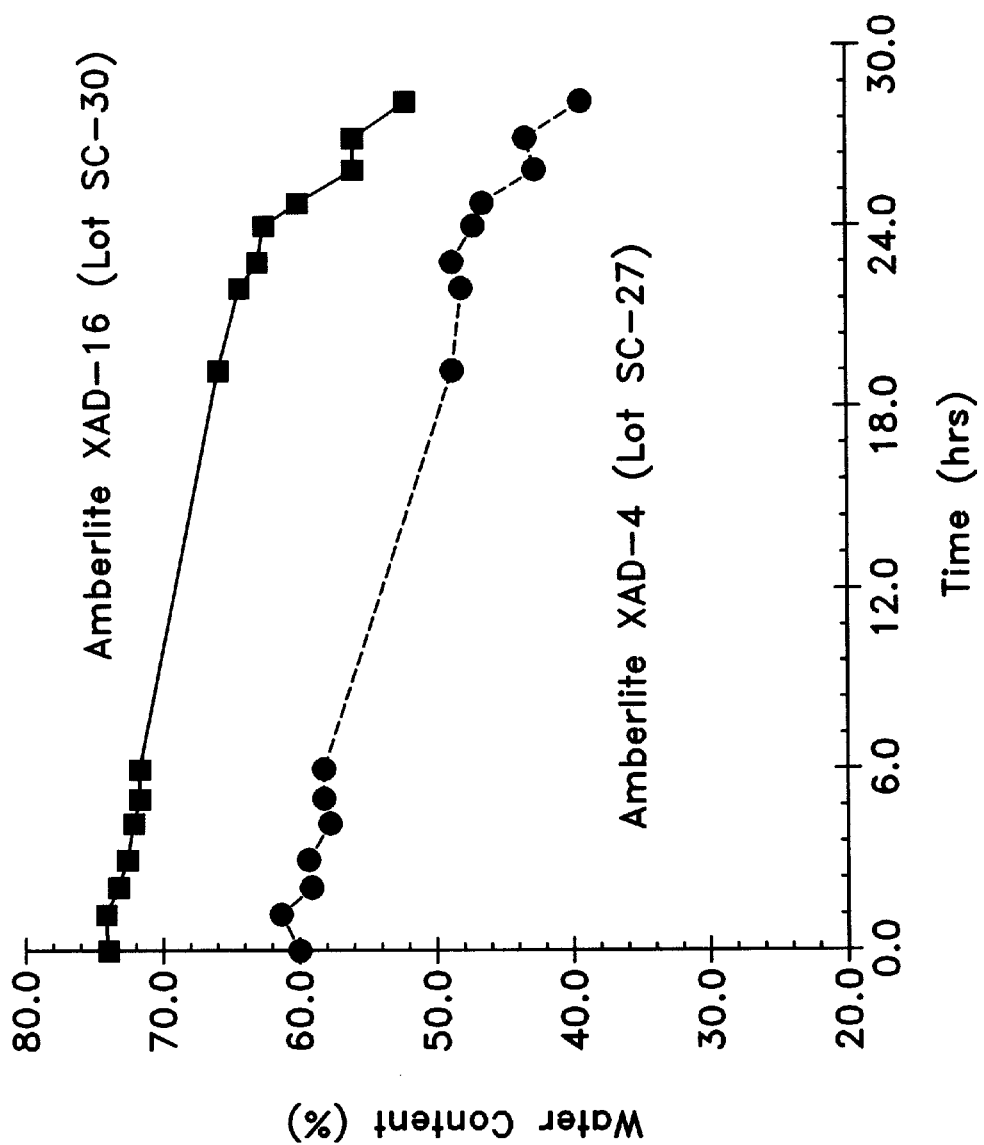
FIG. 33 graphically depicts loss of water by Amberlite® XAD-16 (squares) and Amberlite® XAD-4 (circles) during a 27-hour incubation at room temperature and standard humidity.

The data indicating the kinetics for water loss from both Amberlite® XAD-4 and Amberlite® XAD-16 are presented in FIG. 33. More specifically, FIG. 33 represents loss of water by Amberlite® XAD-16 (squares) and Amberlite™ XAD-4 (circles) during a 27-hour incubation at room temperature and standard humidity. The results of FIG. 33 indicate that water loss is a potential problem that should be considered in both manufacturing and storage of Amberlite-containing RDs.

EXAMPLE 33

Sterilization of Wet Amberlite Adsorbents by Gamma Irradiation

As previously indicated, the storage container containing the assembled RD of the present invention is sealed in a foil overwrap and terminally sterilized. Generally speaking, polystyrene divinyl benzene adsorbents are stable to repeated autoclave cycles. However, some storage containers (e.g., PL 2410 Plastic container (Baxter)) are not autoclavable due to the materials used therein, and must be sterilized by either γ-irradiation, the preferred technique, or E-beam.

This example describes the methods and results of studies performed to determine the suitability of either γ-irdiation or E-beam for sterilizing wet Amberlite adsorbents. Data of the effects of sterilization on a variety of adsorbent characteristics, including adsorption kinetics and adsorption capacity, are presented below.

A. Effect of γ-Irradiation on Adsorption Kinetics

Raw (i.e., unprocessed) adsorbent was processed by Supelco and then subjected to γ-irradiation. Two separate lots of raw adsorbent were processed at Supelco according to the following procedure. First, batches of raw adsorbent (e.g., 18 liters) were placed in a cleaning container with 74 μm sieve retainers and rinsed with deionized water; during rinsing, the conductivity of the effluent is continuously monitored. Rinsing was complete when the resistivity of the rinse effluent rose to 18 MΩ. Second, residual extractables were removed from batches of adsorbent (e.g., 6 liters, 1.6 kg) by a proprietary (Supelco, Inc.) thermal solvent-free cleaning process. Thereafter, the adsorbent was packaged (2 L brown glass containers) and steam sterilized on liquid cycle (20 mins., 121° C.).

Following this procedure, the adsorbent beads contained <10% water. The adsorbents were wetted by suspending in a 30% aqueous ethanol solution for 10 minutes. The adsorbent was thoroughly rinsed with distilled water to remove residual ethanol. Thereafter, the adsorbent samples were placed in glass containers and subjected to two different doses of γ-irradiation (Isomedix; Morton Grove, Ill.): single dose (49.9–50.7 kGy) and double dose (112.4–114.8 kGy).

The irradiated samples were tested for adsorbent function. The first study compared the adsorption kinetics of unsterilized (ie., processed but not subjected to γ-irradiation) and sterilized adsorbent. A fresh unit of platelet concentrate ($4.0 \times 10^{11}$ platelets/300 mL) prepared in 35% autologous plasma, 65% PAS III was spiked with 150 μM $^3$H-S-59. Samples of adsorbent (approximately 0.1 g) were accurately weighed into 5 mL polypropylene tubes. A 3.0 mL aliquot of the platelet mixture was added to each tube and the tubes were placed on a rotator (Barmstead, Thermolyne Model 400110) at room temperature. Samples of PC were removed from the tubes at various time points. Levels of radioactivity were determined by counting 200 μL of each sample in 5.0 mL of HiSafe LSC cocktail (Wallac). Residual S-59 concentrations were measured and the amount of S-59 which had been adsorbed per mass (μmoles/g) of adsorbent was determined by radioactivity balance. In this study, mass of adsorbent was based on the wet weight of the adsorbent samples.

Figure 34A:
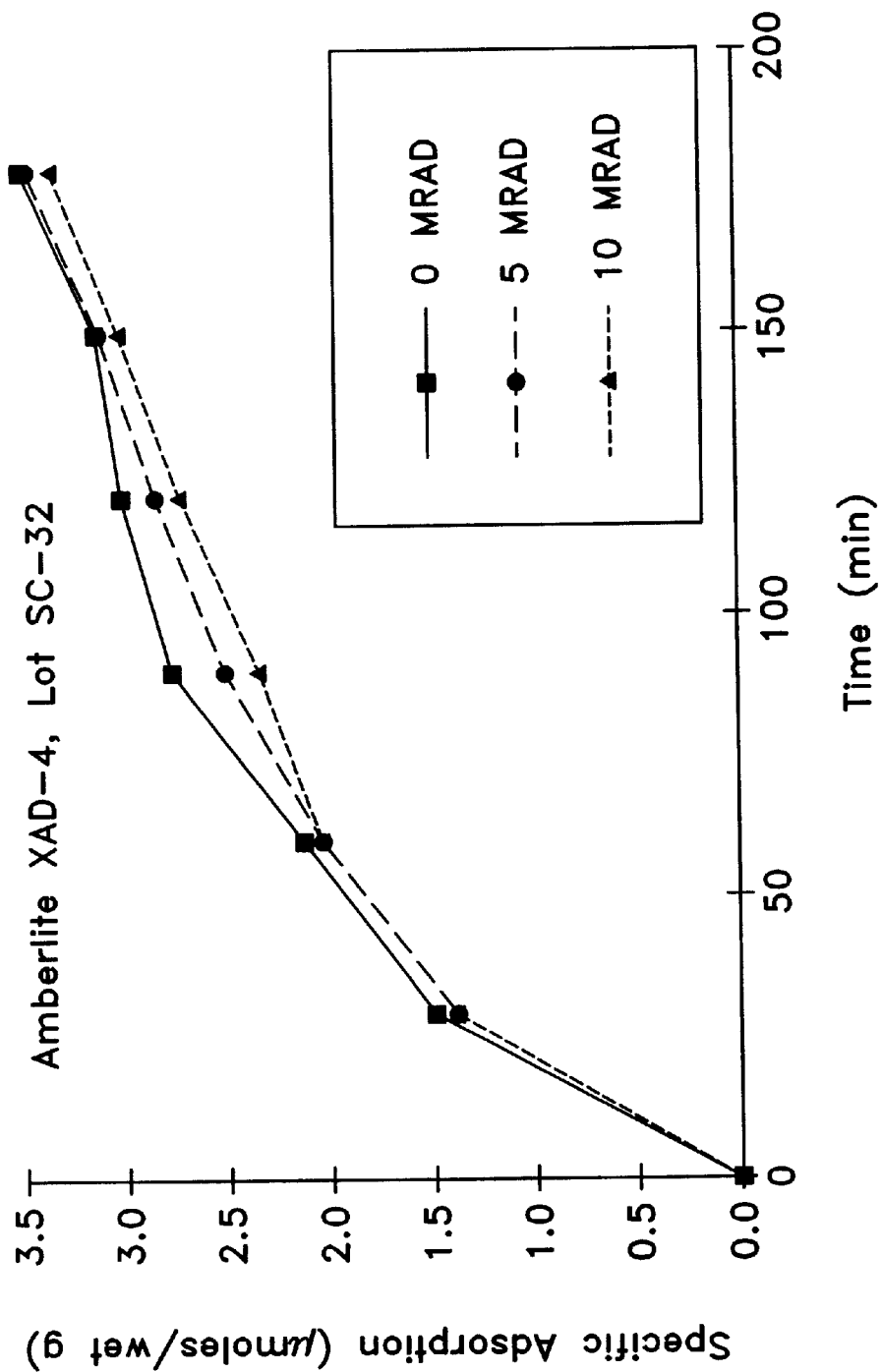
FIGS. 34A and 34B graphically depict the effect of sterilization by γ-irradiation (squares=0 MRad; circles=5 MRad; triangles=10 MRad) on adsorption kinetics for removal of S-59 from 35% platelet concentrate by two different lots of Amberlite® XAD-4.
Figure 34B:
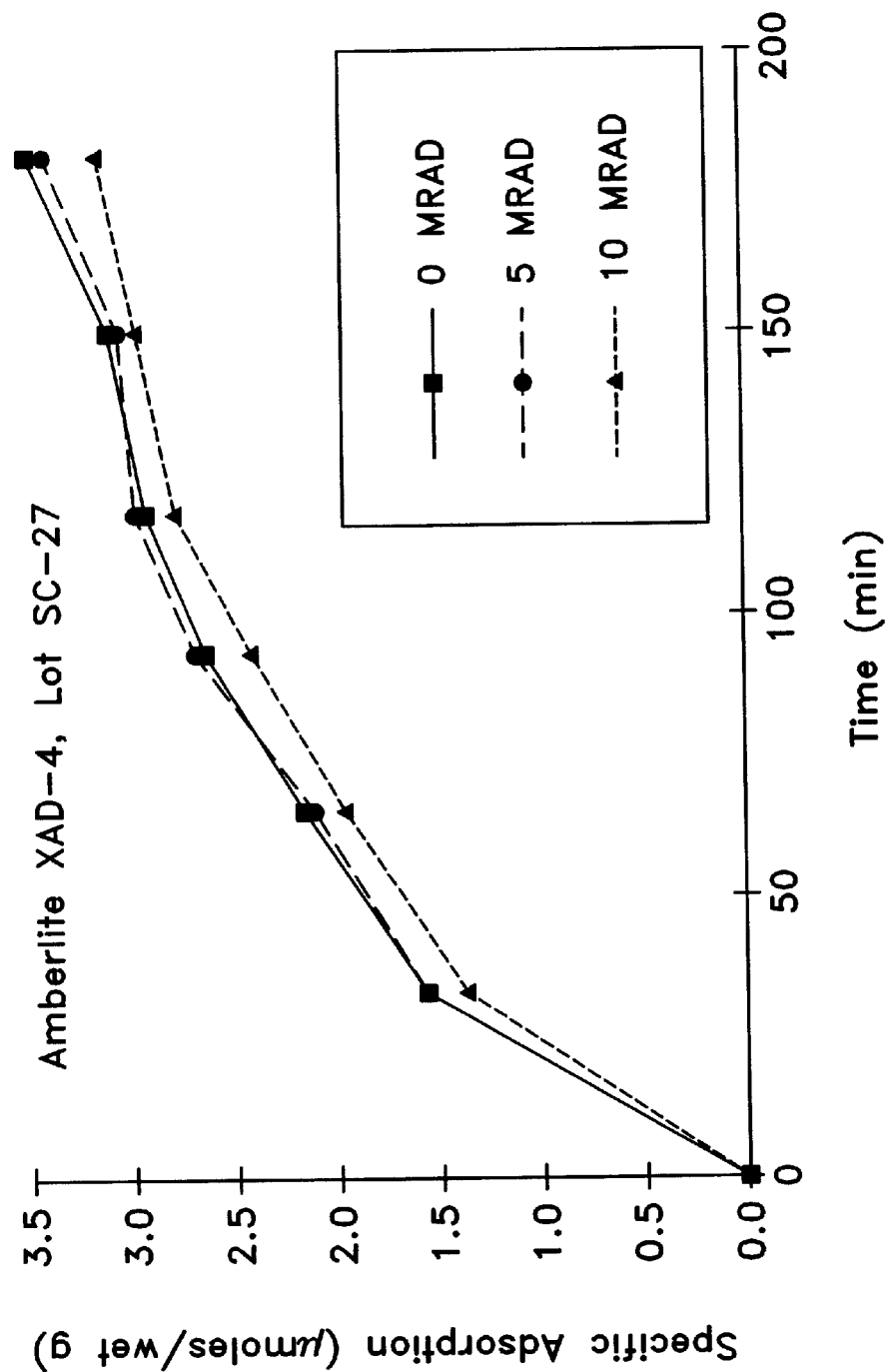
Figure 35A:
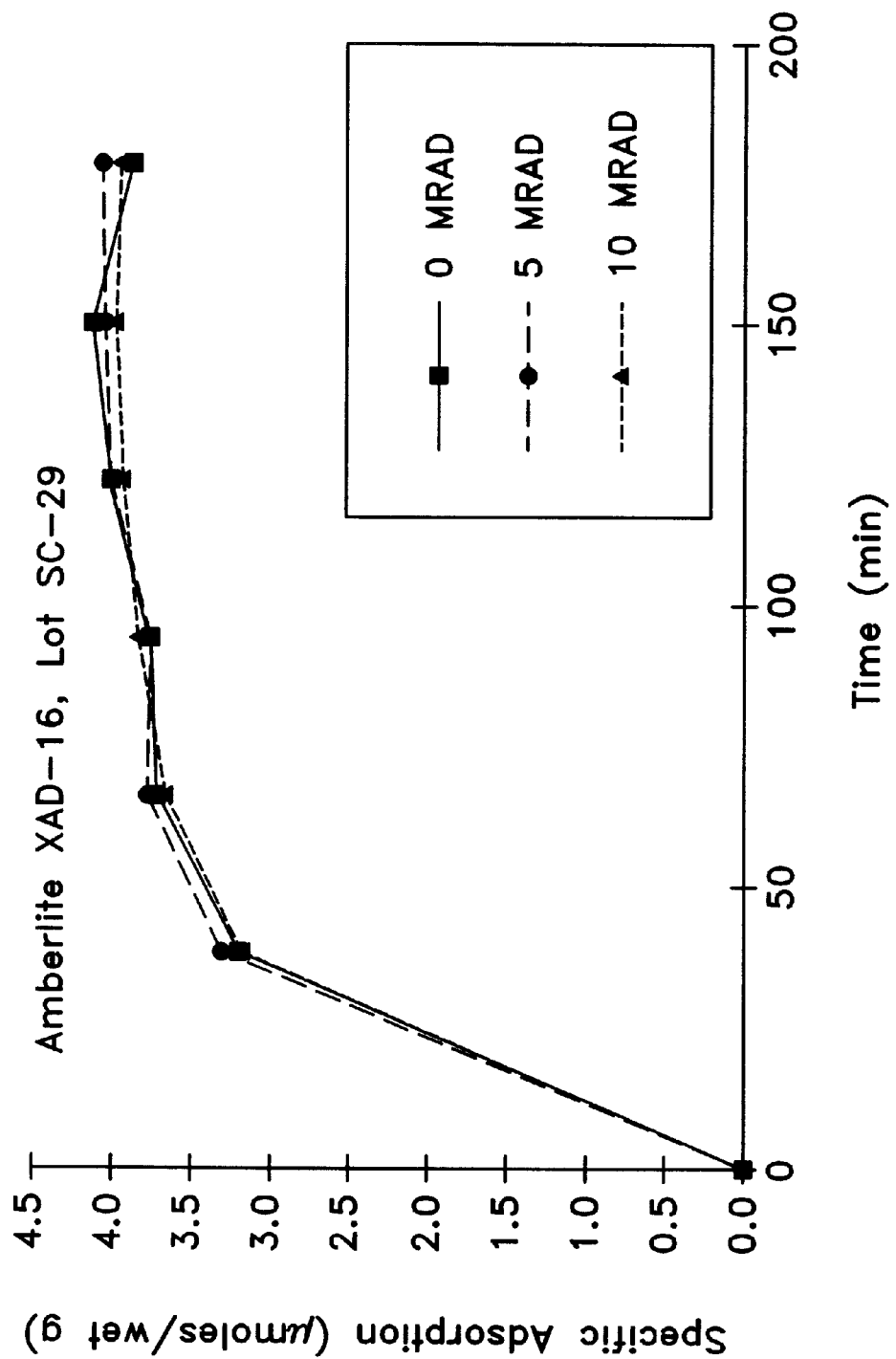
FIGS. 35A and 35B graphically depict the effect of sterilization by γ-irradiation (squares=0 MRad; circles=5 MRad; triangles=10 MRad) on adsorption kinetics for removal of S-59 from 35% platelet concentrate by two different lots of Amberlite® XAD-16.
Figure 35B:
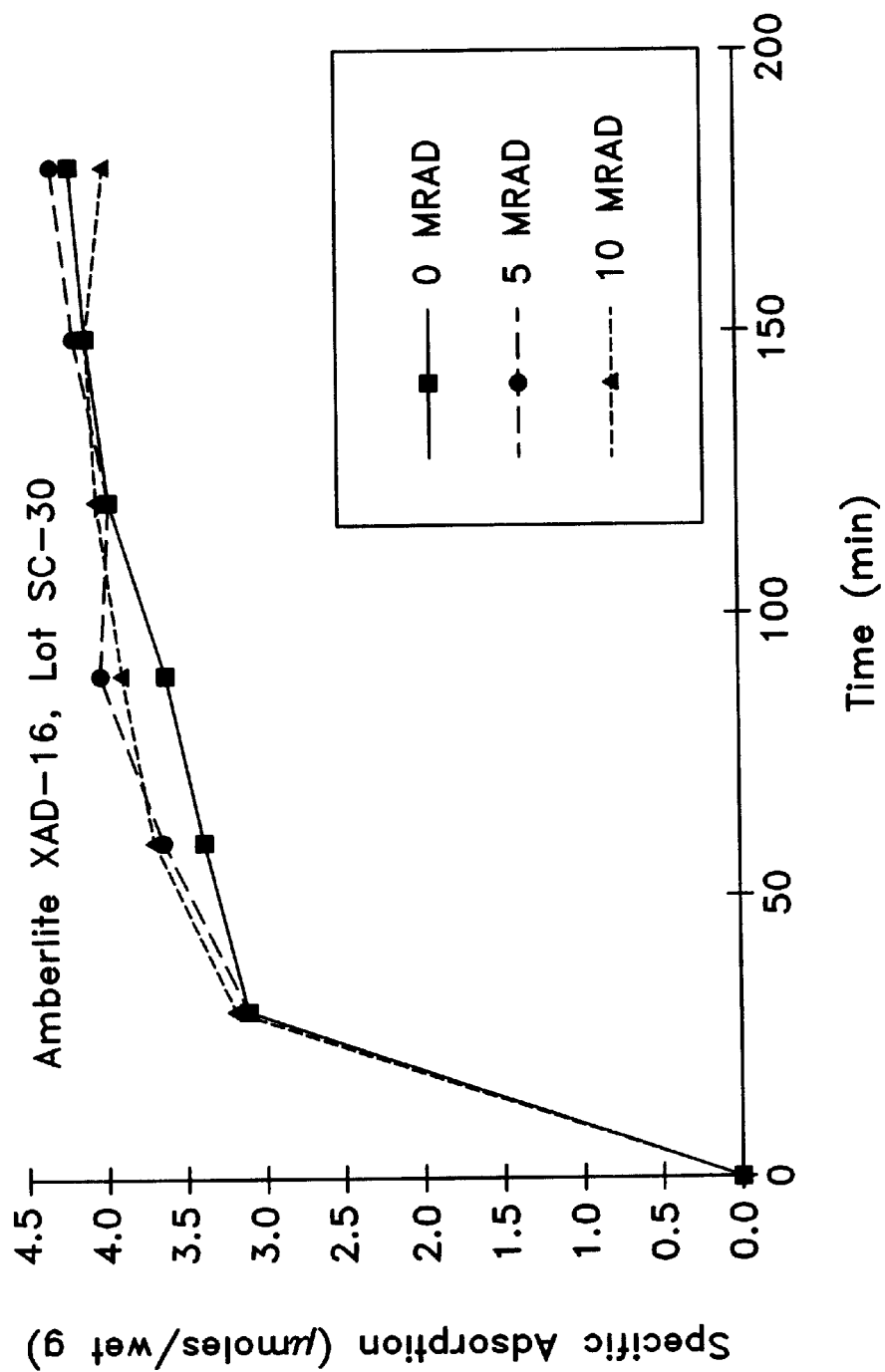

The adsorption kinetic data for removal of S-59 from PC is presented in FIGS. 34A and B and 35A and B. More specifically, the data in FIGS. 34 and 35 depict the effect of sterilization by γ-irradiation on adsorption kinetics for removal of S-59 from 35% platelet concentrate by Amberlite® XAD-4 (two lots, FIGS. 34A and 34B) and Amberlite® XAD-16 (two lots, FIGS. 35A and 35B), respectively. As indicated above, capacities (i.e., amount of S-59 adsorbed per mass of adsorbent; μmoles/g) were determined based on the wet weight of adsorbents.

Overall, sterilization with γ-irradiation did not appear to have a significant effect on adsorption kinetics. Sterilization had a very slight adverse effect on the adsorption kinetics of Amberlite® XAD-4. Conversely, sterilized Amberlite® XAD-16 appeared to have adsorption kinetics as good as or better than unsterilized samples of Amberlite® XAD-16. Comparison of the two adsorbents revealed that sterilized Amberlite® XAD-16 showed substantially better adsorption kinetics and capacities than sterilized Amberlite® XADA4. To illustrate, Amberlite® XAD-16 appeared to reach equilibrium conditions near 120 minutes of incubation, while Amberlite® XAD-4 required more than 180 minutes to reach equilibrium conditions. It is important to emphasize that the calculations were based on wet weight of adsorbent. Since typically contains more water than XAD-4, adsorption capacities based on dry weight would be significantly higher for XAD-16(see FIG. 32).

Amberlite® XAD-16 is thought to be the preferred Amberlite adsorbent because of its rapid adsorption kinetics and relatively high capacity. Importantly, as indicated above and set forth below, Dowex® XUS-43493 is presently considered the preferred adsorbent overall.

B. Effect of γ-Irrdiation on Adsorption Capacity

Samples of each adsorbent were also tested for equilibrium adsorption capacity following sterilization. Approximately 0.1 g of adsorbent was accurately weighed into a 5 mL polypropylene tube. A series of dilutions of S-59 in 35% plasma, 65% PAS III containing concentrations of $^3$H-S-59 from 500 μM down to 15 μM was prepared. A 3.0 mL aliquot of each dilution was added to separate tubes. The tubes were placed on rotators (Barnstead, Thermolyne Model 400110) and incubated for 24 hours at room temperature. Following incubation, a sample was removed from each tube and transferred to an Eppendorf tube. A 200 μL sample of 35% plasma was removed from each Eppendorf tube and diluted in 5.0 mL of HiSafe LSC cocktail (Wallac). Samples were counted on a Wallac LSC to determine residual levels of S-59 in each sample. Capacities were calculated by determining the total μmoles of S-59 which were removed from each sample per mass of wet adsorbent. The adsorption capacities for Amberlite® XAD-4 and Amberlite® XAD-16 treated with doses of 5 and 10 MRad of γ-irradiation are summarized in Table J.

TABLE J

| | Adsorption Capacity @ $C_f$ = 1 μM (μmoles/g) | | |
|---|---|---|---|
| Adsorbent | No γ-Irradiation | 5 MRad γ-Irradiation | 10 MRad γ-Irradiation |
| XAD-4 (Lot SC-27) | 7.6 | 7.2 | 7.9 |
| XAD-16 (Lot SC-30) | 7.5 | 8.6 | 6.3 |

*Capacities are based on wet mass of adsorbent samples.

As indicated by the data in Table J, the effect of γ-irradiation on the adsorption capacity of Amberlite® XAD-4 was very small even at doses of up to 10 MRad. Variations in the adsorption capacity for Amberlite® XAD-16 are probably not significant. The effects of sterilization on adsorption capacity are small enough such that they will not significantly impact either adsorbent in a RD which is sterilized by γ-irradiation.

C. Sterilization of Amberlite Adsorbents by E-beam

As discussed above, γ-irradiation is currently viewed as the preferred sterilization method. The effect of E-beam on the function of the Amberlite adsorbents was examined in a study similar to that performed for gamma sterilization. The methodology and results of this study are reported hereafter.

For this study, samples of Amberlite® XAD-4 and XAD-16 were wetted with aqueous ethanol (30%) and were placed in 25 mL scintillation vials. In addition, mock devices were prepared by placing 10 g of wet adsorbent in polyester mesh pouches (Saati polyester 29/16, 10 cm×10 cm) and heat sealing the open end. The resulting mock removal device was introduced into PL 2410 Plastic containers (Baxter) via a small slit; thereafter, the slit was closed via heat seal.

The adsorbent samples and mock devices were submitted to NIS (San Diego, Calif.), where they were subjected to a 5 MRad dose of E-beam. The samples which were sterilized in vials did not require wetting. However, the adsorbent samples from the mock devices dried during storage because no water barrier was used; these samples were recovered from the mock devices and were wet with aqueous ethanol prior to performing function experiments. The adsorption capacity for removal of S-59 from 35% plasma 65% PAS III was examined as described above. The results of the study are summarized in Table K.

TABLE K

| Adsorbent | Adsorption Capacity @ $C_f$ = 1 μM (μmoles/g) | | |
|---|---|---|---|
| | No E-Beam | 5 MRad Adsorbent | 5 MRad Mock Device |
| XAD-4 (Lot SC-27) | 9.6 | 10.8 μmoles/g | 7.7 |
| XAD-16 (Lot SC-29) | 13.4 | ND | 11.2 |
| XAD-16 HP | 10.3 | 9.2 | 11.2 |

*Capacities are based on wet mass of adsorbent samples; ND = not determined.

As indicated by the data presented in Table K, sterilization by E-beam at 5 MRad did not have a significant impact on adsorbent function when sterilization was performed either on adsorbent alone ("5 MRad Adsorbent") or on adsorbent retained within a polyester mesh pouch housed in a PL 2410 Plastic container (Baxter) ("5 MRad Mock Device").

EXAMPLE 34

S-59 Adsorption Constants and the Effect of Water Content on Adsorbent Function

A previous example was specifically directed at the effect of water content on the function of Amberlite® XAD-4 and XAD-16. This example compares S-59 adsorption constants for several additional adsorbents in both their wet and dry states.

Samples of adsorbent were exhaustively rinsed with distilled water. A portion of each sample was then placed in a drying oven at 120° C. for 4 hours to produce dried adsorbent samples. The water content of each adsorbent, in both wet and dry states, was determined by accurately weighing a sample of adsorbent into a previously dried and pre-weighed container (a scintillation vial). Samples were dried at 120° C. for 24 hours and reweighed to determine the mass of lost water. The mass % water content was then calculated.

Samples of each adsorbent were also tested for equilibrium adsorption capacity. As alluded to above, the equilibrium adsorption capacity refers to the amount of psoralen that a particular resin is able to adsorb; that is, after equilibrium is achieved, the amount of psoralen adsorbed relative to the amount of residual psoralen is essentially unchanged. An incubation period of 24 hours was previously indicated to produce equilibrium conditions.

Figure 36:
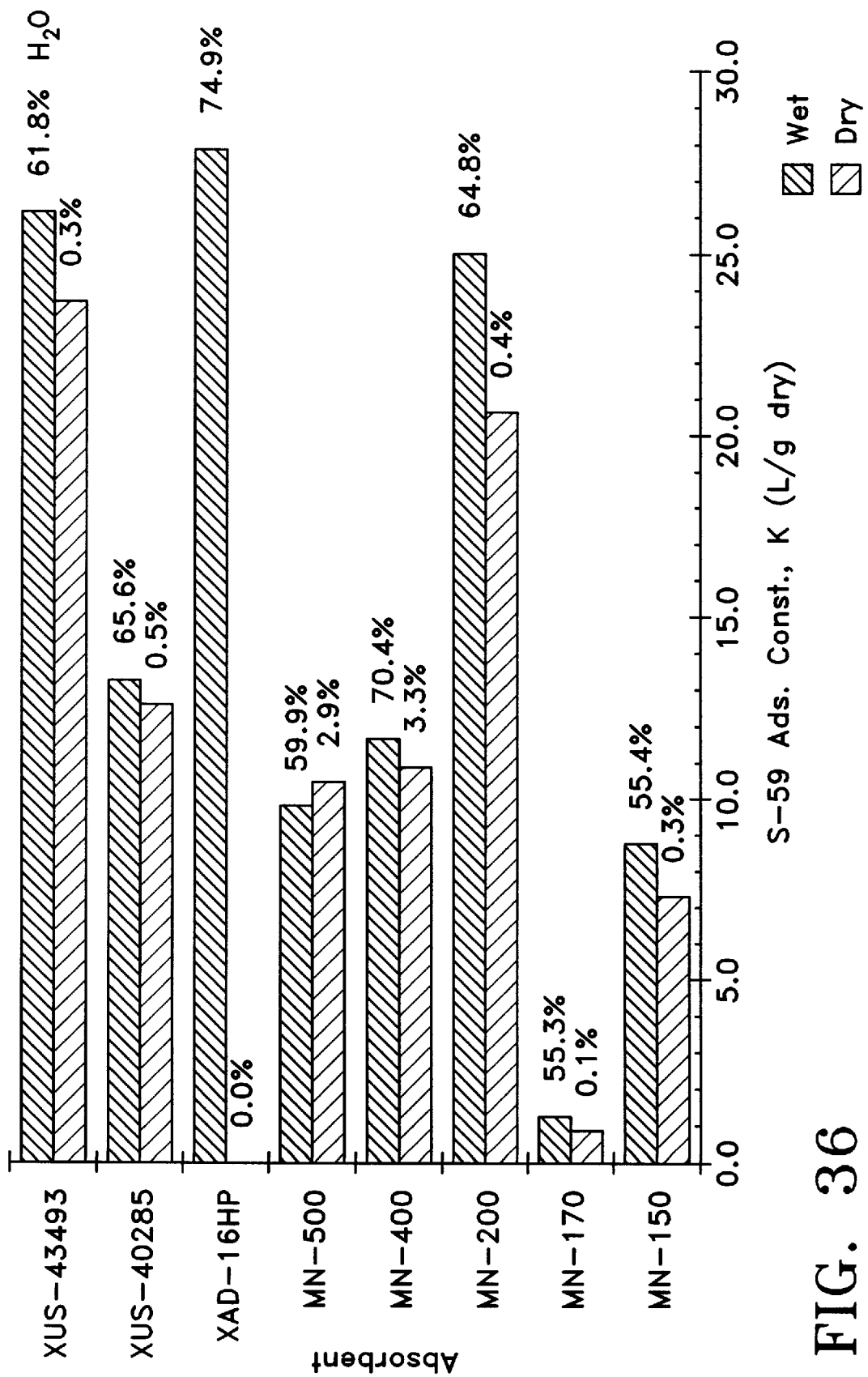
FIG. 36 is a bar graph indicating S-59 adsorption constants for adsorbents in both the wet (dark shading) and dry (light shading) states, the percentages referring to the amount of water in each sample.

Adsorbent (approximately 0.1 g) was weighed and transferred into a 5 mL polypropylene tube. A 3.0 mL aliquot of 35% plasma, 65% PAS III containing 150 μM $^3$H-S-59 was added to each tube. The tubes were placed on rotators and incubated for 24 hours at room temperature. Following incubation, a sample was removed from each tube and transferred into an Eppendorf tube. A 200 μL sample of 35% plasma was removed from each Eppendorf tube and diluted in 5.0 mL of HiSafe LSC cocktail (Wallac). Samples were counted on a Wallac LSC to determine residual levels of S-59 in each sample. Capacities were calculated by determining the total μmoles of S-59 which were removed from each sample per mass of dry adsorbent. The results are depicted in FIG. 36, a bar graph indicating S-59 adsorption constants for adsorbents in both the wet (dark shading) and dry (light shading) states (the percentages referring to the amount of water in each sample), and summarized in Table L (150 μM S-59=61754.725 DPM; Background 30 DPM; $C_f$=final equilibrium solution concentration of S-59).

TABLE L

| Sample | Adsorbent | State | Water Content (%) | Capacity at $C_f$ (μmole/g dry) | Approx. K (L/g) |
|---|---|---|---|---|---|
| 2 | MN-150 (Purolite) | Wet | 55.4 | 7.1 | 8.76 |
| 3 | MN-170 (Purolite) | Wet | 55.3 | 6.7 | 1.17 |
| 5 | MN-200 (Purolite) | Wet | 64.8 | 9.4 | 25.02 |
| 7 | MN-400 (Purolite) | Wet | 70.4 | 11.6 | 11.61 |
| 6 | MN-500 (Purolite) | Wet | 59.9 | 7.7 | 9.78 |
| 8 | XAD-16HP (Rohm & Haas) | Wet | 74.9 | 13.1 | 27.80 |
| 1 | XUS-40285 (Dowex) | Wet | 65.6 | 10.9 | 13.13 |
| 4 | XUS-43493 (Dowex) | Wet | 61.8 | 8.1 | 25.98 |
| 12 | MN-150 (Purolite) | Dry | 0.3 | 6.2 | 7.25 |
| 15 | MN-170 (Purolite) | Dry | 0.1 | 5.8 | 0.78 |
| 9 | MN-200 (Purolite) | Dry | 0.4 | 6.8 | 20.65 |
| 13 | MN-400 (Purolite) | Dry | 3.3 | 6.7 | 10.79 |
| 14 | MN-500 (Purolite) | Dry | 2.9 | 6.0 | 10.43 |
| 16 | XAD-15HP (Rohm & Haas) | Dry | 0.0 | 2.2 | 0.02 |
| 11 | XUS-40285 (Dowex) | Dry | 0.5 | 5.1 | 12.46 |
| 10 | XUS-49493 (Dowex) | Dry | 0.3 | 5.9 | 23.56 |

EXAMPLE 35

Characteristics of a Removal Device Containing Dowex® XUS-43493

The Description of the Invention section described the general features of the RD manufacturing process and its incorporation into a storage container. This example illustrates the specific characteristics of the preferred batch RD and the preferred manufacturing process for a batch RD and its incorporation into a storage container.

Dowex® XUS-43493 Adsorbent

As previously indicated, Dowex® XUS-43493 (Dow Chemical Co.) is the preferred adsorbent. After Supelco, Inc. identifies the uncleaned adsorbent with infrared spectroscopy, it further processes the adsorbent to ensure low levels of extractables and fine particles. In the first step of the process, fine particles and salts are removed by exhaustive rinsing of the adsorbent with distilled water.

Batches of adsorbent (e.g., 2.0 kg) are placed in a container with 74 µm sieve retainers (i.e., the process is able to retain particles approximately 74 µm in diameter or larger) during the rinsing process. The second step of the processing involves removal of residual extractables by a proprietary thermal, solvent-free cleaning process. If desired, the cleaned adsorbent may then be packaged in large bags and steam-sterilized before shipment to the RD manufacturing site.

The Dowex® XUS-43493 adsorbent from Dow Chemical Co. is accompanied by a Certificate of Analysis that specifies water content (50–60%), sphericity (>90%), and particle size limits by sieve analysis (<2% retained on 16 mesh; <3% passed through 50 mesh). The adsorbent that has been subjected to the Supelco, Inc. cleaning process is monitored for potential extractables, such as divinyl benzene (e.g., <50 ppb; 1:1 isopropanol:adsorbent; 2 hr extraction @ 22° C.) and ethylvinylbenzene. In addition, a GC analysis of methylene chloride extracts is used to assess the Total Chromatographic Organics (e.g., <20 µg/mL total extractables).

Additional tests are also performed on the cleaned adsorbent. For example, levels of endotoxin are determined using a Limulus Amaebocyte Lysis (LAL) test. The particle size distribution (e.g., <0.01% below 90 µm diameter; <2.0% above 1400 µm diameter) is measured for each batch of adsorbent, as well as the water content (e.g., mass loss upon drying=10% maximum, 5% minimum). Finally, the functional characteristics of each batch of adsorbent are assessed by an S-59 adsorption assay performed with $^3$H-labeled S-59 in buffered saline containing serum albumin.

The Mesh Pouch and Port Filter

Figure 37:
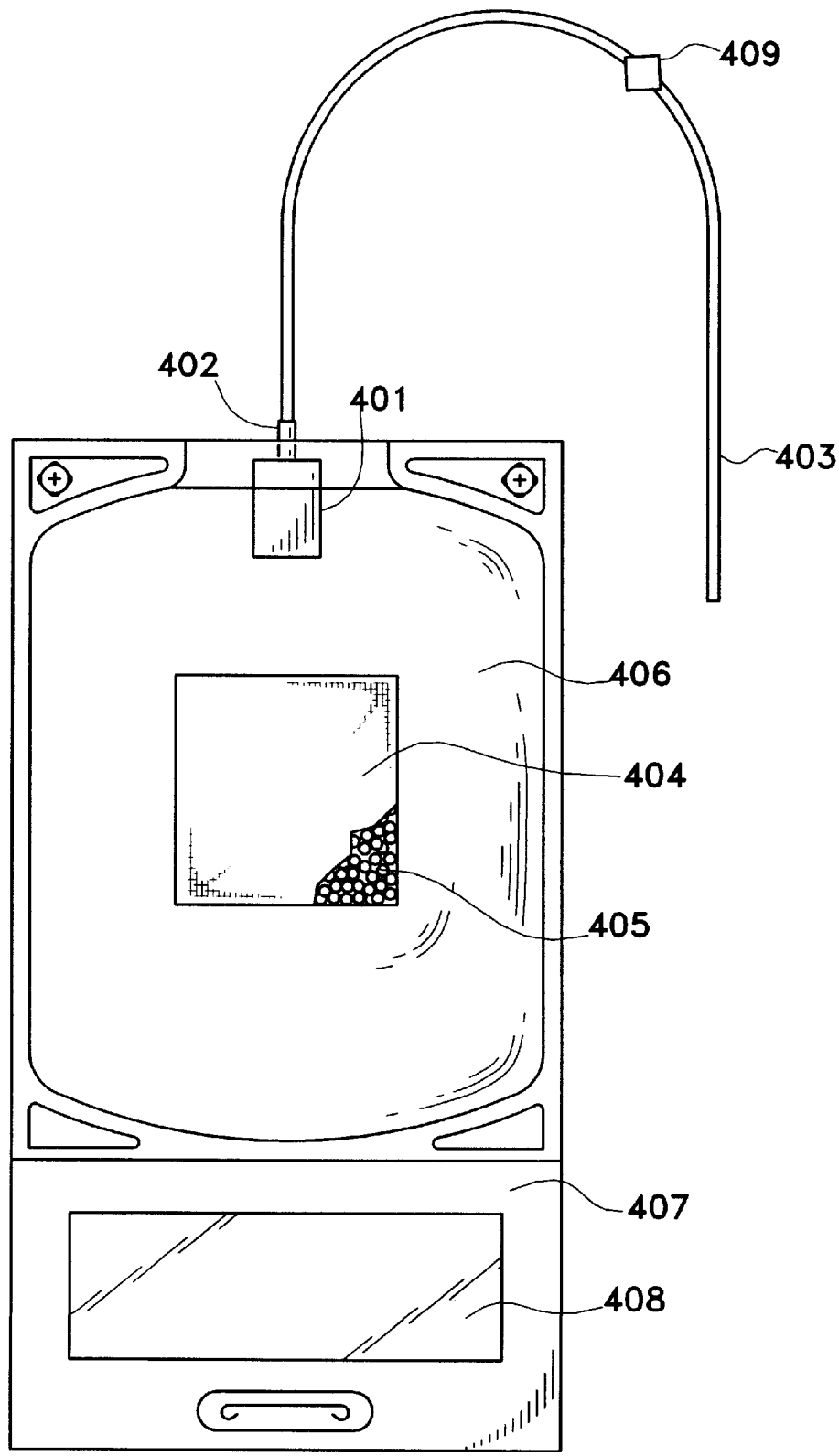
FIG. 37 depicts a removal device of the present invention illustrating how the removal device may be contained within a platelet storage container.
Figure 38B:
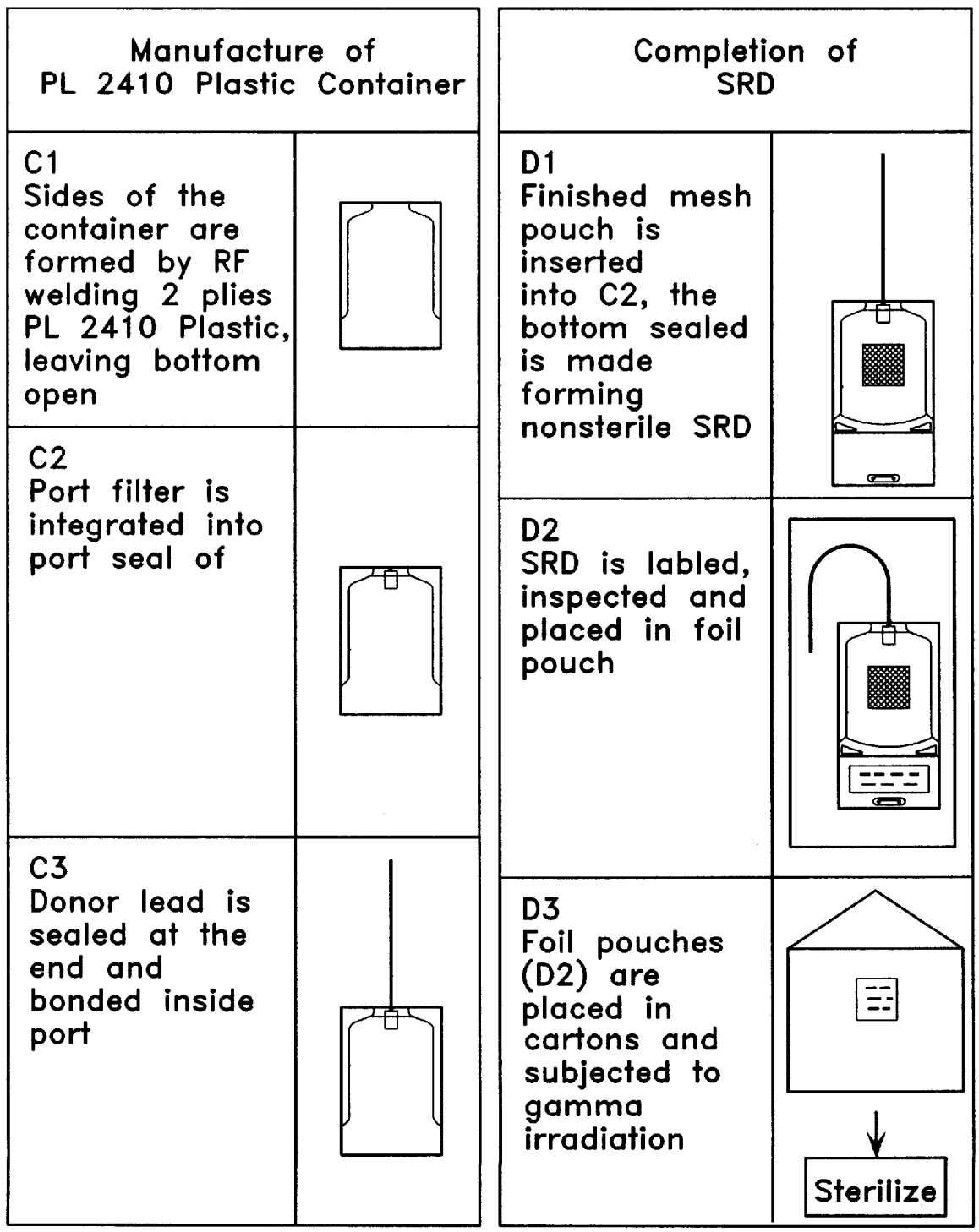

FIG. 37 schematically illustrates the preferred batch RD contained within a platelet storage container (e.g., a PL 2410 Plastic container, Baxter). In addition, a flow chart is presented in FIG. 38 that depicts the prinary steps of the preferred manufacturing process for the batch RD contained within a platelet storage container, including the steps of incorporating the assembled RD and filter port into the platelet storage container. Reference to those figures will assist in understanding the discussion that follows.

The polyester mesh pouch and the port filter are manufactured using the same technique (described below). The mesh pouch is used to confine the adsorbent, thereby preventing adsorbent from subsequently being transfused into the recipient. The port filter serves as a backup mechanism of protecting against transfusion of small particles; solutions entering or exiting the platelet storage container must pass through the port filter. Both the polyester mesh pouch and the port filter utilize the same medical-grade woven polyester with 30 µm pore openings (e.g., Tetko Medifab 07-30/21 designated as PL 1144 Plastic by Baxter). The 30 µm mesh pore-size provides a large safety margin for preventing transfusion of small particles while allowing the plasma/PAS mixture to freely contact the adsorbent. The platelets do not have to actually contact the adsorbent, but allowing the solution to freely pass by the adsorbent aids in removal of residual psoralen and psoralen photoproducts.

For the manufacture of the mesh pouch and port filter, a strip of mesh from a roll is folded longitudinally and sealed transversely with an impulse sealer. While sealing, the impulse sealer simultaneously cuts the mesh in the middle of the seal. This results in a rectangnlar pocket containing i) a lower end that is folded, ii) two edges that are heat-sealed, and iii) a top edge that is open. Depending on the width of the pocket and the distance between the two heatseals, the pocket either becomes the port filter or the adsorbent-containing mesh pouch (i.e., the RD). For example, one embodiment of the present invention utilizes mesh material slit into widths of approximately 76 mm for the port filter and approximately 154 mm for the RD pouch.

Smaller pockets of mesh become the port filter 401. The port filter is sealed to a bushing 402 (ie., the port bushing) that will be used to affix the inlet/outlet line 403 to the plastic container. The plastic container is formed by radiofrequency-welding two plies (i.e., layers) of PL 2410 Plastic (Baxter) over the port filter 401. The back of the PL 2410 Plastic container (Baxter) is left open for insertion of the RD. Thereafter, the inlet/outlet line (i.e., donor lead) 403 is bonded to the port bushing 402 using a solvent (e.g., cyclohexanone) and sealed at the end to prevent any contamination by particles in subsequent steps.

Larger pockets of mesh are used to produce the RD. Briefly, the polyester mesh pouch 404 (e.g., square with 5 cm sides or circular) produced above is filled with adsorbent beads 405 (e.g., 2.5±0.1 g dry) through the unsealed fourth edge. The mesh pouch to be filled is held by a fixture and moved to a filling system (not shown). The present invention contemplates the use of any appropriate filling system, e.g., a vibratory filling system. Filling systems which utilize an auger to dispense the adsorbent are also available, but are not preferred because they can cause mechanical degradation of the adsorbent. The filling system typically consists of a balance, a vibratory feeder unit, and a controller. The open edge of the mesh pouch is then sealed with a heat-sealer. Thereafter, the mesh pouch is subjected to an "ionized air shower" or vacuum to eliminate free particles from the external surfaces of the RD, weighed, and inspected for loose particles and flaws. Of course, any accurate means of filling the mesh pouch can be used in conjunction with the preferred embodiment.

The Fully-assembled Batch RD Contained within a Platelet Storage Container

The RD is then placed inside a PL 2410 Plastic container (Baxter) 406 equipped with a single donor lead 403 (FIG. 37). The final bottom seal is performed to create a rectangular area 407 that will subsequently provide a flap for affixing an identifying label 408. The fully assembled container housing the RD, which is disposable in a preferred embodiment, is visually inspected and submitted to a leak-test with compressed air through the donor lead.

Thereafter, the platelet storage container 406 is evacuated to remove residual air within the container, the donor lead is heat sealed, and the container is placed in a foil pouch which is vacuum-sealed. Storage of the container under vacuum conditions helps eliminate the formation of bubbles (i e., offgassing/foaming) during the initial contacting of the illuminated platelet mixture and the RD. Finally, the assembly contained in the foil pouch is placed in shipping cartons. The packed cartons are then sterilized by γ-irradiation at a dose sufficient to achieve a Sterilization Assurance Level (SAL) of $10^{-6}$ (i.e., fewer than $10^{-6}$ microorganisms are present after γ-irradiation).

The major components of the preferred embodiment are presented in Table M.

TABLE M

| Component/Service (Manufacturer) | Description |
| --- | --- |
| Adsorbent - Dowex ® XUS-43493 (Dow Chemical Co., Midland, MI) | polystyrene-divinyl benzene; bead diameter: 300–850 $\mu$m; surface area: 1100 m$^2$/g; average pore diameter: 46 Å; total porosity: 1.16 cc/g; ash content: <0.01%; crush strength: >500 g/bead*. |
| Processing of Adsorbent (Supelco, Inc., Bellefonte, PA) | Rinse and remove fine particles; clean adsorbent (proprietary process); test for extractables. |
| Mesh Pouch (Tetko, Switzerland) | PL 1144 plastic mesh: medical-grade woven polyester mesh [poly(ethylene terephthalate)] with 30 $\mu$m openings and a 21% open area; 7.5 cm × 7.5 cm square pouch; ultrasonic weld; Certificate of Analysis - LAL: <0.125 EU/mL; Physical inspection of sealed edge, particulate matter, and cosmetic uniformity Microscopic analysis: verify weave type, mesh count, and thread diameter. |
| Mesh Port Filter (Filter Sock) (Tetko, Depew, NY) | PL 1144 Plastic medical-grade polyester mesh as above; 2 cm × 4 cm square sock bonded to tubing. |
| PL 2410 Plastic Container (Baxter Healthcare Corp., Round Lake, IL) | 1 L capacity; monolayer extruded film of ethylene vinyl acetate, ethylene butylene styrene copolymer, and ultra low density polyethylene; single inlet/outlet with filter. |
| Assembly Packaging (Baxter Healthcare Corp., Round Lake, IL) | Assemble port filter; manufacture PL2410 Plastic container with port filter; manufacture mesh pouch; fill and seal mesh pouch; insert filled pouch into PL 2410 Plastic container and finish bottom seal; label; package product in foil pouch. |
| Sterilization (Isomedix, Inc., Libertyville, IL) | Sterilize finished RD-containing platelet storage container, 25–40 kGy; maximum allowable dose of y-irradiation based on the components is 90 kGy. |

*Typical physical and chemical properties for Dowex ® XUS-43493 (Technical Bulletin 3.03).

While the preferred embodiment of the present invention involves placement of the RD inside a platelet storage container (or other container or bag), the present invention also contemplates an embodiment in which the adsorbent is loose within the platelet storage container. The same overall type of design can be used in such an alternative embodiment as was used in the design described above, only without the mesh pouch. More specifically, the free adsorbent is retained in the platelet storage container 406 by the port filter 401. Thus, while the port filter 401 serves as a secondary mode of protection (i e., prevents escape of adsorbent particles) in the embodiment depicted in FIG. 37, it serves as the primary mode of protection in this alternative embodiment because of the absence of the mesh pouch containing the adsorbent. If desired, a macroaggregate filter (or similar filter) 409 can be incorporated into the inlet/outlet line 403; such a filter would serve as a secondary means of protection by retaining particles should the port filter 401 fail.

The alternative embodiment has several advantages over the embodiment utilizing an adsorbent-containing mesh bag. For example, platelet adhesion to the mesh bag is avoided, thus increasing platelet yield. Similarly, there should be less volume loss because there are fewer surfaces for fluid adhesion. In addition, this embodiment also eliminates the problems with gas trapping inside the mesh pouch. Conversely, by lacking the mesh pouch, this alternative embodiment is devoid of a major mechanism of preventing subsequent inadvertent infusion of adsorbent particles or other contaminants.

The present invention also contemplates the use of other means for securing the adsorbent particlesibeads within a blood product storage container. For example, the Dowex® XUS-43493 particles may be incorporated into a fiber network to produce a filtration system that comprises a three-dimensional network of fibers with particles arranged equidistantly within the fiber structure. The fiber network is then placed within a platelet storage container. The preferred fibers are comprised of polyester due to its positive history of use in blood-contacting devices. An adhesive or an adhesive-free process can be utilized to secure the adsorbent to the fiber network. (Hoechst Celanese, Charlotte, N.C.). It is contemplated that a homogeneous fiber network can be produced with known amounts of adsorbent per surface area; due to this homogeneity, the appropriate amount of adsorbent can be measured simply by cutting a predetermined area of the fiber network (i.e., there is no weighing of the adsorbent). Thus, this embodiment also avoids the need for a RD.

EXAMPLE 36

HPLC Analysis of Residual S-59 and S-59 Photoproducts Following Reduction with a RD Containing Dowex® XUS-43493

As previously indicated, photoproducts generated by UVA illumination of PCs containing S-59 can be monitored using an HPLC assay. This example first provides an overview of the photoproducts formed during illumination. Thereafter, this example illustrates the reduction characteristics of a RD containing Dowex® XUS-43493.

A. Characterization of Residual S-59 and S-59 Photoproducts

The photochemical treatment process involves the addition of S-59 (e.g., 15.2 mg) to platelets (approximately $4.0 \times 10^{11}$) suspended in approximately 300 mL of 35% plasma/65% PAS III. During subsequent illumination with UVA light, S-59 is converted into photoproducts in the PC. The photoproducts can be classified as either unbound or bound based on dialysis experiments (see Schematic A). The unbound photoproducts can be monitored and quantified using a standard HPLC assay.

Samples were prepared for HPLC analysis according to the general procedure described in Example 39, infra.

Briefly, the assay involved an initial sample preparation which lyses the platelets and solubilizes the S-59 and photoproducts. The supernatant from the sample preparation was then analyzed on a C-18 reverse phase column with a gradient of increasing methanol in $KH_2PO_4$ buffer. The major peaks were detected by optical absorbance.

Figure 39:
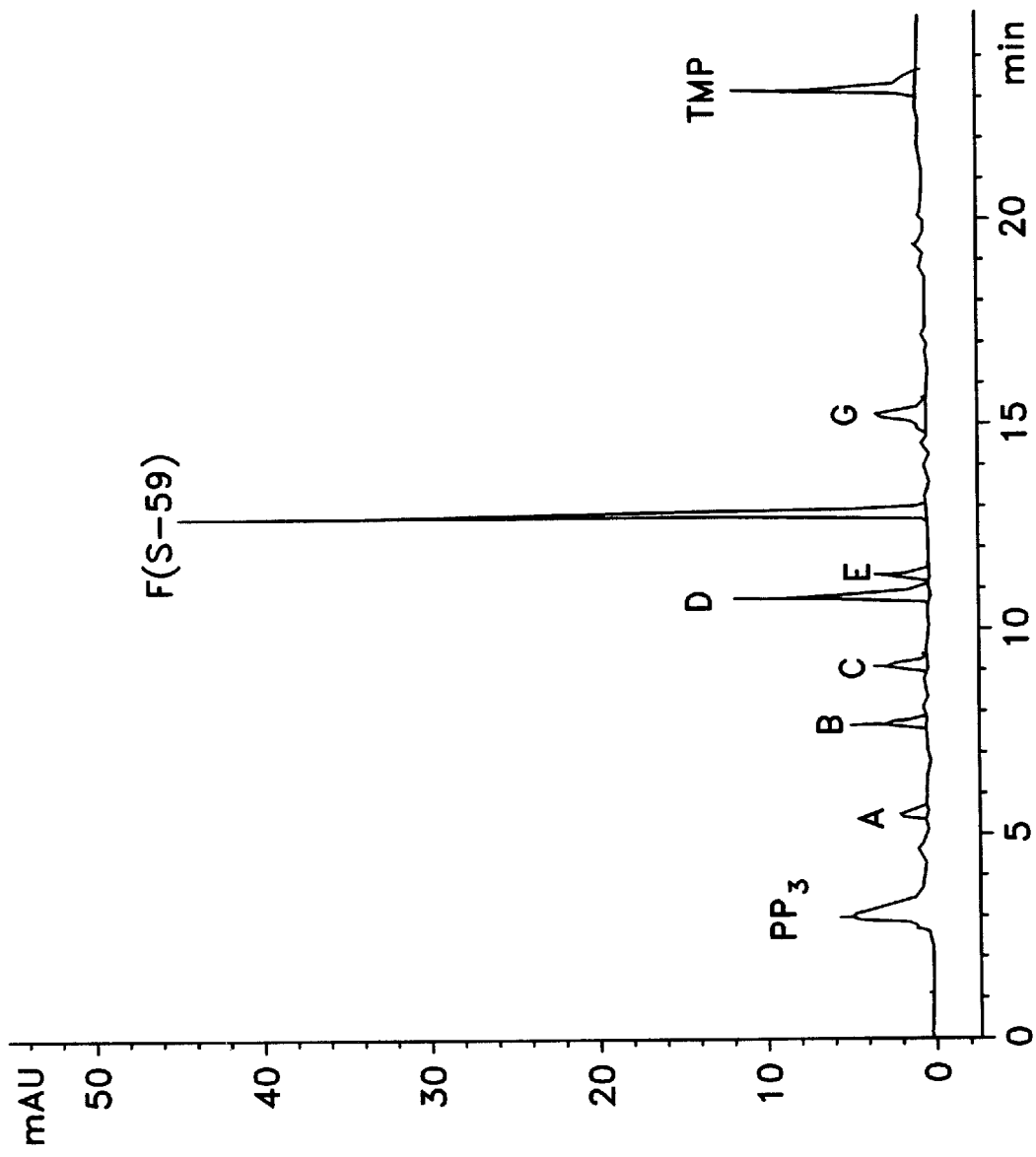
FIG. 39 is a representative HPLC chromatogram of S-59 and S-59 photoproducts formed in a PC (35% plasma/65% PAS III, 150 μM S-59 [15.2 mg/300 mL]) following illumination with 3.0 J/cm² UVA.

FIG. 39 is a representative HPLC chromatogram of S-5-59 and S-59 photoproducts formed in a PC (35% plasmal65% PAS III, 150 $\mu$M S-59 [15.2 mg/300 mL]) following illumination with 3.0 $J/cm^2$ UVA (320–400 nm). Referring to FIG. 39, the ordinate is the optical density at 300 nm while the abscissa represents time; the peaks labeled "PPs" are plasma peaks which are present on HPLC chromatograms of the plasma without S-59, and the peak labeled "TMP" refers to 4,5',8-trimethylpsoralen used as the internal standard. FIG. 39 reveals seven major peaks, which are designated peaks A–G. Residual S-59 is represented by peak F, and the other photoproducts are represented by peaks A–E and G. The amount of residual S-59 in the UVA-treated platelet mixture is reproducible and can be used as an internal dosimeter for monitoring delivery of UVA. Each of the S-59 photoproducts is also formed in reproducible amounts.

Figure 40:
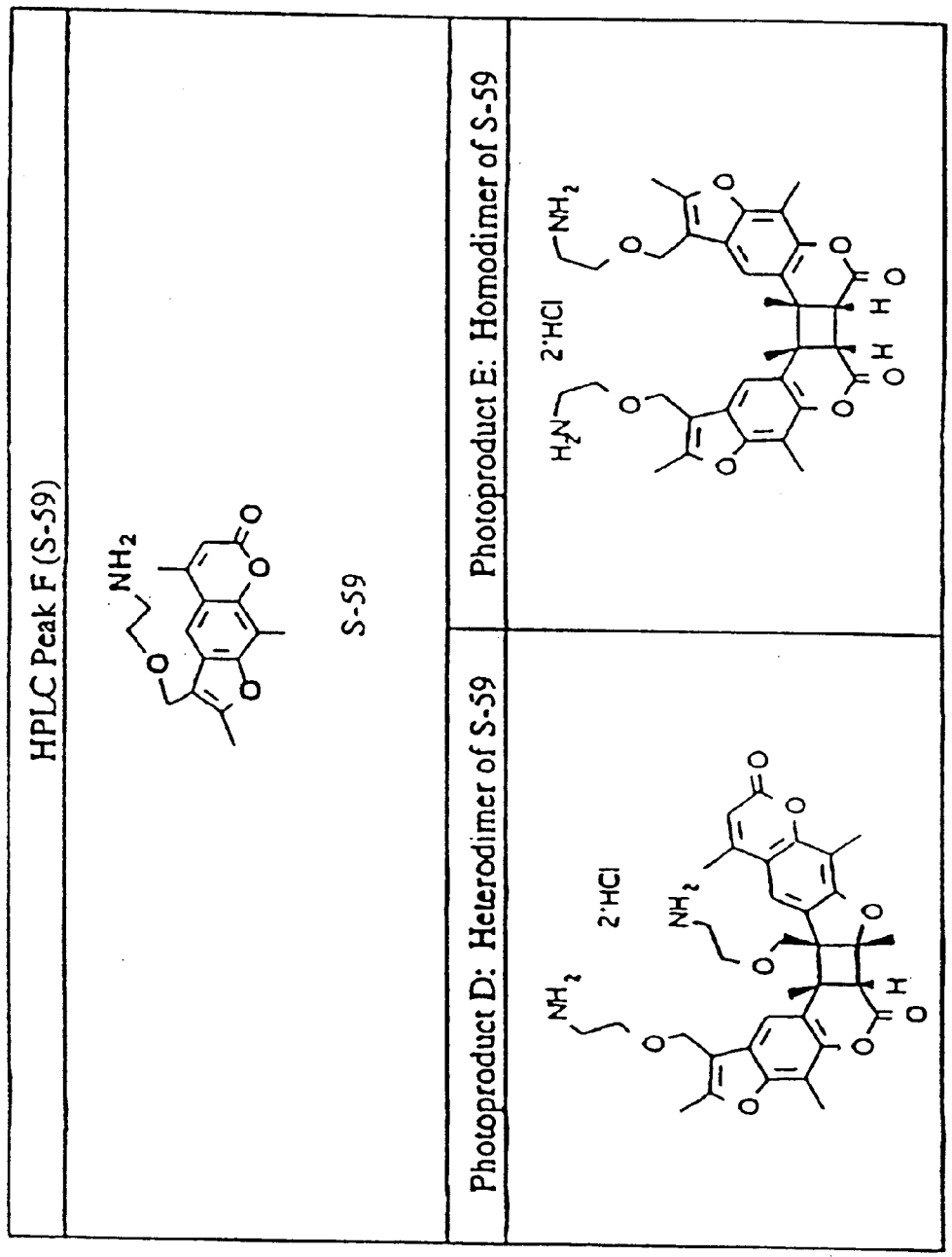
FIG. 40 depicts the chemical structure of the major S-59 photoproduct peaks: i) S-59 (HPLC peak F), ii) the heterodimer of S-59 (HPLC peak D), and iii) the homodimer of S-59 (HPLC peak E).

While it is not necessary that the precise mechanisms and photoproducts be known for successful use of the invention, it is believed that dimerization of S-59 is the principle mode of photochemical breakdown. The two major photoproducts (peaks D and E in the HPLC chromatogram in FIG. 39) have been isolated from illuminated solutions and their structures have been determined by GC/MS and NMR analysis and are presented in FIG. 40. As depicted in FIG. 40, peak D is the heterodimer of S-59 and peak E is the homodimer of S-59 (hereafter "photoproducts D and E"); the structures of the remaining photoproducts are unknown.

As previously indicated, approximately 25% of the S-59 added to PC partitions into the platelets (the actual amount being dependent on the platelet count). Uptake of S-59 by the platelets results in significantly higher concentration of S-59 within the platelets. Moreover, since dimerization is a biomolecular reaction, the yield of dimers (represented by peaks D and E) formed during photochemical treatment is increased within the platelets as well. Thus, an effective RD should be designed to remove S-59 and photoproducts D and E from the platelet interior.

B. Reduction Characteristics of an RD Containing Dowex® XUS-43493

As described above, about 74% of the original 15.2 mg of S-59 is present as residual and unbound S-59 photoproducts following illumination. Adsorption studies have demonstrated that greater than 99% of the initial 15.2 mg of S-59 is removed from PCs following illumination and incubation with the RD. This section addresses the kinetics of removal of S-59 and unbound photoproducts and the final levels of S-59 following treatment with a RD containing Dowex® XUS-43493.

Following illumination with 3.0 $J/cm^2$ UVA of a PC to which 15.2 mg S-59 had been added, the treated PC was incubated with the RD (contained within a PL 2410 Plastic container, Baxter) for 8 hours. Samples of the treated PC were then taken and subjected to HPLC for detection of residual S-59 and S-59 photoproducts. Post-incubation levels of photoproducts D, E, and F (S-59) are presented in Table N; photoproducts A, B, C, and G were not detectable by HPLC. Levels of residual photoproducts are average values taken from six independent, photochemically- and RD-treated platelet units. The Limit of Quantitation (LOQ) for the HPLC assay was 0.3 $\mu$M S-59.

TABLE N

| HPLC Peak | Photoproduct Identification | Concentration Remaining ($\mu$M) (Average ± S.D.) |
|---|---|---|
| D | Heterodimer of S-59 | 2.5 ± 0.4 |
| E | Homodimer of S-59 | 2.5 ± 0.3 |
| F | S-59 | 0.27 ± 0.05* |

*Two measurements were below the LOQ for the assay, while the other four measurements were at the LOQ.

Figure 41A:
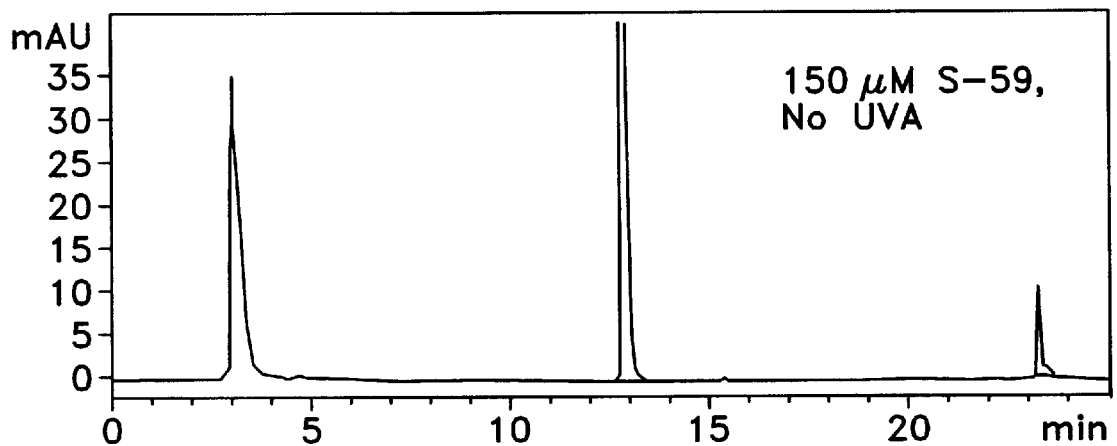
FIGS. 41A, 41B and 41C depict chromatograms of PC, containing 150 μM S-59 (15.2 mg/300 mL), showing levels of S-59 and free photoproducts before illumination with UVA (FIG. 41A), following illumination with UVA (FIG. 41B), and following illumination with UVA and an 8-hour incubation with a RD containing Dowex® XUS-43493 (FIG. 41C) and housed within a PL 2410 Plastic container (Baxter).
Figure 41B:
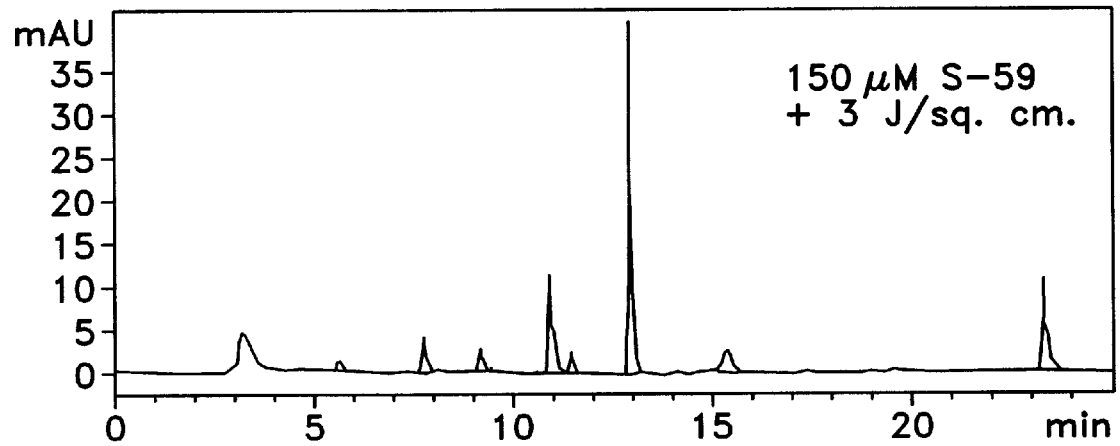
Figure 41C:
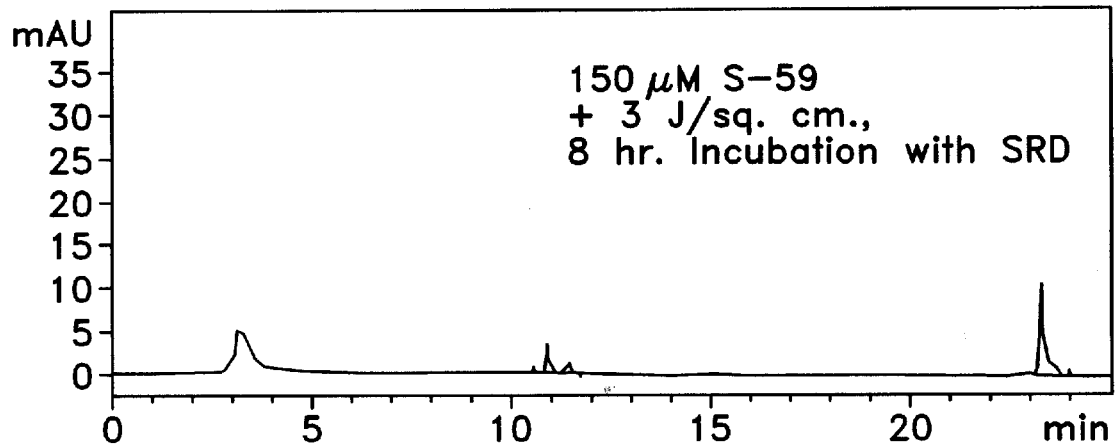

Representative HPLC chromatograms of PC showing levels of S-59 and free photoproducts before and after the 8-hour incubation with the RD are presented in FIG. 41. The chromatograms in FIG. 41 are of PC containing 150 $\mu$M S-59 (15.2 mg/300 mL) before illumination with UVA (top), following illumination with UVA (middle), and following illumination with UVA and incubation with the RD (bottom). The ordinate is optical density at 300 nm as measured by the HPLC detector and the abscissa is time in minutes.

Figure 42:
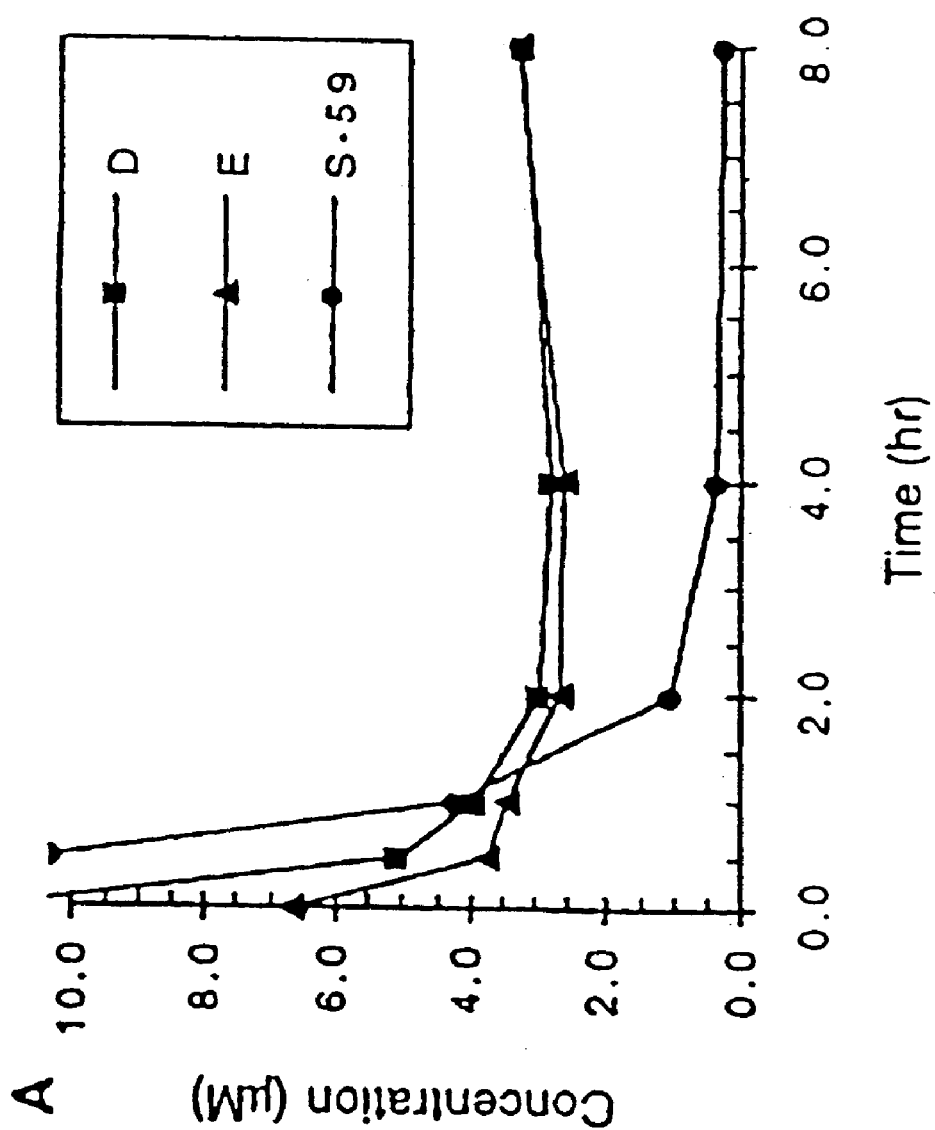
FIG. 42 depicts the kinetics for removal of unbound photoproducts D, E and S-59 from the complete PC (i.e., a PC containing platelets).

The data described above indicate that the levels of residual photoproducts D and E are higher than levels of residual S-59 even thought the initial levels of D and E in the illuminated PC were much lower than S-59. This observation can be more easily understood by examining the kinetics for removal of S-59 and photoproducts D and E from illuminated PCs. For this study, samples of the PC were removed from the PL 2410 Plastic container housing the RD at various time points prior to completion of the 8-hour treatment. The PC was assayed for unbound photoproducts using the HPLC assay discussed above, which quantifies the photoproducts present both within the platelets and in the plasma/PAS III mixture. The results presented in FIG. 42 depict the kinetics for removal of photoproducts D, E and S-59 from the complete PC. Photoproducts D and E appear to reach equilibrium levels while S-59 is almost completely removed.

Figure 43:
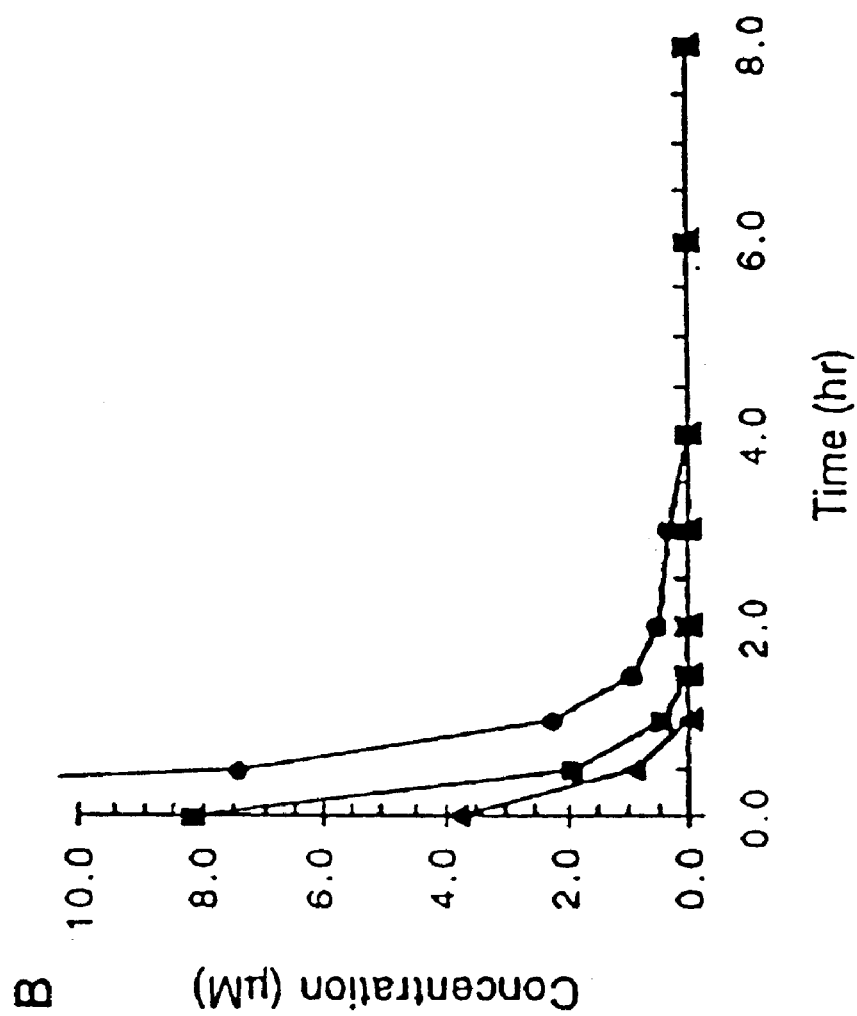
FIG. 43 depicts the kinetics for removal of unbound photoproducts D, E and S-59 from PC centrifuged to remove the platelets to allow separate analysis of unbound photoproducts in the plasma/PAS III.

In addition to assaying the complete PC, samples were centrifuged to remove the platelets so that unbound photoproducts in the plasma/PAS III could be analyzed separately. The results presented in FIG. 43 demonstrate that all of the photoproducts are removed from the plasma/PAS III compartment relatively rapidly. Though it is not necessary that the factors influencing removal of the photoproducts be precisely understood in order to practice the present invention, the results suggest that removal of photoproducts D and E is kinetically limited by migration from the platelet interior to the plasma/PAS III compartment. That it is more difficult to remove photoproducts D and E than S-59 may be due to the fact that photoproducts D and E possess two charged amino groups which must be neutralized when crossing the platelet membrane, while S-59 possesses only a single charged amino group.

The kinetic limitation to removal of photoproducts D and E from the platelet interior indicates that the preferred embodiment involve a batch contacting process rather than a flow process. That is, the use of a batch RD provides sufficient time to allow photoproducts D and E to be depleted from the platelet interior to levels feasible in light of the practical limitations imposed by blood banking procedures that limit the available incubation time with the resin.

EXAMPLE 37

In Vitro Platelet Function Tests Following Batch RD Treatment with Dowex® XUS-43493

This example describes in vitro platelet function testing of PC subjected to photochemical treatment, 8-hour RD treatment (Dowex® XUS-43493), and storage (PL 2410 Plastic container, Baxter). Assay results for platelet mixtures subjected to photochemical and RD treatment were compared to identical platelet mixtures subjected only to photochemical treatment. As described in detail below, each of the parameters was assessed on days 1, 5, and 7; after five days of platelet storage, treated and untreated platelet products demonstrated comparable in vitro function.

Two ABO-matched single donor PCs containing $2-5 \times 10^{11}$ platelets in approximately 300 mL of 35% plasma and 65% PAS III were pooled and redivided into two identical units in PL 2410 Plastic containers (Baxter). One unit (the control) was immediately placed on a platelet shaker and stored at approximately 22° C. The other unit (the test) was treated with 150 μM S-59 and 3 Joules/cm² UVA. After treatment, the platelets suspension was transferred into a second PL 2410 Plastic container containing a RD. Contact between platelets and the RD occurred for a period of approximately 8 hours, then the platelet suspension was transferred to a new PL 2410 Plastic container for storage. The time of blood donation was defined as day 0. Treatment with S-59, UVA (320–400 nm), and the RD was performed on day 1. Six replicate experiments were carried out, each with a different pool of two ABO-matched single-donor platelet concentrates.

For the evaluation of in vitro platelet function, platelet samples were withdrawn from both the control and test units before treatment and after treatment on days 2, 5, and 7. The following parameters were analyzed: pH, $pO_2$, $pCO_2$, bicarbonate concentration, platelet count, morphology, aggregation, platelet shape change, hypotonic shock response, lactate production, glucose consumption, ATP secretion, p-selectin expression, and microvesicle formation. Several of these assays, including pH, morphology score, platelet shape change, and hypotonic shock response, have been reported in the literature to correlate with in-vivo post-transfusion recovery and survival. The Student's paired t-test was used for statistical analysis.

To evaluate the efficacy of the RD for reducing the concentration of S-59, platelet samples from the test unit were analyzed for S-59 content by HPLC. Samples before illumination, after 3 Joules/cm² of illumination, and immediately following the 8-hour RD treatment were analyzed.

The results are set forth in Table O and Table P. Referring to Tables O and P, "ID" refers to whether the sample was a test unit (i.e., "T") or a control unit (i.e., "C"), the "*" indicates $p \leq 0.05$ between the test platelets and the control platelets, and "n.d." indicates that measurements were not done. For platelet count measurement, the volume of the control unit is approximately 5% less than the volume of the paired test unit; thus, for statistical analysis the platelet count per μL for the test unit was adjusted by a factor of 1.05. The pH of the treated platelets was maintained at 6.91±0.05 after seven days of storage following treatment.

The results demonstrate that platelets were not adversely affected by photochemical treatment followed by treatment with the RD of the present invention. There was no statistically significant difference (p>0.05) between the test platelets and the control platelets for platelet count, platelet aggregation, secretory adenosine triphosphate (ATP) and microvesicle formation evaluated over seven days of storage. Measurements in platelet morphology and platelet shape change demonstrated statistically significant ($p \leq 0.05$) improvements over time for the test platelets. Statistically significant differences ($p \leq 0.05$) in $pCO_2$, $pO_2$, $HCO_3-$, plasma glucose and lactate production suggested metabolic slowing for treated platelets which did not appear to be detrimental for platelet property. Statistically significant differences were detected for hypotonic shock response (HSR) on day 2 and for p-selectin expression on days 2 and 5.

TABLE O

| Assay | ID | Mean ± Standard Deviation Deviation²Mean ± Standard | | | |
|---|---|---|---|---|---|
| | | Day 1 | Day 2 | Day 5 | Day 7 |
| pH | C | 7.05 ± 0.06 | 6.98 ± 0.08*³ | 6.93 ± 0.09 | 6.96 ± 0.04* |
| | T | | 6.94 ± 0.05* | 6.92 ± 0.06 | 6.91 ± 0.05* |
| $pCO_2$ (mm Hg) | C | 28.3 ± 4.2 | 31.3 ± 5.3* | 27.0 ± 3.3* | 23.8 ± 2.5* |
| | T | | 29.2 ± 3.8* | 23.7 ± 3.5* | 20.7 ± 2.4* |
| $pO_2$ (mm Hg) | C | 68.8 ± 25.1 | 54.0 ± 14.4* | 73.4 ± 2.8* | 71.5 ± 2.7* |
| | T | | 68.3 ± 19.4* | 84.8 ± 22.5* | 88.8 ± 20.2* |
| Bicarbonate (mM) | C | 7.7 ± 0.4 | 7.3 ± 0.5* | 5.6 ± 0.7* | 5.4 ± 0.8* |
| | T | | 6.3 ± 0.3* | 4.8 ± 0.5* | 4.2 ± 0.7* |
| Platelet count ($\times 10^{-3}/\mu L$) | C | 1574 ± 218 | 1586 ± 239 | 1521 ± 250 | 1524 ± 233 |
| | T | | 1545 ± 247 | 1525 ± 246 | 1500 ± 219 |

TABLE P

| Assay | ID | Mean ± Standard Deviation | | | |
|---|---|---|---|---|---|
| | | Day 1 | Day 2 | Day 5 | Day 7 |
| Morphology (Out Of 400) | C | n.d.5 | 305 ± 18 | 279 ± 20*6 | 268 ± 12 |
| | T | | 302 ± 16 | 290 ± 20* | 274 ± 12 |
| Glucose (mM) | C | n.d. | 4.5 ± 1.1 | 1.6 ± 1.3* | 0.6 ± 0.5 |
| | T | | 4.6 ± 0.9 | 2.1 ± 1.1* | 0.8 ± 0.8 |
| Lactate (mM) | C | n.d. | 5.6 ± 1.9* | 9.9 ± 2.2* | 11.3 ± 1.1 |
| | T | | 4.7 ± 1.2* | 8.5 ± 1.6* | 10.8 ± 1.3 |
| (%) Aggregation | C | n.d. | 92 ± 4 | 80 ± 5 | 79 ± 8 |
| | T | | 88 ± 4 | 81 ± 7 | 81 ± 4 |
| ATP (Nmoles Per $10^8$ Platelets) | C | n.d. | 1.0 ± 0.1 | 0.7 ± 0.1 | 0.6 ± 0.2 |
| | T | | 1.0 ± 0.1 | 0.7 ± 0.2 | 0.6 ± 0.2 |
| Platelet Shape Change | C | n.d. | 1.1 ± 0.2 | 0.8 ± 0.2 | 0.7 ± 0.3* |
| | T | | 1.0 ± 0.1 | 0.9 ± 0.1 | 0.9 ± 0.3* |
| (%) HSR | C | n.d. | 46 ± 6* | 45 ± 5 | 45 ± 6 |
| | T | | 52 ± 5* | 45 ± 3 | 48 ± 8 |
| (%) p-Selectin-Positive | C | n.d. | 45 ± 4* | 51 ± 3 | 58 ± 3 |
| | T | | 49 ± 5* | 58 ± 5 | 60 ± 7 |
| (%) Microvesicle Formation | C | n.d. | 1.0 ± 0.2 | 1.1 ± 0.3 | 1.4 ± 0.5 |
| | T | | 0.9 ± 0.2 | 0.8 ± 0.2 | 1.7 ± 1.7 |

The concentration of S-59 before and after UVA illumination and the reduction in the concentration of residual S-59 following RD treatment were measured by HPLC analysis. At 0 Joule/cm², the initial S-59 concentration in a platelet concentrate was approximately 145±10 μM. After 3 Joule/cm² of illumination, 20.5%±2.3% of the initial S-59 remained unreacted (Table Q). Referring to Table Q, "n.a." means "not applicable" and "n.d." means "not done". The concentration of the remaining S-59 was reduced to 0.27±0.05 μM by treatment with a RD for 8 hours. This level of reduction in S-59 was approximately 100-fold.

TABLE Q

| Sampling Time | Mean ± Standard Deviation | |
|---|---|---|
| | μM S-59 | % Residual S-59 |
| Pre-Treatment | 145 ± 10 | n.a.[2] |
| Post 3 Joule/cm² UVA Illumination | n.d. | 20.5 ± 2.3 |
| Post Treatment With An RD (8 Hours) | 0.27 ± 0.05 | n.a. |

The results indicated that in vitro platelet function following photochemical treatment with 150 μM S-59 and 3 Joules/cm² UVA and depletion of S-59 by treatment with a RD for 8 hours was adequately maintained during seven days of storage.

The measured in vitro platelet function values for the test platelets obtained in this study were comparable to those obtained for photochemically treated platelets without RD exposure in an earlier study (results not shown). Photochemically treated platelets have been evaluated in normal human volunteers and have been shown to have normal in vivo recovery and life span. Based on these in vitro studies, treatment with a RD is not expected to have an additional effect on in vivo platelet function.

Following an 8-hour RD treatment, a 100-fold reduction in S-59 concentration was achieved. The residual S-59 concentration was reduced to ≦0.3 μM. These results demonstrate that the incorporation of a RD into a photochemical treatment process for platelet concentrates provides a viable means to effectively reduce the patient exposure to S-59 and thus increasing the safety margin of platelet transfusion.

EXAMPLE 38

Psoralen Removal from Fresh Frozen Plasma Using a Batch Removal Device

Some of the previous examples address the removal of psoralen from platelet concentrates using batch RDs containing Dowex® adsorbents. This example describes experiments with fresh frozen plasma (FFP) using RDs containing Dowex® XUS 43493 (also known commercially as Optipore® L493). The experiments assessed i) the amount of adsorbent required to remove S-59 to preferred levels, and ii) the effect of the mass of adsorbent determined in i) on clotting factor activity.

As described in detail below, the basic protocol for the experiments of this example is similar as that for the experiments with platelets. However, larger quantities of adsorbent (and larger mesh pouches to accommodate the adsorbent) were used because a very short treatment time, e.g, 1 hour, was desired. Fresh frozen plasma is preferably processed quickly because the clotting factors can degrade over time when at room temperature.

A. Effect of the Mass of Adsorbent on S-59 Removal Kinetics and Retention of Clotting Factor Activity Based on the results of toxicological studies (not shown), the preferred residual level of S-59 following photochemical- and removal device (RD)-treatment is less than 5 μM, preferably less than 1 μM, and most preferably less than or equal to 0.75 μM. In addition, it is preferred to achieve the desired level of ≦0.75 μM in less than 2 hours and preferably approximately one hour due to current FDA restrictions addressing handling of plasma at room temperature. With those goals in mind, the following experiments were performed.

Seven fresh units of plasma, each containing 250–325 mL, were pooled and divided into 250 mL portions of plasma. Each 250 mL portion was added to a PL 2410 Plastic container (Baxter), and a volume of S-59 solution was then added to each container to achieve a final S-59 concentration of 150 μM. The containers were then placed into an Ultraviolet Illumination System (Steritech, Inc. and Baxter Healthcare Corp., Fenwal Division) for photocherical treatment and illuminated (3 J/cm² long wavelength UVA [320–400 nm]).

Thereafter, the plasma/S-59 solution in each container was transferred into a separate PL 2410 Plastic container (Baxter) housing a RD containing 5, 10, 15, or 20 g of dry Dowex® XUS 43493 within a 12 cm×12 cm mesh pouch (polyester mesh with 30 μm openings). The containers were then incubated with shaking at room temperature. Samples were withdrawn from each of the containers pre-illumination and post-illumination at 1 hour and 8 hours. These samples were stored at −80° C. for subsequent analysis.

Samples taken from each bag after a 1-hour incubation were analyzed for S-59 and photoproduct removal. The results (n=7) for residual S-59 and photoproducts D and E (two of primary photoproducts formed during illumination, as described above) are presented in Table R (ND=not detectable; 1 hour incubation).

TABLE R

| | Photoproduct D (μM) | Photoproduct E (μM) | Residual S-59 (μM) |
|---|---|---|---|
| Pre-Removal | 4.80 | 0.52 | 83.30 |
| 5 g | ND | ND | 2.09 |
| 10 g | ND | ND | 0.63 |
| 15 g | ND | ND | 0.35 |
| 20 g | ND | ND | 0.28 |

Samples taken from each bag after an 8-hour incubation with the RD were analyzed for clotting factor activity. The results (n=7) using RDs containing different masses of adsorbent are presented in Table S (8 hour incubation).

TABLE S

| | Fibrogen (mg/dL) | Factor V (%) | Factor VIII (%) | Factor IX (%) | Prothrombin Time (s) | Partial Thromboplastin Time (s) | Thrombin Time (s) |
|---|---|---|---|---|---|---|---|
| Pre-removal | 218 | 99.5 | 70.4 | 149.5 | 12.4 | 30.9 | 37.7 |
| 5 g | 216 | 99.4 | 61.4 | 124.2 | 12.4 | 31.9 | 38.1 |
| 10 g | 213 | 97.7 | 63.4 | 109.8 | 12.4 | 32.2 | 38.0 |

TABLE S-continued

| | Fibrogen (mg/dL) | Factor V (%) | Factor VIII (%) | Factor IX (%) | Prothrombin Time (s) | Partial Thromboplastin Time (s) | Thrombin Time (s) |
|---|---|---|---|---|---|---|---|
| 15 g | 199 | 95.4 | 61.0 | 109.7 | 12.5 | 33.1 | 36.6 |
| 20 g | 203 | 94.9 | 55.9 | 100.5 | 12.5 | 33.8 | 33.8 |

B. S-59 Removal Kinetics and Retention of Clotting Factor Activity with a RD Containing 12.5 g Adsorbent Based on the results of the experiments described above, 12.5 g of Dowex® XUS 43493 was determined to be a preferred amount for the removal of residual S-59 and photoproducts and retention of clotting factor activity given the size of the bag, the volume of plasma, the selected concentration of S-59, and the desired 1-hour limit This section describes experiments to evaluate removal kinetics and retention of clotting factor activity using a RD containing 12.5 g of adsorbent.

The experiments were performed in the manner described above. Samples withdrawn from each of the containers pre-illumination and post-illumination for analysis of residual S-59 and photoproducts and clotting factor activity were stored at −80° C.

The results (n=7) for residual S-59 and photoproducts D and E obtained from samples taken after a 1-hour incubation are set forth in Table T. As indicated in Table T, the RD achieved the desired removal level (residual S-59≦0.75 $\mu$M in approximately one hour) (ND not detectable; 1 hour incubation).

TABLE T

| | Photoproduct D ($\mu$M) | Photoproduct E ($\mu$M) | Residual S-59 ($\mu$M) |
|---|---|---|---|
| Pre-removal (±SD) | 2.65 ± 0.64 | 1.30 ± 0.58 | 88.7 ± 4.1 |
| 12.5 g (±SD) | ND | ND | 0.62 ± 0.11 |

The results (n=7) of clotting factor activity after a 2-hour incubation with the RD are presented in Table U.

TABLE U

| | Fibrogen (mg/dL) | Factor V (%) | Factor VIII (%) | Factor IX (%) | Prothrombin Time (s) | Partial Thromboplastin Time (s) | Thrombin Time (s) |
|---|---|---|---|---|---|---|---|
| Pre-Removal (±SD) | 224 ± 31 | 116.8 ± 19.6 | 78.4 ± 7.8 | 118.4 ± 13.9 | 12.6 ± 0.5 | 31.5 ± 0.8 | 34.5 ± 3.3 |
| 12.5 g (±SD) | 208 ± 31 | 127.8 ± 22.0 | 72.9 ± 8.2 | 81.5 ± 9.1 | 12.6 ± 0.5 | 31.4 ± 1.0 | 29.9 ± 2.1 |

As the results indicate, there was little, if any, effect on prothrombin time, partial thromboplastin time, and Factor V. Moreover, the decreases in activity for the other clotting factors were acceptable. These results indicate that a RD containing Dowex® XUS 43493 can be successfully employed with FFP. Under the conditions tested, greater than 10 g is desired, and more preferably 12.5 g.

EXAMPLE 39

Effect of Psoralen Structural Characteristics on Adsorption

Several of the previous examples discussed the removal of S-59 from platelet concentrates by both batch and flow devices. This example entails a determination of how structural characteristics of psoralens may affect their removal by Amberlite adsorbents during batch adsorption.

Figure 44:
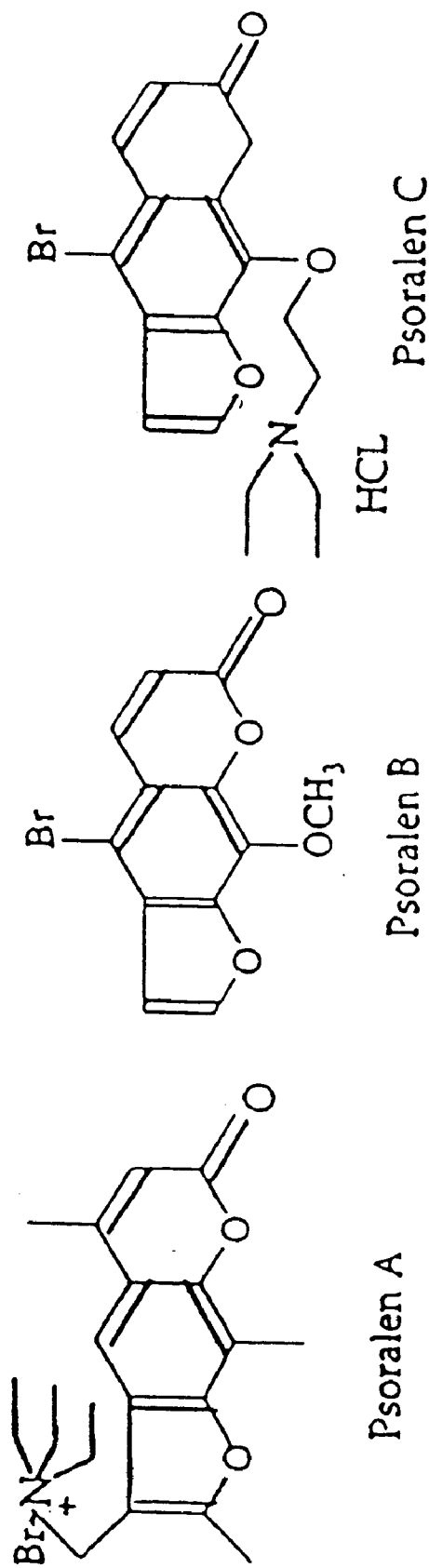
FIG. 44 depicts the chemical structures of three different psoralens used in some of the experiments of the present invention: Psoralen A [4'-(triethylamino) methyl-4,5',8-trimethylpsoralen]; Psoralen B [5-bromo-8-methoxypsoralen]; and Psoralen C [5-bromo-8-(diethylaminopropyloxy)-psoralen].
Figure 45:
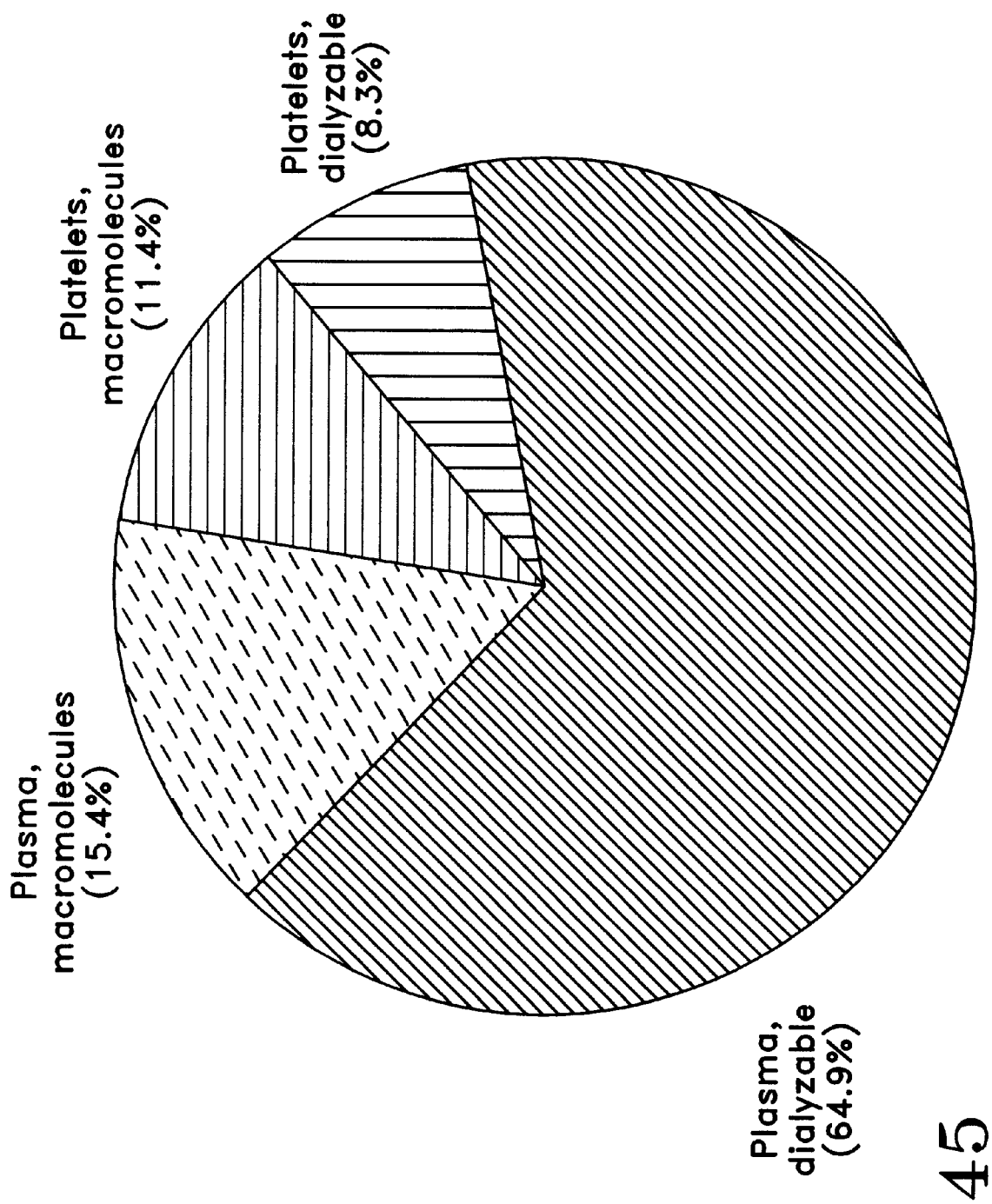
FIG. 45 diagrammatically depicts the distribution of S-59 in platelets suspended in 35% plasma/65% PAS III following illumination with UVA.
Figure 46:
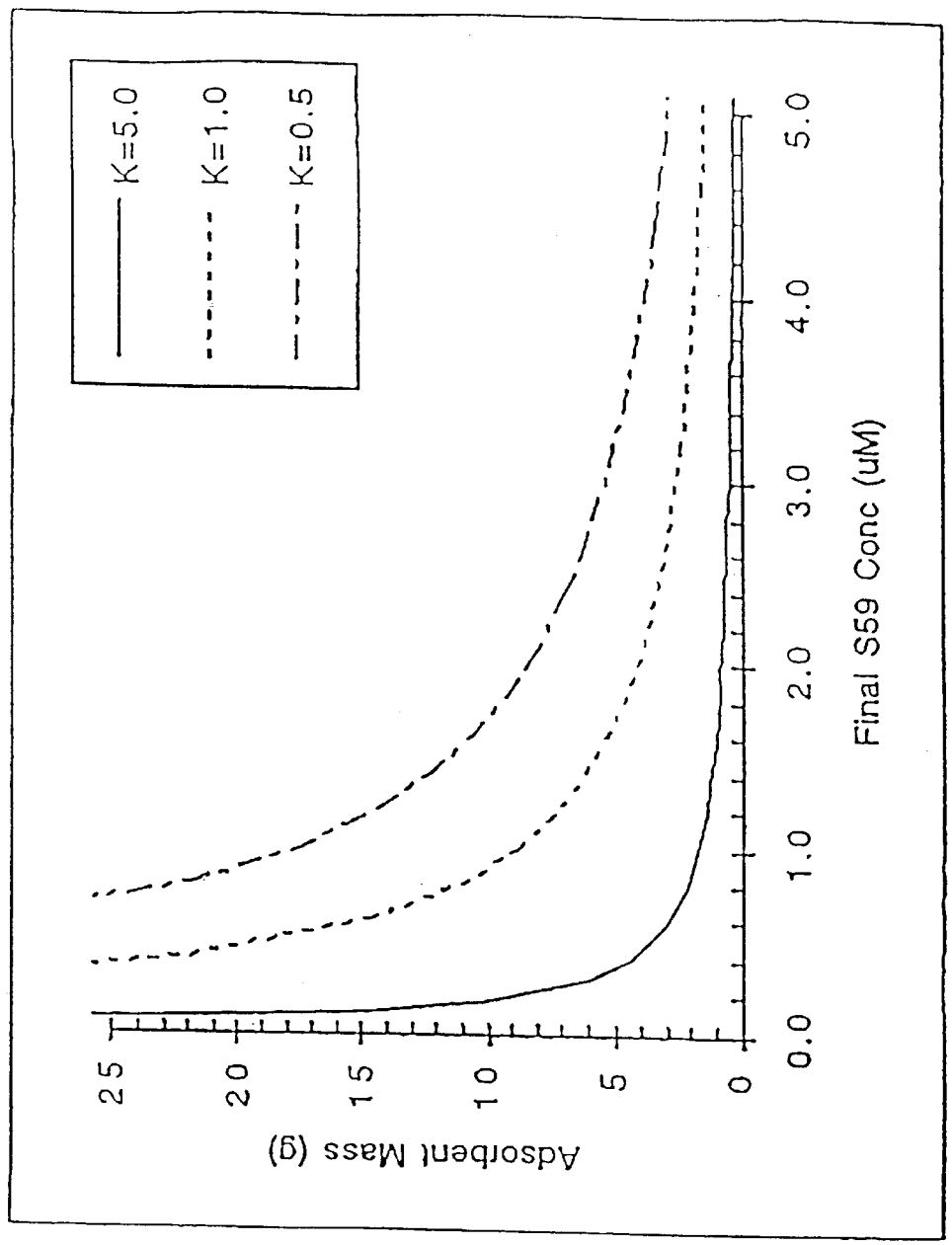
FIG. 46 is a graph showing the effect of the final S-59 concentration on the amount of adsorbent required (initial concentration, $C_o$=30 μM and a volume, V=300 mL). The "K-values" for each curve are listed in the legend.

The following three structurally different psoralens were used in the experiments of this example: Psoralen A, a psoralen with a quaternary amine [4'-(triethylamino) methyl-4,5',8-trimethylpsoralen]; Psoralen B, a brominated psoralen that is uncharged [5-bromo-8-methoxypsoralen]; and Psoralen C, a brominated psoralen that is positively charged [5-bromo-8-(diethylaminopropyloxy)-psoralen]. The chemical structures of these psoralens are set forth in FIG. 44; it should be noted that while Br⁻ is depicted as the counter ion is FIG. 44, Cl⁻ is generally the counter ion. For the adsorption studies, these psoralens were combined with Amberlite ionic and non-ionic adsorbents. More specifically, three non-ionic polystyrene adsorbents (Amberlite® XAD-2, XAD-4, and XAD-16), one non-ionic polyacrylic ester adsorbent (Amberlite® XAD-7), and two polystyrene adsorbents derivatized with ion-exchange groups (Amberlite® 200 [sulfonic acid] and Amberlite® DP-1 [carboxylic acid]) were used. Some of the properties of these adsorbents are set forth in Table A, supra.

For this example, the platelet concentrates contained approximately 4.0×10¹¹ platelets/300 mL in a mixture of 35% plasma/65% PAS III. Stock solutions (15 mM) of each psoralen (i.e., Psoralens A, B, and C) were prepared in DMSO. Serial dilutions of each psoralen were then prepared in the PC in concentrations ranging from 300 $\mu$M to 10 $\mu$M; for purposes of the calculations that follow, these initial concentrations are designated $C_o$. Thereafter, control samples and test samples were prepared for HPLC analysis. Test samples were prepared by adding a 3.0 mL aliquot of each dilution to a 5 mL polypropylene tube containing 0.1 g of adsorbent; control samples were prepared in an analogous manner with the exception that the adsorbent was omitted. The test and control samples were then incubated for 6 hours at 22° C. by rotating gently on a mixer (Barnstead, Thermolyne Model 400110). This incubation resulted in complete equilibrium between the adsorbed and the free psoralen based on previous equilibrium studies with S-59.

Adsorption data were then obtained by HPLC analysis on the test and control samples. Specifically, a 200 $\mu$l sample volume of PC was removed from each tube following the incubation period (special care being taken to ensure that no adsorbent particles were removed with the test samples). Each sample of PC was diluted 5-fold with sample diluent (final concentration: 35% methanol, 25 mM $KH_2PO_4$, pH=3.5) containing trimethylpsoralen (TMP) as the internal standard. The addition of methanol lyses platelets and precipitates plasma proteins so that psoralen contained within the platelets is not excluded by the assay. This sample preparation technique resulted in greater than 90% recovery of each of the psoralens that was used in the study. The samples were centrifuged, and the supernatant was filtered with 0.2 μm filters. The samples were then analyzed on a C-18 reversed phase column (YMC, model ODS-AM, 4.6× 250 mm) by rurning a linear gradient from 65% solvent A (25 mM $KH_2PO_4$, pH=3.5), 35% B (methanol) to 80/% B in 20 minutes.

The HPLC results from the control samples were used to construct calibration curves (not shown) for Psoralens A, B, and C. The calibration curves plotted HPLC area (y-axis) versus concentration (x-axis) for each psoralen. The slopes of the calibration curves were determined by linear least square method (y-intercept constrained to zero). The slopes were then used to calculate the concentration of psoralen remaining after 6 hours of contact time between the psoralen-containing PC and one of the Amberlite adsorbents (see below).

The HPLC results from the test samples were used in conjunction with the slopes of the calibration curves to determine concentrations of residual (i.e., free, non-adsorbed) psoralen, $C_f$ (μmoles/L), following incubation of PC with adsorbent. Specifically, HPLC area was divided by the slope of the calibration curve for that particular adsorbent, yielding $C_f$. The amount (μmoles) of psoralen which the adsorbent had removed from the PC was calculated [$V(C_o-C_f)$]. Adsorption isotherms were then constructed which plotted adsorbent capacity, q (μmoles/g), versus the final concentration of psoralen (μM) in the PC. Linear isotherms were obtained (described by [$q=KC_f$] (Equation 1, previously presented)). As previously discussed, the slope of the adsorbent isotherm, K (L/g), is termed the adsorption constant and can be determined by a linear regression of the adsorption data. Equation 1 can then be used to estimate the capacity of an adsorbent (q) for a given psoralen at a target final concentration, $C_f$. The adsorption capacities (μmoles/g) of various Amberlite adsorbents at 1 μM residual psoralen ($C_f$) are reported in Table V.

TABLE V

| | Adsorption Capacity At $C_f$ = 1 μM (μmoles/g) | | |
|---|---|---|---|
| Adsorbent | Psoralen A | Psoralen B | Psoralen C |
| Amberlite XAD-2 | 1.9 | 1.2 | 14.0 |
| Amberlite XAD-4 | 2.4 | 0.80 | 13.0 |
| Amberlite XAD-7 | 0.3 | 0.22 | 0.84 |
| Amberlite XAD-16 | 1.8 | 1.4 | 9.0 |
| Amberlite 200 | 0.83 | 0.01 | 0.55 |
| Amberlite DP-1 | 0.01 | 0.00 | 0.01 |

Subsequent to calculating the capacity of an adsorbent, the amount of adsorbent required to achieve a particular removal goal (ie., to remove a given amount of a particular psoralen) can be determined. That amount can be calculated using the following equation: [$M=V(C_o-C_f)/q$] (Equation 2, previously presented). For purposes of Equation 2, M is the mass of adsorbent (g) and V is the volume of sample to be treated (L).

In a typical situation wherein one wishes to achieve viral inactivation in a PC, the psoralen is added to the PC to a concentration of about 150 μM. However, during illumination, the psoralen undergoes photodegradation; the photodegradation process results in a lower concentration for $C_o$ of approximately 30–50 μM. Thus, one can determine the amount of adsorbent required to reduce the psoralen concentration from $C_o$=50 μM to a desired $C_f$ value. Table W lists the amount (g) of adsorbent required to reach a $C_f$ of 1 μM using Equation 2. The amounts in Table W were calculated using the adsorption capacities (q) listed in Table V, $C_o$=50 μM, and V=0.3 L (a typical therapeutic dose of PC).

TABLE W

| | Required Adsorbent Mass (g) $C_o$ = 50 μM, $C_f$= 1μM, V = 0.3 L, 1 from Table V | | |
|---|---|---|---|
| Adsorbent | Psoralen A | Psoralen B | Psoralen C |
| Amberlite XAD-2 | 7.7 | 12.2 | 1.0 |
| Amberlite XAD-4 | 6.1 | 18.4 | 1.1 |
| Amberlite XAD-7 | 49.0 | 66.8 | 17.5 |
| Amberlite XAD-16 | 8.2 | 10.5 | 1.6 |
| Amberlite 200 | 17.7 | 1470.0 | 26.7 |
| Amberlite DP-1 | 1470.0 | Not Removable | 1470.0 |

*Amount (g) of adsorbent required to achieve $C_f$ = 1 μM.

From the data presented in Table W, several conclusions can be drawn regarding (i) the characteristics of the adsorbents themselves and (ii) how psoralen structure affects the psoralens' removal capability. First, the polystyrene adsorbents, Amberlite® XAD-2, XAD-4, and XAD-16, appear to be capable of removing any of the psoralens to satisfactory levels. The performance of Amberlite® XAD-7, a polyacrylic adsorbent which is more polar that polystyrene, was not as effective as the more hydrophobic polystyrene adsorbents. Similarly, adsorption with the ion-exchange resins (Amberlite® 200 and Amberlite® DP-1) did not result in psoralen removal comparable to the hydrophobic polystyrene adsorbents. Though the present invention is not limited to any particular mechanism, the primary mechanism of psoralen removal is probably hydrophobic interaction involving aromatic stacking of the psoralen and the polystyrene side chains of the adsorbent. This explains, in part, the effectiveness of the hydrophobic polystyrene adsorbents.

Examination of psoralen properties reveals that HPLC retention time can be used as a rough estimate of hydrophobicity. Since each of the psoralens were analyzed using the same type of BPLC assay, one can use the psoralens' relative retention times to rank them according to increasing hydrophobicity. The HPLC retention times in order of increasing hydrophobicity were as follows: Psoralen A—7.8 min, Psoralen C—12.0 min, and Psoralen B—20.0 min. If hydrophobicity were the main factor in determining removability of a psoralen from PC, one would expect Psoralen B to be most easily removed since it is the most hydrophobic. However, despite being intermediate in hydrophobicity, Psoralen C was the most easily removed from PC. One possible explanation for this result is that Psoralen C does not interact as strongly as Psoralen B with cells or plasma proteins (e g., serum albumin) which are present in the PC. Strong interactions with cells or plasma proteins could compete with adsorption, thereby interfering with resin binding.

In addition, psoralens which are very polar, such as Psoralen A, may be more difficult to remove since they have decreased affinity for hydrophobic adsorbents. Moreover, the cationic exchange resins tested (Amberlite® DP-1 and Amberlite® 200) also gave poor removal for all psoralens tested. The results of this example demonstrate that psoralens having a wide range of structural characteristics are capable of being removed from PC.

EXAMPLE 40

Use of a RD in Conjunction with an Apheresis System

As previously indicated, the present invention contemplates the use of a RD in conjunction with an apheresis system. This example first describes the concurrent collection of single donor platelets and plasma via apheresis. Thereafter, the addition of PAS III and S-59 to the platelet preparation is described, followed by a discussion of the illumination and RD-treatment processes.

Methodology

The experiments of this example utilized a Baxter Biotech CS-3000™ Plus Blood Cell Separator with Access Management System™ (Baxter Healthcare Corp., Fenwal Division) in conjunction with a Closed System Apheresis Kit (Baxter Healthcare Corp., Fenwal Division). The components included two empty 1000 mL platelet collection bags (PL 3014 Plastic, Baxter), a PL 2410 Plastic container (Baxter), and a bag (PL 2411, Baxter) containing PAS III. Additional components of the apheresis system included a TNX-6™ Separation Chamber, a PLT-30™ Collection Chamber, an Accessory Weight Scale (all of Baxter Healthcare Corp., Fenwal Division), and a Terumo SCD 312 Sterile Tubing Welder. The operating parameters of the apheresis system were as follows: whole blood flow rate of 50–55 mL/min; interface detector offset set at 6; yield calibration factor of 1.13; plasma collection volume of 155 mL, and a platelet yield of $3.7 \times 10^{11}$ platelets. The equipment was set up and operated according to manufacturer's instructions, unless otherwise noted.

After calibration, the Accessory Weight Scale was used to tare the first platelet storage container; as used in this example, the term "tare" means to determine the weight of the storage container and to deduct that weight from the gross weight of the storage container and the solution to allow accurate measurement of the weight of the solution. The roller clamp was then closed. The second platelet storage container and the transfer pack were placed on separate hooks in front of the saline and ACD bags, respectively; the roller clamp of the second platelet storage container was closed, while that on the transfer pack was opened. The plasma transfer pack was used to collect the prime saline. The inlet and return lines were then primed with the saline, and the ACD ratio was adjusted to deliver an anticoagulant ratio of approximately 10:1.

Collection of Platelets and Plasma

Following venipuncture, whole blood was withdrawn from the donor and pumped through the inlet line of the multiple lumen tubing into the separation container of the centrifuge. The separation container separated the whole blood into two distinct phases, one containing plasma and platelets (i.e., platelet-rich plasma) and the other containing red blood cells; the red blood cells were returned to the donor. The platelet-rich plasma was then pumped from the separation container to the centrifuge's collection container. While the platelet-rich plasma passed through the collection container, the platelets were concentrated as the plasma was withdrawn. The concentrated platelets in the collection container were associated with approximately 30 mL of residual plasma. Of course, different operating parameters and different apheresis systems may result in other amounts of residual plasma being associated with the platelets.

When using the PLT-30™ Collection Chamber, an additional amount of plasma must be collected during the procedure for subsequent platelet resuspension and storage. Thus, after 400 mL of plasma had been processed over the plasma pump and the apheresis system was not in a spillover, the plasma option was selected and the system was programmed to collect 155 mL of plasma. After opening the appropriate clamps, 55 g of plasma (as weighed on the accessory scale) were collected in the first platelet storage container for later platelet resuspension, and 100 mL were subsequently collected in the second platelet storage container. Following plasma collection, the Reinfuse Mode of the Baxter Biotech CS-300™ Plus Blood Cell Separator was initiated. The return line needle was removed from the donor's arm.

After the separation and collection containers were removed from their respective clamp assemblies, the concentrated platelets in the collection container were resuspended until no platelet aggregates were visible. This was performed by adding the 55 g of plasma from the first platelet collection bag to the collection container. The platelet storage container and plasma transfer pack assembly were then placed in the bottom of the centrifuge compartment and the concentrated platelets were transferred to the first platelet collection bag. Finally, this platelet storage assembly was detached from the apheresis kit by making three hermetic seals approximately 12 inches below the manifold, resulting in a 12-inch length of tubing that was later used to connect the assembly via sterile docking to the PAS III solution. The tubing was cut between seals such that two seals were left on the platelet storage container assembly.

Transfer of PAS III Solution to the PC Followed by Transfer to Storage Container The PAS III solution was then added to the PC through a sterile docking procedure. U.S. Pat. No. 4,412,835 to Spencer, hereby incorporated by reference, describes a sterile docking apparatus. First, the 12-inch length of tubing from the platelet storage container assembly was placed into the back slot of the sterile connection device (SCD). The two platelet storage containers and the plasma transfer pack were hung to the right of the SCD, and their roller clamps were checked to assure that they were closed. The line from the PL 2411 Plastic container (Baxter) with the PAS III solution was placed into the front slot of the SCD so that the PL 2411 Plastic container (Baxter) was on the left side of the SCD. The sterile welding operation was then performed (Terumo SCD 312 Sterile Tubing Welder), and the fluidic connection was checked for leaks. After opening the roller clamp for the PC container, the PAS III solution was passed into the PC, and residual air from the PC was burped back into the empty PAS III container. Finally, the connection tubing was heat sealed and the PAS III container was discarded.

Next, the platelet storage container containing the PC/PAS III solution was connected to the PL 2410 Plastic container (Baxter). After weighing the empty PL 2410 Plastic container (Baxter), that container was sterile docked (using the procedure described above) to the plasma transfer pack (comprising the platelet storage container containing the PC/PAS III solution). Following completion of the sterile welding operation (Terumo SCD 312 Sterile Tubing Welder), the plasma transfer pack was discarded. The PC/PAS III solution in the first platelet container was then transferred into the PL 2410 Plastic container (Baxter), burping air back into the now empty first platelet storage container.

The PC/PAS III solution was then weighed. The total volume (excluding the tare weight of the PL 2410 Plastic container (Baxter)) should be 300±10 mL. If the total volume (measured by weight) is less than 290 mL, an amount of plasma can be added from the second platelet storage container (used to collect concurrent plasma) to achieve the desired volume. This results in a final platelet concentrate of approximately 35% plasma/65% PAS III solution. Finally, the line from the PL 2410 Plastic container (Baxter) was hermetically sealed as far from the container as possible, and the PC/PAS III solution was stored on a flat bed agitator at 22±2° C.

Sterile Connection of PC/PAS III Solution to S-59 Solution

The PC/PAS III solution was added to the S-59 solution and immediately transferred into an empty container for subsequent illumination. First, the above-described sterile docking/welding procedure was performed to create a fluidic connection between the line from the PCIPAS III container and one line of the plastic container (PL 2411 Plastic container, Baxter) with the S-59 (15 mL; 3 mM). The sterile welding operation was performed, and the line was checked for leaks. Next, the sterile welding procedure was used to connect the unattached line from the S-59 container to the shorter tubing of an empty PL 2410 Plastic container (Baxter). Again, the sterile welding operation was performed, and the line was checked for leaks. After removal of the appropriate clamp, the PC/PAS III solution was passed through the S-59 container and into the empty PL 2410 Plastic container (Baxter). The tubing between the S-59 container and the PL 2410 Plastic container (Baxter) was heat sealed as close to the S-59 container as possible, and the two empty containers were discarded. The S-59/PC/PAS III solution container was then placed on a flat bed agitator for a minimum of 5 minutes and a maximum of 1 hour.

As described above, this example involved the transfer of the PC/PAS III solution through the S-59 container, allowing the two solutions to mix, and into a separate PL 2410 Plastic container (Baxter). However, if the PC/PAS III solution is in a PL 2410 Plastic container (Baxter) prior to mixing with S-59 solution, it is not necessary to transfer the solutions into a separate container for illumination. Rather, the PL 2410 Plastic container (Baxter) containing the PC/PAS III solution can be sterile docked to the container with the S-59 solution, the two solutions thoroughly mixed, and the entire volume collected in the PL 2410 Plastic container (Baxter) for subsequent illumination.

If desired, samples of the resulting solution can be evaluated (e.g., pre-illuminations S-59 concentration by HPLC). The sampling procedure entails stripping (stripper/sealer model 1301; Sebra) the line to the platelet product to draw up a platelet sample into the remaining long piece of tubing on the S-59/PC/PAS III solution container. Thereafter, the tubing is heat sealed at least 12 inches away from the solution container, and samples may be prepared and processed. For example, the tubing ends can be cut over a sterile 15 mL centrifuge tube, allowing the solution to drain into the tube, and aliquots placed in 5 mL microcentrifuge tubes (Vacutainer, Becton-Dickinson). Samples of solution (e.g., 200 μl aliquots) can then be transferred to polypropylene microcentrifiuge tubes and stored at −20° C. prior to HPLC analysis.

Photochemical Treatment

The S-59/PC/PAS III solution container was then placed into an Ultraviolet Illumination System (Steritech, Inc. and Baxter Healthcare Corp., Fenwal Division) for photochemical treatment. The container was illuminated (3 J/cm$^2$ long wavelength UVA [320–400 nm]), with the temperature (before and after) and duration of treatment being recorded. The illuminated solution was then stored in the dark on a flat bed agitator at approximately 22° C. (22±2° C.) until being added to the container housing the RD.

S-59 Reduction with a RD

Prior to its use, the container housing the RD was inspected for particulate matter, the integrity of the RD, and integrity of the port filter. In addition, care was taken not to manipulate or crush the beads in the RD. FIG. 37 illustrates the type of container housing the batch removal device (RD) used in this example.

The above-described sterile docking/welding procedure was performed between the line from the treated S-59/PC/PAS III solution container and the line from the container housing the RD. The sterile welding operation was performed, and the line was checked for leaks. The treated S-59/PC/PAS III solution was transferred into the container housing the RD, and residual air was burped back into the now empty S-59/PC/PAS III solution container. If the container housing the RD was packaged under vacuum, there usually is not residual air. The line connecting the two bags was heat sealed, and the empty S-59/PC/PAS III solution container was discarded. The container now containing the S-59/PC/PAS III solution was then agitated continuously for 8 hours at 22° C. (flatbed platelet agitator model #PF48; Helmer Lab Co.).

Following the 8-hour agitation period, the line from the container housing the RD was sterile docked/welded (using the procedure described above) to the line from an empty PL 2410 Plastic container (Baxter). After checking the line for leaks, the RD-treated PC was transferred into the storage container. The connecting tubing was heat sealed, and the now empty container housing the RD was discarded. The storage container containing the final PC was then stored on a flat bed agitator at 22° C. The final treated solution can be stored (up to five days from the time of whole blood withdrawal from the donor) for subsequent infusion into a recipient.

EXAMPLE 41

Use of a RD in Conjunction with an Apheresis System

Though similar in many respects, this example involves a variation of the apheresis procedure presented in the preceding example. To illustrate, the protocol of this example utilized only one of the two platelet storage bags for plasma collection, while both platelet collection bags in the preceding example were used. In addition, while the platelet storage bags in the preceding example were PL 2410 Plastic containers (Baxter), the protocol of this example utilizes PL 3014 Plastic containers (Baxter) that are not suitable for photochemical treatment. These differences and others relating to the procedure and equipment used in collecting the blood products from the donor and the procedure for adding the various agents to those products are described in detail below.

Methodology

The experiments of this example utilized a Baxter Biotech CS-3000™ Plus Blood Cell Separator with Access Management System (Baxter Healthcare Corp., Fenwal Division) in conjunction with a Closed System Apheresis Kit (Baxter Healthcare Corp., Fenwal Division). The components included two empty 1000 mL platelet collection bags (PL 3014 Plastic container, Baxter), a PL 2410 Plastic container (Baxter), and a bag containing PAS III (PL-2411 Plastic container, Baxter). Additional components of the apheresis system included a TNX-6™ Separation Chamber (Baxter Healthcare Corp., Fenwal Division), a PLT-30™ Collection Chamber (Baxter Healthcare Corp., Fenwal Division), an Accessory Weight Scale (Baxter Healthcare Corp.), sterile connecting device (model SCD 312; Terumo) and a tubing sealer (model #1090; Sebra Engineering and Research Associates). These components were used in conjunction with an Access System Apheresis Kit (model 4R2295; Baxter Healthcare Corp., Fenwal Division). The operating parameters of the apheresis system were as follows: whole blood flow rate of 50–55 mL/min; interface detector offset set at 6; yield calibration factor of 1.13; plasma collection volume of 155 mL, and a platelet yield of $3.7 \times 10^{11}$ platelets. The equipment was set up and operated according to manufacturer's instructions, unless otherwise noted.

After calibration, the Accessory Weight Scale was used to tare the first platelet storage container; as used in this example, the term "tare" means to determine the weight of the storage container and to deduct that weight from the gross weight of the storage container and the solution to allow accurate measurement of the weight of the solution. The roller clamp was then closed. The second platelet storage container and the transfer pack were placed on separate hooks in front of the saline and ACD bags, respectively; the roller clamp of the second platelet storage container was opened, while that on the transfer pack was closed. The second platelet storage container was used for "spillovers" throughout the procedure, including the saline used to prime the inlet and return lines. The inlet and return lines were then primed with the saline, and the ACD ratio was adjusted to deliver an anticoagulant ratio of approximately 10:1–11:1.

Collection of Platelets and Plasma

Following venipuncture, whole blood was withdrawn from the donor and pumped through the inlet line of the multiple lumen tubing into the separation container of the centrifuge. The separation container separated the whole blood into platelet-rich plasma and red blood cells, the latter being returned to the donor. The platelet-rich plasma was then pumped from the separation container to the centrifuge's collection container. While the platelet-rich plasma passed through the collection container, the platelets were concentrated as the plasma was withdrawn.

When the apheresis system was ready to collect plasma (i.e., after 400 mL of plasma had been processed over the plasma pump), the plasma option was selected and a plasma volume of about 200 mL was entered. After closing the spillover bag and opening the first platelet collection bag hanging on the accessory weight scale, 54 g of plasma were collected for later platelet resuspension; the clamp on that bag was then closed. Immediately thereafter, the clamp to the transfer pack was opened and the remaining concurrent plasma was collected. Following concurrent plasma collection, the clamp was closed and the clamp to the spillover collection bag was reopened. At the completion of collection, all clamps were closed and the donor was disconnected from the apheresis system.

After the collection container was removed from the clamp assembly, the concentrated platelets therein were mixed by hand until they were homogeneously suspended in the residual plasma present in the collection container. Next, the clamp to the first platelet collection bag containing the 54 g of plasma was opened and the plasma was drained into the collection container. After mixing the platelets and plasma well, they were transferred back into first platelet storage container. Additional plasma collected in the transfer pack was then added to achieve a total of 105 mL plasma. The spillover collection bag was heat-sealed, disconnected, and discarded. Following the clamping off of the plasma lines going to the collection chamber, the tubing going to each bag was sealed (leaving enough tubing to be able to sterile dock the bags to one another). The PL 3014 Plastic container (Baxter) and the concurrent plasma transfer pack were kept attached to each other, and the collection and separation chambers were removed and discarded from those bags. Finally, the weight in the bag containing the PC was measured for determination of plasma volume.

Transfer of PAS III Solution and S-59 to the PC

In this example, in order to conserve plasma and to facilitate effective decontamination, platelets were concentrated into 105 mL of autologous plasma and 180 mL of PAS III (the preparation also contained 15 mL of ACD). A photochemical treatment system comprising one PL 2410 Plastic container (Baxter), a bag with 180 mL PAS III solution, and a bag with 15 mL (3 mM) S-59 solution was used. After weighing the empty platelet storage bag, a SCD was used to attach the transfer pack containing the 180 mL PAS III to the single donor plateletpheresis unit in the PL 3014 Plastic container (Baxter). The PAS III solution was then added to the PC, and the tubing between the empty PAS III bag and the PC was heat sealed, leaving enough tubing to the PL 3014 (Baxter) to subsequently sterile dock it to the S-59 bag. The empty PAS III bag was discarded, and the platelets were allowed to rest for less than 2 hours on a flatbed shaker (model #PF48; Helmer Lab Co.) until they disaggregated sufficiently.

It is preferred that S-59 not bind to the bag so that the desired amount of S-59 in the S-59 bag is available to mix with the blood product solution. Thus, in preferred embodiments of the present invention, non-psoralen binding polymers are used in the construction of the S-59 bag (and in the bags used to house other psoralens).

The S-59 bag was then sterile docked with a sterile connection device (SCD) (using the procedure prevously described) to the PL 3014 Plastic container (Baxter) containing the PC/PAS III solution. It is preferred that S-59 not bind to the bag so that the desired amount of S-59 in the S-59 bag is available to mix with the blood product solution. Thus, in prefeffed embodiments of the present invention, non-psoralen binding polymers are used in the construction of the S-59 bag (and in the bags used to house other psoralens). For the sterile docking procedure, the SCD was used to attach the shorter tubing on the PL 2410 Plastic container (Baxter) (the longer tubing can later be used for sampling, if desired) to the free line of the S-59 bag. The PC/PAS III solution in the PL 3014 Plastic container (Baxter) was then transferred through the S-59 bag into the PL 2410 Plastic container (B3axter). This transfer was necessary because the PL 3014 Plastic container is unsuitable for illumination. The line between the S-59 bag and the PL 2410 Plastic container (Baxter) now containing S-59/PC/PAS III was then heat sealed as close as possible to the S-59 bag, while the empty storage bag and S-59 bag were discarded. The S-59/PC/PAS III bag was then placed on a platelet shaker (minimum of 5 min., maximum of 1 hour).

If desired, samples of the resulting solution can be removed for analysis (e.g., pre-illumination S-59 concentration by HPLC). The sampling procedure entails stripping (stripper/sealer model 1301; Sebra) the line to the platelet product to draw up a platelet sample into the remaining long piece of tubing on the S-59/PC/PAS III solution container. Thereafter, the tubing is heat sealed at least 12 inches away from the solution container, and samples may be prepared and processed. For example, the tubing ends can be cut over a sterile 15 mL centrifuge tube, allowing the solution to drain into the tube, and aliquots placed in 5 mL microcentrifuge tubes (Vacutainer, Becton-Dickinson). Samples of solution (e.g., 200 µl aliquots) can then be transferred to polypropylene microcentrifuge tubes and stored at −20° C. prior to HPLC analysis.

The S-59/PC/PAS III solution container was then placed into an Ultraviolet Illumination System (Steritech, Inc. and Baxter Healthcare Corp., Fenwal Division). The container was illuminated (3 J/cm$^2$), and the illuminated solution was then stored in the dark on a flat bed agitator at 20–24° C.

At this point, the autologous plasma can be tested in vitro for platelet function. For this, the concurrent autologous plasma previously collected was subjected to centrifugation. Specifically, the SCD was used to attach the tubing of the plasma containing transfer pack to an empty 150 mL transfer pack container. The autologous plasma/new transfer pack were centrifuged (model #RC-3B with HA 6000 rotor; Sorvall Instruments) at 3000 g (3800 rmp) for 10 minutes at room temperature. The centrifuged plasma was then placed in the plasma extractor, and approximately half of the platelet-poor plasma was expressed into the new transfer pack. The tubing was heat sealed and the new transfer pack was disconnected from the original plasma transfer pack. Finally, the spike end (i.e., the end of a piece of tubing adapted to be inserted into the receiving port of another element, e.g., a blood storage container, to create a fluidic connection between the tubing and the element) of a plasma transfer set (4C2240, Baxter Healthcare Corp., Fenwal Division) was inserted into the port of the plasma transfer bag. A minimum of 20 mL of platelet poor plasma was expressed into a sterile centrifuge tube, covered, and stored at approximately 4° C. in preparation for platelet function tests.

S-59 Reduction with a RD

As previously indicated, a container housing the RD is stored in a vacuum-sealed foil overwrap in a preferred embodiment Prior to its use, the container housing the RD was removed from its overwrap and inspected for particulate matter, the integrity of the RD, and integrity of the port filter. In addition, care was taken not to manipulate or crush the beads in the RD. FIG. 37 illustrates the type of container housing the batch removal device (RD) used in this example.

The above-described sterile docking/welding procedure was performed between the line from the treated S-59/PC/PAS III solution container and the single inlet/outlet line of the container housing the RD. Prior to welding, the inlet/outlet line of the container housing the RD was rolled between two fingers to assure that it was not excessively collapsed before being placed in the SCD. The sterile welding operation was performed, the line was checked for leaks, and the connection between the two containers was rolled between two fingers to open the line. The treated S-59/PC/PAS III solution was then transferred into the container housing the RD, and residual solution was hand-expressed into that container. The line connecting the two bags was heat sealed (leaving enough tubing connected to the container housing the RD to allow transfer to the final platelet storage container), and the empty S-59/PC/PAS III solution container was discarded. The container containing the S-59/PC/PAS III solution was then agitated continuously for 8 hours at 22° C. (flatbed platelet agitator model #PF48; Helmer Lab Co.).

Following the 8-hour agitation period, the single line from the container housing the RD was sterile docked/welded (using the procedure previously described) to the line from an empty PL 2410 Plastic container (Baxter). After checking the line for leaks, the RD-treated PC was transferred into the storage container, residual solution being hand-expressed into the storage container. The connecting tubing was heat sealed, and the now empty container housing the RD was discarded. The storage container containing the final PC was then stored on a flat bed agitator at 22° C. (to be used in less than 4 days and no more than 5 days after withdrawal of whole blood from the donor). If desired, a platelet sample can be drawn up into the remaining piece of tubing on the storage container using the sampling procedure described above.

EXAMPLE 42

Addition of PAS III to a PC During Platelet Collection in an Apheresis System

As previously indicated, PAS III (or other suitable) synthetic media can be added to collected platelets following apheresis to produce a preparation suitable for illumination. However, such procedures require waiting until the platelets have been collected before utilizing a sterile docking procedure to add the PAS III to the collected platelets. This example describes an alternative embodiment in which PAS III is added during the platelet collection process during apheresis so that the platelets ultimately collected already contain the appropriate amount of PAS III.

Except for the deviations to be discussed, all of the equipment and procedures in Example 41 are equally applicable here. The process of this example utilizes a three-bag arrangement like that described above and depicted in FIG. 49. The first bag contains 180 mL of PAS III; the second bag is used to collect autologous plasma in a pre-determined amount; the third bag is the platelet collection bag in which all of the additives are combined.

The apheresis system is programmed to collect a predetermined volume of plasma to be used for platelet resuspension. However, the necessary volume must take into consideration the residual plasma associated with the platelets in the collection container following centrifugation and in the tubing of the apheresis system. For example, if it is desired that the collected platelets ultimately be suspended in 105 mL of plasma, the approximately 30 mL of residual plasma associated with the platelets in the collection container and the approximately 18–20 mL of residual plasma in the apheresis system's tubing must be subtracted. Thus, the apheresis system should be programmed to concurrently collect approximately 55–57 mL of plasma from the donor for subsequent platelet resuspension.

Following collection of the plasma, the concentrated platelets (approximately $4.0 \times 10^{11}$) in the collection chamber of the centrifuge are resuspended in the 105 mL (total) of plasma and transferred to the platelet storage container. While that mixture is being transferred, the required amount of PAS III is added from the PAS III container to provide the desired final concentration of plasma-to-PAS III. The final collected platelet bag contains approximately 300 mL and is composed of the following (in approximately the amounts indicated): 35% autologous plasma, 60% PAS III, 5% ACD, and $4.0 \times 10^{11}$ platelets.

Thereafter, the PC/PAS III solution may be processed using the procedures described in Example 41. Briefly, the resulting PC/PAS III solution is combined with S-59, agitated, and illuminated. The illuminated platelet preparation is then transferred to the container housing the RD for about 8 hours to allow removal of S-59 and photoproducts. Finally, the treated platelet preparation is transferred to a platelet storage bag from which it can be infused into a recipient.

It is to be understood that the invention is not to be limited to the exact details of operation or exact compounds, composition, methods, or procedures shown and described, as modifications and equivalents will be apparent to one skilled in the art.

I claim:

1. A blood-processing system that removes free psoralen and low molecular-weight psoralen photoproducts from a blood product to produce a blood product suitable for use in a human, said system comprising:
  a) a hemocompatible housing having walls that form a chamber;
  b) a hemocompatible resin comprising a hemocompatible macroreticular adsorbent resin having a network pore structure, wherein said hemocompatible resin resides within said chamber, wherein said hemocompatible resin possesses an affinity for said free psoralen and said low molecular-weight psoralen photoproducts, and wherein said hemocompatible resin does not require prewetting in a wetting solution to enable the resin to adsorb the free psoralen; and
  c) a hemocompatible filter that is configured to separate said hemocompatible resin from said blood product to provide treated blood product that is free of said resin.

2. The system of claim 1 wherein the resin has sufficient adsorption capacity that contact of said blood product with the system for less than or equal to 10 hours results in a residual concentration of psoralen in said blood product less than or equal to 1 $\mu$M.

3. The system of claim 1 wherein the blood product comprises platelets, and wherein contact of said platelets with the system for less than or equal to 10 hours results in a pH for said blood product of at least 6.5.

4. The system of claim 1 wherein the housing is adapted to receive said blood product from a blood storage bag.

5. The system of claim 1 wherein the housing has at least one inlet and at least one outlet and wherein said resin is positioned within the housing so that the blood product contacts said resin without bypassing said resin when the blood product flows through said at least one inlet and out said at least one outlet.

6. The system of claim 1 wherein said resin comprises a hypercrosslinked macroreticular adsorbent polyaromatic resin.

7. The system of claim 1 wherein said resin comprises a resin formed using styrene monomer.

8. The system of claim 7 wherein said resin comprises a resin formed using styrene and divinylbenzene monomers.

9. The system of claim 1 wherein said filter comprises a mesh enclosure that contains said adsorbent resin.

10. The system of claim 9 wherein said mesh enclosure has openings approximately 10 to 100 $\mu$m in size.

11. The system of claim 1 further comprising an agitator that is capable of agitating said blood product.

12. The system of claim 11 wherein the agitator comprises a stirrer positioned within said housing.

13. The system of claim 11 wherein the agitator comprises a shaker that is configured to hold and shake said housing.

14. The blood-processing system of claim 1 wherein said filter resides within said housing.

15. The blood-processing system of claim 1 wherein said hemocompatible macroreticular adsorbent resin comprises a cross-linked resin.

16. The blood-processing system of claim 1 wherein said hemocompatible macroreticular adsorbent resin comprises a non-ionic resin.

17. The blood-processing system of claim 1 wherein the resin has a surface area between about 725 and 1100 m²/g.

18. The blood processing system of claim 1 or claim 17 wherein the resin has a pore diameter between about 40 and 100 Å.

19. The blood processing system of claim 18 wherein the resin has a mean diameter between about 250 and 850 micron.

20. The blood processing system of claim 1 wherein the resin has a mean diameter between about 250 and 850 micron.

21. A blood-processing system that removes free psoralen and low molecular-weight psoralen photoproducts from a blood product to produce a blood product suitable for use in a human, said system comprising:
  a) a hemocompatible housing having walls that form a chamber;
  b) a hemocompatible resin comprising a hemocompatible hypercrosslinked resin having a network pore structure, wherein said hemocompatible resin resides within said chamber and wherein said hemocompatible resin possesses an affinity for said free psoralen and said low molecular-weight psoralen photoproducts; and
  c) a hemocompatible filter that is configured to separate said hemocompatible resin from said blood product to provide treated blood product that is free of said resin.

22. The system of claim 21 wherein contact of said blood product with the system for less than or equal to 10 hours results in a residual concentration of psoralen in said blood product less than or equal to 1 $\mu$M.

23. The system of claim 21 wherein the blood product comprises platelets, and wherein contact of said platelets with the system for less than or equal to 10 hours results in a pH of at least 6.5.

24. The system of claim 21 wherein the housing is adapted to receive said blood product from a blood storage bag.

25. The system of claim 21 wherein the housing has at least one inlet and at least one outlet and wherein said resin is positioned within the housing so that the blood product contacts said resin without bypassing said resin when the blood product flows through said at least one inlet and out said at least one outlet.

26. The system of claim 21 wherein said resin is selected from the group consisting of: a polyaromatic resin having a mean surface area of about 1100 m²/gm and a mean pore diameter of about 46 Å; and a functionalized polyaromatic resin having a mean surface area of about 800 m²/gm and a mean pore diameter of about 25 Å.

27. The system of claim 21 wherein said resin comprises a nonionic hypercrosslinked macroreticular adsorbent polyaromatic resin having a pore structure that does not require prewetting in a wetting solution to enable the resin to adsorb the free psoralen.

28. The blood-processing system of claim 27 wherein said housing, said resin, and said filter are sterile.

29. The system of claim 21 wherein said resin comprises a resin formed using styrene monomer.

30. The system of claim 29 wherein said resin comprises a resin formed using styrene and divinylbenzene monomers.

31. The system of claim 21 wherein said filter comprises a mesh enclosure that contains said adsorbent resin.

32. The system of claim 31 wherein said mesh enclosure has openings approximately 10 to 100 $\mu$m in size.

33. The system of claim 21 further comprising an agitator that is capable of agitating said blood product.

34. The system of claim 33 wherein the agitator comprises a stirrer positioned within said housing.

35. The system of claim 33 wherein the agitator comprises a shaker that is configured to hold and shake said housing.

36. The blood-processing system of claim 21 wherein said filter resides within said housing.

37. The blood-processing system of claim 21 wherein said hemocompatible hypercrosslinked resin comprises a non-ionic resin.

38. A functioning blood purification system comprising the blood-processing system of claim 1 or claim 21 and said blood product, which blood product is within said chamber and which blood product is in contact with the hemocompatible resin of said blood-processing system.

39. A functioning blood purification system comprising the blood-processing system of claim 1 or claim 21 and said blood product, wherein said free psoralen comprises an aminopsoralen selected from the group consisting of 4'-primary amino-substituted psoralen and 5'-primary amino-substituted psoralen.

40. The blood purification system of claim 39 wherein said aminopsoralen comprises 4'-(4-amino-2-oxa)butyl-4,5', 8-trimethylpsoralen.

41. A functioning blood purification system comprising the blood-processing system of claim 1 or claim 21 and said blood product, wherein said blood product comprises plasma.

42. A functioning blood purification system comprising the blood-processing system of claim 1 or claim 21 said blood product, wherein said blood product comprises platelets.

43. The blood purification system of claim 42 wherein said blood product further comprises a synthetic medium containing phosphate.

44. A functioning blood purification system comprising the blood-processing system of claim 1 or claim 21 and said blood product, wherein said hemocompatible resin has not been pre-wetted prior to said blood product contacting said hemocompatible resin.

45. The blood-processing system of claim 44 wherein said housing, said resin, and said filter are sterile.

46. The blood-processing system of claim 1 or claim 21 wherein the resin has sufficient adsorption capacity that contact of said blood product with said blood-processing system for less than or equal to 10 hours removes said psoralen to a level so that less than about 1% of the original amount of psoralen added to said blood product remains as free psoralen.

47. The blood-processing system of claim 1 or claim 21 wherein the resin has sufficient adsorption capacity that contact of said blood product with said blood-processing system for about 24 hours removes said psoralen to a level so that less than about 9% of the original amount of psoralen added to said blood product remains as free psoralen.

* * * * *

SEQUENCE LISTING

```
<160> NUMBER OF SEQ ID NOS:  4

<210> SEQ ID NO 1
<211> LENGTH: 20
<212> TYPE: DNA
<213> ORGANISM: Artificial Sequence
<220> FEATURE:
<223> OTHER INFORMATION: PCR product from dHBV source.

<400> SEQUENCE: 1
actagaaaac ctcgtggact                                              20

<210> SEQ ID NO 2
<211> LENGTH: 20
<212> TYPE: DNA
<213> ORGANISM: Artificial Sequence
<220> FEATURE:
<223> OTHER INFORMATION: PCR product from dHBV source.

<400> SEQUENCE: 2
gggagagggg agcccgcacg                                              20

<210> SEQ ID NO 3
<211> LENGTH: 20
<212> TYPE: DNA
<213> ORGANISM: Artificial Sequence
<220> FEATURE:
<223> OTHER INFORMATION: PCR product from dHBV source.

<400> SEQUENCE: 3
caatttcggg aagggcactc                                              20

<210> SEQ ID NO 4
<211> LENGTH: 20
<212> TYPE: DNA
<213> ORGANISM: Artificial Sequence
<220> FEATURE:
<223> OTHER INFORMATION: PCR product from dHBV source.

<400> SEQUENCE: 4
gctagtattc ccccgaaggt                                              20
```